US011254740B2

(12) United States Patent
Stevens et al.

(10) Patent No.: US 11,254,740 B2
(45) Date of Patent: *Feb. 22, 2022

(54) METHODS OF TREATMENT USING IL-23P19 MONOCLONAL ANTIBODIES

(71) Applicant: Bristol-Myers Squibb Company, Princeton, NJ (US)

(72) Inventors: Brenda L. Stevens, Seattle, WA (US); Mark W. Rixon, Issaquah, WA (US); Scott R. Presnell, Tacoma, WA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 168 days.

This patent is subject to a terminal disclaimer.

(21) Appl. No.: 16/435,960

(22) Filed: Jun. 10, 2019

(65) Prior Publication Data

US 2020/0040072 A1 Feb. 6, 2020

Related U.S. Application Data

(62) Division of application No. 15/620,358, filed on Jun. 12, 2017, now Pat. No. 10,358,489, which is a division of application No. 14/402,322, filed as application No. PCT/US2013/041928 on May 21, 2013, now Pat. No. 9,708,401.

(60) Provisional application No. 61/787,890, filed on Mar. 15, 2013, provisional application No. 61/784,600, filed on Mar. 14, 2013, provisional application No. 61/650,286, filed on May 22, 2012.

(51) Int. Cl.
*A61K 39/395* (2006.01)
*C07K 16/24* (2006.01)
*C07K 16/46* (2006.01)
*A61K 39/00* (2006.01)

(52) U.S. Cl.
CPC .......... *C07K 16/244* (2013.01); *C07K 16/468* (2013.01); *A61K 2039/505* (2013.01); *C07K 2317/21* (2013.01); *C07K 2317/24* (2013.01); *C07K 2317/31* (2013.01); *C07K 2317/34* (2013.01); *C07K 2317/55* (2013.01); *C07K 2317/565* (2013.01); *C07K 2317/76* (2013.01); *C07K 2317/92* (2013.01)

(58) Field of Classification Search
CPC ............ C07K 16/244; C07K 2317/565; A61K 2039/505; A61K 39/395
See application file for complete search history.

(56) References Cited

U.S. PATENT DOCUMENTS

| | | |
|---|---|---|
| 5,658,739 A | 8/1997 | Woods |
| 6,291,189 B1 | 9/2001 | Woods |
| 6,331,400 B1 | 12/2001 | Woods |
| 6,797,482 B2 | 9/2004 | Woods |
| 6,902,735 B1 | 6/2005 | Jacobs et al. |
| 7,491,391 B2 | 2/2009 | Benson et al. |
| 7,501,247 B2 | 3/2009 | Kastelein et al. |
| 7,601,818 B2 | 10/2009 | Wild et al. |
| 7,612,181 B2 | 11/2009 | Wu et al. |
| 7,619,071 B2 | 11/2009 | Presnell et al. |
| 7,750,126 B2 | 7/2010 | Hirata |
| 7,790,163 B2 | 9/2010 | Jaspers et al. |
| 7,790,862 B2 | 9/2010 | Lewis et al. |
| 7,807,155 B2 | 10/2010 | Di Padova et al. |
| 7,807,160 B2 | 10/2010 | Presta et al. |
| 7,807,414 B2 | 10/2010 | Benson et al. |
| 7,838,638 B2 | 11/2010 | Allan et al. |
| 7,846,443 B2 | 12/2010 | Presta et al. |
| 7,872,102 B2 | 1/2011 | Beidler et al. |
| 7,910,540 B2 | 3/2011 | Levin et al. |
| 7,910,703 B2 | 3/2011 | Lewis et al. |
| 7,943,745 B2 | 5/2011 | Tahara et al. |
| 8,012,477 B2 | 9/2011 | Cooreman et al. |
| 8,119,131 B2 | 2/2012 | Di Padova et al. |
| 8,178,095 B2 | 5/2012 | Kastelein et al. |
| 8,258,268 B2 | 9/2012 | Wu et al. |
| 8,268,773 B2 | 9/2012 | Presnell et al. |
| 8,333,968 B2 | 12/2012 | Lewis et al. |
| 8,362,212 B2 | 1/2013 | Presta |
| 8,496,936 B2 | 7/2013 | Lewis et al. |
| 8,557,544 B2 | 10/2013 | Jaspers et al. |
| 8,609,099 B2 | 12/2013 | Jaspers et al. |
| 8,835,610 B2 | 9/2014 | Hsieh et al. |
| 8,865,166 B2 | 10/2014 | Cochrane et al. |
| 8,871,467 B2 | 10/2014 | Jaspers et al. |
| 2002/0004587 A1 | 1/2002 | Miller et al. |
| 2006/0270003 A1 | 11/2006 | Arnott et al. |

(Continued)

FOREIGN PATENT DOCUMENTS

| | | |
|---|---|---|
| WO | WO 2004/071517 A2 | 8/2004 |
| WO | WO 2005/010044 A2 | 2/2005 |

(Continued)

OTHER PUBLICATIONS

Beyer et al., Crystal Structures of the Pro-Inflammatory Cytokine Interleukin-23 and Its Complex with a High-Affinity Neutralizing Antibody, J. Mol. Biol. , 2008, pp. 942-955, vol. 382.

(Continued)

*Primary Examiner* — Dong Jiang
(74) *Attorney, Agent, or Firm* — Brian J. Walsh

(57) ABSTRACT

The present invention relates to antagonizing the activity of IL-17A, IL-17F and IL-23 using bispecific antibodies that comprise a binding entity that is cross-reactive for IL-17A and IL-17F and a binding entity that binds IL-23p19. The present invention relates to novel bispecific antibody formats and methods of using the same.

24 Claims, 13 Drawing Sheets

Specification includes a Sequence Listing.

(56) References Cited

U.S. PATENT DOCUMENTS

| | | |
|---|---|---|
| 2009/0317400 A1 | 12/2009 | Masternak et al. |
| 2011/0076722 A1 | 3/2011 | Takahashi |
| 2012/0237442 A1 | 9/2012 | Rossi et al. |
| 2013/0209470 A1 | 8/2013 | Jaspers et al. |

FOREIGN PATENT DOCUMENTS

| | | | |
|---|---|---|---|
| WO | WO 2005/056772 A1 | 6/2005 | |
| WO | WO 2006/088833 A2 | 8/2006 | |
| WO | WO 2007/027761 A2 | 3/2007 | |
| WO | WO2007/147019 A2 | 12/2007 | |
| WO | WO2008/133684 A1 | 11/2008 | |
| WO | WO2008/134659 A2 | 11/2008 | |
| WO | WO2009/082624 A2 | 7/2009 | |
| WO | WO2009/149189 A1 | 12/2009 | |

OTHER PUBLICATIONS

Coloma et al., Design and production of novel tetravalent bispecific antibodies, Nature Biotechnology, Feb. 1997, pp. 159-163, vol. 15.
Davis et al, Engineering Optimized Biotherapeutics, Eighth Annual PEGS, Apr. 29, 2012, pp. 1-32.
Ding et al., Interleukin-17 contributes to cardiovascular diseases, Mol. Biol. Rep., published on line Feb. 14, 2012, pp. 1-6.
Gross et al., TACI-lg Neutralizes Molecules Critical for B Cell Development and Autoimmune Disease: Impaired B Cell Maturation in Mice Lacking BLyS, Immunity, Aug. 2001, pp. 289-302, vol. 15.
Horton et al., Engineering hybrid genes without the use of restriction enzymes: gene splicing by overlap extension, Gene, Apr. 15, 1989, pp. 61-68, vol. 77, Iss. 1.
Hu et al., The IL-17 pathway as a major therapeutic target in autoimmune diseases. Ann. N.Y. Acad. Sci., 2011, pp. 60-76, vol. 1217.
Hueber et al., Secukinumab, a human anti-IL-17A monoclonal antibody, for moderate to severe Crohn's disease: unexpected results of a randomised, double-blind placebo-controlled trial, GUT, 2012, pp. 1-8.
Leng et al., IL-23: A Promising Therapeutic Target for Systemic Lupus Erythematosus, Archives of Medical Research, 2010, pp. 221-225, vol. 41.
Liang et al., An IL-17F/A Heterodimer Protein Is Produced by Mouse Th17 Cells and Induces Airway Neutrophil Recruitment, J. Of Immunol., 2007, pp. 7791-7799, 2007.
Lundy et al., Cells of the synovium in rheumatoid arthritis T lymphocytes, Arthritis Res. Ther., 2007, pp. 1-11, vol. 9, No. 1.
Lupardus et al., The structure of Interleukin-23 reveals the molecular basis of p40 subunit sharing with IL-12, J. Mol Biol. Oct. 17, 2008, pp. 931-941, vol. 382, No. 4.
Mabry et al., Engineering of stable bispecific antibodies targeting IL-17A and IL-23, Protein Engineering, Design & Selection, Mar. 2010, pp. 115-137, vol. 23, No. 3.
Mc Geachy et al., Th17 Cell Differentiation: The Long and Winding Road, Immunity, Apr. 2008, pp. 445-453, vol. 28.
Mc Kenzie et al., Understanding the IL-23-IL-17 immune pathway, Trends in Immunology, Jan. 2006, pp. 1-7, vol. 27, No. 1.
Meng et al., Interleukin-17 Signaling in Inflammatory, Kupffer Cells, and Hepatic Stellate Cells Exacerbates Liver Fibrosis in Mice, Gastroenterology, 2012, pp. 765-776, vol. 143.
Miller et al., Design, Construction, and in Vitro Analyses of Multivalent Antibodies, J. of Immunol., 2003, pp. 4854-4861, vol. 170.
Ouyang et al., The Biological Functions of T Helpher 17 Cell Effector Cytokines in Inflammation, Immunity, Apr. 2008, pp. 454-467, vol. 28.
Paradowska-Gorycka et al., IL-23 in the Pathogenesis of Rheumatoid Arthritis, Scandinavian Journal of Immunology, 2010, pp. 134-145, vol. 71, Issue 3.
Parker et al., MALDI/MS-Based Epitope Mapping of Antigens Bound to Immobilized Antibodies, Mol. Biotechnol., Jan. 2002, pp. 49-62, vol. 20, No. 1.
Rutitzky et al., Severe CD4 T Cell-Mediated Immunopathology in Murine Schistosomiasis Is Dependent on IL-12p40 and Correlates with High Levels of IL-17 [1], J. Of Immunol., 2005, pp. 3920-3926, vol. 175.
Sandborn et al., Ustekinumab Induction and Maintenance Therapy in Refractory Crohn's Disease, NEJM, Oct. 18, 2012, pp. 1519-1528.
Shahrara, TH-17 cells in rheumatoid arthritis, Arthritis Research & Therapy, 2008, pp. 1-7, vol. 10, No. 4.
Songsivilai et al., Bispecific antibody: a tool for diagnosis and treatment of disease, Clin. Exp. Immunol., 1990, pp. 315-321, vol. 79.
Sotomayor, E., "Skulls and bones" new member: Th17, Blood, 2010, pp. 3380-3382, vol. 116.
Tan et al., The Th17 Pathway in Cystic Fibrosis Lung Disease, Am. J. Respir. CritCare Med., 2011, pp. 252-258, vol. 184.
Valente et al., Interleukin-17A stimulates cardiac fibroblast proliferation and migration via negative regulation of the dual-specificity phosphatase MKP-1/DUSP-1, Cellular Signalling, 2012, pp. 560-568, vol. 24.
Wei et al., Hypomethylation of the IL17RC Promoter Associates with Age-Related Macular Degeneration, Cell Reports, Nov. 29, 2012, pp. 1151-1158, vol. 2.
Wells, J., Systemic Mutational Analyses of Protein-Protein Interfaces, Methods in Enzymology, 1991, pp. 390-411, vol. 202.
West et al., Mutational Analysis of the Transferrin Receptor Reveals Overlapping HFE and Transferrin Binding sites, J. Mol. Biol., 2001, pp. 385-397, vol. 313.
West et al., Crystal Structure and Immunoglobulin G Binding Properties of the Human Major Histocompatibility Complex-Related Fc Receptor, Biochemistry, 2000, pp. 9698-9708, vol. 39, No. 32.
Kostelny et al., Formation of A Bispecific Antibody By The Use of Leucine Zippers, J. of Immunology, Mar. 1, 1992, pp. 1547-1553, vol. 148, No. 5.
Chan et al., Therapeutic antibodies for autoimmunity and inflammation, Nat Rev Immuol. May 2010, vol. 10, Issue 5, pp. 301-316.
Paul, Fundamental Immunology, 3$^{rd}$ Ediition, 1993, pp. 292-295.
Pascalis et al., Grafting "Abbreviated" Complementarity-Determining Regions Containing Specificity-Determining Residues Essential for Ligand Contact to Engineer a Less Immunogenic Humanized Monoclonal Antibody, J. Immunol. 2002, vol. 169, pp. 3076-3084.
Dixon et al. IL-17a and IL-22 Induce Expression of Antimicrobials in Gastrointestinal Epithelial Cells and May Contribute to Epithelial Cell Defense against Helicobacter pylori. PLoS One. Feb. 11, 2016;11(2):e0148514.
Contreras et al., Role of IL-17 during Helicobacter pylori infection (MPF2P.750). J. Immunol., May 2015; 194 (1 Supplement) 63.9 (meeting abstract).

SEQUENCE LISTING

<160> NUMBER OF SEQ ID NOS: 128

<210> SEQ ID NO 1
<211> LENGTH: 468
<212> TYPE: DNA
<213> ORGANISM: Homo sapiens
<220> FEATURE:
<221> NAME/KEY: CDS
<222> LOCATION: (1)..(468)
<220> FEATURE:
<221> NAME/KEY: sig_peptide
<222> LOCATION: (1)..(69)

<400> SEQUENCE: 1

```
atg act cct ggg aag acc tca ttg gtg tca ctg cta ctg ctg ctg agc      48
Met Thr Pro Gly Lys Thr Ser Leu Val Ser Leu Leu Leu Leu Leu Ser
1               5                   10                  15 ctg gag gcc ata gtg aag gca gga atc aca atc cca cga aat cca gga      96
Leu Glu Ala Ile Val Lys Ala Gly Ile Thr Ile Pro Arg Asn Pro Gly
                20                  25                  30 tgc cca aat tct gag gac aag aac ttc ccc cgg act gtg atg gtc aac     144
Cys Pro Asn Ser Glu Asp Lys Asn Phe Pro Arg Thr Val Met Val Asn
            35                  40                  45 ctg aac atc cat aac cgg aat acc aat acc aat ccc aaa agg tcc tca     192
Leu Asn Ile His Asn Arg Asn Thr Asn Thr Asn Pro Lys Arg Ser Ser
        50                  55                  60 gat tac tac aac cga tcc acc tca cct tgg aat ctc cac cgc aat gag     240
Asp Tyr Tyr Asn Arg Ser Thr Ser Pro Trp Asn Leu His Arg Asn Glu
65                  70                  75                  80 gac cct gag aga tat ccc tct gtg atc tgg gag gca aag tgc cgc cac     288
Asp Pro Glu Arg Tyr Pro Ser Val Ile Trp Glu Ala Lys Cys Arg His
                85                  90                  95 ttg ggc tgc atc aac gct gat ggg aac gtg gac tac cac atg aac tct     336
Leu Gly Cys Ile Asn Ala Asp Gly Asn Val Asp Tyr His Met Asn Ser
                100                 105                 110 gtc ccc atc cag caa gag atc ctg gtc ctg cgc agg gag cct cca cac     384
Val Pro Ile Gln Gln Glu Ile Leu Val Leu Arg Arg Glu Pro Pro His
            115                 120                 125 tgc ccc aac tcc ttc cgg ctg gag aag ata ctg gtg tcc gtg ggc tgc     432
Cys Pro Asn Ser Phe Arg Leu Glu Lys Ile Leu Val Ser Val Gly Cys
        130                 135                 140 acc tgt gtc acc ccg att gtc cac cat gtg gcc taa                     468
Thr Cys Val Thr Pro Ile Val His His Val Ala
145                 150                 155
```

<210> SEQ ID NO 2
<211> LENGTH: 155
<212> TYPE: PRT
<213> ORGANISM: Homo sapiens

<400> SEQUENCE: 2

```
Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80
```

```
Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 3
<211> LENGTH: 492
<212> TYPE: DNA
<213> ORGANISM: Homo sapiens
<220> FEATURE:
<221> NAME/KEY: CDS
<222> LOCATION: (1)..(492)
<220> FEATURE:
<221> NAME/KEY: sig_peptide
<222> LOCATION: (1)..(90)

<400> SEQUENCE: 3 atg aca gtg aag acc ctg cat ggc cca gcc atg gtc aag tac ttg ctg      48
Met Thr Val Lys Thr Leu His Gly Pro Ala Met Val Lys Tyr Leu Leu
1               5                   10                  15 ctg tcg ata ttg ggg ctt gcc ttt ctg agt gag gcg gca gct cgg aaa      96
Leu Ser Ile Leu Gly Leu Ala Phe Leu Ser Glu Ala Ala Ala Arg Lys
            20                  25                  30 atc ccc aaa gta gga cat act ttt ttc caa aag cct gag agt tgc ccg     144
Ile Pro Lys Val Gly His Thr Phe Phe Gln Lys Pro Glu Ser Cys Pro
        35                  40                  45 cct gtg cca gga ggt agt atg aag ctt gac att ggc atc atc aat gaa     192
Pro Val Pro Gly Gly Ser Met Lys Leu Asp Ile Gly Ile Ile Asn Glu
    50                  55                  60 aac cag cgc gtt tcc atg tca cgt aac atc gag agc cgc tcc acc tcc     240
Asn Gln Arg Val Ser Met Ser Arg Asn Ile Glu Ser Arg Ser Thr Ser
65                  70                  75                  80 ccc tgg aat tac act gtc act tgg gac ccc aac cgg tac ccc tcg gaa     288
Pro Trp Asn Tyr Thr Val Thr Trp Asp Pro Asn Arg Tyr Pro Ser Glu
                85                  90                  95 gtt gta cag gcc cag tgt agg aac ttg ggc tgc atc aat gct caa gga     336
Val Val Gln Ala Gln Cys Arg Asn Leu Gly Cys Ile Asn Ala Gln Gly
            100                 105                 110 aag gaa gac atc tcc atg aat tcc gtt ccc atc cag caa gag acc ctg     384
Lys Glu Asp Ile Ser Met Asn Ser Val Pro Ile Gln Gln Glu Thr Leu
        115                 120                 125 gtc gtc cgg agg aag cac caa ggc tgc tct gtt tct ttc cag ttg gag     432
Val Val Arg Arg Lys His Gln Gly Cys Ser Val Ser Phe Gln Leu Glu
    130                 135                 140 aag gtg ctg gtg act gtt ggc tgc acc tgc gtc acc cct gtc atc cac     480
Lys Val Leu Val Thr Val Gly Cys Thr Cys Val Thr Pro Val Ile His
145                 150                 155                 160 cat gtg cag taa                                                     492
His Val Gln <210> SEQ ID NO 4
<211> LENGTH: 163
<212> TYPE: PRT
<213> ORGANISM: Homo sapiens

<400> SEQUENCE: 4
```

```
Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Arg Lys
            20                  25                  30

Ile Pro Lys Val Gly His Thr Phe Phe Gln Lys Pro Glu Ser Cys Pro
            35                  40                  45

Pro Val Pro Gly Gly Ser Met Lys Leu Asp Ile Gly Ile Ile Asn Glu
        50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
            115                 120                 125

Val Val Arg Arg Lys His Gln Gly Cys Ser Val Ser Phe Gln Leu Glu
        130                 135                 140

Lys Val Leu Val Thr Val Gly Cys Thr Cys Val Thr Pro Val Ile His
145                 150                 155                 160

His Val Gln

<210> SEQ ID NO 5
<211> LENGTH: 570
<212> TYPE: DNA
<213> ORGANISM: Homo sapiens
<220> FEATURE:
<221> NAME/KEY: CDS
<222> LOCATION: (1)..(570)
<220> FEATURE:
<221> NAME/KEY: sig_peptide
<222> LOCATION: (1)..(57)

<400> SEQUENCE: 5 atg ctg ggg agc aga gct gta atg ctg ctg ttg ctg ctg ccc tgg aca    48
Met Leu Gly Ser Arg Ala Val Met Leu Leu Leu Leu Leu Pro Trp Thr
1               5                   10                  15 gct cag ggc aga gct gtg cct ggg ggc agc agc cct gcc tgg act cag    96
Ala Gln Gly Arg Ala Val Pro Gly Gly Ser Ser Pro Ala Trp Thr Gln
            20                  25                  30 tgc cag cag ctt tca cag aag ctc tgc aca ctg gcc tgg agt gca cat   144
Cys Gln Gln Leu Ser Gln Lys Leu Cys Thr Leu Ala Trp Ser Ala His
        35                  40                  45 cca cta gtg gga cac atg gat cta aga gaa gag gga gat gaa gag act   192
Pro Leu Val Gly His Met Asp Leu Arg Glu Glu Gly Asp Glu Glu Thr
    50                  55                  60 aca aat gat gtt ccc cat atc cag tgt gga gat ggc tgt gac ccc caa   240
Thr Asn Asp Val Pro His Ile Gln Cys Gly Asp Gly Cys Asp Pro Gln
65                  70                  75                  80 gga ctc agg gac aac agt cag ttc tgc ttg caa agg atc cac cag ggt   288
Gly Leu Arg Asp Asn Ser Gln Phe Cys Leu Gln Arg Ile His Gln Gly
                85                  90                  95 ctg att ttt tat gag aag ctg cta gga tcg gat att ttc aca ggg gag   336
Leu Ile Phe Tyr Glu Lys Leu Leu Gly Ser Asp Ile Phe Thr Gly Glu
            100                 105                 110 cct tct ctg ctc cct gat agc cct gtg ggc cag ctt cat gcc tcc cta   384
Pro Ser Leu Leu Pro Asp Ser Pro Val Gly Gln Leu His Ala Ser Leu
            115                 120                 125
```

```
ctg ggc ctc agc caa ctc ctg cag cct gag ggt cac cac tgg gag act      432
Leu Gly Leu Ser Gln Leu Leu Gln Pro Glu Gly His His Trp Glu Thr
130                 135                 140 cag cag att cca agc ctc agt ccc agc cag cca tgg cag cgt ctc ctt      480
Gln Gln Ile Pro Ser Leu Ser Pro Ser Gln Pro Trp Gln Arg Leu Leu
145                 150                 155                 160 ctc cgc ttc aaa atc ctt cgc agc ctc cag gcc ttt gtg gct gta gcc      528
Leu Arg Phe Lys Ile Leu Arg Ser Leu Gln Ala Phe Val Ala Val Ala
                165                 170                 175 gcc cgg gtc ttt gcc cat gga gca gca acc ctg agt ccc taa              570
Ala Arg Val Phe Ala His Gly Ala Ala Thr Leu Ser Pro
            180                 185
```

<210> SEQ ID NO 6
<211> LENGTH: 189
<212> TYPE: PRT
<213> ORGANISM: Homo sapiens

<400> SEQUENCE: 6

```
Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Glu Thr
        50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 7
<211> LENGTH: 122
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE

```
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(111)
<223> OTHER INFORMATION: CDR3
<220> FEATURE:
<221> NAME/KEY: MISC_FEATURE
<222> LOCATION: (112)..(122)
<223> OTHER INFORMATION: FR4

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Gly Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser
        115                 120

<210> SEQ ID NO 8
<211> LENGTH: 327
<212> TYPE: PRT
<213> ORGANISM: Homo sapiens

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 9
<211> LENGTH: 107
<212> TYPE: PRT
<213> ORGANISM: Homo sapiens
<220> FEATURE:
<221> NAME/KEY: MISC_FEATURE
<222> LOCATION: (1)..(23)
<223> OTHER INFORMATION: FR1
<220> FEATURE:
<221> NAME/KEY: MISC_FEATURE
<222> LOCATION: (24)..(35)
<223> OTHER INFORMATION: CDR1
<220> FEATURE:
<221> NAME/KEY: MISC_FEATURE
<222> LOCATION: (36)..(50)
<223> OTHER INFORMATION: FR2
<220> FEATURE:
<221> NAME/KEY: MISC_FEATURE
<222> LOCATION: (51)..(57)
<223> OTHER INFORMATION: CDR2
<220> FEATURE:
<221> NAME/KEY: MISC_FEATURE
<222> LOCATION: (58)..(89)
<223> OTHER INFORMATION: FR3
<220> FEATURE:
<221> NAME/KEY: MISC_FEATURE
<222> LOCATION: (90)..(97)
<223> OTHER INFORMATION: CDR3
<220> FEATURE:
<221> NAME/KEY: MISC_FEATURE
<222> LOCATION: (98)..(107)
<223> OTHER INFORMATION: FR4

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

```
                    50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Tyr
                 85                  90                  95

Thr Phe Gly Gln Gly Thr Lys Leu Glu Ile Lys
                100                 105

<210> SEQ ID NO 10
<211> LENGTH: 107
<212> TYPE: PRT
<213> ORGANISM: Homo sapiens

<400> SEQUENCE: 10

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 11
<211> LENGTH: 329
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Ala Glu Gly Ala Pro Ser Val Phe Leu Phe Pro Pro
             115                 120                 125

Lys Pro Lys Asp Thr Leu Met Ile Ser Arg Thr Pro Glu Val Thr Cys
         130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                    165                 170                 175
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ser Ser Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 12
<211> LENGTH: 10
<212> TYPE: PRT
<213> ORGANISM: Homo sapiens

<400> SEQUENCE: 12

Gly Gly Gly Gly Ser Gly Gly Gly Gly Ser
1               5                   10

<210> SEQ ID NO 13
<211> LENGTH: 123
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 13
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ala Pro Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser
            115                 120
```

<210> SEQ ID NO 14
<211> LENGTH: 103
<212> TYPE: PRT
<213> ORGANISM: Homo sapiens
<220> FEATURE:
<221> NAME/KEY: MISC_FEATURE
<222> LOCATION: (1)..(103)
<223> OTHER INFORMATION: IgG1 CH1

<400> SEQUENCE: 14

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

<210> SEQ ID NO 15
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: IgG4 CH1

<400> SEQUENCE: 15

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
                50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val

<210> SEQ ID NO 16
<211> LENGTH: 680
<212> TYPE: PRT
<213> ORGANISM: Homo sapiens

<400> SEQUENCE: 16

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Ser Tyr
                20                  25                  30

Ala Met His Trp Val Arg Gln Ala Pro Gly Lys Gly Leu Glu Trp Val
             35                  40                  45

Ala Val Ile Ser Tyr Gly Gly Ser Lys Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser Ala Ser Thr Lys Gly Pro
         115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
```

325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys Gly Gly Gly Gly Ser Gly Gly Gly Gly Ser Gln Val Gln Leu Val
            450                 455                 460

Gln Ser Gly Ala Glu Val Lys Lys Pro Gly Ala Ser Val Lys Val Ser
465                 470                 475                 480

Cys Lys Ala Ser Gly Tyr Thr Phe Asn Glu Tyr Thr Met His Trp Val
                485                 490                 495

Lys Gln Ala Pro Gly Gln Arg Leu Glu Trp Met Gly Gly Ile Asn Pro
            500                 505                 510

Asn Ser Gly Gly Val Ser Tyr Asn Gln Asn Phe Lys Gly Lys Ala Thr
            515                 520                 525

Leu Thr Val Asp Thr Ser Ala Ser Thr Ala Tyr Met Glu Leu Ser Ser
        530                 535                 540

Leu Arg Ser Glu Asp Thr Ala Val Tyr Tyr Cys Ala Arg Gly Gly Asp
545                 550                 555                 560

Gly Tyr Tyr Thr Asn Tyr Phe Asp Ile Asp Tyr Trp Gly Gln Gly Thr
                565                 570                 575

Thr Val Thr Val Ser Ser Ala Ser Thr Lys Gly Pro Ser Val Phe Pro
            580                 585                 590

Leu Ala Pro Cys Ser Arg Ser Thr Ser Glu Ser Thr Ala Ala Leu Gly
            595                 600                 605

Cys Leu Val Lys Asp Tyr Phe Pro Glu Pro Val Thr Val Ser Trp Asn
        610                 615                 620

Ser Gly Ala Leu Thr Ser Gly Val His Thr Phe Pro Ala Val Leu Gln
625                 630                 635                 640

Ser Ser Gly Leu Tyr Ser Leu Ser Ser Val Val Thr Val Pro Ser Ser
                645                 650                 655

Ser Leu Gly Thr Lys Thr Tyr Thr Cys Asn Val Asp His Lys Pro Ser
            660                 665                 670

Asn Thr Lys Val Asp Lys Arg Val
            675                 680

<210> SEQ ID NO 17
<211> LENGTH: 214
<212> TYPE: PRT
<213> ORGANISM: Homo sapiens

<400> SEQUENCE: 17

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 687
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
                20                  25                  30

Thr Met His Trp Val Lys Gln Ala Pro Gly Gln Arg Leu Glu Trp Met
            35                  40                  45

Gly Gly Ile Asn Pro Asn Ser Gly Gly Val Ser Tyr Asn Gln Asn Phe
 50                  55                  60

Lys Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

-continued

```
Pro Ala Val Leu Gln Ser Ser Gly Leu Tyr Ser Leu Ser Val Val
                180                 185                 190

Thr Val Pro Ser Ser Leu Gly Thr Gln Thr Tyr Ile Cys Asn Val
            195                 200                 205

Asn His Lys Pro Ser Asn Thr Lys Val Asp Lys Val Glu Pro Lys
        210                 215                 220

Ser Cys Asp Lys Thr His Thr Cys Pro Pro Cys Pro Ala Pro Glu Ala
225                 230                 235                 240

Glu Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
    435                 440                 445

Leu Ser Pro Gly Gly Gly Gly Ser Gly Gly Gly Gly Ser Gln Val
450                 455                 460

Gln Leu Val Glu Ser Gly Gly Val Val Gln Pro Gly Arg Ser Leu
465                 470                 475                 480

Arg Leu Ser Cys Ala Ala Ser Gly Phe Ser Phe Ser Ser Tyr Ala Met
                485                 490                 495

His Trp Val Arg Gln Ala Pro Gly Lys Gly Leu Glu Trp Val Ala Val
            500                 505                 510

Ile Ser Tyr Gly Gly Ser Lys Lys Tyr Tyr Ala Asp Ser Val Lys Gly
    515                 520                 525

Arg Phe Thr Ile Ser Arg Asp Asn Ser Lys Asn Thr Leu Tyr Leu Gln
    530                 535                 540

Met Asn Ser Leu Arg Ala Glu Asp Thr Ala Val Tyr Tyr Cys Ala Arg
545                 550                 555                 560

Met Gly Tyr Tyr Asp Ile Leu Thr Gly Pro Phe Asp Tyr Trp Gly Gln
                565                 570                 575

Gly Thr Leu Val Thr Val Ser Ser Ala Ser Thr Lys Gly Pro Ser Val
            580                 585                 590
```

-continued

```
Phe Pro Leu Ala Pro Ser Ser Lys Ser Thr Ser Gly Thr Ala Ala
            595                 600                 605

Leu Gly Cys Leu Val Lys Asp Tyr Phe Pro Glu Pro Val Thr Val Ser
    610                 615                 620

Trp Asn Ser Gly Ala Leu Thr Ser Gly Val His Thr Phe Pro Ala Val
625                 630                 635                 640

Leu Gln Ser Ser Gly Leu Tyr Ser Leu Ser Ser Val Val Thr Val Pro
                645                 650                 655

Ser Ser Ser Leu Gly Thr Gln Thr Tyr Ile Cys Asn Val Asn His Lys
            660                 665                 670

Pro Ser Asn Thr Lys Val Asp Lys Lys Val Glu Pro Lys Ser Cys
        675                 680                 685

<210> SEQ ID NO 19
<211> LENGTH: 5
<212> TYPE: PRT
<213> ORGANISM: Homo sapiens

<400> SEQUENCE: 19

Ser Tyr Ala Met His
1               5

<210> SEQ ID NO 20
<211> LENGTH: 17
<212> TYPE: PRT
<213> ORGANISM: Homo sapiens

<400> SEQUENCE: 20

Val Ile Ser Tyr Gly Gly Ser Lys Lys Tyr Tyr Ala Asp Ser Val Lys
1               5                   10                  15

Gly

<210> SEQ ID NO 21
<211> LENGTH: 13
<212> TYPE: PRT
<213> ORGANISM: Homo sapiens

<400> SEQUENCE: 21

Met Gly Tyr Tyr Asp Ile Leu Thr Gly Pro Phe Asp Tyr
1               5                   10

<210> SEQ ID NO 22
<211> LENGTH: 12
<212> TYPE: PRT
<213> ORGANISM: Homo sapiens

<400> SEQUENCE: 22

Arg Ala Ser Gln Ser Val Ser Ser Ser Tyr Leu Ala
1               5                   10

<210> SEQ ID NO 23
<211> LENGTH: 7
<212> TYPE: PRT
<213> ORGANISM: Homo sapiens

<400> SEQUENCE: 23

Gly Ala Ser Ser Arg Ala Thr
1               5

<210> SEQ ID NO 24
<211> LENGTH: 8
<212> TYPE: PRT
```

<213> ORGANISM: Homo sapiens

<400> SEQUENCE: 24

Gln Gln Tyr Gly Ser Ser Tyr Thr
1               5

<210> SEQ ID NO 25
<211> LENGTH: 5
<212> TYPE: PRT
<213> ORGANISM: Homo sapiens

<400> SEQUENCE: 25

Glu Tyr Thr Met His
1               5

<210> SEQ ID NO 26
<211> LENGTH: 17
<212> TYPE: PRT
<213> ORGANISM: Homo sapiens

<400> SEQUENCE: 26

Gly Ile Asn Pro Asn Ser Gly Gly Val Ser Tyr Asn Gln Asn Phe Lys
1               5                   10                  15

Gly

<210> SEQ ID NO 27
<211> LENGTH: 14
<212> TYPE: PRT
<213> ORGANISM: Homo sapiens

<400> SEQUENCE: 27

Gly Gly Asp Gly Tyr Tyr Thr Asn Tyr Phe Asp Ile Asp Tyr
1               5                   10

<210> SEQ ID NO 28
<211> LENGTH: 687
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(111)
<223> OTHER INFORMATION: CDR3
<220> FEATURE:
<221> NAME/KEY: MISC_FEATURE
<222> LOCATION: (112)..(122)
<223> OTHER INFORMATION: FR4
<220> FEATURE:
<221> NAME/KEY: MISC_FEATURE
<222> LOCATION: (462)..(491)
<223> OTHER INFORMATION: FR1

```
<220> FEATURE:
<221> NAME/KEY: MISC_FEATURE
<222> LOCATION: (492)..(496)
<223> OTHER INFORMATION: CDR1
<220> FEATURE:
<221> NAME/KEY: MISC_FEATURE
<222> LOCATION: (497)..(510)
<223> OTHER INFORMATION: FR2
<220> FEATURE:
<221> NAME/KEY: MISC_FEATURE
<222> LOCATION: (511)..(527)
<223> OTHER INFORMATION: CDR2
<220> FEATURE:
<221> NAME/KEY: MISC_FEATURE
<222> LOCATION: (528)..(559)
<223> OTHER INFORMATION: FR3
<220> FEATURE:
<221> NAME/KEY: MISC_FEATURE
<222> LOCATION: (560)..(573)
<223> OTHER INFORMATION: CDR3
<220> FEATURE:
<221> NAME/KEY: MISC_FEATURE
<222> LOCATION: (574)..(584)
<223> OTHER INFORMATION: FR4
<220> FEATURE:
<221> NAME/KEY: MISC_FEATURE
<222> LOCATION: (585)..(687)
<223> OTHER INFORMATION: IgG1 CH1

<400> SEQUENCE: 28

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Gly Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Glu
225                 230                 235                 240

Gly Ala Pro Ser Val Phe Leu Phe Pro Pro Lys Pro Lys Asp Thr Leu
                245                 250                 255
```

```
Met Ile Ser Arg Thr Pro Glu Val Thr Cys Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Gly Gly Gly Ser Gly Gly Gly Ser Gln Val Gln
        450                 455                 460

Leu Val Gln Ser Gly Ala Glu Val Lys Lys Pro Gly Ala Ser Val Lys
465                 470                 475                 480

Val Ser Cys Lys Ala Ser Gly Tyr Thr Phe Asn Glu Tyr Thr Met His
                485                 490                 495

Trp Val Lys Gln Ala Pro Gly Gln Arg Leu Glu Trp Met Gly Gly Ile
            500                 505                 510

Asn Pro Asn Ser Gly Gly Val Ser Tyr Asn Gln Asn Phe Lys Gly Lys
        515                 520                 525

Ala Thr Leu Thr Val Asp Thr Ser Ala Ser Thr Ala Tyr Met Glu Leu
        530                 535                 540

Ser Ser Leu Arg Ser Glu Asp Thr Ala Val Tyr Tyr Cys Ala Arg Gly
545                 550                 555                 560

Gly Asp Gly Tyr Tyr Thr Asn Tyr Phe Asp Ile Asp Tyr Trp Gly Gln
                565                 570                 575

Gly Thr Thr Val Thr Val Ser Ser Ala Ser Thr Lys Gly Pro Ser Val
            580                 585                 590

Phe Pro Leu Ala Pro Ser Ser Lys Ser Thr Ser Gly Gly Thr Ala Ala
        595                 600                 605

Leu Gly Cys Leu Val Lys Asp Tyr Phe Pro Glu Pro Val Thr Val Ser
        610                 615                 620

Trp Asn Ser Gly Ala Leu Thr Ser Gly Val His Thr Phe Pro Ala Val
625                 630                 635                 640

Leu Gln Ser Ser Gly Leu Tyr Ser Leu Ser Ser Val Val Thr Val Pro
                645                 650                 655

Ser Ser Ser Leu Gly Thr Gln Thr Tyr Ile Cys Asn Val Asn His Lys
            660                 665                 670

Pro Ser Asn Thr Lys Val Asp Lys Lys Val Glu Pro Lys Ser Cys
```

<210> SEQ ID NO 29
<211> LENGTH: 679
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4
<220> FEATURE:
<221> NAME/KEY: MISC_FEATURE
<222> LOCATION: (461)..(490)
<223> OTHER INFORMATION: FR1
<220> FEATURE:
<221> NAME/KEY: MISC_FEATURE
<222> LOCATION: (491)..(495)
<223> OTHER INFORMATION: CDR1
<220> FEATURE:
<221> NAME/KEY: MISC_FEATURE
<222> LOCATION: (496)..(499)
<223> OTHER INFORMATION: FR2
<220> FEATURE:
<221> NAME/KEY: MISC_FEATURE
<222> LOCATION: (510)..(526)
<223> OTHER INFORMATION: CDR2
<220> FEATURE:
<221> NAME/KEY: MISC_FEATURE
<222> LOCATION: (527)..(558)
<223> OTHER INFORMATION: FR3
<220> FEATURE:
<221> NAME/KEY: MISC_FEATURE
<222> LOCATION: (559)..(571)
<223> OTHER INFORMATION: CDR3
<220> FEATURE:
<221> NAME/KEY: MISC_FEATURE
<222> LOCATION: (572)..(582)
<223> OTHER INFORMATION: FR4
<220> FEATURE:
<221> NAME/KEY: MISC_FEATURE
<222> LOCATION: (583)..(680)
<223> OTHER INFORMATION: IgG4 CH1

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ala Pro Gly Gln Arg Leu Glu Trp Met
        35                  40                  45

```
Gly Gly Ile Asn Pro Asn Ser Gly Gly Val Ser Tyr Asn Gln Asn Phe
 50                  55                  60
Lys Gly Lys Ala Thr Leu Thr Val Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Asp Gly Tyr Tyr Thr Asn Tyr Phe Asp Ile Asp Tyr
            100                 105                 110
Trp Gly Gln Gly Thr Thr Val Thr Val Ser Ser Ala Ser Thr Lys Gly
            115                 120                 125
Pro Ser Val Phe Pro Leu Ala Pro Cys Ser Arg Ser Thr Ser Glu Ser
130                 135                 140
Thr Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Lys Thr Tyr Thr Cys Asn Val
            195                 200                 205
Asp His Lys Pro Ser Asn Thr Lys Val Asp Lys Arg Val Glu Ser Lys
210                 215                 220
Tyr Gly Pro Pro Cys Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
            275                 280                 285
Asn Ala Lys Thr Lys Pro Arg Glu Glu Gln Phe Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Glu Glu Met Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
            435                 440                 445
Gly Gly Gly Gly Ser Gly Gly Gly Ser Gln Val Gln Leu Val
450                 455                 460
Glu Ser Gly Gly Gly Val Val Gln Pro Gly Arg Ser Leu Arg Leu Ser
```

```
                465                 470                 475                 480
Cys Ala Ala Ser Gly Phe Ser Phe Ser Ser Tyr Ala Met His Trp Val
                    485                 490                 495

Arg Gln Ala Pro Gly Lys Gly Leu Glu Trp Val Ala Val Ile Ser Tyr
                500                 505                 510

Gly Gly Ser Lys Lys Tyr Tyr Ala Asp Ser Val Lys Gly Arg Phe Thr
            515                 520                 525

Ile Ser Arg Asp Asn Ser Lys Asn Thr Leu Tyr Leu Gln Met Asn Ser
        530                 535                 540

Leu Arg Ala Glu Asp Thr Ala Val Tyr Tyr Cys Ala Arg Met Gly Tyr
545                 550                 555                 560

Tyr Asp Ile Leu Thr Gly Pro Phe Asp Tyr Trp Gly Gln Gly Thr Leu
                565                 570                 575

Val Thr Val Ser Ser Ala Ser Thr Lys Gly Pro Ser Val Phe Pro Leu
                580                 585                 590

Ala Pro Cys Ser Arg Ser Thr Ser Glu Ser Thr Ala Ala Leu Gly Cys
                595                 600                 605

Leu Val Lys Asp Tyr Phe Pro Glu Pro Val Thr Val Ser Trp Asn Ser
    610                 615                 620

Gly Ala Leu Thr Ser Gly Val His Thr Phe Pro Ala Val Leu Gln Ser
625                 630                 635                 640

Ser Gly Leu Tyr Ser Leu Ser Ser Val Val Thr Val Pro Ser Ser Ser
                645                 650                 655

Leu Gly Thr Lys Thr Tyr Thr Cys Asn Val Asp His Lys Pro Ser Asn
                660                 665                 670

Thr Lys Val Asp Lys Arg Val
                675

<210> SEQ ID NO 30
<211> LENGTH: 66
<212> TYPE: DNA
<213> ORGANISM: Homo sapiens

<400> SEQUENCE: 30
atgcggcgga gaggctggtc ctggatcttc ctgtttctgc tgagcggaac agccggcgtg      60
ctgagc                                                                66

<210> SEQ ID NO 31
<211> LENGTH: 22
<212> TYPE: PRT
<213> ORGANISM: Homo sapiens

<400> SEQUENCE: 31

Met Arg Arg Arg Gly Trp Ser Trp Ile Phe Leu Phe Leu Leu Ser Gly
1               5                   10                  15

Thr Ala Gly Val Leu Ser
            20

<210> SEQ ID NO 32
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 32 gag gtc cag ctg caa cag tca gga cct gag ctg gtg aag cct ggg gct      48
```

```
Glu Val Gln Leu Gln Gln Ser Gly Pro Glu Leu Val Lys Pro Gly Ala
1               5                   10                  15 tca gtg aag ata tcc tgt aag act tct gga tac aca ttc aat gaa tac       96
Ser Val Lys Ile Ser Cys Lys Thr Ser Gly Tyr Thr Phe Asn Glu Tyr
                20                  25                  30 acc atg cac tgg gtg aag cag agc cat gga aag cgc ctt gag tgg att      144
Thr Met His Trp Val Lys Gln Ser His Gly Lys Arg Leu Glu Trp Ile
            35                  40                  45 gga ggt att aat cct aac agt ggt ggt gtt agc tac aac cag aac ttc      192
Gly Gly Ile Asn Pro Asn Ser Gly Gly Val Ser Tyr Asn Gln Asn Phe
        50                  55                  60 aag ggc aag gcc aca ttg act gta gac aag tcc tcc agc aca gcc tcc      240
Lys Gly Lys Ala Thr Leu Thr Val Asp Lys Ser Ser Ser Thr Ala Ser
65                  70                  75                  80 atg gag ctc cgc agc ctg aca tct gag gat tct gca gtc ttt tac tgt      288
Met Glu Leu Arg Ser Leu Thr Ser Glu Asp Ser Ala Val Phe Tyr Cys
                85                  90                  95 gca aga ggg gga gat ggt tac tac acc aat tac ttt gat att gac tac      336
Ala Arg Gly Gly Asp Gly Tyr Tyr Thr Asn Tyr Phe Asp Ile Asp Tyr
                100                 105                 110 tgg ggt caa gga acc tca gtc acc gtc tcc tca                          369
Trp Gly Gln Gly Thr Ser Val Thr Val Ser Ser
            115                 120

<210> SEQ ID NO 33
<211> LENGTH: 123
<212> TYPE: PRT
<213> ORGANISM: Homo sapiens

<400> SEQUENCE: 33

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Asn Glu Tyr
                20                  25                  30

Thr Met His Trp Val Lys Gln Ser His Gly Lys Arg Leu Glu Trp Ile
            35                  40                  45

Gly Gly Ile Asn Pro Asn Ser Gly Gly Val Ser Tyr Asn Gln Asn Phe
        50                  55                  60

Lys Gly Lys Ala Thr Leu Thr Val Asp Lys Ser Ser Ser Thr Ala Ser
65                  70                  75                  80

Met Glu Leu Arg Ser Leu Thr Ser Glu Asp Ser Ala Val Phe Tyr Cys
                85                  90                  95

Ala Arg Gly Gly Asp Gly Tyr Tyr Thr Asn Tyr Phe Asp Ile Asp Tyr
                100                 105                 110

Trp Gly Gln Gly Thr Ser Val Thr Val Ser Ser
            115                 120

<210> SEQ ID NO 34
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 34 caa att gtt ctc acc cag tct cca gca atc atg tct gca tct cca ggg       48
Gln Ile Val Leu Thr Gln Ser Pro Ala Ile Met Ser Ala Ser Pro Gly
1               5                   10                  15 gag aag gtc acc atg tcc tgc agt gcc agc tca agt gta aat tac atg       96
```

|  |  |  |  |  |  |  |  |  |  |  |  |  |  |  |  |
|---|---|---|---|---|---|---|---|---|---|---|---|---|---|---|---|
| Glu | Lys | Val | Thr | Met | Ser | Cys | Ser | Ala | Ser | Ser | Ser | Val | Asn | Tyr | Met |
|  |  |  | 20 |  |  |  |  | 25 |  |  |  |  | 30 |  |  |

```
cac tgg ttc cag cag aag tca ggc acc tcc ccc aaa cga tgg att tat      144
His Trp Phe Gln Gln Lys Ser Gly Thr Ser Pro Lys Arg Trp Ile Tyr
         35                  40                  45 gac aca tcc aaa ctg gct tct gga gtc cct gct cgc ttc agt ggc agt      192
Asp Thr Ser Lys Leu Ala Ser Gly Val Pro Ala Arg Phe Ser Gly Ser
 50                  55                  60 ggg tct ggg acc tct tac tct ctc aca atc acc gac atg gag gct gag      240
Gly Ser Gly Thr Ser Tyr Ser Leu Thr Ile Thr Asp Met Glu Ala Glu
 65                  70                  75                  80 gat gct gcc act tat tac tgc cag cag tgg aat agt cac cca ctc acg      288
Asp Ala Ala Thr Tyr Tyr Cys Gln Gln Trp Asn Ser His Pro Leu Thr
                 85                  90                  95 ttc ggt gct ggg acc aag ctg gag ctg ata                              318
Phe Gly Ala Gly Thr Lys Leu Glu Leu Ile
            100                 105

<210> SEQ ID NO 35
<211> LENGTH: 106
<212> TYPE: PRT
<213> ORGANISM: Homo sapiens

<400> SEQUENCE: 35

Gln Ile Val Leu Thr Gln Ser Pro Ala Ile Met Ser Ala Ser Pro Gly
1               5                  10                  15

Glu Lys Val Thr Met Ser Cys Ser Ala Ser Ser Ser Val Asn Tyr Met
            20                  25                  30

His Trp Phe Gln Gln Lys Ser Gly Thr Ser Pro Lys Arg Trp Ile Tyr
         35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Thr Asp Met Glu Ala Glu
 65                  70                  75                  80

Asp Ala Ala Thr Tyr Tyr Cys Gln Gln Trp Asn Ser His Pro Leu Thr
                 85                  90                  95

Phe Gly Ala Gly Thr Lys Leu Glu Leu Ile
            100                 105

<210> SEQ ID NO 36
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 36 cag gtg cag ctg gtg cag agc gga gcc gaa gtg aag aaa cct ggc gcc      48
Gln Val Gln Leu Val Gln Ser Gly Ala Glu Val Lys Lys Pro Gly Ala
1               5                  10                  15 agc gtg aag gtg tcc tgc aag gcc agc ggc tac acc ttc acc gag tac      96
Ser Val Lys Val Ser Cys Lys Ala Ser Gly Tyr Thr Phe Thr Glu Tyr
            20                  25                  30 acc atg cac tgg gtg cgc cag gct cca ggc cag aga ctg gaa tgg atg     144
Thr Met His Trp Val Arg Gln Ala Pro Gly Gln Arg Leu Glu Trp Met
         35                  40                  45 ggc ggc atc aac ccc aat agc gga ggt gtg agc tac aac cag aac ttc     192
Gly Gly Ile Asn Pro Asn Ser Gly Gly Val Ser Tyr Asn Gln Asn Phe
 50                  55                  60
```

| | | | | | | | | | | | | | | | |
|---|---|---|---|---|---|---|---|---|---|---|---|---|---|---|---|
| aag | ggc | aga | gtg | acc | atc | acc | cgg | gac | aca | agc | gcc | agc | acc | gcc | tac | 240 |
| Lys | Gly | Arg | Val | Thr | Ile | Thr | Arg | Asp | Thr | Ser | Ala | Ser | Thr | Ala | Tyr | |
| 65 | | | | 70 | | | | 75 | | | | 80 | | | |

| atg | gaa | ctg | agc | agc | ctg | aga | agc | gag | gac | acc | gcc | gtg | tac | tac | tgc | 288 |
| Met | Glu | Leu | Ser | Ser | Leu | Arg | Ser | Glu | Asp | Thr | Ala | Val | Tyr | Tyr | Cys | |
| | | | | 85 | | | | 90 | | | | 95 | | | |

| gcc | aga | ggc | ggc | gac | ggc | tac | tac | acc | aac | tac | ttc | gac | atc | gac | tac | 336 |
| Ala | Arg | Gly | Gly | Asp | Gly | Tyr | Tyr | Thr | Asn | Tyr | Phe | Asp | Ile | Asp | Tyr | |
| | | | 100 | | | | | 105 | | | | 110 | | | |

| tgg | ggc | cag | ggc | acc | acc | gtg | acc | gtg | tcc | agc | | | | | | 369 |
| Trp | Gly | Gln | Gly | Thr | Thr | Val | Thr | Val | Ser | Ser | | | | | | |
| | | | 115 | | | | | 120 | | | | | | | |

<210> SEQ ID NO 37
<211> LENGTH: 123
<212> TYPE: PRT
<213> ORGANISM: Homo sapiens

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser
        115                 120

<210> SEQ ID NO 38
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 38

| | | | | | | | | | | | | | | | |
|---|---|---|---|---|---|---|---|---|---|---|---|---|---|---|---|
| gag | atc | gtg | ctg | acc | cag | agc | ccc | gac | ttc | cag | agc | gtg | acc | ccc | aaa | 48 |
| Glu | Ile | Val | Leu | Thr | Gln | Ser | Pro | Asp | Phe | Gln | Ser | Val | Thr | Pro | Lys | |
| 1 | | | | 5 | | | | 10 | | | | 15 | | | |

| gaa | aaa | gtg | acc | atc | acc | tgt | agc | gcc | agc | agc | agc | gtg | aac | tac | atg | 96 |
| Glu | Lys | Val | Thr | Ile | Thr | Cys | Ser | Ala | Ser | Ser | Ser | Val | Asn | Tyr | Met | |
| | | | 20 | | | | 25 | | | | 30 | | | | | |

| cac | tgg | tat | cag | cag | aag | ccc | gac | cag | agc | ccc | aag | ctg | ctg | atc | aag | 144 |
| His | Trp | Tyr | Gln | Gln | Lys | Pro | Asp | Gln | Ser | Pro | Lys | Leu | Leu | Ile | Lys | |
| | | | 35 | | | | 40 | | | | 45 | | | | | |

| gac | acc | agc | aag | ctg | gcc | agc | ggc | gtg | ccc | agc | aga | ttt | tct | ggc | agc | 192 |
| Asp | Thr | Ser | Lys | Leu | Ala | Ser | Gly | Val | Pro | Ser | Arg | Phe | Ser | Gly | Ser | |
| | | | 50 | | | | 55 | | | | 60 | | | | | |

| ggc | agc | ggc | acc | gac | ttc | acc | ctg | acc | atc | aac | agc | ctg | gaa | gcc | gag | 240 |
| Gly | Ser | Gly | Thr | Asp | Phe | Thr | Leu | Thr | Ile | Asn | Ser | Leu | Glu | Ala | Glu | |
| 65 | | | | 70 | | | | 75 | | | | 80 | | | |

```
gac gcc gcc acc tac tac tgc cag cag tgg aac agc cac ccc ctg acc      288
Asp Ala Ala Thr Tyr Tyr Cys Gln Gln Trp Asn Ser His Pro Leu Thr
                85                  90                  95 ttt ggc cag ggc acc aag ctg gaa atc aag                              318
Phe Gly Gln Gly Thr Lys Leu Glu Ile Lys
            100                 105

<210> SEQ ID NO 39
<211> LENGTH: 106
<212> TYPE: PRT
<213> ORGANISM: Homo sapiens

<400> SEQUENCE: 39

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Val Asn Tyr Met
            20                  25                  30

His Trp Tyr Gln Gln Lys Pro Asp Gln Ser Pro Lys Leu Leu Ile Lys
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Trp Asn Ser His Pro Leu Thr
                85                  90                  95

Phe Gly Gln Gly Thr Lys Leu Glu Ile Lys
            100                 105

<210> SEQ ID NO 40
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 40 gac atc cag atg acc cag tcc ccc tcc tcc ctg tcc gcc tcc gtg ggc       48
Asp Ile Gln Met Thr Gln Ser Pro Ser Ser Leu Ser Ala Ser Val Gly
1               5                   10                  15 gac aga gtg acc atc acc tgc tcc gcc tcc agc tcc gtg aac tac atg       96
Asp Arg Val Thr Ile Thr Cys Ser Ala Ser Ser Ser Val Asn Tyr Met
            20                  25                  30 cac tgg tat cag cag aaa cct ggc aag gtg ccc aag ctg ctg atc tac      144
His Trp Tyr Gln Gln Lys Pro Gly Lys Val Pro Lys Leu Leu Ile Tyr
        35                  40                  45 gac acc tcc aag ctg gcc tcc ggc gtg cct tcc cgg ttc tcc ggc tcc      192
Asp Thr Ser Lys Leu Ala Ser Gly Val Pro Ser Arg Phe Ser Gly Ser
    50                  55                  60 ggc tct ggc acc gac ttc acc ctg acc atc tcc agc ctg cag cct gag      240
Gly Ser Gly Thr Asp Phe Thr Leu Thr Ile Ser Ser Leu Gln Pro Glu
65                  70                  75                  80 gac gtg gcc acc tac tac tgc cag cag tgg aac tcc cac cct ctg acc      288
Asp Val Ala Thr Tyr Tyr Cys Gln Gln Trp Asn Ser His Pro Leu Thr
                85                  90                  95 ttc gga cag ggc acc aag ctg gag atc aaa                              318
Phe Gly Gln Gly Thr Lys Leu Glu Ile Lys
            100                 105

<210> SEQ ID NO 41
<211> LENGTH: 106
```

```
<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Asn Tyr Met
            20                  25                  30

His Trp Tyr Gln Gln Lys Pro Gly Lys Val Pro Lys Leu Leu Ile Tyr
        35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Gln Trp Asn Ser His Pro Leu Thr
                85                  90                  95

Phe Gly Gln Gly Thr Lys Leu Glu Ile Lys
            100                 105

<210> SEQ ID NO 42
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 42 gat gtt gtg atg aca cag tcc cct gcc ttc ctg tcc gtg acc cct ggc      48
Asp Val Val Met Thr Gln Ser Pro Ala Phe Leu Ser Val Thr Pro Gly
1               5                   10                  15 gag aag gtg acc atc acc tgc tcc gcc tcc agc tcc gtg aac tac atg      96
Glu Lys Val Thr Ile Thr Cys Ser Ala Ser Ser Ser Val Asn Tyr Met
            20                  25                  30 cac tgg tat cag cag aag cct gac cag gcc cct aag ctg ctg atc aag     144
His Trp Tyr Gln Gln Lys Pro Asp Gln Ala Pro Lys Leu Leu Ile Lys
        35                  40                  45 gac acc tcc aag ctg gcc tcc ggc gtg cct tcc cgg ttc tcc ggc tcc     192
Asp Thr Ser Lys Leu Ala Ser Gly Val Pro Ser Arg Phe Ser Gly Ser
        50                  55                  60 ggc tct ggc acc gac ttc acc ttc acc atc tcc agc ctg gag gcc gag     240
Gly Ser Gly Thr Asp Phe Thr Phe Thr Ile Ser Ser Leu Glu Ala Glu
65                  70                  75                  80 gac gcc gcc acc tac tac tgc cag cag tgg aac tcc cac cct ctg acc     288
Asp Ala Ala Thr Tyr Tyr Cys Gln Gln Trp Asn Ser His Pro Leu Thr
                85                  90                  95 ttc gga cag ggc acc aag ctg gag atc aaa                             318
Phe Gly Gln Gly Thr Lys Leu Glu Ile Lys
            100                 105

<210> SEQ ID NO 43
<211> LENGTH: 106
<212> TYPE: PRT
<213> ORGANISM: Homo sapiens

<400> SEQUENCE: 43

Asp Val Val Met Thr Gln Ser Pro Ala Phe Leu Ser Val Thr Pro Gly
1               5                   10                  15

Glu Lys Val Thr Ile Thr Cys Ser Ala Ser Ser Ser Val Asn Tyr Met
            20                  25                  30
```

```
His Trp Tyr Gln Gln Lys Pro Asp Gln Ala Pro Lys Leu Leu Ile Lys
        35                  40                  45

Asp Thr Ser Lys Leu Ala Ser Gly Val Pro Ser Arg Phe Ser Gly Ser
 50                  55                  60

Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln Trp Asn Ser His Pro Leu Thr
                 85                  90                  95

Phe Gly Gln Gly Thr Lys Leu Glu Ile Lys
            100                 105

<210> SEQ ID NO 44
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 44 gag atc gtg ctg acc cag agc cct gcc acc ctg tct ctg agc cct ggc     48
Glu Ile Val Leu Thr Gln Ser Pro Ala Thr Leu Ser Leu Ser Pro Gly
 1               5                  10                  15 gag aga gcc aca ctg agc tgc agc gcc agc agc agc gtg aac tac atg     96
Glu Arg Ala Thr Leu Ser Cys Ser Ala Ser Ser Ser Val Asn Tyr Met
             20                  25                  30 cac tgg tat cag cag aag ccc ggc cag gcc ccc aga ctg ctg atc tac    144
His Trp Tyr Gln Gln Lys Pro Gly Gln Ala Pro Arg Leu Leu Ile Tyr
        35                  40                  45 gac acc agc aag ctg gcc agc ggc atc cct gcc aga ttc agc ggc agc    192
Asp Thr Ser Lys Leu Ala Ser Gly Ile Pro Ala Arg Phe Ser Gly Ser
 50                  55                  60 ggc tcc ggc acc gac ttc acc ctg acc atc agc agc ctg gaa ccc gag    240
Gly Ser Gly Thr Asp Phe Thr Leu Thr Ile Ser Ser Leu Glu Pro Glu
 65                  70                  75                  80 gac ttc gcc gtg tac tac tgc cag cag tgg aac agc cac ccc ctg acc    288
Asp Phe Ala Val Tyr Tyr Cys Gln Gln Trp Asn Ser His Pro Leu Thr
                 85                  90                  95 ttt ggc cag ggc acc aag ctg gaa atc aag                            318
Phe Gly Gln Gly Thr Lys Leu Glu Ile Lys
            100                 105

<210> SEQ ID NO 45
<211> LENGTH: 106
<212> TYPE: PRT
<213> ORGANISM: Homo sapiens

<400> SEQUENCE: 45

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Asn Tyr Met
             20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Trp Asn Ser His Pro Leu Thr
                 85                  90                  95
```

-continued

```
Phe Gly Gln Gly Thr Lys Leu Glu Ile Lys
            100                 105

<210> SEQ ID NO 46
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 46 aac atc cag atg acc cag agc cct agc gcc atg agc gcc agc gtg ggc      48
Asn Ile Gln Met Thr Gln Ser Pro Ser Ala Met Ser Ala Ser Val Gly
1               5                   10                  15 gac aga gtg acc atc acc tgt agc gcc agc agc agc gtg aac tac atg      96
Asp Arg Val Thr Ile Thr Cys Ser Ala Ser Ser Ser Val Asn Tyr Met
            20                  25                  30 cac tgg ttc cag cag aaa ccc ggc aag gtg ccc aag cac ctg atc tac     144
His Trp Phe Gln Gln Lys Pro Gly Lys Val Pro Lys His Leu Ile Tyr
        35                  40                  45 gac acc agc aag ctg gcc tcc ggc gtg ccc agc aga ttt tct ggc agc     192
Asp Thr Ser Lys Leu Ala Ser Gly Val Pro Ser Arg Phe Ser Gly Ser
    50                  55                  60 ggc agc ggc acc gag ttc acc ctg acc atc agc agc ctg cag ccc gag     240
Gly Ser Gly Thr Glu Phe Thr Leu Thr Ile Ser Ser Leu Gln Pro Glu
65                  70                  75                  80 gac ttc gcc acc tac tac tgc cag cag tgg aac agc cac ccc ctg acc     288
Asp Phe Ala Thr Tyr Tyr Cys Gln Gln Trp Asn Ser His Pro Leu Thr
                85                  90                  95 ttt ggc cag ggc acc aag ctg gaa atc aag                             318
Phe Gly Gln Gly Thr Lys Leu Glu Ile Lys
            100                 105

<210> SEQ ID NO 47
<211> LENGTH: 106
<212> TYPE: PRT
<213> ORGANISM: Homo sapiens

<400> SEQUENCE: 47

Asn Ile Gln Met Thr Gln Ser Pro Ser Ala Met Ser Ala Ser Val Gly
1               5                   10                  15

Asp Arg Val Thr Ile Thr Cys Ser Ala Ser Ser Ser Val Asn Tyr Met
            20                  25                  30

His Trp Phe Gln Gln Lys Pro Gly Lys Val Pro Lys His Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Asn Ser His Pro Leu Thr
                85                  90                  95

Phe Gly Gln Gly Thr Lys Leu Glu Ile Lys
            100                 105

<210> SEQ ID NO 48
<211> LENGTH: 369
<212> TYPE: DNA
<213> ORGANISM: Homo sapiens
<220> FEATURE:
<221> NAME/KEY: CDS
```

<222> LOCATION: (1)..(369)

<400> SEQUENCE: 48

```
cag gtg cag ctg gtg cag agc gga gcc gaa gtg aag aaa cct ggc gcc      48
Gln Val Gln Leu Val Gln Ser Gly Ala Glu Val Lys Lys Pro Gly Ala
1               5                   10                  15 agc gtg aag gtg tcc tgc aag gcc agc ggc tac acc ttc aac gag tac      96
Ser Val Lys Val Ser Cys Lys Ala Ser Gly Tyr Thr Phe Asn Glu Tyr
                20                  25                  30 acc atg cac tgg gtg aag cag agc cac ggc cag aga ctg gaa tgg atg     144
Thr Met His Trp Val Lys Gln Ser His Gly Gln Arg Leu Glu Trp Met
            35                  40                  45 ggc ggc atc aac ccc aat agc gga ggc gtg agc tac aac cag aac ttc     192
Gly Gly Ile Asn Pro Asn Ser Gly Gly Val Ser Tyr Asn Gln Asn Phe
        50                  55                  60 aag ggc aga gtg acc atc acc cgg gac aca agc gcc agc acc gcc tac     240
Lys Gly Arg Val Thr Ile Thr Arg Asp Thr Ser Ala Ser Thr Ala Tyr
65                  70                  75                  80 atg gaa ctg agc agc ctg aga agc gag gac acc gcc gtg tac tac tgc     288
Met Glu Leu Ser Ser Leu Arg Ser Glu Asp Thr Ala Val Tyr Tyr Cys
                85                  90                  95 gcc aga ggc ggc gac ggc tac tac acc aac tac ttc gac atc gac tac     336
Ala Arg Gly Gly Asp Gly Tyr Tyr Thr Asn Tyr Phe Asp Ile Asp Tyr
                100                 105                 110 tgg ggc cag ggc acc acc gtg acc gtg tcc agc                         369
Trp Gly Gln Gly Thr Thr Val Thr Val Ser Ser
            115                 120
```

<210> SEQ ID NO 49
<211> LENGTH: 123
<212> TYPE: PRT
<213> ORGANISM: Homo sapiens

<400> SEQUENCE: 49

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
                20                  25                  30

Thr Met His Trp Val Lys Gln Ser His Gly Gln Arg Leu Glu Trp Met
            35                  40                  45

Gly Gly Ile Asn Pro Asn Ser Gly Gly Val Ser Tyr Asn Gln Asn Phe
        50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
                100                 105                 110

Trp Gly Gln Gly Thr Thr Val Thr Val Ser Ser
            115                 120
```

<210> SEQ ID NO 50
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 50

```
cag gtg cag ctg gtg cag agc gga gcc gaa gtg aag aaa cct ggc gcc      48
Gln Val Gln Leu Val Gln Ser Gly Ala Glu Val Lys Lys Pro Gly Ala
1               5                   10                  15 agc gtg aag gtg tcc tgc aag gcc agc ggc tac acc ttc acc gag tac      96
Ser Val Lys Val Ser Cys Lys Ala Ser Gly Tyr Thr Phe Thr Glu Tyr
            20                  25                  30 acc atg cac tgg gtg cgc cag gct cca ggc cag aga ctg gaa tgg atg     144
Thr Met His Trp Val Arg Gln Ala Pro Gly Gln Arg Leu Glu Trp Met
        35                  40                  45 ggc ggc atc aac ccc aat agc gga ggc gtg agc tac aac cag aac ttc     192
Gly Gly Ile Asn Pro Asn Ser Gly Gly Val Ser Tyr Asn Gln Asn Phe
    50                  55                  60 aag ggc aag gcc acc ctg acc gtc gac aca agc gcc agc acc gcc tac     240
Lys Gly Lys Ala Thr Leu Thr Val Asp Thr Ser Ala Ser Thr Ala Tyr
65                  70                  75                  80 atg gaa ctg agc agc ctg aga agc gag gac acc gcc gtg tac tac tgc     288
Met Glu Leu Ser Ser Leu Arg Ser Glu Asp Thr Ala Val Tyr Tyr Cys
                85                  90                  95 gcc aga ggc ggc gac ggc tac tac acc aac tac ttc gac atc gac tac     336
Ala Arg Gly Gly Asp Gly Tyr Tyr Thr Asn Tyr Phe Asp Ile Asp Tyr
            100                 105                 110 tgg ggc cag ggc acc acc gtg acc gtg tcc agc                         369
Trp Gly Gln Gly Thr Thr Val Thr Val Ser Ser
        115                 120
```

<210> SEQ ID NO 51
<211> LENGTH: 123
<212> TYPE: PRT
<213> ORGANISM: Homo sapiens

<400> SEQUENCE: 51

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser
        115                 120
```

<210> SEQ ID NO 52
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 52

```
cag gtg cag ctg gtg cag agc gga gcc gaa gtg aag aaa cct ggc gcc      48
Gln Val Gln Leu Val Gln Ser Gly Ala Glu Val Lys Lys Pro Gly Ala
1               5                   10                  15
```

| | | |
|---|---|---|
| agc gtg aag gtg tcc tgc aag gcc agc ggc tac acc ttc acc gag tac<br>Ser Val Lys Val Ser Cys Lys Ala Ser Gly Tyr Thr Phe Thr Glu Tyr<br>20 25 30 | | 96 |
| acc atg cac tgg gtg cgc cag gct cca ggc cag aga ctg gaa tgg atg<br>Thr Met His Trp Val Arg Gln Ala Pro Gly Gln Arg Leu Glu Trp Met<br>35 40 45 | | 144 |
| ggc ggc atc aac ccc aat agc gga ggc gtg agc tac aac cag aac ttc<br>Gly Gly Ile Asn Pro Asn Ser Gly Gly Val Ser Tyr Asn Gln Asn Phe<br>50 55 60 | | 192 |
| aag ggc aga gtg acc atc acc cgg gac aca agc tct agc acc gcc tac<br>Lys Gly Arg Val Thr Ile Thr Arg Asp Thr Ser Ser Ser Thr Ala Tyr<br>65 70 75 80 | | 240 |
| atg gaa ctg agc agc ctg aga agc gag gac acc gcc gtg ttc tac tgc<br>Met Glu Leu Ser Ser Leu Arg Ser Glu Asp Thr Ala Val Phe Tyr Cys<br>85 90 95 | | 288 |
| gcc aga ggc ggc gac ggc tac tac acc aac tac ttc gac atc gac tac<br>Ala Arg Gly Gly Asp Gly Tyr Tyr Thr Asn Tyr Phe Asp Ile Asp Tyr<br>100 105 110 | | 336 |
| tgg ggc cag ggc acc acc gtg acc gtg tcc agc<br>Trp Gly Gln Gly Thr Thr Val Thr Val Ser Ser<br>115 120 | | 369 |

<210> SEQ ID NO 53
<211> LENGTH: 123
<212> TYPE: PRT
<213> ORGANISM: Homo sapiens

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Val Arg Gln Ala Pro Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Arg Val Thr Ile Thr Arg Asp Thr Ser Ser Ser Thr Ala Tyr
65                  70                  75                  80

Met Glu Leu Ser Ser Leu Arg Ser Glu Asp Thr Ala Val Phe Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser
        115                 120

<210> SEQ ID NO 54
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 54

| | | |
|---|---|---|
| cag gtg cag ctg gtg cag agc gga gcc gaa gtg aag aaa cct ggc gcc<br>Gln Val Gln Leu Val Gln Ser Gly Ala Glu Val Lys Lys Pro Gly Ala<br>1               5                   10                  15 | | 48 |
| agc gtg aag gtg tcc tgc aag gcc agc ggc tac acc ttc aac gag tac<br>Ser Val Lys Val Ser Cys Lys Ala Ser Gly Tyr Thr Phe Asn Glu Tyr<br>20                  25                  30 | | 96 |

| | | |
|---|---|---|
| acc atg cac tgg gtg aag cag agc cac ggc cag aga ctg gaa tgg atg<br>Thr Met His Trp Val Lys Gln Ser His Gly Gln Arg Leu Glu Trp Met<br>35 40 45 | | 144 |
| ggc ggc atc aac ccc aat agc gga ggc gtg agc tac aac cag aac ttc<br>Gly Gly Ile Asn Pro Asn Ser Gly Gly Val Ser Tyr Asn Gln Asn Phe<br>50 55 60 | | 192 |
| aag ggc aag gcc acc ctg acc gtc gac aca agc gcc agc acc gcc tac<br>Lys Gly Lys Ala Thr Leu Thr Val Asp Thr Ser Ala Ser Thr Ala Tyr<br>65 70 75 80 | | 240 |
| atg gaa ctg agc agc ctg aga agc gag gac acc gcc gtg tac tac tgc<br>Met Glu Leu Ser Ser Leu Arg Ser Glu Asp Thr Ala Val Tyr Tyr Cys<br>85 90 95 | | 288 |
| gcc aga ggc ggc gac ggc tac tac acc aac tac ttc gac atc gac tac<br>Ala Arg Gly Gly Asp Gly Tyr Tyr Thr Asn Tyr Phe Asp Ile Asp Tyr<br>100 105 110 | | 336 |
| tgg ggc cag ggc acc acc gtg acc gtg tcc agc<br>Trp Gly Gln Gly Thr Thr Val Thr Val Ser Ser<br>115 120 | | 369 |

<210> SEQ ID NO 55
<211> LENGTH: 123
<212> TYPE: PRT
<213> ORGANISM: Homo sapiens

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ser His Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser
        115                 120

<210> SEQ ID NO 56
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 56

| | | |
|---|---|---|
| cag gtg cag ctg gtg cag agc gga gcc gaa gtg aag aaa cct ggc gcc<br>Gln Val Gln Leu Val Gln Ser Gly Ala Glu Val Lys Lys Pro Gly Ala<br>1               5                   10                  15 | | 48 |
| agc gtg aag gtg tcc tgc aag gcc agc ggc tac acc ttc aac gag tac<br>Ser Val Lys Val Ser Cys Lys Ala Ser Gly Tyr Thr Phe Asn Glu Tyr<br>20                  25                  30 | | 96 |
| acc atg cac tgg gtg aag cag agc cac ggc cag aga ctg gaa tgg atg<br>Thr Met His Trp Val Lys Gln Ser His Gly Gln Arg Leu Glu Trp Met<br>35                  40                  45 | | 144 |

| | | |
|---|---|---|
| ggc ggc atc aac ccc aat agc gga ggc gtg agc tac aac cag aac ttc<br>Gly Gly Ile Asn Pro Asn Ser Gly Gly Val Ser Tyr Asn Gln Asn Phe<br>        50                        55                        60 | | 192 |
| aag ggc aag gcc acc ctg acc gtc gac aca agc tct agc acc gcc tac<br>Lys Gly Lys Ala Thr Leu Thr Val Asp Thr Ser Ser Ser Thr Ala Tyr<br>65                      70                        75                        80 | | 240 |
| atg gaa ctg agc agc ctg aga agc gag gac acc gcc gtg ttc tac tgc<br>Met Glu Leu Ser Ser Leu Arg Ser Glu Asp Thr Ala Val Phe Tyr Cys<br>                    85                        90                        95 | | 288 |
| gcc aga ggc ggc gac ggc tac tac acc aac tac ttc gac atc gac tac<br>Ala Arg Gly Gly Asp Gly Tyr Tyr Thr Asn Tyr Phe Asp Ile Asp Tyr<br>                        100                      105                    110 | | 336 |
| tgg ggc cag ggc acc acc gtg acc gtg tcc agc<br>Trp Gly Gln Gly Thr Thr Val Thr Val Ser Ser<br>           115                    120 | | 369 |

<210> SEQ ID NO 57
<211> LENGTH: 123
<212> TYPE: PRT
<213> ORGANISM: Homo sapiens

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ser His Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Lys Ala Thr Leu Thr Val Asp Thr Ser Ser Ser Thr Ala Tyr
65                  70                  75                  80

Met Glu Leu Ser Ser Leu Arg Ser Glu Asp Thr Ala Val Phe Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser
        115                 120

<210> SEQ ID NO 58
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 58

| | | |
|---|---|---|
| cag gtg cag ctg gtg cag agc gga gcc gaa gtg aag aaa cct ggc gcc<br>Gln Val Gln Leu Val Gln Ser Gly Ala Glu Val Lys Lys Pro Gly Ala<br>1                      5                        10                        15 | | 48 |
| agc gtg aag gtg tcc tgc aag gcc agc ggc tac acc ttc aac gag tac<br>Ser Val Lys Val Ser Cys Lys Ala Ser Gly Tyr Thr Phe Asn Glu Tyr<br>                    20                        25                        30 | | 96 |
| acc atg cac tgg gtg aag cag gcc ccc ggc cag aga ctg gaa tgg atg<br>Thr Met His Trp Val Lys Gln Ala Pro Gly Gln Arg Leu Glu Trp Met<br>        35                        40                        45 | | 144 |
| ggc ggc atc aac ccc aat agc gga ggc gtg agc tac aac cag aac ttc<br>Gly Gly Ile Asn Pro Asn Ser Gly Gly Val Ser Tyr Asn Gln Asn Phe<br>                  50                        55                        60 | | 192 |

```
aag ggc aag gcc acc ctg acc gtc gac aca agc gcc agc acc gcc tac      240
Lys Gly Lys Ala Thr Leu Thr Val Asp Thr Ser Ala Ser Thr Ala Tyr
 65                  70                  75                  80 atg gaa ctg agc agc ctg aga agc gag gac acc gcc gtg tac tac tgc      288
Met Glu Leu Ser Ser Leu Arg Ser Glu Asp Thr Ala Val Tyr Tyr Cys
                 85                  90                  95 gcc aga ggc ggc gac ggc tac tac acc aac tac ttc gac atc gac tac      336
Ala Arg Gly Gly Asp Gly Tyr Tyr Thr Asn Tyr Phe Asp Ile Asp Tyr
            100                 105                 110 tgg ggc cag ggc acc acc gtg acc gtg tcc agc                          369
Trp Gly Gln Gly Thr Thr Val Thr Val Ser Ser
        115                 120
```

<210> SEQ ID NO 59
<211> LENGTH: 123
<212> TYPE: PRT
<213> ORGANISM: Homo sapiens

<400> SEQUENCE: 59

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Glu Tyr
             20                  25                  30

Thr Met His Trp Val Lys Gln Ala Pro Gly Gln Arg Leu Glu Trp Met
         35                  40                  45

Gly Gly Ile Asn Pro Asn Ser Gly Gly Val Ser Tyr Asn Gln Asn Phe
     50                  55                  60

Lys Gly Lys Ala Thr Leu Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser
        115                 120
```

<210> SEQ ID NO 60
<211> LENGTH: 1347
<212> TYPE: DNA
<213> ORGANISM: Homo sapiens
<220> FEATURE:
<221> NAME/KEY: CDS
<222> LOCATION: (1)..(1347)

<400> SEQUENCE: 60

```
cag gtg cag ctg gtg gaa agc ggc ggc ggc gtg gtg cag ccg ggc cgc       48
Gln Val Gln Leu Val Glu Ser Gly Gly Gly Val Val Gln Pro Gly Arg
 1               5                  10                  15 agc ctg cgc ctg agc tgc gcg gcg agc ggc ttt agc ttt agc agc tat       96
Ser Leu Arg Leu Ser Cys Ala Ala Ser Gly Phe Ser Phe Ser Ser Tyr
             20                  25                  30 gcg atg cat tgg gtg cgc cag gcg ccg ggc aaa ggc ctg gaa tgg gtg      144
Ala Met His Trp Val Arg Gln Ala Pro Gly Lys Gly Leu Glu Trp Val
         35                  40                  45 gcg gtg att agc tat ggc ggc agc aaa aaa tat tat gcg gat agc gtg      192
Ala Val Ile Ser Tyr Gly Gly Ser Lys Lys Tyr Tyr Ala Asp Ser Val
     50                  55                  60 aaa ggc cgc ttt acc att agc cgc gat aac agc aaa aac acc ctg tat      240
Lys Gly Arg Phe Thr Ile Ser Arg Asp Asn Ser Lys Asn Thr Leu Tyr
 65                  70                  75                  80
```

| | | |
|---|---|---|
| ctg cag atg aac agc ctg cgc gcg gaa gat acc gcg gtg tat tat tgc<br>Leu Gln Met Asn Ser Leu Arg Ala Glu Asp Thr Ala Val Tyr Tyr Cys<br>85 90 95 | | 288 |
| gcg cgc atg ggc tat tat gat att ctg acc ggc ccg ttt gat tat tgg<br>Ala Arg Met Gly Tyr Tyr Asp Ile Leu Thr Gly Pro Phe Asp Tyr Trp<br>100 105 110 | | 336 |
| ggc cag ggc acc ctg gtg acc gtg agc agc gcc tcc act aaa gga cct<br>Gly Gln Gly Thr Leu Val Thr Val Ser Ser Ala Ser Thr Lys Gly Pro<br>115 120 125 | | 384 |
| agc gtg ttt ccg cta gcc ccc tgt tca aga agc aca agc gag tca acc<br>Ser Val Phe Pro Leu Ala Pro Cys Ser Arg Ser Thr Ser Glu Ser Thr<br>130 135 140 | | 432 |
| gcc gca ctg gga tgc ctg gtg aag gac tac ttc cct gag cca gtc aca<br>Ala Ala Leu Gly Cys Leu Val Lys Asp Tyr Phe Pro Glu Pro Val Thr<br>145 150 155 160 | | 480 |
| gtg tcc tgg aac tct gga gcc ctg aca tct ggc gtc cac act ttt ccc<br>Val Ser Trp Asn Ser Gly Ala Leu Thr Ser Gly Val His Thr Phe Pro<br>165 170 175 | | 528 |
| gct gtg ctg cag agc tcc gga ctg tac agc ctg tct agt gtg gtc acc<br>Ala Val Leu Gln Ser Ser Gly Leu Tyr Ser Leu Ser Ser Val Val Thr<br>180 185 190 | | 576 |
| gtg cct tca agc tcc ctg ggc act aag acc tat aca tgc aac gtg gac<br>Val Pro Ser Ser Ser Leu Gly Thr Lys Thr Tyr Thr Cys Asn Val Asp<br>195 200 205 | | 624 |
| cat aaa cca tcc aat aca aag gtc gat aaa cga gtg gag tct aag tac<br>His Lys Pro Ser Asn Thr Lys Val Asp Lys Arg Val Glu Ser Lys Tyr<br>210 215 220 | | 672 |
| gga cca cct tgc cca cca tgt cca gct cct gag ttc ctg gga gga cct<br>Gly Pro Pro Cys Pro Pro Cys Pro Ala Pro Glu Phe Leu Gly Gly Pro<br>225 230 235 240 | | 720 |
| tcc gtg ttc ctg ttt cct cca aag cca aaa gac act ctg atg atc tcc<br>Ser Val Phe Leu Phe Pro Pro Lys Pro Lys Asp Thr Leu Met Ile Ser<br>245 250 255 | | 768 |
| aga act cca gag gtc acc tgc gtg gtc gtg gac gtg tct cag gag gat<br>Arg Thr Pro Glu Val Thr Cys Val Val Val Asp Val Ser Gln Glu Asp<br>260 265 270 | | 816 |
| ccc gaa gtc cag ttc aac tgg tac gtg gat ggg gtc gaa gtg cac aat<br>Pro Glu Val Gln Phe Asn Trp Tyr Val Asp Gly Val Glu Val His Asn<br>275 280 285 | | 864 |
| gcc aag acc aaa ccc agg gag gaa cag ttt aac agc act tac cgc gtc<br>Ala Lys Thr Lys Pro Arg Glu Glu Gln Phe Asn Ser Thr Tyr Arg Val<br>290 295 300 | | 912 |
| gtg tcc gtc ctg acc gtg ctg cat cag gat tgg ctg aac ggg aag gag<br>Val Ser Val Leu Thr Val Leu His Gln Asp Trp Leu Asn Gly Lys Glu<br>305 310 315 320 | | 960 |
| tat aag tgc aaa gtg agt aat aag gga ctg cct tct agt atc gag aaa<br>Tyr Lys Cys Lys Val Ser Asn Lys Gly Leu Pro Ser Ser Ile Glu Lys<br>325 330 335 | | 1008 |
| aca att tcc aag gca aaa ggc cag cca cgg gaa ccc cag gtg tac act<br>Thr Ile Ser Lys Ala Lys Gly Gln Pro Arg Glu Pro Gln Val Tyr Thr<br>340 345 350 | | 1056 |
| ctg ccc cct agt cag gag gaa atg acc aag aac cag gtc tca ctg aca<br>Leu Pro Pro Ser Gln Glu Glu Met Thr Lys Asn Gln Val Ser Leu Thr<br>355 360 365 | | 1104 |
| tgt ctg gtg gat ggc ttc tat ccc tca gat atc gcc gtg gag tgg gaa<br>Cys Leu Val Asp Gly Phe Tyr Pro Ser Asp Ile Ala Val Glu Trp Glu<br>370 375 380 | | 1152 |
| agc aat ggg cag cct gag aac aat tac gat acc aca cca ccc gtg ctg<br>Ser Asn Gly Gln Pro Glu Asn Asn Tyr Asp Thr Thr Pro Pro Val Leu<br>385 390 395 400 | | 1200 |

-continued

```
gac agt gat ggg tca ttc ttt ctg tat tct gat ctg acc gtg gat aaa    1248
Asp Ser Asp Gly Ser Phe Phe Leu Tyr Ser Asp Leu Thr Val Asp Lys
            405                 410                 415 agt aga tgg cag gaa gga aat gtc ttt tca tgc agc gtg atg cac gaa    1296
Ser Arg Trp Gln Glu Gly Asn Val Phe Ser Cys Ser Val Met His Glu
        420                 425                 430 gca ctg cac aat cat tac act cag aag tcc ctg tca ctg tcc ctg ggc    1344
Ala Leu His Asn His Tyr Thr Gln Lys Ser Leu Ser Leu Ser Leu Gly
    435                 440                 445 aaa                                                                 1347
Lys

<210> SEQ ID NO 61
<211> LENGTH: 449
<212> TYPE: PRT
<213> ORGANISM: Homo sapiens

<400> SEQUENCE: 61

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Gly Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
```

```
                    290                 295                 300
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Asp Gly Phe Tyr Pro Ser Asp Ile Ala Val Glu Trp Glu
        370                 375                 380

Ser Asn Gly Gln Pro Glu Asn Asn Tyr Asp Thr Thr Pro Pro Val Leu
385                 390                 395                 400

Asp Ser Asp Gly Ser Phe Phe Leu Tyr Ser Asp Leu Thr Val Asp Lys
                    405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

Lys

<210> SEQ ID NO 62
<211> LENGTH: 1356
<212> TYPE: DNA
<213> ORGANISM: Homo sapiens
<220> FEATURE:
<221> NAME/KEY: CDS
<222> LOCATION: (1)..(1356)

<400> SEQUENCE: 62 cag gtg cag ctg gtg gaa agc ggc ggc ggc gtg gtg cag ccg ggc cgc      48
Gln Val Gln Leu Val Glu Ser Gly Gly Gly Val Val Gln Pro Gly Arg
1               5                   10                  15 agc ctg cgc ctg agc tgc gcg gcg agc ggc ttt agc ttt agc agc tat      96
Ser Leu Arg Leu Ser Cys Ala Ala Ser Gly Phe Ser Phe Ser Ser Tyr
            20                  25                  30 gcg atg cat tgg gtg cgc cag gcg ccg ggc aaa ggc ctg gaa tgg gtg     144
Ala Met His Trp Val Arg Gln Ala Pro Gly Lys Gly Leu Glu Trp Val
        35                  40                  45 gcg gtg att agc tat ggc ggc agc aaa aaa tat tat gcg gat agc gtg     192
Ala Val Ile Ser Tyr Gly Gly Ser Lys Lys Tyr Tyr Ala Asp Ser Val
    50                  55                  60 aaa ggc cgc ttt acc att agc cgc gat aac agc aaa aac acc ctg tat     240
Lys Gly Arg Phe Thr Ile Ser Arg Asp Asn Ser Lys Asn Thr Leu Tyr
65                  70                  75                  80 ctg cag atg aac agc ctg cgc gcg gaa gat acc gcg gtg tat tat tgc     288
Leu Gln Met Asn Ser Leu Arg Ala Glu Asp Thr Ala Val Tyr Tyr Cys
                85                  90                  95 gcg cgc atg ggc tat tat gat att ctg acc ggc ccg ttt gat tat tgg     336
Ala Arg Met Gly Tyr Tyr Asp Ile Leu Thr Gly Pro Phe Asp Tyr Trp
            100                 105                 110 ggc cag ggc acc ctg gtg acc gtg agc agc gct tct acc aag ggc ccc     384
Gly Gln Gly Thr Leu Val Thr Val Ser Ser Ala Ser Thr Lys Gly Pro
        115                 120                 125 agc gtg ttc ccg cta gcc ccc agc agc aag agc aca agc gga ggc aca     432
Ser Val Phe Pro Leu Ala Pro Ser Ser Lys Ser Thr Ser Gly Gly Thr
    130                 135                 140 gcc gcc ctg ggc tgc ctg gtg aag gac tac ttc ccc gag ccc gtg aca     480
```

```
Ala Ala Leu Gly Cys Leu Val Lys Asp Tyr Phe Pro Glu Pro Val Thr
145                 150                 155                 160 gtg tcc tgg aac agc gga gcc ctg acc agc ggc gtg cac acc ttt cca      528
Val Ser Trp Asn Ser Gly Ala Leu Thr Ser Gly Val His Thr Phe Pro
                165                 170                 175 gcc gtg ctg cag agc agc ggc ctg tac agc ctg agc agc gtg gtg acc      576
Ala Val Leu Gln Ser Ser Gly Leu Tyr Ser Leu Ser Ser Val Val Thr
            180                 185                 190 gtg cct agc agc agc ctg ggc acc cag acc tac atc tgc aac gtg aac      624
Val Pro Ser Ser Ser Leu Gly Thr Gln Thr Tyr Ile Cys Asn Val Asn
        195                 200                 205 cac aag ccc agc aac acc aag gtg gac aag aag gtg gag ccc aag agc      672
His Lys Pro Ser Asn Thr Lys Val Asp Lys Lys Val Glu Pro Lys Ser
    210                 215                 220 tgc gac aag acc cac acc tgt ccc cct tgt cct gcc cct gaa gcc gaa      720
Cys Asp Lys Thr His Thr Cys Pro Pro Cys Pro Ala Pro Glu Ala Glu
225                 230                 235                 240 ggc gcc cct tcc gtg ttc ctg ttc ccc cca aag ccc aag gac acc ctg      768
Gly Ala Pro Ser Val Phe Leu Phe Pro Pro Lys Pro Lys Asp Thr Leu
                245                 250                 255 atg atc agc cgg acc ccc gaa gtg acc tgc gtg gtg gtg gac gtg tcc      816
Met Ile Ser Arg Thr Pro Glu Val Thr Cys Val Val Val Asp Val Ser
            260                 265                 270 cac gag gac cct gaa gtg aag ttc aat tgg tac gtg gac ggc gtg gag      864
His Glu Asp Pro Glu Val Lys Phe Asn Trp Tyr Val Asp Gly Val Glu
        275                 280                 285 gtg cac aac gcc aag acc aag ccc cgg gag gaa cag tac aac agc acc      912
Val His Asn Ala Lys Thr Lys Pro Arg Glu Glu Gln Tyr Asn Ser Thr
    290                 295                 300 tac cgg gtg gtg tcc gtg ctg acc gtg ctg cac cag gac tgg ctg aac      960
Tyr Arg Val Val Ser Val Leu Thr Val Leu His Gln Asp Trp Leu Asn
305                 310                 315                 320 ggc aaa gag tac aag tgc aag gtc tcc aac aag gcc ctg ccc agc agc     1008
Gly Lys Glu Tyr Lys Cys Lys Val Ser Asn Lys Ala Leu Pro Ser Ser
                325                 330                 335 atc gag aaa acc atc agc aag gcc aag ggc cag ccc aga gaa ccc cag     1056
Ile Glu Lys Thr Ile Ser Lys Ala Lys Gly Gln Pro Arg Glu Pro Gln
            340                 345                 350 gtg tac acc ctg ccc cct agc agg gac gag ctg acc aag aac cag gtg     1104
Val Tyr Thr Leu Pro Pro Ser Arg Asp Glu Leu Thr Lys Asn Gln Val
        355                 360                 365 tcc ctg acc tgt ctg gtg gat ggc ttc tac ccc agc gat atc gcc gtg     1152
Ser Leu Thr Cys Leu Val Asp Gly Phe Tyr Pro Ser Asp Ile Ala Val
    370                 375                 380 gag tgg gag agc aac ggc cag ccc gaa aac aac tac gat acc acc ccc     1200
Glu Trp Glu Ser Asn Gly Gln Pro Glu Asn Asn Tyr Asp Thr Thr Pro
385                 390                 395                 400 cct gtg ctg gac agc gac ggc agc ttc ttc ctg tac tcc gat ctg acc     1248
Pro Val Leu Asp Ser Asp Gly Ser Phe Phe Leu Tyr Ser Asp Leu Thr
                405                 410                 415 gtg gac aag agc cgg tgg cag cag ggc aac gtg ttc agc tgc agc gtg     1296
Val Asp Lys Ser Arg Trp Gln Gln Gly Asn Val Phe Ser Cys Ser Val
            420                 425                 430 atg cac gag gcc ctg cac aac cac tac acc cag aag tcc ctg agc ctg     1344
Met His Glu Ala Leu His Asn His Tyr Thr Gln Lys Ser Leu Ser Leu
        435                 440                 445 agc ccc ggc aag                                                     1356
Ser Pro Gly Lys
    450
```

<210> SEQ ID NO 63
<211> LENGTH: 452
<212> TYPE: PRT
<213> ORGANISM: Homo sapiens

<400> SEQUENCE: 63

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Gly Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Glu
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Asp Gly Phe Tyr Pro Ser Asp Ile Ala Val
    370                 375                 380
```

```
Glu Trp Glu Ser Asn Gly Gln Pro Glu Asn Asn Tyr Asp Thr Thr Pro
385                 390                 395                 400

Pro Val Leu Asp Ser Asp Gly Ser Phe Phe Leu Tyr Ser Asp Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 64
<211> LENGTH: 1359
<212> TYPE: DNA
<213> ORGANISM: Homo sapiens
<220> FEATURE:
<221> NAME/KEY: CDS
<222> LOCATION: (1)..(1359)

<400> SEQUENCE: 64 cag gtg cag ctg gtg cag agc gga gcc gaa gtg aag aaa cct ggc gcc     48
Gln Val Gln Leu Val Gln Ser Gly Ala Glu Val Lys Lys Pro Gly Ala
1               5                   10                  15 agc gtg aag gtg tcc tgc aag gcc agc ggc tac acc ttc aac gag tac     96
Ser Val Lys Val Ser Cys Lys Ala Ser Gly Tyr Thr Phe Asn Glu Tyr
            20                  25                  30 acc atg cac tgg gtg aag cag gcc ccc ggc cag aga ctg gaa tgg atg    144
Thr Met His Trp Val Lys Gln Ala Pro Gly Gln Arg Leu Glu Trp Met
        35                  40                  45 ggc ggc atc aac ccc aat agc gga ggc gtg agc tac aac cag aac ttc    192
Gly Gly Ile Asn Pro Asn Ser Gly Gly Val Ser Tyr Asn Gln Asn Phe
    50                  55                  60 aag ggc aag gcc acc ctg acc gtc gac aca agc gcc agc acc gcc tac    240
Lys Gly Lys Ala Thr Leu Thr Val Asp Thr Ser Ala Ser Thr Ala Tyr
65                  70                  75                  80 atg gaa ctg agc agc ctg aga agc gag gac acc gcc gtg tac tac tgc    288
Met Glu Leu Ser Ser Leu Arg Ser Glu Asp Thr Ala Val Tyr Tyr Cys
                85                  90                  95 gcc aga ggc ggc gac ggc tac tac acc aac tac ttc gac atc gac tac    336
Ala Arg Gly Gly Asp Gly Tyr Tyr Thr Asn Tyr Phe Asp Ile Asp Tyr
            100                 105                 110 tgg ggc cag ggc acc acc gtg acc gtg tcc agc gct tct acc aag ggc    384
Trp Gly Gln Gly Thr Thr Val Thr Val Ser Ser Ala Ser Thr Lys Gly
        115                 120                 125 ccc agc gtg ttc ccg cta gcc ccc agc agc aag agc aca agc gga ggc    432
Pro Ser Val Phe Pro Leu Ala Pro Ser Ser Lys Ser Thr Ser Gly Gly
    130                 135                 140 aca gcc gcc ctg ggc tgc ctg gtg aag gac tac ttc ccc gag ccc gtg    480
Thr Ala Ala Leu Gly Cys Leu Val Lys Asp Tyr Phe Pro Glu Pro Val
145                 150                 155                 160 aca gtg tcc tgg aac agc gga gcc ctg acc agc ggc gtg cac acc ttt    528
Thr Val Ser Trp Asn Ser Gly Ala Leu Thr Ser Gly Val His Thr Phe
                165                 170                 175 cca gcc gtg ctg cag agc agc ggc ctg tac agc ctg agc agc gtg gtg    576
Pro Ala Val Leu Gln Ser Ser Gly Leu Tyr Ser Leu Ser Ser Val Val
            180                 185                 190 acc gtg cct agc agc agc ctg ggc acc cag acc tac atc tgc aac gtg    624
Thr Val Pro Ser Ser Ser Leu Gly Thr Gln Thr Tyr Ile Cys Asn Val
        195                 200                 205
```

| | | | | | | | | | | | | | | |
|---|---|---|---|---|---|---|---|---|---|---|---|---|---|---|
| aac | cac | aag | ccc | agc | aac | acc | aag | gtg | gac | aag | aag | gtg | gag | ccc | aag | 672 |
| Asn | His | Lys | Pro | Ser | Asn | Thr | Lys | Val | Asp | Lys | Lys | Val | Glu | Pro | Lys |
| | 210 | | | | 215 | | | | 220 | | | | | | |

| agc | tgc | gac | aag | acc | cac | acc | tgt | ccc | cct | tgt | cct | gcc | cct | gaa | gcc | 720 |
| Ser | Cys | Asp | Lys | Thr | His | Thr | Cys | Pro | Pro | Cys | Pro | Ala | Pro | Glu | Ala |
| 225 | | | | | 230 | | | | 235 | | | | 240 | | |

| gaa | ggc | gcc | cct | tcc | gtg | ttc | ctg | ttc | ccc | cca | aag | ccc | aag | gac | acc | 768 |
| Glu | Gly | Ala | Pro | Ser | Val | Phe | Leu | Phe | Pro | Pro | Lys | Pro | Lys | Asp | Thr |
| | | | | 245 | | | | 250 | | | | 255 | | | |

| ctg | atg | atc | agc | cgg | acc | ccc | gaa | gtg | acc | tgc | gtg | gtg | gtg | gac | gtg | 816 |
| Leu | Met | Ile | Ser | Arg | Thr | Pro | Glu | Val | Thr | Cys | Val | Val | Val | Asp | Val |
| | | | 260 | | | | 265 | | | | 270 | | | | |

| tcc | cac | gag | gac | cct | gaa | gtg | aag | ttc | aat | tgg | tac | gtg | gac | ggc | gtg | 864 |
| Ser | His | Glu | Asp | Pro | Glu | Val | Lys | Phe | Asn | Trp | Tyr | Val | Asp | Gly | Val |
| | 275 | | | | 280 | | | | 285 | | | | | | |

| gag | gtg | cac | aac | gcc | aag | acc | aag | ccc | cgg | gag | gaa | cag | tac | aac | agc | 912 |
| Glu | Val | His | Asn | Ala | Lys | Thr | Lys | Pro | Arg | Glu | Glu | Gln | Tyr | Asn | Ser |
| 290 | | | | | 295 | | | | 300 | | | | | | |

| acc | tac | cgg | gtg | gtg | tcc | gtg | ctg | acc | gtg | ctg | cac | cag | gac | tgg | ctg | 960 |
| Thr | Tyr | Arg | Val | Val | Ser | Val | Leu | Thr | Val | Leu | His | Gln | Asp | Trp | Leu |
| 305 | | | | 310 | | | | 315 | | | | | 320 | | |

| aac | ggc | aaa | gag | tac | aag | tgc | aag | gtc | tcc | aac | aag | gcc | ctg | ccc | agc | 1008 |
| Asn | Gly | Lys | Glu | Tyr | Lys | Cys | Lys | Val | Ser | Asn | Lys | Ala | Leu | Pro | Ser |
| | | | | 325 | | | | 330 | | | | 335 | | | |

| agc | atc | gag | aaa | acc | atc | agc | aag | gcc | aag | ggc | cag | ccc | aga | gaa | ccc | 1056 |
| Ser | Ile | Glu | Lys | Thr | Ile | Ser | Lys | Ala | Lys | Gly | Gln | Pro | Arg | Glu | Pro |
| | | | 340 | | | | 345 | | | | 350 | | | | |

| cag | gtg | tac | acc | ctg | ccc | cct | agc | agg | gac | gag | ctg | acc | aag | aac | cag | 1104 |
| Gln | Val | Tyr | Thr | Leu | Pro | Pro | Ser | Arg | Asp | Glu | Leu | Thr | Lys | Asn | Gln |
| | | 355 | | | | 360 | | | | 365 | | | | | |

| gtg | tcc | ctg | acc | tgt | ctg | gtg | aag | ggc | ttc | tac | ccc | agc | gat | atc | gcc | 1152 |
| Val | Ser | Leu | Thr | Cys | Leu | Val | Lys | Gly | Phe | Tyr | Pro | Ser | Asp | Ile | Ala |
| 370 | | | | 375 | | | | 380 | | | | | | | |

| gtg | gag | tgg | gag | agc | aac | ggc | cag | ccc | gaa | aac | aac | tac | aag | acc | acc | 1200 |
| Val | Glu | Trp | Glu | Ser | Asn | Gly | Gln | Pro | Glu | Asn | Asn | Tyr | Lys | Thr | Thr |
| 385 | | | | 390 | | | | 395 | | | | 400 | | | |

| ccc | cct | gtg | ctg | gac | agc | gac | ggc | agc | ttc | ttc | ctg | tac | tcc | aaa | ctg | 1248 |
| Pro | Pro | Val | Leu | Asp | Ser | Asp | Gly | Ser | Phe | Phe | Leu | Tyr | Ser | Lys | Leu |
| | | | 405 | | | | 410 | | | | 415 | | | | |

| acc | gtg | gac | aag | agc | cgg | tgg | cag | cag | ggc | aac | gtg | ttc | agc | tgc | agc | 1296 |
| Thr | Val | Asp | Lys | Ser | Arg | Trp | Gln | Gln | Gly | Asn | Val | Phe | Ser | Cys | Ser |
| | | 420 | | | | 425 | | | | 430 | | | | | |

| gtg | atg | cac | gag | gcc | ctg | cac | aac | cac | tac | acc | cag | aag | tcc | ctg | agc | 1344 |
| Val | Met | His | Glu | Ala | Leu | His | Asn | His | Tyr | Thr | Gln | Lys | Ser | Leu | Ser |
| 435 | | | | | 440 | | | | 445 | | | | | | |

| ctg | agc | ccc | ggc | aag | | | | | | | | | | | | 1359 |
| Leu | Ser | Pro | Gly | Lys | | | | | | | | | | | |
| | 450 | | | | | | | | | | | | | | |

<210> SEQ ID NO 65
<211> LENGTH: 453
<212> TYPE: PRT
<213> ORGANISM: Homo sapiens

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ala Pro Gly Gln Arg Leu Glu Trp Met

```
                35                  40                  45
Gly Gly Ile Asn Pro Asn Ser Gly Gly Val Ser Tyr Asn Gln Asn Phe
 50                  55                  60
Lys Gly Lys Ala Thr Leu Thr Val Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Asp Gly Tyr Tyr Thr Asn Tyr Phe Asp Ile Asp Tyr
                100                 105                 110
Trp Gly Gln Gly Thr Thr Val Thr Val Ser Ser Ala Ser Thr Lys Gly
                115                 120                 125
Pro Ser Val Phe Pro Leu Ala Pro Ser Ser Lys Ser Thr Ser Gly Gly
                130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Lys Val Glu Pro Lys
210                 215                 220
Ser Cys Asp Lys Thr His Thr Cys Pro Pro Cys Pro Ala Pro Glu Ala
225                 230                 235                 240
Glu Gly Ala Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn Ser
                290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ser
                325                 330                 335
Ser Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
                355                 360                 365
Val Ser Leu Thr Cys Leu Val Lys Gly Phe Tyr Pro Ser Asp Ile Ala
                370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
                435                 440                 445
Leu Ser Pro Gly Lys
                450
```

<210> SEQ ID NO 66
<211> LENGTH: 639
<212> TYPE: DNA
<213> ORGANISM: Homo sapiens
<220> FEATURE:
<221> NAME/KEY: CDS
<222> LOCATION: (1)..(639)

<400> SEQUENCE: 66

| | | | | | | | | | | | | | | | | |
|---|---|---|---|---|---|---|---|---|---|---|---|---|---|---|---|---|
| gac | atc | cag | atg | acc | cag | tcc | ccc | tcc | tcc | ctg | tcc | gcc | tcc | gtg | ggc | 48 |
| Asp | Ile | Gln | Met | Thr | Gln | Ser | Pro | Ser | Ser | Leu | Ser | Ala | Ser | Val | Gly | |
| 1 | | | | 5 | | | | | 10 | | | | | 15 | | |
| gac | aga | gtg | acc | atc | acc | tgc | tcc | gcc | tcc | agc | tcc | gtg | aac | tac | atg | 96 |
| Asp | Arg | Val | Thr | Ile | Thr | Cys | Ser | Ala | Ser | Ser | Ser | Val | Asn | Tyr | Met | |
| | | | 20 | | | | | 25 | | | | | 30 | | | |
| cac | tgg | tat | cag | cag | aaa | cct | ggc | aag | gtg | ccc | aag | ctg | ctg | atc | tac | 144 |
| His | Trp | Tyr | Gln | Gln | Lys | Pro | Gly | Lys | Val | Pro | Lys | Leu | Leu | Ile | Tyr | |
| | | 35 | | | | | 40 | | | | | 45 | | | | |
| gac | acc | tcc | aag | ctg | gcc | tcc | ggc | gtg | cct | tcc | cgg | ttc | tcc | ggc | tcc | 192 |
| Asp | Thr | Ser | Lys | Leu | Ala | Ser | Gly | Val | Pro | Ser | Arg | Phe | Ser | Gly | Ser | |
| | 50 | | | | | 55 | | | | | 60 | | | | | |
| ggc | tct | ggc | acc | gac | ttc | acc | ctg | acc | atc | tcc | agc | ctg | cag | cct | gag | 240 |
| Gly | Ser | Gly | Thr | Asp | Phe | Thr | Leu | Thr | Ile | Ser | Ser | Leu | Gln | Pro | Glu | |
| 65 | | | | | 70 | | | | | 75 | | | | | 80 | |
| gac | gtg | gcc | acc | tac | tac | tgc | cag | cag | tgg | aac | tcc | cac | cct | ctg | acc | 288 |
| Asp | Val | Ala | Thr | Tyr | Tyr | Cys | Gln | Gln | Trp | Asn | Ser | His | Pro | Leu | Thr | |
| | | | | 85 | | | | | 90 | | | | | 95 | | |
| ttc | gga | cag | ggc | acc | aag | ctg | gag | atc | aaa | cga | act | gtg | gct | gca | cca | 336 |
| Phe | Gly | Gln | Gly | Thr | Lys | Leu | Glu | Ile | Lys | Arg | Thr | Val | Ala | Ala | Pro | |
| | | | 100 | | | | | 105 | | | | | 110 | | | |
| tct | gtc | ttc | atc | ttc | ccg | cca | tct | gat | gag | cag | ttg | aaa | tct | gga | act | 384 |
| Ser | Val | Phe | Ile | Phe | Pro | Pro | Ser | Asp | Glu | Gln | Leu | Lys | Ser | Gly | Thr | |
| | | 115 | | | | | 120 | | | | | 125 | | | | |
| gcc | tct | gtt | gtg | tgc | ctg | ctg | aat | aac | ttc | tat | ccc | aga | gag | gcc | aaa | 432 |
| Ala | Ser | Val | Val | Cys | Leu | Leu | Asn | Asn | Phe | Tyr | Pro | Arg | Glu | Ala | Lys | |
| | 130 | | | | | 135 | | | | | 140 | | | | | |
| gta | cag | tgg | aag | gtg | gat | aac | gcc | ctc | caa | tcg | ggt | aac | tcc | cag | gag | 480 |
| Val | Gln | Trp | Lys | Val | Asp | Asn | Ala | Leu | Gln | Ser | Gly | Asn | Ser | Gln | Glu | |
| 145 | | | | | 150 | | | | | 155 | | | | | 160 | |
| agt | gtc | aca | gag | cag | gac | agc | aag | gac | agc | acc | tac | agc | ctc | agc | agc | 528 |
| Ser | Val | Thr | Glu | Gln | Asp | Ser | Lys | Asp | Ser | Thr | Tyr | Ser | Leu | Ser | Ser | |
| | | | | 165 | | | | | 170 | | | | | 175 | | |
| acc | ctg | acg | ctg | agc | aaa | gca | gac | tac | gag | aaa | cac | aaa | gtc | tac | gcc | 576 |
| Thr | Leu | Thr | Leu | Ser | Lys | Ala | Asp | Tyr | Glu | Lys | His | Lys | Val | Tyr | Ala | |
| | | | 180 | | | | | 185 | | | | | 190 | | | |
| tgc | gaa | gtc | acc | cat | cag | ggc | ctg | agc | tcg | ccc | gtc | aca | aag | agc | ttc | 624 |
| Cys | Glu | Val | Thr | His | Gln | Gly | Leu | Ser | Ser | Pro | Val | Thr | Lys | Ser | Phe | |
| | | 195 | | | | | 200 | | | | | 205 | | | | |
| aac | agg | gga | gag | tgt | | | | | | | | | | | | 639 |
| Asn | Arg | Gly | Glu | Cys | | | | | | | | | | | | |
| | 210 | | | | | | | | | | | | | | | |

<210> SEQ ID NO 67
<211> LENGTH: 213
<212> TYPE: PRT
<213> ORGANISM: Homo sapiens

<400> SEQUENCE: 67

Asp Ile Gln Met Thr Gln Ser Pro Ser Ser Leu Ser Ala Ser Val Gly
1               5                   10                  15

```
Asp Arg Val Thr Ile Thr Cys Ser Ala Ser Ser Ser Val Asn Tyr Met
            20                  25                  30

His Trp Tyr Gln Gln Lys Pro Gly Lys Val Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Gln Trp Asn Ser His Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 68
<211> LENGTH: 1356
<212> TYPE: DNA
<213> ORGANISM: Homo sapiens
<220> FEATURE:
<221> NAME/KEY: CDS
<222> LOCATION: (1)..(1356)

<400> SEQUENCE: 68

```
cag gtg cag ctg gtg gaa agc ggc ggc ggc gtg gtg cag ccg ggc cgc      48
Gln Val Gln Leu Val Glu Ser Gly Gly Gly Val Val Gln Pro Gly Arg
1               5                   10                  15 agc ctg cgc ctg agc tgc gcg gcg agc ggc ttt agc ttt agc agc tat      96
Ser Leu Arg Leu Ser Cys Ala Ala Ser Gly Phe Ser Phe Ser Ser Tyr
            20                  25                  30 gcg atg cat tgg gtg cgc cag gcg ccg ggc aaa ggc ctg gaa tgg gtg     144
Ala Met His Trp Val Arg Gln Ala Pro Gly Lys Gly Leu Glu Trp Val
        35                  40                  45 gcg gtg att agc tat ggc ggc agc aaa aaa tat tat gcg gat agc gtg     192
Ala Val Ile Ser Tyr Gly Gly Ser Lys Lys Tyr Tyr Ala Asp Ser Val
    50                  55                  60 aaa ggc cgc ttt acc att agc cgc gat aac agc aaa aac acc ctg tat     240
Lys Gly Arg Phe Thr Ile Ser Arg Asp Asn Ser Lys Asn Thr Leu Tyr
65                  70                  75                  80 ctg cag atg aac agc ctg cgc gcg gaa gat acc gcg gtg tat tat tgc     288
Leu Gln Met Asn Ser Leu Arg Ala Glu Asp Thr Ala Val Tyr Tyr Cys
                85                  90                  95 gcg cgc atg ggc tat tat gat att ctg acc ggc ccg ttt gat tat tgg     336
Ala Arg Met Gly Tyr Tyr Asp Ile Leu Thr Gly Pro Phe Asp Tyr Trp
            100                 105                 110 ggc cag ggc acc ctg gtg acc gtg agc agc gct tct acc aag ggc ccc     384
Gly Gln Gly Thr Leu Val Thr Val Ser Ser Ala Ser Thr Lys Gly Pro
```

```
Gly Gln Gly Thr Leu Val Thr Val Ser Ser Ala Ser Thr Lys Gly Pro
        115                 120                 125 agc gtg ttc ccg cta gcc ccc agc agc aag agc aca agc gga ggc aca      432
Ser Val Phe Pro Leu Ala Pro Ser Ser Lys Ser Thr Ser Gly Gly Thr
        130                 135                 140 gcc gcc ctg ggc tgc ctg gtg aag gac tac ttc ccc gag ccc gtg aca      480
Ala Ala Leu Gly Cys Leu Val Lys Asp Tyr Phe Pro Glu Pro Val Thr
145                 150                 155                 160 gtg tcc tgg aac agc gga gcc ctg acc agc ggc gtg cac acc ttt cca      528
Val Ser Trp Asn Ser Gly Ala Leu Thr Ser Gly Val His Thr Phe Pro
                165                 170                 175 gcc gtg ctg cag agc agc ggc ctg tac agc ctg agc agc gtg gtg acc      576
Ala Val Leu Gln Ser Ser Gly Leu Tyr Ser Leu Ser Ser Val Val Thr
            180                 185                 190 gtg cct agc agc agc ctg ggc acc cag acc tac atc tgc aac gtg aac      624
Val Pro Ser Ser Ser Leu Gly Thr Gln Thr Tyr Ile Cys Asn Val Asn
                195                 200                 205 cac aag ccc agc aac acc aag gtg gac aag aag gtg gag ccc aag agc      672
His Lys Pro Ser Asn Thr Lys Val Asp Lys Lys Val Glu Pro Lys Ser
        210                 215                 220 tgc gac aag acc cac acc tgt ccc cct tgt cct gcc cct gaa gcc gaa      720
Cys Asp Lys Thr His Thr Cys Pro Pro Cys Pro Ala Pro Glu Ala Glu
225                 230                 235                 240 ggc gcc cct tcc gtg ttc ctg ttc ccc cca aag ccc aag gac acc ctg      768
Gly Ala Pro Ser Val Phe Leu Phe Pro Pro Lys Pro Lys Asp Thr Leu
                245                 250                 255 atg atc agc cgg acc ccc gaa gtg acc tgc gtg gtg gtg gac gtg tcc      816
Met Ile Ser Arg Thr Pro Glu Val Thr Cys Val Val Val Asp Val Ser
            260                 265                 270 cac gag gac cct gaa gtg aag ttc aat tgg tac gtg gac ggc gtg gag      864
His Glu Asp Pro Glu Val Lys Phe Asn Trp Tyr Val Asp Gly Val Glu
        275                 280                 285 gtg cac aac gcc aag acc aag ccc cgg gag gaa cag tac aac agc acc      912
Val His Asn Ala Lys Thr Lys Pro Arg Glu Glu Gln Tyr Asn Ser Thr
        290                 295                 300 tac cgg gtg gtg tcc gtg ctg acc gtg ctg cac cag gac tgg ctg aac      960
Tyr Arg Val Val Ser Val Leu Thr Val Leu His Gln Asp Trp Leu Asn
305                 310                 315                 320 ggc aaa gag tac aag tgc aag gtc tcc aac aag gcc ctg ccc agc agc     1008
Gly Lys Glu Tyr Lys Cys Lys Val Ser Asn Lys Ala Leu Pro Ser Ser
                325                 330                 335 atc gag aaa acc atc agc aag gcc aag ggc cag ccc aga gaa ccc cag     1056
Ile Glu Lys Thr Ile Ser Lys Ala Lys Gly Gln Pro Arg Glu Pro Gln
            340                 345                 350 gtg tac acc ctg ccc cct agc agg gac gag ctg acc aag aac cag gtg     1104
Val Tyr Thr Leu Pro Pro Ser Arg Asp Glu Leu Thr Lys Asn Gln Val
        355                 360                 365 tcc ctg acc tgt ctg gtg aag ggc ttc tac ccc agc gat atc gcc gtg     1152
Ser Leu Thr Cys Leu Val Lys Gly Phe Tyr Pro Ser Asp Ile Ala Val
        370                 375                 380 gag tgg gag agc aac ggc cag ccc gaa aac aac tac aag acc acc ccc     1200
Glu Trp Glu Ser Asn Gly Gln Pro Glu Asn Asn Tyr Lys Thr Thr Pro
385                 390                 395                 400 cct gtg ctg gac agc gac ggc agc ttc ttc ctg tac tcc aaa ctg acc     1248
Pro Val Leu Asp Ser Asp Gly Ser Phe Phe Leu Tyr Ser Lys Leu Thr
                405                 410                 415 gtg gac aag agc cgg tgg cag cag ggc aac gtg ttc agc tgc agc gtg     1296
Val Asp Lys Ser Arg Trp Gln Gln Gly Asn Val Phe Ser Cys Ser Val
            420                 425                 430
```

```
atg cac gag gcc ctg cac aac cac tac acc cag aag tcc ctg agc ctg     1344
Met His Glu Ala Leu His Asn His Tyr Thr Gln Lys Ser Leu Ser Leu
    435                 440                 445 agc ccc ggc aag                                                      1356
Ser Pro Gly Lys
    450
```

<210> SEQ ID NO 69
<211> LENGTH: 452
<212> TYPE: PRT
<213> ORGANISM: Homo sapiens

<400> SEQUENCE: 69

```
Gln Val Gln Leu Val Glu Ser Gly Gly Gly Val Gln Pro Gly Arg
1               5                   10                  15

Ser Leu Arg Leu Ser Cys Ala Ala Ser Gly Phe Ser Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Gly Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Ala Glu
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ser Ser
                325                 330                 335
```

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 70
<211> LENGTH: 642
<212> TYPE: DNA
<213> ORGANISM: Homo sapiens

<400> SEQUENCE: 70
gaaattgtgc tgacccagag cccgggcacc ctgagcctga gcccgggcga acgcgcgacc    60
ctgagctgcc gcgcgagcca gagcgtgagc agcagctatc tggcgtggta tcagcagaaa   120
ccgggccagg cgccgcgcct gctgatttat ggcgcgagca gccgcgcgac cggcattccg   180
gatcgcttta gcggcagcgg cagcggcacc gattttaccc tgaccattag ccgcctggaa   240
ccggaagatt ttgcggtgta ttattgccag cagtatggca gcagctatac ctttggccag   300
ggcaccaaac tggaaattaa acggaccgtg gccgctccca gcgtgttcat cttcccaccc   360
agcgacgagc agctgaagtc cggtaccgcc agcgtggtgt gcctgctgaa caacttctac   420
ccgcgggagg ccaaggtgca gtggaaggtg gacaacgccc tgcagagcgg caactcccag   480
gaaagcgtca ccgagcagga cagcaaggac tccacctaca gcctgagcag caccctgacc   540
ctgagcaagg ccgactacga gaagcacaag gtgtacgcct gcgaagtgac ccaccagggc   600
ctgtccagcc ccgtgaccaa gagcttcaac cggggcgagt gt                      642

<210> SEQ ID NO 71
<211> LENGTH: 2061
<212> TYPE: DNA
<213> ORGANISM: Homo sapiens

<400> SEQUENCE: 71
caggtgcagc tggtggaaag cggcggcggc gtggtgcagc cgggccgcag cctgcgcctg    60
agctgcgcgg cgagcggctt tagctttagc agctatgcga tgcattgggt gcgccaggcg   120
ccgggcaaag gcctggaatg ggtggcggtg attagctatg cggcagcaa aaaatattat    180 gcggatagcg tgaaaggccg ctttaccatt agccgcgata acagcaaaaa caccctgtat   240
ctgcagatga acagcctgcg cgcggaagat accgcggtgt attattgcgc gcgcatgggc   300
tattatgata ttctgaccgg cccgtttgat tattggggcc agggcaccct ggtgaccgtg   360
agcagcgctt ctaccaaggg cccatccgtg ttccccctag cccccagcag caagagcaca   420
agcggaggca gccccgccct gggctgcctg gtgaaggact acttccccga gcccgtgaca   480
gtgtcctgga acagcggagc cctgaccagc ggcgtgcaca cctttccagc cgtgctgcag   540

```
agcagcggcc tgtacagcct gagcagcgtg gtgaccgtgc ctagcagcag cctgggcacc    600
cagacctaca tctgcaacgt gaaccacaag cccagcaaca ccaaggtgga caagaaggtg    660
gagcccaaga gctgcgacaa gacccacacc tgtcccccct tgtcctgccc tgaagccgaa    720
ggcgcccctt ccgtgttcct gttcccccca agcccaagg acaccctgat gatcagccgg    780 accccgaag tgacctgcgt ggtggtggac gtgtcccacg aggaccctga agtgaagttc    840
aattggtacg tggacggcgt ggaggtgcac aacgccaaga ccaagccccg ggaggaacag    900
tacaacagca cctaccgggt ggtgtccgtg ctgaccgtgc tgcaccagga ctggctgaac    960
ggcaaagagt acaagtgcaa ggtctccaac aaggccctgc cagcagcat cgagaaaacc    1020 atcagcaagg ccaagggcca gccagagaa ccccaggtgt acaccctgcc ccctagcagg    1080
gacgagctga ccaagaacca ggtgtccctg acctgtctgg tgaagggctt ctaccccagc    1140
gatatcgccg tggagtggga gagcaacggc cagcccgaaa acaactacaa gaccaccccc    1200
cctgtgctgg acagcgacgg cagcttcttc ctgtactcca aactgaccgt ggacaagagc    1260
cggtggcagc agggcaacgt gttcagctgc agcgtgatgc acgaggccct gcacaaccac    1320
tacacccaga agtccctgag cctgagcccc ggcgtggcg ggggttcggg tggaggaggt    1380
tctcaggtgc agctggtgca gagcggagcc gaagtgaaga acctggcgc cagcgtgaag    1440 gtgtcctgca aggccagcgg ctacaccttc aacgagtaca ccatgcactg ggtgaagcag    1500
gcccccggcc agagactgga atggatgggc ggcatcaacc ccaatagcgg aggcgtgagc    1560
tacaaccaga acttcaaggg caaggccacc ctgaccgtcg acacaagcgc cagcaccgcc    1620
tacatggaac tgagcagcct gagaagcgag gacaccgccg tgtactactg cgccagaggc    1680
ggcgacggct actacaccaa ctacttcgac atcgactact ggggccaggg caccaccgtg    1740
accgtgtcca gcgcctctac caagggcccc agcgtgttcc ctctggcccc cagcagcaag    1800
agcacaagcg gaggcacagc cgccctgggc tgcctggtga aggactactt ccccgagccc    1860
gtgacagtgt cctggaacag cggagccctg accagcggcg tgcacacctt ccagccgtg    1920 ctgcagagca gcggcctgta cagcctgagc agcgtggtga ccgtgcctag cagcagcctg    1980
ggcacccaga cctacatctg caacgtgaac cacaagccca gcaaccacaa ggtggacaag    2040
aaggtggagc ccaagagctg c                                             2061
```

<210> SEQ ID NO 72
<211> LENGTH: 2061
<212> TYPE: DNA
<213> ORGANISM: Homo sapiens

<400> SEQUENCE: 72

```
caggtgcagc tggtgcagag cggagccgaa gtgaagaaac tggcgccag cgtgaaggtg     60 tcctgcaagg ccagcggcta caccttcaac gagtacacca tgcactgggt gaagcaggcc    120
cccggccaga gactggaatg gatgggcggc atcaaccca atagcggagg cgtgagctac    180
aaccagaact tcaagggcaa ggccaccctg accgtcgaca agcgccag caccgcctac    240 atggaactga gcagcctgag aagcgaggac accgccgtgt actactgcgc cagaggcggc    300
gacggctact acaccaacta cttcgacatc gactactggg gccagggcac caccgtgacc    360
gtgtccagcg cttctaccaa gggcccagc gtgttcccgc tagcccccag cagcaagagc    420
acaagcggag gcacagccgc cctgggctgc ctggtgaagg actacttccc cgagcccgtg    480
acagtgtcct ggaacagcgg agccctgacc agcggcgtgc acacctttcc agccgtgctg    540
```

```
cagagcagcg gcctgtacag cctgagcagc gtggtgaccg tgcctagcag cagcctgggc    600
acccagacct acatctgcaa cgtgaaccac aagcccagca acaccaaggt ggacaagaag    660
gtggagccca agagctgcga caagacccac acctgtcccc cttgtcctgc ccctgaagcc    720
gaaggcgccc cttccgtgtt cctgttcccc ccaaagccca aggacaccct gatgatcagc    780
cggacccccg aagtgacctg cgtggtggtg gacgtgtccc acgaggaccc tgaagtgaag    840
ttcaattggt acgtggacgg cgtggaggtg cacaacgcca agaccaagcc ccgggaggaa    900
cagtacaaca gcacctaccg ggtggtgtcc gtgctgaccg tgctgcacca ggactggctg    960
aacggcaaag agtacaagtg caaggtctcc aacaaggccc tgcccagcag catcgagaaa   1020
accatcagca aggccaaggg ccagcccaga gaaccccagg tgtacaccct gcccccctag   1080
agggacgagc tgaccaagaa ccaggtgtcc ctgacctgtc tggtgaaggg cttctacccc   1140
agcgatatcg ccgtggagtg ggagagcaac ggccagcccg aaaacaacta caagaccacc   1200
cccctgtgc tggacagcga cggcagcttc ttcctgtact ccaaactgac cgtggacaag   1260
agccggtggc agcagggcaa cgtgttcagc tgcagcgtga tgcacgaggc cctgcacaac   1320
cactacaccc agaagtccct gagcctgagc cccggcggtg cgggggttc gggtggagga   1380
ggttctcagg tgcagctggt ggaaagcggc ggcgcgtgg tgcagccggg ccgcagcctg   1440
cgcctgagct gcgcggcgag cggctttagc tttagcagct atgcgatgca ttgggtgcgc   1500
caggcgccgg gcaaaggcct ggaatgggtg gcggtgatta gctatggcgg cagcaaaaaa   1560
tattatgcgg atagcgtgaa aggccgcttt accattagcc gcgataacag caaaaacacc   1620
ctgtatctgc agatgaacag cctgcgcgcg gaagataccg cggtgtatta ttgcgcgcgc   1680
atgggctatt atgatattct gaccggcccg tttgattatt ggggccaggg caccctggtg   1740
accgtgagca gcgcctctac caagggcccc agcgtgttcc ctctggcccc cagcagcaag   1800
agcacaagcg gaggcacagc cgccctgggc tgcctggtga aggactactt ccccgagccc   1860
gtgacagtgt cctggaacag cggagccctg accagcggcg tgcacacctt ccagccgtg    1920
ctgcagagca gcggcctgta cagcctgagc agcgtggtga ccgtgcctag cagcagcctg   1980
ggcacccaga cctacatctg caacgtgaac cacaagccca gcaacaccaa ggtggacaag   2040
aaggtggagc ccaagagctg c                                              2061
```

<210> SEQ ID NO 73
<211> LENGTH: 2037
<212> TYPE: DNA
<213> ORGANISM: Homo sapiens
<220> FEATURE:
<221> NAME/KEY: CDS
<222> LOCATION: (1)..(2037)

<400> SEQUENCE: 73

```
cag gtg cag ctg gtg gaa agc ggc ggc ggc gtg gtg cag ccg ggc cgc      48
Gln Val Gln Leu Val Glu Ser Gly Gly Gly Val Val Gln Pro Gly Arg
1               5                   10                  15 agc ctg cgc ctg agc tgc gcg gcg agc ggc ttt agc ttt agc agc tat      96
Ser Leu Arg Leu Ser Cys Ala Ala Ser Gly Phe Ser Phe Ser Ser Tyr
            20                  25                  30 gcg atg cat tgg gtg cgc cag gcg ccg ggc aaa ggc ctg gaa tgg gtg     144
Ala Met His Trp Val Arg Gln Ala Pro Gly Lys Gly Leu Glu Trp Val
        35                  40                  45 gcg gtg att agc tat ggc ggc agc aaa aaa tat tat gcg gat agc gtg     192
Ala Val Ile Ser Tyr Gly Gly Ser Lys Lys Tyr Tyr Ala Asp Ser Val
    50                  55                  60
```

```
aaa ggc cgc ttt acc att agc cgc gat aac agc aaa aac acc ctg tat       240
Lys Gly Arg Phe Thr Ile Ser Arg Asp Asn Ser Lys Asn Thr Leu Tyr
 65                  70                  75                  80 ctg cag atg aac agc ctg cgc gcg gaa gat acc gcg gtg tat tat tgc       288
Leu Gln Met Asn Ser Leu Arg Ala Glu Asp Thr Ala Val Tyr Tyr Cys
                 85                  90                  95 gcg cgc atg ggc tat tat gat att ctg acc ggc ccg ttt gat tat tgg       336
Ala Arg Met Gly Tyr Tyr Asp Ile Leu Thr Gly Pro Phe Asp Tyr Trp
            100                 105                 110 ggc cag ggc acc ctg gtg acc gtg agc agc gct tcc acc aag ggc cca       384
Gly Gln Gly Thr Leu Val Thr Val Ser Ser Ala Ser Thr Lys Gly Pro
        115                 120                 125 tcc gtc ttc ccc ctg gcg ccc tgc tcc agg agc acc tcc gag agc aca       432
Ser Val Phe Pro Leu Ala Pro Cys Ser Arg Ser Thr Ser Glu Ser Thr
    130                 135                 140 gcc gcc ctg ggc tgc ctg gtc aag gac tac ttc ccc gaa ccg gtg acg       480
Ala Ala Leu Gly Cys Leu Val Lys Asp Tyr Phe Pro Glu Pro Val Thr
145                 150                 155                 160 gtg tcg tgg aac tca ggc gcc ctg acc agc ggc gtg cac acc ttc ccg       528
Val Ser Trp Asn Ser Gly Ala Leu Thr Ser Gly Val His Thr Phe Pro
                165                 170                 175 gct gtc cta cag tcc tca gga ctc tac tcc ctc agc agc gtg gtg acc       576
Ala Val Leu Gln Ser Ser Gly Leu Tyr Ser Leu Ser Ser Val Val Thr
            180                 185                 190 gtg ccc tcc agc agc ttg ggc acg aag acc tac acc tgc aac gta gat       624
Val Pro Ser Ser Ser Leu Gly Thr Lys Thr Tyr Thr Cys Asn Val Asp
        195                 200                 205 cac aag ccc agc aac acc aag gtg gac aag aga gtt gag tcc aaa tat       672
His Lys Pro Ser Asn Thr Lys Val Asp Lys Arg Val Glu Ser Lys Tyr
    210                 215                 220 ggt ccc cca tgc cca cca tgc cca gca cct gag ttc ctg ggg gga cca       720
Gly Pro Pro Cys Pro Pro Cys Pro Ala Pro Glu Phe Leu Gly Gly Pro
225                 230                 235                 240 tca gtc ttc ctg ttc ccc cca aaa ccc aag gac act ctc atg atc tcc       768
Ser Val Phe Leu Phe Pro Pro Lys Pro Lys Asp Thr Leu Met Ile Ser
                245                 250                 255 cgg acc cct gag gtc acg tgc gtg gtg gtg gac gtg agc cag gaa gac       816
Arg Thr Pro Glu Val Thr Cys Val Val Val Asp Val Ser Gln Glu Asp
            260                 265                 270 ccc gag gtc cag ttc aac tgg tac gtg gat ggc gtg gag gtg cat aat       864
Pro Glu Val Gln Phe Asn Trp Tyr Val Asp Gly Val Glu Val His Asn
        275                 280                 285 gcc aag aca aag ccg cgg gag gag cag ttc aac agc acg tac cgt gtg       912
Ala Lys Thr Lys Pro Arg Glu Glu Gln Phe Asn Ser Thr Tyr Arg Val
    290                 295                 300 gtc agc gtc ctc acc gtc ctg cac cag gac tgg ctg aac ggc aag gag       960
Val Ser Val Leu Thr Val Leu His Gln Asp Trp Leu Asn Gly Lys Glu
305                 310                 315                 320 tac aag tgc aag gtc tcc aac aaa ggc ctc ccg tcc tcc atc gag aaa      1008
Tyr Lys Cys Lys Val Ser Asn Lys Gly Leu Pro Ser Ser Ile Glu Lys
                325                 330                 335 acc atc tcc aaa gcc aaa ggg cag ccc cga gag cca cag gtg tac acc      1056
Thr Ile Ser Lys Ala Lys Gly Gln Pro Arg Glu Pro Gln Val Tyr Thr
            340                 345                 350 ctg ccc cca tcc cag gag gag atg acc aag aac cag gtc agc ctg acc      1104
Leu Pro Pro Ser Gln Glu Glu Met Thr Lys Asn Gln Val Ser Leu Thr
        355                 360                 365 tgc ctg gtc aaa ggc ttc tac ccc agc gac atc gcc gtg gag tgg gag      1152
Cys Leu Val Lys Gly Phe Tyr Pro Ser Asp Ile Ala Val Glu Trp Glu
    370                 375                 380
```

```
agc aat ggg cag ccg gag aac aac tac aag acc acg cct ccc gtg ctg      1200
Ser Asn Gly Gln Pro Glu Asn Asn Tyr Lys Thr Thr Pro Pro Val Leu
385                 390                 395                 400 gac tcc gac ggc tcc ttc ttc ctc tac agc agg cta acc gtg gac aag      1248
Asp Ser Asp Gly Ser Phe Phe Leu Tyr Ser Arg Leu Thr Val Asp Lys
                405                 410                 415 agc agg tgg cag gag ggg aat gtc ttc tca tgc tcc gtg atg cat gag      1296
Ser Arg Trp Gln Glu Gly Asn Val Phe Ser Cys Ser Val Met His Glu
            420                 425                 430 gct ctg cac aac cac tac aca cag aag agc ctc tcc ctg tct ctg ggt      1344
Ala Leu His Asn His Tyr Thr Gln Lys Ser Leu Ser Leu Ser Leu Gly
                435                 440                 445 ggt ggc ggg ggt tcg ggt gga gga ggt tct cag gtg cag ctg gtg cag      1392
Gly Gly Gly Gly Ser Gly Gly Gly Gly Ser Gln Val Gln Leu Val Gln
        450                 455                 460 agc gga gcc gaa gtg aag aaa cct ggc gcc agc gtg aag gtg tcc tgc      1440
Ser Gly Ala Glu Val Lys Lys Pro Gly Ala Ser Val Lys Val Ser Cys
465                 470                 475                 480 aag gcc agc ggc tac acc ttc aac gag tac acc atg cac tgg gtg aag      1488
Lys Ala Ser Gly Tyr Thr Phe Asn Glu Tyr Thr Met His Trp Val Lys
                485                 490                 495 cag gcc ccc ggc cag aga ctg gaa tgg atg ggc ggc atc aac ccc aat      1536
Gln Ala Pro Gly Gln Arg Leu Glu Trp Met Gly Gly Ile Asn Pro Asn
            500                 505                 510 agc gga ggc gtg agc tac aac cag aac ttc aag ggc aag gcc acc ctg      1584
Ser Gly Gly Val Ser Tyr Asn Gln Asn Phe Lys Gly Lys Ala Thr Leu
        515                 520                 525 acc gtc gac aca agc gcc agc acc gcc tac atg gaa ctg agc agc ctg      1632
Thr Val Asp Thr Ser Ala Ser Thr Ala Tyr Met Glu Leu Ser Ser Leu
530                 535                 540 aga agc gag gac acc gcc gtg tac tac tgc gcc aga ggc ggc gac ggc      1680
Arg Ser Glu Asp Thr Ala Val Tyr Tyr Cys Ala Arg Gly Gly Asp Gly
545                 550                 555                 560 tac tac acc aac tac ttc gac atc gac tac tgg ggc cag ggc acc acc      1728
Tyr Tyr Thr Asn Tyr Phe Asp Ile Asp Tyr Trp Gly Gln Gly Thr Thr
                565                 570                 575 gtg acc gtg tcc agc gct tcc acc aag ggc cca tcc gtc ttc ccc ctg      1776
Val Thr Val Ser Ser Ala Ser Thr Lys Gly Pro Ser Val Phe Pro Leu
            580                 585                 590 gcg ccc tgc tcc agg agc acc tcc gag agc aca gcc gcc ctg ggc tgc      1824
Ala Pro Cys Ser Arg Ser Thr Ser Glu Ser Thr Ala Ala Leu Gly Cys
        595                 600                 605 ctg gtc aag gac tac ttc ccc gaa ccg gtg acg gtg tcg tgg aac tca      1872
Leu Val Lys Asp Tyr Phe Pro Glu Pro Val Thr Val Ser Trp Asn Ser
610                 615                 620 ggc gcc ctg acc agc ggc gtg cac acc ttc ccg gct gtc cta cag tcc      1920
Gly Ala Leu Thr Ser Gly Val His Thr Phe Pro Ala Val Leu Gln Ser
625                 630                 635                 640 tca gga ctc tac tcc ctc agc agc gtg gtg acc gtg ccc tcc agc agc      1968
Ser Gly Leu Tyr Ser Leu Ser Ser Val Val Thr Val Pro Ser Ser Ser
                645                 650                 655 ttg ggc acg aag acc tac acc tgc aac gta gat cac aag ccc agc aac      2016
Leu Gly Thr Lys Thr Tyr Thr Cys Asn Val Asp His Lys Pro Ser Asn
            660                 665                 670 acc aag gtg gac aag aga gtt                                           2037
Thr Lys Val Asp Lys Arg Val
        675

<210> SEQ ID NO 74
```

```
<211> LENGTH: 679
<212> TYPE: PRT
<213> ORGANISM: Homo sapiens

<400> SEQUENCE: 74

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Gly Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
            385                 390                 395                 400
Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
                435                 440                 445

Gly Gly Gly Gly Ser Gly Gly Gly Ser Gln Val Gln Leu Val Gln
450                 455                 460

Ser Gly Ala Glu Val Lys Lys Pro Gly Ala Ser Val Lys Val Ser Cys
465                 470                 475                 480

Lys Ala Ser Gly Tyr Thr Phe Asn Glu Tyr Thr Met His Trp Val Lys
                485                 490                 495

Gln Ala Pro Gly Gln Arg Leu Glu Trp Met Gly Gly Ile Asn Pro Asn
            500                 505                 510

Ser Gly Gly Val Ser Tyr Asn Gln Asn Phe Lys Gly Lys Ala Thr Leu
            515                 520                 525

Thr Val Asp Thr Ser Ala Ser Thr Ala Tyr Met Glu Leu Ser Ser Leu
        530                 535                 540

Arg Ser Glu Asp Thr Ala Val Tyr Tyr Cys Ala Arg Gly Gly Asp Gly
545                 550                 555                 560

Tyr Tyr Thr Asn Tyr Phe Asp Ile Asp Tyr Trp Gly Gln Gly Thr Thr
                565                 570                 575

Val Thr Val Ser Ser Ala Ser Thr Lys Gly Pro Ser Val Phe Pro Leu
            580                 585                 590

Ala Pro Cys Ser Arg Ser Thr Ser Glu Ser Thr Ala Ala Leu Gly Cys
        595                 600                 605

Leu Val Lys Asp Tyr Phe Pro Glu Pro Val Thr Val Ser Trp Asn Ser
            610                 615                 620

Gly Ala Leu Thr Ser Gly Val His Thr Phe Pro Ala Val Leu Gln Ser
625                 630                 635                 640

Ser Gly Leu Tyr Ser Leu Ser Ser Val Val Thr Val Pro Ser Ser Ser
                645                 650                 655

Leu Gly Thr Lys Thr Tyr Thr Cys Asn Val Asp His Lys Pro Ser Asn
            660                 665                 670

Thr Lys Val Asp Lys Arg Val
            675

<210> SEQ ID NO 75
<211> LENGTH: 2037
<212> TYPE: DNA
<213> ORGANISM: Homo sapiens

<400> SEQUENCE: 75
caggtgcagc tggtgcagag cggagccgaa gtgaagaaac tggcgccag cgtgaaggtg      60 tcctgcaagg ccagcggcta caccttcaac gagtacacca tgcactgggt gaagcaggcc    120
cccggccaga gactggaatg gatgggcggc atcaacccca atagcggagg cgtgagctac    180
aaccagaact tcaagggcaa ggccaccctg accgtcgaca agagcgccag caccgcctac    240
atggaactga gcagcctgag aagcgaggac accgccgtgt actactgcgc cagaggcggc    300
gacggctact acaccaacta cttcgacatc gactactggg gccagggcac caccgtgacc    360
gtgtccagcg cttccaccaa gggcccatcc gtcttccccc tggcgccctg ctccaggagc    420
acctccgaga gcacagccgc cctgggctgc ctggtcaagg actacttccc cgaaccggtg    480
```

-continued

```
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acgaagacct acacctgcaa cgtagatcac aagcccagca acaccaaggt ggacaagaga      660
gttgagtcca aatatggtcc cccatgccca ccatgcccag cacctgagtt cctgggggga      720
ccatcagtct tcctgttccc cccaaaaccc aaggacactc tcatgatctc ccggacccct      780
gaggtcacgt gcgtggtggt ggacgtgagc caggaagacc ccgaggtcca gttcaactgg      840
tacgtggatg gcgtggaggt gcataatgcc aagacaaagc cgcgggagga gcagttcaac      900
agcacgtacc gtgtggtcag cgtcctcacc gtcctgcacc aggactggct gaacggcaag      960
gagtacaagt gcaaggtctc caacaaaggc ctcccgtcct ccatcgagaa aaccatctcc     1020
aaagccaaag gcagccccg agagccacag gtgtacaccc tgcccccatc ccaggaggag     1080
atgaccaaga accaggtcag cctgacctgc ctggtcaaag gcttctaccc cagcgacatc     1140
gccgtggagt gggagagcaa tgggcagccg gagaacaact acaagaccac gcctcccgtg     1200
ctggactccg acggctcctt cttcctctac agcaggctaa ccgtggacaa gagcaggtgg     1260
caggagggga atgtcttctc atgctccgtg atgcatgagg ctctgcacaa ccactacaca     1320
cagaagagcc tctccctgtc tctgggtggt ggcgggggtt cgggtggagg aggttctcag     1380
gtgcagctgg tggaaagcgg cggcggcgtg gtgcagccgg gccgcagcct cgcctgagc     1440 tgcgcggcga gcggctttag ctttagcagc tatgcgatgc attgggtgcg ccaggcgccg     1500
ggcaaaggcc tggaatgggt ggcggtgatt agctatggcg gcagcaaaaa atattatgcg     1560
gatagcgtga aaggccgctt taccattagc cgcgataaca gcaaaaacac cctgtatctg     1620
cagatgaaca gcctgcgcgc ggaagatacc gcggtgtatt attgcgcgcg catgggctat     1680
tatgatattc tgaccggccc gtttgattat tggggccagg gcaccctggt gaccgtgagc     1740
agcgcttcca ccaagggccc atccgtcttc cccctggcgc cctgctccag gagcacctcc     1800
gagagcacag ccgccctggg ctgcctggtc aaggactact tccccgaacc ggtgacggtg     1860
tcgtggaact caggcgccct gaccagcggc gtgcacacct tcccggctgt cctacagtcc     1920
tcaggactct actccctcag cagcgtggtg accgtgccct ccagcagctt gggcacgaag     1980
acctacacct gcaacgtaga tcacaagccc agcaacacca aggtggacaa gagagtt       2037
```

```
<210> SEQ ID NO 76
<211> LENGTH: 2064
<212> TYPE: DNA
<213> ORGANISM: Homo sapiens
<220> FEATURE:
<221> NAME/KEY: CDS
<222> LOCATION: (1)..(2064)

<400> SEQUENCE: 76
```

```
cag gtg cag ctg gtg gaa agc ggc ggc ggc gtg gtg cag ccg ggc cgc       48
Gln Val Gln Leu Val Glu Ser Gly Gly Gly Val Val Gln Pro Gly Arg
1               5                   10                  15 agc ctg cgc ctg agc tgc gcg gcg agc ggc ttt agc ttt agc agc tat       96
Ser Leu Arg Leu Ser Cys Ala Ala Ser Gly Phe Ser Phe Ser Ser Tyr
            20                  25                  30 gcg atg cat tgg gtg cgc cag gcg ccg ggc aaa ggc ctg gaa tgg gtg      144
Ala Met His Trp Val Arg Gln Ala Pro Gly Lys Gly Leu Glu Trp Val
        35                  40                  45 gcg gtg att agc tat ggc ggc agc aaa aaa tat tat gcg gat agc gtg      192
Ala Val Ile Ser Tyr Gly Gly Ser Lys Lys Tyr Tyr Ala Asp Ser Val
    50                  55                  60
```

-continued

```
aaa ggc cgc ttt acc att agc cgc gat aac agc aaa aac acc ctg tat        240
Lys Gly Arg Phe Thr Ile Ser Arg Asp Asn Ser Lys Asn Thr Leu Tyr
65                  70                  75                  80 ctg cag atg aac agc ctg cgc gcg gaa gat acc gcg gtg tat tat tgc        288
Leu Gln Met Asn Ser Leu Arg Ala Glu Asp Thr Ala Val Tyr Tyr Cys
                85                  90                  95 gcg cgc atg ggc tat tat gat att ctg acc ggc ccg ttt gat tat tgg        336
Ala Arg Met Gly Tyr Tyr Asp Ile Leu Thr Gly Pro Phe Asp Tyr Trp
            100                 105                 110 ggc cag ggc acc ctg gtg acc gtg agc agc gcc tct acc aag ggc ccc        384
Gly Gln Gly Thr Leu Val Thr Val Ser Ser Ala Ser Thr Lys Gly Pro
        115                 120                 125 agc gtg ttc cct ctg gcc ccc agc agc aag agc aca agc gga ggc aca        432
Ser Val Phe Pro Leu Ala Pro Ser Ser Lys Ser Thr Ser Gly Gly Thr
    130                 135                 140 gcc gcc ctg ggc tgc ctg gtg aag gac tac ttc ccc gag ccc gtg aca        480
Ala Ala Leu Gly Cys Leu Val Lys Asp Tyr Phe Pro Glu Pro Val Thr
145                 150                 155                 160 gtg tcc tgg aac agc gga gcc ctg acc agc ggc gtg cac acc ttt cca        528
Val Ser Trp Asn Ser Gly Ala Leu Thr Ser Gly Val His Thr Phe Pro
                165                 170                 175 gcc gtg ctg cag agc agc ggc ctg tac agc ctg agc agc gtg gtg acc        576
Ala Val Leu Gln Ser Ser Gly Leu Tyr Ser Leu Ser Ser Val Val Thr
            180                 185                 190 gtg cct agc agc agc ctg ggc acc cag acc tac atc tgc aac gtg aac        624
Val Pro Ser Ser Ser Leu Gly Thr Gln Thr Tyr Ile Cys Asn Val Asn
        195                 200                 205 cac aag ccc agc aac acc aag gtg gac aag aag gtg gag ccc aag agc        672
His Lys Pro Ser Asn Thr Lys Val Asp Lys Lys Val Glu Pro Lys Ser
    210                 215                 220 tgc ggt ggc ggg ggt tcg ggt gga gga ggt tct cag gtg cag ctg gtg        720
Cys Gly Gly Gly Gly Ser Gly Gly Gly Gly Ser Gln Val Gln Leu Val
225                 230                 235                 240 cag agc gga gcc gaa gtg aag aaa cct ggc gcc agc gtg aag gtg tcc        768
Gln Ser Gly Ala Glu Val Lys Lys Pro Gly Ala Ser Val Lys Val Ser
                245                 250                 255 tgc aag gcc agc ggc tac acc ttc aac gag tac acc atg cac tgg gtg        816
Cys Lys Ala Ser Gly Tyr Thr Phe Asn Glu Tyr Thr Met His Trp Val
            260                 265                 270 aag cag gcc ccc ggc cag aga ctg gaa tgg atg ggc ggc atc aac ccc        864
Lys Gln Ala Pro Gly Gln Arg Leu Glu Trp Met Gly Gly Ile Asn Pro
        275                 280                 285 aat agc gga ggc gtg agc tac aac cag aac ttc aag ggc aag gcc acc        912
Asn Ser Gly Gly Val Ser Tyr Asn Gln Asn Phe Lys Gly Lys Ala Thr
    290                 295                 300 ctg acc gtc gac aca agc gcc agc acc gcc tac atg gaa ctg agc agc        960
Leu Thr Val Asp Thr Ser Ala Ser Thr Ala Tyr Met Glu Leu Ser Ser
305                 310                 315                 320 ctg aga agc gag gac acc gcc gtg tac tac tgc gcc aga ggc ggc gac       1008
Leu Arg Ser Glu Asp Thr Ala Val Tyr Tyr Cys Ala Arg Gly Gly Asp
                325                 330                 335 ggc tac tac acc aac tac ttc gac atc gac tac tgg ggc cag ggc acc       1056
Gly Tyr Tyr Thr Asn Tyr Phe Asp Ile Asp Tyr Trp Gly Gln Gly Thr
            340                 345                 350 acc gtg acc gtg tcc agc gct tct acc aag ggc ccc agc gtg ttc ccg       1104
Thr Val Thr Val Ser Ser Ala Ser Thr Lys Gly Pro Ser Val Phe Pro
        355                 360                 365 cta gcc ccc agc agc aag agc aca agc gga ggc aca gcc gcc ctg ggc       1152
Leu Ala Pro Ser Ser Lys Ser Thr Ser Gly Gly Thr Ala Ala Leu Gly
```

-continued

```
                370                 375                 380
tgc ctg gtg aag gac tac ttc ccc gag ccc gtg aca gtg tcc tgg aac        1200
Cys Leu Val Lys Asp Tyr Phe Pro Glu Pro Val Thr Val Ser Trp Asn
385                 390                 395                 400 agc gga gcc ctg acc agc ggc gtg cac acc ttt cca gcc gtg ctg cag        1248
Ser Gly Ala Leu Thr Ser Gly Val His Thr Phe Pro Ala Val Leu Gln
            405                 410                 415 agc agc ggc ctg tac agc ctg agc agc gtg gtg acc gtg cct agc agc        1296
Ser Ser Gly Leu Tyr Ser Leu Ser Ser Val Val Thr Val Pro Ser Ser
        420                 425                 430 agc ctg ggc acc cag acc tac atc tgc aac gtg aac cac aag ccc agc        1344
Ser Leu Gly Thr Gln Thr Tyr Ile Cys Asn Val Asn His Lys Pro Ser
    435                 440                 445 aac acc aag gtg gac aag aag gtg gag ccc aag agc tgc gac aag acc        1392
Asn Thr Lys Val Asp Lys Lys Val Glu Pro Lys Ser Cys Asp Lys Thr
450                 455                 460 cac acc tgt ccc cct tgt cct gcc cct gaa gcc gaa ggc gcc cct tcc        1440
His Thr Cys Pro Pro Cys Pro Ala Pro Glu Ala Glu Gly Ala Pro Ser
465                 470                 475                 480 gtg ttc ctg ttc ccc cca aag ccc aag gac acc ctg atg atc agc cgg        1488
Val Phe Leu Phe Pro Pro Lys Pro Lys Asp Thr Leu Met Ile Ser Arg
            485                 490                 495 acc ccc gaa gtg acc tgc gtg gtg gtg gac gtg tcc cac gag gac cct        1536
Thr Pro Glu Val Thr Cys Val Val Val Asp Val Ser His Glu Asp Pro
        500                 505                 510 gaa gtg aag ttc aat tgg tac gtg gac ggc gtg gag gtg cac aac gcc        1584
Glu Val Lys Phe Asn Trp Tyr Val Asp Gly Val Glu Val His Asn Ala
    515                 520                 525 aag acc aag ccc cgg gag gaa cag tac aac agc acc tac cgg gtg gtg        1632
Lys Thr Lys Pro Arg Glu Glu Gln Tyr Asn Ser Thr Tyr Arg Val Val
530                 535                 540 tcc gtg ctg acc gtg ctg cac cag gac tgg ctg aac ggc aaa gag tac        1680
Ser Val Leu Thr Val Leu His Gln Asp Trp Leu Asn Gly Lys Glu Tyr
545                 550                 555                 560 aag tgc aag gtc tcc aac aag gcc ctg ccc agc agc atc gag aaa acc        1728
Lys Cys Lys Val Ser Asn Lys Ala Leu Pro Ser Ser Ile Glu Lys Thr
            565                 570                 575 atc agc aag gcc aag ggc cag ccc aga gaa ccc cag gtg tac acc ctg        1776
Ile Ser Lys Ala Lys Gly Gln Pro Arg Glu Pro Gln Val Tyr Thr Leu
        580                 585                 590 ccc cct agc agg gac gag ctg acc aag aac cag gtg tcc ctg acc tgt        1824
Pro Pro Ser Arg Asp Glu Leu Thr Lys Asn Gln Val Ser Leu Thr Cys
    595                 600                 605 ctg gtg aag ggc ttc tac ccc agc gat atc gcc gtg gag tgg gag agc        1872
Leu Val Lys Gly Phe Tyr Pro Ser Asp Ile Ala Val Glu Trp Glu Ser
610                 615                 620 aac ggc cag ccc gaa aac aac tac aag acc acc ccc cct gtg ctg gac        1920
Asn Gly Gln Pro Glu Asn Asn Tyr Lys Thr Thr Pro Pro Val Leu Asp
625                 630                 635                 640 agc gac ggc agc ttc ttc ctg tac tcc aaa ctg acc gtg gac aag agc        1968
Ser Asp Gly Ser Phe Phe Leu Tyr Ser Lys Leu Thr Val Asp Lys Ser
            645                 650                 655 cgg tgg cag cag ggc aac gtg ttc agc tgc agc gtg atg cac gag gcc        2016
Arg Trp Gln Gln Gly Asn Val Phe Ser Cys Ser Val Met His Glu Ala
        660                 665                 670 ctg cac aac cac tac acc cag aag tcc ctg agc ctg agc ccc ggc aag        2064
Leu His Asn His Tyr Thr Gln Lys Ser Leu Ser Leu Ser Pro Gly Lys
    675                 680                 685
```

```
<210> SEQ ID NO 77
<211> LENGTH: 688
<212> TYPE: PRT
<213> ORGANISM: Homo sapiens

<400> SEQUENCE: 77

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Gly Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Gly Gly Gly Ser Gly Gly Gly Ser Gln Val Gln Leu Val
225                 230                 235                 240

Gln Ser Gly Ala Glu Val Lys Lys Pro Gly Ala Ser Val Lys Val Ser
                245                 250                 255

Cys Lys Ala Ser Gly Tyr Thr Phe Asn Glu Tyr Thr Met His Trp Val
            260                 265                 270

Lys Gln Ala Pro Gly Gln Arg Leu Glu Trp Met Gly Ile Asn Pro
        275                 280                 285

Asn Ser Gly Gly Val Ser Tyr Asn Gln Asn Phe Lys Gly Lys Ala Thr
    290                 295                 300

Leu Thr Val Asp Thr Ser Ala Ser Thr Ala Tyr Met Glu Leu Ser Ser
305                 310                 315                 320

Leu Arg Ser Glu Asp Thr Ala Val Tyr Tyr Cys Ala Arg Gly Gly Asp
                325                 330                 335

Gly Tyr Tyr Thr Asn Tyr Phe Asp Ile Asp Tyr Trp Gly Gln Gly Thr
            340                 345                 350

Thr Val Thr Val Ser Ser Ala Ser Thr Lys Gly Pro Ser Val Phe Pro
        355                 360                 365

Leu Ala Pro Ser Ser Lys Ser Thr Ser Gly Gly Thr Ala Ala Leu Gly
    370                 375                 380
```

```
Cys Leu Val Lys Asp Tyr Phe Pro Glu Pro Val Thr Val Ser Trp Asn
385                 390                 395                 400

Ser Gly Ala Leu Thr Ser Gly Val His Thr Phe Pro Ala Val Leu Gln
            405                 410                 415

Ser Ser Gly Leu Tyr Ser Leu Ser Ser Val Val Thr Val Pro Ser Ser
            420                 425                 430

Ser Leu Gly Thr Gln Thr Tyr Ile Cys Asn Val Asn His Lys Pro Ser
            435                 440                 445

Asn Thr Lys Val Asp Lys Lys Val Glu Pro Lys Ser Cys Asp Lys Thr
        450                 455                 460

His Thr Cys Pro Pro Cys Pro Ala Pro Glu Ala Glu Gly Ala Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Val Asp Val Ser His Glu Asp Pro
                500                 505                 510

Glu Val Lys Phe Asn Trp Tyr Val Asp Gly Val Glu Val His Asn Ala
            515                 520                 525

Lys Thr Lys Pro Arg Glu Glu Gln Tyr Asn Ser Thr Tyr Arg Val Val
        530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ser Ser Ile Glu Lys Thr
                565                 570                 575

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser
610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

<210> SEQ ID NO 78
<211> LENGTH: 1311
<212> TYPE: DNA
<213> ORGANISM: Homo sapiens
<220> FEATURE:
<221> NAME/KEY: CDS
<222> LOCATION: (1)..(1311)

<400> SEQUENCE: 78 gaa att gtg ctg acc cag agc ccg ggc acc ctg agc ctg agc ccg ggc    48
Glu Ile Val Leu Thr Gln Ser Pro Gly Thr Leu Ser Leu Ser Pro Gly
1               5                   10                  15 gaa cgc gcg acc ctg agc tgc cgc gcg agc cag agc gtg agc agc agc    96
Glu Arg Ala Thr Leu Ser Cys Arg Ala Ser Gln Ser Val Ser Ser Ser
            20                  25                  30 tat ctg gcg tgg tat cag cag aaa ccg ggc cag gcg ccg cgc ctg ctg    144
Tyr Leu Ala Trp Tyr Gln Gln Lys Pro Gly Gln Ala Pro Arg Leu Leu
        35                  40                  45
```

-continued

| | | |
|---|---|---|
| att tat ggc gcg agc agc cgc gcg acc ggc att ccg gat cgc ttt agc<br>Ile Tyr Gly Ala Ser Ser Arg Ala Thr Gly Ile Pro Asp Arg Phe Ser<br>50                              55                            60 | | 192 |
| ggc agc ggc agc ggc acc gat ttt acc ctg acc att agc cgc ctg gaa<br>Gly Ser Gly Ser Gly Thr Asp Phe Thr Leu Thr Ile Ser Arg Leu Glu<br>65                              70                            75                            80 | | 240 |
| ccg gaa gat ttt gcg gtg tat tat tgc cag cag tat ggc agc agc tat<br>Pro Glu Asp Phe Ala Val Tyr Tyr Cys Gln Gln Tyr Gly Ser Ser Tyr<br>                        85                            90                            95 | | 288 |
| acc ttt ggc cag ggc acc aaa ctg gaa att aaa cga act gtg gct gca<br>Thr Phe Gly Gln Gly Thr Lys Leu Glu Ile Lys Arg Thr Val Ala Ala<br>                        100                        105                        110 | | 336 |
| cca tct gtc ttc atc ttc ccg cca tct gat gag cag ttg aaa tct gga<br>Pro Ser Val Phe Ile Phe Pro Pro Ser Asp Glu Gln Leu Lys Ser Gly<br>         115                        120                        125 | | 384 |
| act gcc tct gtt gtg tgc ctg ctg aat aac ttc tat ccc aga gag gcc<br>Thr Ala Ser Val Val Cys Leu Leu Asn Asn Phe Tyr Pro Arg Glu Ala<br>130                            135                        140 | | 432 |
| aaa gta cag tgg aag gtg gat aac gcc ctc caa tcg ggt aac tcc cag<br>Lys Val Gln Trp Lys Val Asp Asn Ala Leu Gln Ser Gly Asn Ser Gln<br>145                            150                        155                        160 | | 480 |
| gag agt gtc aca gag cag gac agc aag gac agc acc tac agc ctc agc<br>Glu Ser Val Thr Glu Gln Asp Ser Lys Asp Ser Thr Tyr Ser Leu Ser<br>                        165                        170                        175 | | 528 |
| agc acc ctg acg ctg agc aaa gca gac tac gag aaa cac aaa gtc tac<br>Ser Thr Leu Thr Leu Ser Lys Ala Asp Tyr Glu Lys His Lys Val Tyr<br>                        180                        185                        190 | | 576 |
| gcc tgc gaa gtc acc cat cag ggc ctg agc tcg ccc gtc aca aag agc<br>Ala Cys Glu Val Thr His Gln Gly Leu Ser Ser Pro Val Thr Lys Ser<br>         195                        200                        205 | | 624 |
| ttc aac agg gga gag tgt ggt ggc ggg ggt tcg ggt gga gga ggt tct<br>Phe Asn Arg Gly Glu Cys Gly Gly Gly Gly Ser Gly Gly Gly Gly Ser<br>210                            215                        220 | | 672 |
| gac atc cag atg acc cag tcc ccc tcc tcc ctg tcc gcc tcc gtg ggc<br>Asp Ile Gln Met Thr Gln Ser Pro Ser Ser Leu Ser Ala Ser Val Gly<br>225                            230                        235                        240 | | 720 |
| gac aga gtg acc atc acc tgc tcc gcc tcc agc tcc gtg aac tac atg<br>Asp Arg Val Thr Ile Thr Cys Ser Ala Ser Ser Ser Val Asn Tyr Met<br>                        245                        250                        255 | | 768 |
| cac tgg tat cag cag aaa cct ggc aag gtg ccc aag ctg ctg atc tac<br>His Trp Tyr Gln Gln Lys Pro Gly Lys Val Pro Lys Leu Leu Ile Tyr<br>                        260                        265                        270 | | 816 |
| gac acc tcc aag ctg gcc tcc ggc gtg cct tcc cgg ttc tcc ggc tcc<br>Asp Thr Ser Lys Leu Ala Ser Gly Val Pro Ser Arg Phe Ser Gly Ser<br>         275                        280                        285 | | 864 |
| ggc tct ggc acc gac ttc acc ctg acc atc tcc agc ctg cag cct gag<br>Gly Ser Gly Thr Asp Phe Thr Leu Thr Ile Ser Ser Leu Gln Pro Glu<br>         290                        295                        300 | | 912 |
| gac gtg gcc acc tac tac tgc cag cag tgg aac tcc cac cct ctg acc<br>Asp Val Ala Thr Tyr Tyr Cys Gln Gln Trp Asn Ser His Pro Leu Thr<br>305                            310                        315                        320 | | 960 |
| ttc gga cag ggc acc aag ctg gag atc aaa cgg acc gtg gcc gct ccc<br>Phe Gly Gln Gly Thr Lys Leu Glu Ile Lys Arg Thr Val Ala Ala Pro<br>                        325                        330                        335 | | 1008 |
| agc gtg ttc atc ttc cca ccc agc gac gag cag ctg aag tcc ggt acc<br>Ser Val Phe Ile Phe Pro Pro Ser Asp Glu Gln Leu Lys Ser Gly Thr<br>         340                        345                        350 | | 1056 |
| gcc agc gtg gtg tgc ctg ctg aac aac ttc tac ccg cgg gag gcc aag<br>Ala Ser Val Val Cys Leu Leu Asn Asn Phe Tyr Pro Arg Glu Ala Lys | | 1104 |

```
              355                 360                 365
gtg cag tgg aag gtg gac aac gcc ctg cag agc ggc aac tcc cag gaa      1152
Val Gln Trp Lys Val Asp Asn Ala Leu Gln Ser Gly Asn Ser Gln Glu
    370                 375                 380 agc gtc acc gag cag gac agc aag gac tcc acc tac agc ctg agc agc      1200
Ser Val Thr Glu Gln Asp Ser Lys Asp Ser Thr Tyr Ser Leu Ser Ser
385                 390                 395                 400 acc ctg acc ctg agc aag gcc gac tac gag aag cac aag gtg tac gcc      1248
Thr Leu Thr Leu Ser Lys Ala Asp Tyr Glu Lys His Lys Val Tyr Ala
                405                 410                 415 tgc gaa gtg acc cac cag ggc ctg tcc agc ccc gtg acc aag agc ttc      1296
Cys Glu Val Thr His Gln Gly Leu Ser Ser Pro Val Thr Lys Ser Phe
            420                 425                 430 aac cgg ggc gag tgt                                                  1311
Asn Arg Gly Glu Cys
            435

<210> SEQ ID NO 79
<211> LENGTH: 437
<212> TYPE: PRT
<213> ORGANISM: Homo sapiens

<400> SEQUENCE: 79

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Gly Ser
        210                 215                 220

Asp Ile Gln Met Thr Gln Ser Pro Ser Ser Leu Ser Ala Ser Val Gly
225                 230                 235                 240

Asp Arg Val Thr Ile Thr Cys Ser Ala Ser Ser Val Asn Tyr Met
                245                 250                 255

His Trp Tyr Gln Gln Lys Pro Gly Lys Val Pro Lys Leu Leu Ile Tyr
```

```
                260                 265                 270
Asp Thr Ser Lys Leu Ala Ser Gly Val Pro Ser Arg Phe Ser Gly Ser
            275                 280                 285

Gly Ser Gly Thr Asp Phe Thr Leu Thr Ile Ser Ser Leu Gln Pro Glu
        290                 295                 300

Asp Val Ala Thr Tyr Tyr Cys Gln Gln Trp Asn Ser His Pro Leu Thr
305                 310                 315                 320

Phe Gly Gln Gly Thr Lys Leu Glu Ile Lys Arg Thr Val Ala Ala Pro
                325                 330                 335

Ser Val Phe Ile Phe Pro Pro Ser Asp Glu Gln Leu Lys Ser Gly Thr
            340                 345                 350

Ala Ser Val Val Cys Leu Leu Asn Asn Phe Tyr Pro Arg Glu Ala Lys
        355                 360                 365

Val Gln Trp Lys Val Asp Asn Ala Leu Gln Ser Gly Asn Ser Gln Glu
    370                 375                 380

Ser Val Thr Glu Gln Asp Ser Lys Asp Ser Thr Tyr Ser Leu Ser Ser
385                 390                 395                 400

Thr Leu Thr Leu Ser Lys Ala Asp Tyr Glu Lys His Lys Val Tyr Ala
                405                 410                 415

Cys Glu Val Thr His Gln Gly Leu Ser Ser Pro Val Thr Lys Ser Phe
            420                 425                 430

Asn Arg Gly Glu Cys
        435

<210> SEQ ID NO 80
<211> LENGTH: 1350
<212> TYPE: DNA
<213> ORGANISM: Homo sapiens
<220> FEATURE:
<221> NAME/KEY: CDS
<222> LOCATION: (1)..(1350)

<400> SEQUENCE: 80 cag gtg cag ctg gtg cag agc gga gcc gaa gtg aag aaa cct ggc gcc      48
Gln Val Gln Leu Val Gln Ser Gly Ala Glu Val Lys Lys Pro Gly Ala
1               5                   10                  15 agc gtg aag gtg tcc tgc aag gcc agc ggc tac acc ttc aac gag tac      96
Ser Val Lys Val Ser Cys Lys Ala Ser Gly Tyr Thr Phe Asn Glu Tyr
            20                  25                  30 acc atg cac tgg gtg aag cag gcc ccc ggc cag aga ctg gaa tgg atg     144
Thr Met His Trp Val Lys Gln Ala Pro Gly Gln Arg Leu Glu Trp Met
        35                  40                  45 ggc ggc atc aac ccc aat agc gga ggc gtg agc tac aac cag aac ttc     192
Gly Gly Ile Asn Pro Asn Ser Gly Gly Val Ser Tyr Asn Gln Asn Phe
    50                  55                  60 aag ggc aag gcc acc ctg acc gtc gac aca agc gcc agc acc gcc tac     240
Lys Gly Lys Ala Thr Leu Thr Val Asp Thr Ser Ala Ser Thr Ala Tyr
65                  70                  75                  80 atg gaa ctg agc agc ctg aga agc gag gac acc gcc gtg tac tac tgc     288
Met Glu Leu Ser Ser Leu Arg Ser Glu Asp Thr Ala Val Tyr Tyr Cys
                85                  90                  95 gcc aga ggc ggc gac ggc tac tac acc aac tac ttc gac atc gac tac     336
Ala Arg Gly Gly Asp Gly Tyr Tyr Thr Asn Tyr Phe Asp Ile Asp Tyr
            100                 105                 110 tgg ggc cag ggc acc acc gtg acc gtg tcc agc gcc tcc act aaa gga     384
Trp Gly Gln Gly Thr Thr Val Thr Val Ser Ser Ala Ser Thr Lys Gly
        115                 120                 125 cct agc gtg ttt ccg cta gcc ccc tgt tca aga agc aca agc gag tca     432
```

```
                Pro Ser Val Phe Pro Leu Ala Pro Cys Ser Arg Ser Thr Ser Glu Ser
                    130                 135                 140 acc gcc gca ctg gga tgc ctg gtg aag gac tac ttc cct gag cca gtc      480
Thr Ala Ala Leu Gly Cys Leu Val Lys Asp Tyr Phe Pro Glu Pro Val
145                 150                 155                 160 aca gtg tcc tgg aac tct gga gcc ctg aca tct ggc gtc cac act ttt      528
Thr Val Ser Trp Asn Ser Gly Ala Leu Thr Ser Gly Val His Thr Phe
                165                 170                 175 ccc gct gtg ctg cag agc tcc gga ctg tac agc ctg tct agt gtg gtc      576
Pro Ala Val Leu Gln Ser Ser Gly Leu Tyr Ser Leu Ser Ser Val Val
            180                 185                 190 acc gtg cct tca agc tcc ctg ggc act aag acc tat aca tgc aac gtg      624
Thr Val Pro Ser Ser Ser Leu Gly Thr Lys Thr Tyr Thr Cys Asn Val
        195                 200                 205 gac cat aaa cca tcc aat aca aag gtc gat aaa cga gtg gag tct aag      672
Asp His Lys Pro Ser Asn Thr Lys Val Asp Lys Arg Val Glu Ser Lys
    210                 215                 220 tac gga cca cct tgc cca cca tgt cca gct cct gag ttc ctg gga gga      720
Tyr Gly Pro Pro Cys Pro Pro Cys Pro Ala Pro Glu Phe Leu Gly Gly
225                 230                 235                 240 cct tcc gtg ttc ctg ttt cct cca aag cca aaa gac act ctg atg atc      768
Pro Ser Val Phe Leu Phe Pro Pro Lys Pro Lys Asp Thr Leu Met Ile
                245                 250                 255 tcc aga act cca gag gtc acc tgc gtg gtc gtg gac gtg tct cag gag      816
Ser Arg Thr Pro Glu Val Thr Cys Val Val Val Asp Val Ser Gln Glu
            260                 265                 270 gat ccc gaa gtc cag ttc aac tgg tac gtg gat ggg gtc gaa gtg cac      864
Asp Pro Glu Val Gln Phe Asn Trp Tyr Val Asp Gly Val Glu Val His
        275                 280                 285 aat gcc aag acc aaa ccc agg gag gaa cag ttt aac agc act tac cgc      912
Asn Ala Lys Thr Lys Pro Arg Glu Glu Gln Phe Asn Ser Thr Tyr Arg
    290                 295                 300 gtc gtg tcc gtc ctg acc gtg ctg cat cag gat tgg ctg aac ggg aag      960
Val Val Ser Val Leu Thr Val Leu His Gln Asp Trp Leu Asn Gly Lys
305                 310                 315                 320 gag tat aag tgc aaa gtg agt aat aag gga ctg cct tct agt atc gag     1008
Glu Tyr Lys Cys Lys Val Ser Asn Lys Gly Leu Pro Ser Ser Ile Glu
                325                 330                 335 aaa aca att tcc aag gca aaa ggc cag cca cgg gaa ccc cag gtg tac     1056
Lys Thr Ile Ser Lys Ala Lys Gly Gln Pro Arg Glu Pro Gln Val Tyr
            340                 345                 350 act ctg ccc cct agt cag aag aag atg acc aag aac cag gtc tca ctg     1104
Thr Leu Pro Pro Ser Gln Lys Lys Met Thr Lys Asn Gln Val Ser Leu
        355                 360                 365 aca tgt ctg gtg aaa ggc ttc tat ccc tca gat atc gcc gtg gag tgg     1152
Thr Cys Leu Val Lys Gly Phe Tyr Pro Ser Asp Ile Ala Val Glu Trp
    370                 375                 380 gaa agc aat ggg cag cct gag aac aat tac aag acc aca cca ccc gtg     1200
Glu Ser Asn Gly Gln Pro Glu Asn Asn Tyr Lys Thr Thr Pro Pro Val
385                 390                 395                 400 ctg aag agt gat ggg tca ttc ttt ctg tat tct cgg ctg acc gtg gat     1248
Leu Lys Ser Asp Gly Ser Phe Phe Leu Tyr Ser Arg Leu Thr Val Asp
                405                 410                 415 aaa agt aga tgg cag gaa gga aat gtc ttt tca tgc agc gtg atg cac     1296
Lys Ser Arg Trp Gln Glu Gly Asn Val Phe Ser Cys Ser Val Met His
            420                 425                 430 gaa gca ctg cac aat cat tac act cag aag tcc ctg tca ctg tcc ctg     1344
Glu Ala Leu His Asn His Tyr Thr Gln Lys Ser Leu Ser Leu Ser Leu
        435                 440                 445
```

```
                                                                        1350
ggc aaa
Gly Lys
    450

<210> SEQ ID NO 81
<211> LENGTH: 450
<212> TYPE: PRT
<213> ORGANISM: Homo sapiens

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ala Pro Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Lys Met Thr Lys Asn Gln Val Ser Leu
```

```
                355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Lys Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
    450

<210> SEQ ID NO 82
<211> LENGTH: 990
<212> TYPE: DNA
<213> ORGANISM: Homo sapiens

<400> SEQUENCE: 82
gcctccacca agggcccatc ggtcttcccc ctggcaccct cctccaagag cacctctggg      60
ggcacagcag ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaagc cgaggggggca    360 ccgtcagtct tcctcttccc cccaaaaccc aaggacaccc tcatgatctc ccggaccccct    420 gaggtcacat gcgtggtggt ggacgtgagc cacgaagacc ctgaggtcaa gttcaactgg    480
tacgtggacg gcgtggaggt gcataatgcc aagacaaagc cgcggggagga gcagtacaac    540 agcacgtacc gtgtggtcag cgtcctcacc gtcctgcacc aggactggct gaatggcaag    600
gagtacaagt gcaaggtctc caacaaagcc ctcccatcct ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990

<210> SEQ ID NO 83
<211> LENGTH: 321
<212> TYPE: DNA
<213> ORGANISM: Homo sapiens

<400> SEQUENCE: 83
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
```
agcttcaaca ggggagagtg t                                          321

<210> SEQ ID NO 84
<211> LENGTH: 679
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4
<220> FEATURE:
<221> NAME/KEY: MISC_FEATURE
<222> LOCATION: (460)..(489)
<223> OTHER INFORMATION: FR1
<220> FEATURE:
<221> NAME/KEY: MISC_FEATURE
<222> LOCATION: (490)..(494)
<223> OTHER INFORMATION: CDR1
<220> FEATURE:
<221> NAME/KEY: MISC_FEATURE
<222> LOCATION: (495)..(498)
<223> OTHER INFORMATION: FR2
<220> FEATURE:
<221> NAME/KEY: MISC_FEATURE
<222> LOCATION: (509)..(525)
<223> OTHER INFORMATION: CDR2
<220> FEATURE:
<221> NAME/KEY: MISC_FEATURE
<222> LOCATION: (526)..(557)
<223> OTHER INFORMATION: FR3
<220> FEATURE:
<221> NAME/KEY: MISC_FEATURE
<222> LOCATION: (558)..(570)
<223> OTHER INFORMATION: CDR3
<220> FEATURE:
<221> NAME/KEY: MISC_FEATURE
<222> LOCATION: (571)..(581)
<223> OTHER INFORMATION: FR4
<220> FEATURE:
<221> NAME/KEY: MISC_FEATURE
<222> LOCATION: (584)..(679)
<223> OTHER INFORMATION: IgG4 CH1

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ala Pro Gly Gln Arg Leu Glu Trp Met
        35                  40                  45

```
Gly Gly Ile Asn Pro Asn Ser Gly Gly Val Ser Tyr Asn Gln Asn Phe
        50                  55                  60
Lys Gly Lys Ala Thr Leu Thr Val Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Asp Gly Tyr Tyr Thr Asn Tyr Phe Asp Ile Asp Tyr
                100                 105                 110
Trp Gly Gln Gly Thr Thr Val Thr Val Ser Ser Ala Ser Thr Lys Gly
                115                 120                 125
Pro Ser Val Phe Pro Leu Ala Pro Cys Ser Arg Ser Thr Ser Glu Ser
130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Lys Thr Tyr Thr Cys Asn Val
                195                 200                 205
Asp His Lys Pro Ser Asn Thr Lys Val Asp Lys Arg Val Glu Ser Lys
210                 215                 220
Tyr Gly Pro Pro Cys Pro Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
                260                 265                 270
Asp Pro Glu Val Gln Phe Asn Trp Tyr Val Asp Gly Val Glu Val His
                275                 280                 285
Asn Ala Lys Thr Lys Pro Arg Glu Glu Gln Phe Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Gln Glu Glu Met Thr Lys Asn Gln Val Ser Leu
                355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
                420                 425                 430
Glu Ala Leu His Asn His Tyr Thr Gln Lys Ser Leu Ser Leu Ser Leu
                435                 440                 445
Gly Gly Gly Gly Gly Ser Gly Gly Gly Ser Gln Val Gln Leu Val
450                 455                 460
```

Glu Ser Gly Gly Gly Val Val Gln Pro Gly Arg Ser Leu Arg Leu Ser
465                 470                 475                 480

Cys Ala Ala Ser Gly Phe Ser Phe Ser Ser Tyr Ala Met His Trp Val
            485                 490                 495

Arg Gln Ala Pro Gly Lys Gly Leu Glu Trp Val Ala Val Ile Ser Tyr
            500                 505                 510

Gly Gly Ser Lys Lys Tyr Tyr Ala Asp Ser Val Lys Gly Arg Phe Thr
            515                 520                 525

Ile Ser Arg Asp Asn Ser Lys Asn Thr Leu Tyr Leu Gln Met Asn Ser
        530                 535                 540

Leu Arg Ala Glu Asp Thr Ala Val Tyr Tyr Cys Ala Arg Met Gly Tyr
545                 550                 555                 560

Tyr Asp Ile Leu Thr Gly Pro Phe Asp Tyr Trp Gly Gln Gly Thr Leu
                565                 570                 575

Val Thr Val Ser Ser Ala Ser Thr Lys Gly Pro Ser Val Phe Pro Leu
            580                 585                 590

Ala Pro Cys Ser Arg Ser Thr Ser Glu Ser Thr Ala Ala Leu Gly Cys
            595                 600                 605

Leu Val Lys Asp Tyr Phe Pro Glu Pro Val Thr Val Ser Trp Asn Ser
610                 615                 620

Gly Ala Leu Thr Ser Gly Val His Thr Phe Pro Ala Val Leu Gln Ser
625                 630                 635                 640

Ser Gly Leu Tyr Ser Leu Ser Ser Val Val Thr Val Pro Ser Ser Ser
                645                 650                 655

Leu Gly Thr Lys Thr Tyr Thr Cys Asn Val Asp His Lys Pro Ser Asn
            660                 665                 670

Thr Lys Val Asp Lys Arg Val
            675

<210> SEQ ID NO 85
<211> LENGTH: 7
<212> TYPE: PRT
<213> ORGANISM: Homo sapiens

<400> SEQUENCE: 85

Arg Thr Val Ala Ala Pro Ser
1               5

<210> SEQ ID NO 86
<211> LENGTH: 9
<212> TYPE: PRT
<213> ORGANISM: Homo sapiens

<400> SEQUENCE: 86

Ser Ser Ala Ser Thr Lys Gly Pro Ser
1               5

<210> SEQ ID NO 87
<211> LENGTH: 1770
<212> TYPE: DNA
<213> ORGANISM: Homo sapiens
<220> FEATURE:
<221> NAME/KEY: CDS
<222> LOCATION: (1)..(1770)

<400> SEQUENCE: 87 cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15

-continued

| | | |
|---|---|---|
| tcc ctg aga ctc tcc tgt gca gcc tct gga ttc tcc ttc agt agc tat<br>Ser Leu Arg Leu Ser Cys Ala Ala Ser Gly Phe Ser Phe Ser Ser Tyr<br>20　　　　　　　　25　　　　　　　　30 | | 96 |
| gct atg cac tgg gtc cgc cag gct cca ggc aag ggg ctg gag tgg gtg<br>Ala Met His Trp Val Arg Gln Ala Pro Gly Lys Gly Leu Glu Trp Val<br>　　35　　　　　　　　40　　　　　　　　45 | | 144 |
| gca gtt ata tca tat ggt gga agc aaa aaa tac tac gca gac tcc gtg<br>Ala Val Ile Ser Tyr Gly Gly Ser Lys Lys Tyr Tyr Ala Asp Ser Val<br>50　　　　　　　　55　　　　　　　　60 | | 192 |
| aag ggc cga ttc acc atc tcc aga gac aat tcc aag aac acg ctg tat<br>Lys Gly Arg Phe Thr Ile Ser Arg Asp Asn Ser Lys Asn Thr Leu Tyr<br>65　　　　　　　　70　　　　　　　75　　　　　　　　80 | | 240 |
| ctg caa atg aac agc ctg aga gct gag gac acg gct gtg tat tac tgt<br>Leu Gln Met Asn Ser Leu Arg Ala Glu Asp Thr Ala Val Tyr Tyr Cys<br>　　85　　　　　　　　90　　　　　　　　95 | | 288 |
| gcg aga atg ggg tat tac gat att ttg act ggt ccc ttt gac tac tgg<br>Ala Arg Met Gly Tyr Tyr Asp Ile Leu Thr Gly Pro Phe Asp Tyr Trp<br>　　　　100　　　　　　　　105　　　　　　　110 | | 336 |
| ggc cag gga acc ctg gtc acc gtc tcc tca gcc tct acc aag ggc ccc<br>Gly Gln Gly Thr Leu Val Thr Val Ser Ser Ala Ser Thr Lys Gly Pro<br>　　　115　　　　　　　　120　　　　　　　　125 | | 384 |
| agc gtg ttc cct ctg gcc ccc agc agc aag agc aca agc gga ggc aca<br>Ser Val Phe Pro Leu Ala Pro Ser Ser Lys Ser Thr Ser Gly Gly Thr<br>130　　　　　　　　135　　　　　　　　140 | | 432 |
| gcc gcc ctg ggc tgc ctg gtg aag gac tac ttc ccc gag ccc gtg aca<br>Ala Ala Leu Gly Cys Leu Val Lys Asp Tyr Phe Pro Glu Pro Val Thr<br>145　　　　　　　　150　　　　　　　155　　　　　　　　160 | | 480 |
| gtg tcc tgg aac agc gga gcc ctg acc agc ggc gtg cac acc ttt cca<br>Val Ser Trp Asn Ser Gly Ala Leu Thr Ser Gly Val His Thr Phe Pro<br>　　　　165　　　　　　　　170　　　　　　　175 | | 528 |
| gcc gtg ctg cag agc agc ggc ctg tac agc ctg agc agc gtg gtg acc<br>Ala Val Leu Gln Ser Ser Gly Leu Tyr Ser Leu Ser Ser Val Val Thr<br>　　　180　　　　　　　　185　　　　　　　　190 | | 576 |
| gtg cct agc agc agc ctg ggc acc cag acc tac atc tgc aac gtg aac<br>Val Pro Ser Ser Ser Leu Gly Thr Gln Thr Tyr Ile Cys Asn Val Asn<br>195　　　　　　　　200　　　　　　　　205 | | 624 |
| cac aag ccc agc aac acc aag gtg gac aag aag gtg gag ccc aag agc<br>His Lys Pro Ser Asn Thr Lys Val Asp Lys Lys Val Glu Pro Lys Ser<br>210　　　　　　　　215　　　　　　　　220 | | 672 |
| tgc ggt ggc ggg ggt tcg ggt gga gga ggt tct cag gtg cag ctg gtg<br>Cys Gly Gly Gly Gly Ser Gly Gly Gly Gly Ser Gln Val Gln Leu Val<br>225　　　　　　　　230　　　　　　　235　　　　　　　　240 | | 720 |
| cag agc gga gcc gaa gtg aag aaa cct ggc gcc agc gtg aag gtg tcc<br>Gln Ser Gly Ala Glu Val Lys Lys Pro Gly Ala Ser Val Lys Val Ser<br>　　　　245　　　　　　　　250　　　　　　　255 | | 768 |
| tgc aag gcc agc ggc tac acc ttc aac gag tac acc atg cac tgg gtg<br>Cys Lys Ala Ser Gly Tyr Thr Phe Asn Glu Tyr Thr Met His Trp Val<br>　　　260　　　　　　　　265　　　　　　　　270 | | 816 |
| aag cag gcc ccc ggc cag aga ctg gaa tgg atg ggc ggc atc aac ccc<br>Lys Gln Ala Pro Gly Gln Arg Leu Glu Trp Met Gly Gly Ile Asn Pro<br>275　　　　　　　　280　　　　　　　　285 | | 864 |
| aat agc gga ggc gtg agc tac aac cag aac ttc aag ggc aag gcc acc<br>Asn Ser Gly Gly Val Ser Tyr Asn Gln Asn Phe Lys Gly Lys Ala Thr<br>290　　　　　　　　295　　　　　　　　300 | | 912 |
| ctg acc gtc gac aca agc gcc agc acc gcc tac atg gaa ctg agc agc<br>Leu Thr Val Asp Thr Ser Ala Ser Thr Ala Tyr Met Glu Leu Ser Ser<br>305　　　　　　　　310　　　　　　　315　　　　　　　　320 | | 960 |
| ctg aga agc gag gac acc gcc gtg tac tac tgc gcc aga ggc ggc gac<br>Leu Arg Ser Glu Asp Thr Ala Val Tyr Tyr Cys Ala Arg Gly Gly Asp<br>　　　　325　　　　　　　　330　　　　　　　335 | | 1008 |

-continued

```
ggc tac tac acc aac tac ttc gac atc gac tac tgg ggc cag ggc acc      1056
Gly Tyr Tyr Thr Asn Tyr Phe Asp Ile Asp Tyr Trp Gly Gln Gly Thr
            340                 345                 350 acc gtg acc gtg tcc agc gag ccc aag agc agc gac aag acc cac acc      1104
Thr Val Thr Val Ser Ser Glu Pro Lys Ser Ser Asp Lys Thr His Thr
        355                 360                 365 tgt ccc cct tgt cct gcc cct gaa gcc gaa ggc gcg cct tcc gtg ttc      1152
Cys Pro Pro Cys Pro Ala Pro Glu Ala Glu Gly Ala Pro Ser Val Phe
    370                 375                 380 ctg ttc ccc cca aag ccc aag gac acc ctg atg atc agc cgg acc ccc      1200
Leu Phe Pro Pro Lys Pro Lys Asp Thr Leu Met Ile Ser Arg Thr Pro
385                 390                 395                 400 gaa gtg acc tgc gtg gtg gtg gac gtg tcc cac gag gac cct gaa gtg      1248
Glu Val Thr Cys Val Val Val Asp Val Ser His Glu Asp Pro Glu Val
                405                 410                 415 aag ttc aat tgg tac gtg gac ggc gtg gag gtg cac aac gcc aag acc      1296
Lys Phe Asn Trp Tyr Val Asp Gly Val Glu Val His Asn Ala Lys Thr
            420                 425                 430 aag ccc cgg gag gaa cag tac aac agc acc tac cgg gtg gtg tcc gtg      1344
Lys Pro Arg Glu Glu Gln Tyr Asn Ser Thr Tyr Arg Val Val Ser Val
        435                 440                 445 ctg acc gtg ctg cac cag gac tgg ctg aac ggc aaa gag tac aag tgc      1392
Leu Thr Val Leu His Gln Asp Trp Leu Asn Gly Lys Glu Tyr Lys Cys
    450                 455                 460 aag gtc tcc aac aag gcc ctg ccc agc agc atc gag aaa acc atc agc      1440
Lys Val Ser Asn Lys Ala Leu Pro Ser Ser Ile Glu Lys Thr Ile Ser
465                 470                 475                 480 aag gcc aag ggc cag ccc aga gaa ccc cag gtg tac acc ctg ccc cct      1488
Lys Ala Lys Gly Gln Pro Arg Glu Pro Gln Val Tyr Thr Leu Pro Pro
                485                 490                 495 agc agg gac gag ctg acc aag aac cag gtg tcc ctg acc tgt ctg gtg      1536
Ser Arg Asp Glu Leu Thr Lys Asn Gln Val Ser Leu Thr Cys Leu Val
            500                 505                 510 aag ggc ttc tac ccc agc gat atc gcc gtg gag tgg gag agc aac ggc      1584
Lys Gly Phe Tyr Pro Ser Asp Ile Ala Val Glu Trp Glu Ser Asn Gly
        515                 520                 525 cag ccc gaa aac aac tac aag acc acc ccc cct gtg ctg gac agc gac      1632
Gln Pro Glu Asn Asn Tyr Lys Thr Thr Pro Pro Val Leu Asp Ser Asp
    530                 535                 540 ggc agc ttc ttc ctg tac tcc aaa ctg acc gtg gac aag agc cgg tgg      1680
Gly Ser Phe Phe Leu Tyr Ser Lys Leu Thr Val Asp Lys Ser Arg Trp
545                 550                 555                 560 cag cag ggc aac gtg ttc agc tgc agc gtg atg cac gag gcc ctg cac      1728
Gln Gln Gly Asn Val Phe Ser Cys Ser Val Met His Glu Ala Leu His
                565                 570                 575 aac cac tac acc cag aag tcc ctg agc ctg agc ccc ggc aag              1770
Asn His Tyr Thr Gln Lys Ser Leu Ser Leu Ser Pro Gly Lys
            580                 585                 590

<210> SEQ ID NO 88
<211> LENGTH: 590
<212> TYPE: PRT
<213> ORGANISM: Homo sapiens

<400> SEQUENCE: 88

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30
```

```
Ala Met His Trp Val Arg Gln Ala Pro Gly Lys Gly Leu Glu Trp Val
         35                  40                  45
Ala Val Ile Ser Tyr Gly Gly Ser Lys Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Met Gly Tyr Tyr Asp Ile Leu Thr Gly Pro Phe Asp Tyr Trp
             100                 105                 110
Gly Gln Gly Thr Leu Val Thr Val Ser Ser Ala Ser Thr Lys Gly Pro
         115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Gly Gly Gly Ser Gly Gly Gly Ser Gln Val Gln Leu Val
225                 230                 235                 240
Gln Ser Gly Ala Glu Val Lys Lys Pro Gly Ala Ser Val Lys Val Ser
                245                 250                 255
Cys Lys Ala Ser Gly Tyr Thr Phe Asn Glu Tyr Thr Met His Trp Val
            260                 265                 270
Lys Gln Ala Pro Gly Gln Arg Leu Glu Trp Met Gly Gly Ile Asn Pro
        275                 280                 285
Asn Ser Gly Gly Val Ser Tyr Asn Gln Asn Phe Lys Gly Lys Ala Thr
    290                 295                 300
Leu Thr Val Asp Thr Ser Ala Ser Thr Ala Tyr Met Glu Leu Ser Ser
305                 310                 315                 320
Leu Arg Ser Glu Asp Thr Ala Val Tyr Tyr Cys Ala Arg Gly Gly Asp
                325                 330                 335
Gly Tyr Tyr Thr Asn Tyr Phe Asp Ile Asp Tyr Trp Gly Gln Gly Thr
            340                 345                 350
Thr Val Thr Val Ser Ser Glu Pro Lys Ser Ser Asp Lys Thr His Thr
        355                 360                 365
Cys Pro Pro Cys Pro Ala Pro Glu Ala Glu Gly Ala Pro Ser Val Phe
    370                 375                 380
Leu Phe Pro Pro Lys Pro Lys Asp Thr Leu Met Ile Ser Arg Thr Pro
385                 390                 395                 400
Glu Val Thr Cys Val Val Val Asp Val Ser His Glu Asp Pro Glu Val
                405                 410                 415
Lys Phe Asn Trp Tyr Val Asp Gly Val Glu Val His Asn Ala Lys Thr
            420                 425                 430
Lys Pro Arg Glu Glu Gln Tyr Asn Ser Thr Tyr Arg Val Val Ser Val
        435                 440                 445
Leu Thr Val Leu His Gln Asp Trp Leu Asn Gly Lys Glu Tyr Lys Cys
```

```
                450             455             460
Lys Val Ser Asn Lys Ala Leu Pro Ser Ser Ile Glu Lys Thr Ile Ser
465                 470                 475                 480

Lys Ala Lys Gly Gln Pro Arg Glu Pro Gln Val Tyr Thr Leu Pro Pro
                485                 490                 495

Ser Arg Asp Glu Leu Thr Lys Asn Gln Val Ser Leu Thr Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
    530                 535                 540

Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys
            580                 585                 590

<210> SEQ ID NO 89
<211> LENGTH: 990
<212> TYPE: DNA
<213> ORGANISM: Homo sapiens
<220> FEATURE:
<221> NAME/KEY: CDS
<222> LOCATION: (1)..(990)

<400> SEQUENCE: 89 gaa att gtg ttg acg cag tct cca ggc acc ctg tct ttg tct cca ggg        48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc        96
Glu Arg Ala Thr Leu Ser Cys Arg Ala Ser Gln Ser Val Ser Ser Ser
            20                  25                  30 tac tta gcc tgg tat cag cag aaa cct ggc cag gct ccc agg ctc ctc       144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt       192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag       240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca tac       288
Pro Glu Asp Phe Ala Val Tyr Tyr Cys Gln Gln Tyr Gly Ser Ser Tyr
                85                  90                  95 act ttt ggc cag ggg acc aag ctg gag atc aaa cgg acc gtg gcc gct       336
Thr Phe Gly Gln Gly Thr Lys Leu Glu Ile Lys Arg Thr Val Ala Ala
            100                 105                 110 ccc agc gtg ttc atc ttc cca ccc agc gac gag cag ctg aag tcc ggt       384
Pro Ser Val Phe Ile Phe Pro Pro Ser Asp Glu Gln Leu Lys Ser Gly
        115                 120                 125 acc gcc agc gtg gtg tgc ctg ctg aac aac ttc tac ccg cgg gag gcc       432
Thr Ala Ser Val Val Cys Leu Leu Asn Asn Phe Tyr Pro Arg Glu Ala
    130                 135                 140 aag gtg cag tgg aag gtg gac aac gcc ctg cag agc ggc aac tcc cag       480
Lys Val Gln Trp Lys Val Asp Asn Ala Leu Gln Ser Gly Asn Ser Gln
145                 150                 155                 160 gaa agc gtc acc gag cag gac agc aag gac tcc acc tac agc ctg agc       528
Glu Ser Val Thr Glu Gln Asp Ser Lys Asp Ser Thr Tyr Ser Leu Ser
```

-continued

|   |   |   | 165 |   |   |   | 170 |   |   |   | 175 |   |   |
|---|---|---|---|---|---|---|---|---|---|---|---|---|---|

```
agc acc ctg acc ctg agc aag gcc gac tac gag aag cac aag gtg tac    576
Ser Thr Leu Thr Leu Ser Lys Ala Asp Tyr Glu Lys His Lys Val Tyr
        180                 185                 190 gcc tgc gaa gtg acc cac cag ggc ctg tcc agc ccc gtg acc aag agc    624
Ala Cys Glu Val Thr His Gln Gly Leu Ser Ser Pro Val Thr Lys Ser
            195                 200                 205 ttc aac cgg ggc gag tgt ggt ggc ggg ggt tcg ggt gga gga ggt tct    672
Phe Asn Arg Gly Glu Cys Gly Gly Gly Gly Ser Gly Gly Gly Gly Ser
        210                 215                 220 gac atc cag atg acc cag tcc ccc tcc tcc ctg tcc gcc tcc gtg ggc    720
Asp Ile Gln Met Thr Gln Ser Pro Ser Ser Leu Ser Ala Ser Val Gly
225                 230                 235                 240 gac aga gtg acc atc acc tgc tcc gcc tcc agc tcc gtg aac tac atg    768
Asp Arg Val Thr Ile Thr Cys Ser Ala Ser Ser Ser Val Asn Tyr Met
                245                 250                 255 cac tgg tat cag cag aaa cct ggc aag gtg ccc aag ctg ctg atc tac    816
His Trp Tyr Gln Gln Lys Pro Gly Lys Val Pro Lys Leu Leu Ile Tyr
            260                 265                 270 gac acc tcc aag ctg gcc tcc ggc gtg cct tcc cgg ttc tcc ggc tcc    864
Asp Thr Ser Lys Leu Ala Ser Gly Val Pro Ser Arg Phe Ser Gly Ser
        275                 280                 285 ggc tct ggc acc gac ttc acc ctg acc atc tcc agc ctg cag cct gag    912
Gly Ser Gly Thr Asp Phe Thr Leu Thr Ile Ser Ser Leu Gln Pro Glu
    290                 295                 300 gac gtg gcc acc tac tac tgc cag cag tgg aac tcc cac cct ctg acc    960
Asp Val Ala Thr Tyr Tyr Cys Gln Gln Trp Asn Ser His Pro Leu Thr
305                 310                 315                 320 ttc gga cag ggc acc aag ctg gag atc aaa                            990
Phe Gly Gln Gly Thr Lys Leu Glu Ile Lys
                325                 330
```

<210> SEQ ID NO 90
<211> LENGTH: 330
<212> TYPE: PRT
<213> ORGANISM: Homo sapiens

<400> SEQUENCE: 90

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Asp Ile Gln Met Thr Gln Ser Pro Ser Ser Leu Ser Ala Ser Val Gly
225                 230                 235                 240

Asp Arg Val Thr Ile Thr Cys Ser Ala Ser Ser Val Asn Tyr Met
                245                 250                 255

His Trp Tyr Gln Gln Lys Pro Gly Lys Val Pro Lys Leu Leu Ile Tyr
                260                 265                 270

Asp Thr Ser Lys Leu Ala Ser Gly Val Pro Ser Arg Phe Ser Gly Ser
            275                 280                 285

Gly Ser Gly Thr Asp Phe Thr Leu Thr Ile Ser Ser Leu Gln Pro Glu
        290                 295                 300

Asp Val Ala Thr Tyr Tyr Cys Gln Gln Trp Asn Ser His Pro Leu Thr
305                 310                 315                 320

Phe Gly Gln Gly Thr Lys Leu Glu Ile Lys
                325                 330

<210> SEQ ID NO 91
<211> LENGTH: 1770
<212> TYPE: DNA
<213> ORGANISM: Homo sapiens
<220> FEATURE:
<221> NAME/KEY: CDS
<222> LOCATION: (1)..(1770)

<400> SEQUENCE: 91 cag gtg cag ctg gtg cag agc gga gcc gaa gtg aag aaa cct ggc gcc      48
Gln Val Gln Leu Val Gln Ser Gly Ala Glu Val Lys Lys Pro Gly Ala
1               5                   10                  15 agc gtg aag gtg tcc tgc aag gcc agc ggc tac acc ttc aac gag tac      96
Ser Val Lys Val Ser Cys Lys Ala Ser Gly Tyr Thr Phe Asn Glu Tyr
            20                  25                  30 acc atg cac tgg gtg aag cag gcc ccc ggc cag aga ctg gaa tgg atg     144
Thr Met His Trp Val Lys Gln Ala Pro Gly Gln Arg Leu Glu Trp Met
        35                  40                  45 ggc ggc atc aac ccc aat agc gga ggc gtg agc tac aac cag aac ttc     192
Gly Gly Ile Asn Pro Asn Ser Gly Gly Val Ser Tyr Asn Gln Asn Phe
    50                  55                  60 aag ggc aag gcc acc ctg acc gtc gac aca agc gcc agc acc gcc tac     240
Lys Gly Lys Ala Thr Leu Thr Val Asp Thr Ser Ala Ser Thr Ala Tyr
65                  70                  75                  80 atg gaa ctg agc agc ctg aga agc gag gac acc gcc gtg tac tac tgc     288
Met Glu Leu Ser Ser Leu Arg Ser Glu Asp Thr Ala Val Tyr Tyr Cys
                85                  90                  95 gcc aga ggc ggc gac ggc tac tac acc aac tac ttc gac atc gac tac     336
Ala Arg Gly Gly Asp Gly Tyr Tyr Thr Asn Tyr Phe Asp Ile Asp Tyr
            100                 105                 110 tgg ggc cag ggc acc acc gtg acc gtg tcc agc gcc tct acc aag ggc     384
Trp Gly Gln Gly Thr Thr Val Thr Val Ser Ser Ala Ser Thr Lys Gly
        115                 120                 125 ccc agc gtg ttc cct ctg gcc ccc agc agc aag agc aca agc gga ggc     432
Pro Ser Val Phe Pro Leu Ala Pro Ser Ser Lys Ser Thr Ser Gly Gly
```

|  |  |
|---|---|
| aca gcc gcc ctg ggc tgc ctg gtg aag gac tac ttc ccc gag ccc gtg<br>Thr Ala Ala Leu Gly Cys Leu Val Lys Asp Tyr Phe Pro Glu Pro Val<br>145                150                    155                160 | 480 |
| aca gtg tcc tgg aac agc gga gcc ctg acc agc ggc gtg cac acc ttt<br>Thr Val Ser Trp Asn Ser Gly Ala Leu Thr Ser Gly Val His Thr Phe<br>                165                    170                    175 | 528 |
| cca gcc gtg ctg cag agc agc ggc ctg tac agc ctg agc agc gtg gtg<br>Pro Ala Val Leu Gln Ser Ser Gly Leu Tyr Ser Leu Ser Ser Val Val<br>            180                    185                    190 | 576 |
| acc gtg cct agc agc agc ctg ggc acc cag acc tac atc tgc aac gtg<br>Thr Val Pro Ser Ser Ser Leu Gly Thr Gln Thr Tyr Ile Cys Asn Val<br>195                200                    205 | 624 |
| aac cac aag ccc agc aac acc aag gtg gac aag aag gtg gag ccc aag<br>Asn His Lys Pro Ser Asn Thr Lys Val Asp Lys Lys Val Glu Pro Lys<br>        210                    215                    220 | 672 |
| agc tgc ggt ggc ggg ggt tcg ggt gga gga ggt tct cag gtg cag ctg<br>Ser Cys Gly Gly Gly Gly Ser Gly Gly Gly Gly Ser Gln Val Gln Leu<br>225                230                    235                    240 | 720 |
| gtg gag tct ggg gga ggc gtg gtc cag cct ggg agg tcc ctg aga ctc<br>Val Glu Ser Gly Gly Gly Val Val Gln Pro Gly Arg Ser Leu Arg Leu<br>                245                    250                    255 | 768 |
| tcc tgt gca gcc tct gga ttc tcc ttc agt agc tat gct atg cac tgg<br>Ser Cys Ala Ala Ser Gly Phe Ser Phe Ser Ser Tyr Ala Met His Trp<br>            260                    265                    270 | 816 |
| gtc cgc cag gct cca ggc aag ggg ctg gag tgg gtg gca gtt ata tca<br>Val Arg Gln Ala Pro Gly Lys Gly Leu Glu Trp Val Ala Val Ile Ser<br>275                280                    285 | 864 |
| tat ggt gga agc aaa aaa tac tac gca gac tcc gtg aag ggc cga ttc<br>Tyr Gly Gly Ser Lys Lys Tyr Tyr Ala Asp Ser Val Lys Gly Arg Phe<br>        290                    295                    300 | 912 |
| acc atc tcc aga gac aat tcc aag aac acg ctg tat ctg caa atg aac<br>Thr Ile Ser Arg Asp Asn Ser Lys Asn Thr Leu Tyr Leu Gln Met Asn<br>305                310                    315                    320 | 960 |
| agc ctg aga gct gag gac acg gct gtg tat tac tgt gcg aga atg ggg<br>Ser Leu Arg Ala Glu Asp Thr Ala Val Tyr Tyr Cys Ala Arg Met Gly<br>                325                    330                    335 | 1008 |
| tat tac gat att ttg act ggt ccc ttt gac tac tgg ggc cag gga acc<br>Tyr Tyr Asp Ile Leu Thr Gly Pro Phe Asp Tyr Trp Gly Gln Gly Thr<br>            340                    345                    350 | 1056 |
| ctg gtc acc gtc tcc tca gag ccc aag agc agc gac aag acc cac acc<br>Leu Val Thr Val Ser Ser Glu Pro Lys Ser Ser Asp Lys Thr His Thr<br>                355                    360                    365 | 1104 |
| tgt ccc cct tgt cct gcc cct gaa gcc gaa ggc gcg cct tcc gtg ttc<br>Cys Pro Pro Cys Pro Ala Pro Glu Ala Glu Gly Ala Pro Ser Val Phe<br>370                375                    380 | 1152 |
| ctg ttc ccc cca aag ccc aag gac acc ctg atg atc agc cgg acc ccc<br>Leu Phe Pro Pro Lys Pro Lys Asp Thr Leu Met Ile Ser Arg Thr Pro<br>385                390                    395                    400 | 1200 |
| gaa gtg acc tgc gtg gtg gtg gac gtg tcc cac gag gac cct gaa gtg<br>Glu Val Thr Cys Val Val Val Asp Val Ser His Glu Asp Pro Glu Val<br>                405                    410                    415 | 1248 |
| aag ttc aat tgg tac gtg gac ggc gtg gag gtg cac aac gcc aag acc<br>Lys Phe Asn Trp Tyr Val Asp Gly Val Glu Val His Asn Ala Lys Thr<br>        420                    425                    430 | 1296 |
| aag ccc cgg gag gaa cag tac aac agc acc tac cgg gtg gtg tcc gtg<br>Lys Pro Arg Glu Glu Gln Tyr Asn Ser Thr Tyr Arg Val Val Ser Val<br>            435                    440                    445 | 1344 |
| ctg acc gtg ctg cac cag gac tgg ctg aac ggc aaa gag tac aag tgc | 1392 |

```
Leu Thr Val Leu His Gln Asp Trp Leu Asn Gly Lys Glu Tyr Lys Cys
            450                 455                 460 aag gtc tcc aac aag gcc ctg ccc agc agc atc gag aaa acc atc agc      1440
Lys Val Ser Asn Lys Ala Leu Pro Ser Ser Ile Glu Lys Thr Ile Ser
465                 470                 475                 480 aag gcc aag ggc cag ccc aga gaa ccc cag gtg tac acc ctg ccc cct      1488
Lys Ala Lys Gly Gln Pro Arg Glu Pro Gln Val Tyr Thr Leu Pro Pro
                485                 490                 495 agc agg gac gag ctg acc aag aac cag gtg tcc ctg acc tgt ctg gtg      1536
Ser Arg Asp Glu Leu Thr Lys Asn Gln Val Ser Leu Thr Cys Leu Val
            500                 505                 510 aag ggc ttc tac ccc agc gat atc gcc gtg gag tgg gag agc aac ggc      1584
Lys Gly Phe Tyr Pro Ser Asp Ile Ala Val Glu Trp Glu Ser Asn Gly
            515                 520                 525 cag ccc gaa aac aac tac aag acc acc ccc cct gtg ctg gac agc gac      1632
Gln Pro Glu Asn Asn Tyr Lys Thr Thr Pro Pro Val Leu Asp Ser Asp
530                 535                 540 ggc agc ttc ttc ctg tac tcc aaa ctg acc gtg gac aag agc cgg tgg      1680
Gly Ser Phe Phe Leu Tyr Ser Lys Leu Thr Val Asp Lys Ser Arg Trp
545                 550                 555                 560 cag cag ggc aac gtg ttc agc tgc agc gtg atg cac gag gcc ctg cac      1728
Gln Gln Gly Asn Val Phe Ser Cys Ser Val Met His Glu Ala Leu His
                565                 570                 575 aac cac tac acc cag aag tcc ctg agc ctg agc ccc ggc aag              1770
Asn His Tyr Thr Gln Lys Ser Leu Ser Leu Ser Pro Gly Lys
            580                 585                 590

<210> SEQ ID NO 92
<211> LENGTH: 590
<212> TYPE: PRT
<213> ORGANISM: Homo sapiens

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ala Pro Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Gly Gly Gly Ser Gly Gly Gly Ser Gln Val Gln Leu
225                 230                 235                 240

Val Glu Ser Gly Gly Gly Val Val Gln Pro Gly Arg Ser Leu Arg Leu
                245                 250                 255

Ser Cys Ala Ala Ser Gly Phe Ser Phe Ser Ser Tyr Ala Met His Trp
                260                 265                 270

Val Arg Gln Ala Pro Gly Lys Gly Leu Glu Trp Val Ala Val Ile Ser
            275                 280                 285

Tyr Gly Gly Ser Lys Lys Tyr Tyr Ala Asp Ser Val Lys Gly Arg Phe
290                 295                 300

Thr Ile Ser Arg Asp Asn Ser Lys Asn Thr Leu Tyr Leu Gln Met Asn
305                 310                 315                 320

Ser Leu Arg Ala Glu Asp Thr Ala Val Tyr Tyr Cys Ala Arg Met Gly
                325                 330                 335

Tyr Tyr Asp Ile Leu Thr Gly Pro Phe Asp Tyr Trp Gly Gln Gly Thr
            340                 345                 350

Leu Val Thr Val Ser Ser Glu Pro Lys Ser Ser Asp Lys Thr His Thr
        355                 360                 365

Cys Pro Pro Cys Pro Ala Pro Glu Ala Glu Gly Ala Pro Ser Val Phe
370                 375                 380

Leu Phe Pro Pro Lys Pro Lys Asp Thr Leu Met Ile Ser Arg Thr Pro
385                 390                 395                 400

Glu Val Thr Cys Val Val Val Asp Val Ser His Glu Asp Pro Glu Val
                405                 410                 415

Lys Phe Asn Trp Tyr Val Asp Gly Val Glu Val His Asn Ala Lys Thr
            420                 425                 430

Lys Pro Arg Glu Glu Gln Tyr Asn Ser Thr Tyr Arg Val Val Ser Val
        435                 440                 445

Leu Thr Val Leu His Gln Asp Trp Leu Asn Gly Lys Glu Tyr Lys Cys
450                 455                 460

Lys Val Ser Asn Lys Ala Leu Pro Ser Ser Ile Glu Lys Thr Ile Ser
465                 470                 475                 480

Lys Ala Lys Gly Gln Pro Arg Glu Pro Gln Val Tyr Thr Leu Pro Pro
                485                 490                 495

Ser Arg Asp Glu Leu Thr Lys Asn Gln Val Ser Leu Thr Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
530                 535                 540

Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys
            580                 585                 590

<210> SEQ ID NO 93
<211> LENGTH: 990
<212> TYPE: DNA
```

```
<213> ORGANISM: Homo sapiens
<220> FEATURE:
<221> NAME/KEY: CDS
<222> LOCATION: (1)..(990)

<400> SEQUENCE: 93 gac atc cag atg acc cag tcc ccc tcc tcc ctg tcc gcc tcc gtg ggc       48
Asp Ile Gln Met Thr Gln Ser Pro Ser Ser Leu Ser Ala Ser Val Gly
1               5                   10                  15 gac aga gtg acc atc acc tgc tcc gcc tcc agc tcc gtg aac tac atg       96
Asp Arg Val Thr Ile Thr Cys Ser Ala Ser Ser Ser Val Asn Tyr Met
            20                  25                  30 cac tgg tat cag cag aaa cct ggc aag gtg ccc aag ctg ctg atc tac      144
His Trp Tyr Gln Gln Lys Pro Gly Lys Val Pro Lys Leu Leu Ile Tyr
        35                  40                  45 gac acc tcc aag ctg gcc tcc ggc gtg cct tcc cgg ttc tcc ggc tcc      192
Asp Thr Ser Lys Leu Ala Ser Gly Val Pro Ser Arg Phe Ser Gly Ser
    50                  55                  60 ggc tct ggc acc gac ttc acc ctg acc atc tcc agc ctg cag cct gag      240
Gly Ser Gly Thr Asp Phe Thr Leu Thr Ile Ser Ser Leu Gln Pro Glu
65                  70                  75                  80 gac gtg gcc acc tac tac tgc cag cag tgg aac tcc cac cct ctg acc      288
Asp Val Ala Thr Tyr Tyr Cys Gln Gln Trp Asn Ser His Pro Leu Thr
                85                  90                  95 ttc gga cag ggc acc aag ctg gag atc aaa cgg acc gtg gcc gct ccc      336
Phe Gly Gln Gly Thr Lys Leu Glu Ile Lys Arg Thr Val Ala Ala Pro
            100                 105                 110 agc gtg ttc atc ttc cca ccc agc gac gag cag ctg aag tcc ggt acc      384
Ser Val Phe Ile Phe Pro Pro Ser Asp Glu Gln Leu Lys Ser Gly Thr
        115                 120                 125 gcc agc gtg gtg tgc ctg ctg aac aac ttc tac ccg cgg gag gcc aag      432
Ala Ser Val Val Cys Leu Leu Asn Asn Phe Tyr Pro Arg Glu Ala Lys
    130                 135                 140 gtg cag tgg aag gtg gac aac gcc ctg cag agc ggc aac tcc cag gaa      480
Val Gln Trp Lys Val Asp Asn Ala Leu Gln Ser Gly Asn Ser Gln Glu
145                 150                 155                 160 agc gtc acc gag cag gac agc aag gac tcc acc tac agc ctg agc agc      528
Ser Val Thr Glu Gln Asp Ser Lys Asp Ser Thr Tyr Ser Leu Ser Ser
                165                 170                 175 acc ctg acc ctg agc aag gcc gac tac gag aag cac aag gtg tac gcc      576
Thr Leu Thr Leu Ser Lys Ala Asp Tyr Glu Lys His Lys Val Tyr Ala
            180                 185                 190 tgc gaa gtg acc cac cag ggc ctg tcc agc ccc gtg acc aag agc ttc      624
Cys Glu Val Thr His Gln Gly Leu Ser Ser Pro Val Thr Lys Ser Phe
        195                 200                 205 aac cgg ggc gag tgt ggt ggc ggg ggt tcg ggt gga gga ggt tct gaa      672
Asn Arg Gly Glu Cys Gly Gly Gly Gly Ser Gly Gly Gly Gly Ser Glu
    210                 215                 220 att gtg ttg acg cag tct cca ggc acc ctg tct ttg tct cca ggg gaa      720
Ile Val Leu Thr Gln Ser Pro Gly Thr Leu Ser Leu Ser Pro Gly Glu
225                 230                 235                 240 aga gcc acc ctc tcc tgc agg gcc agt cag agt gtt agc agc agc tac      768
Arg Ala Thr Leu Ser Cys Arg Ala Ser Gln Ser Val Ser Ser Ser Tyr
                245                 250                 255 tta gcc tgg tat cag cag aaa cct ggc cag gct ccc agg ctc ctc atc      816
Leu Ala Trp Tyr Gln Gln Lys Pro Gly Gln Ala Pro Arg Leu Leu Ile
            260                 265                 270 tat ggt gca tcc agc agg gcc act ggc atc cca gac agg ttc agt ggc      864
Tyr Gly Ala Ser Ser Arg Ala Thr Gly Ile Pro Asp Arg Phe Ser Gly
        275                 280                 285
```

```
agt ggg tct ggg aca gac ttc act ctc acc atc agc aga ctg gag cct    912
Ser Gly Ser Gly Thr Asp Phe Thr Leu Thr Ile Ser Arg Leu Glu Pro
    290                 295                 300 gaa gat ttt gca gtg tat tac tgt cag cag tat ggt agc tca tac act    960
Glu Asp Phe Ala Val Tyr Tyr Cys Gln Gln Tyr Gly Ser Ser Tyr Thr
305                 310                 315                 320 ttt ggc cag ggg acc aag ctg gag atc aaa                            990
Phe Gly Gln Gly Thr Lys Leu Glu Ile Lys
                325                 330

<210> SEQ ID NO 94
<211> LENGTH: 330
<212> TYPE: PRT
<213> ORGANISM: Homo sapiens

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Asn Tyr Met
            20                  25                  30

His Trp Tyr Gln Gln Lys Pro Gly Lys Val Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Gln Trp Asn Ser His Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser Gly Gly Gly Ser Glu
    210                 215                 220

Ile Val Leu Thr Gln Ser Pro Gly Thr Leu Ser Leu Ser Pro Gly Glu
225                 230                 235                 240

Arg Ala Thr Leu Ser Cys Arg Ala Ser Gln Ser Val Ser Ser Ser Tyr
                245                 250                 255

Leu Ala Trp Tyr Gln Gln Lys Pro Gly Gln Ala Pro Arg Leu Leu Ile
            260                 265                 270

Tyr Gly Ala Ser Ser Arg Ala Thr Gly Ile Pro Asp Arg Phe Ser Gly
        275                 280                 285

Ser Gly Ser Gly Thr Asp Phe Thr Leu Thr Ile Ser Arg Leu Glu Pro
    290                 295                 300

Glu Asp Phe Ala Val Tyr Tyr Cys Gln Gln Tyr Gly Ser Ser Tyr Thr
305                 310                 315                 320
```

```
                Phe Gly Gln Gly Thr Lys Leu Glu Ile Lys
                                325                 330

<210> SEQ ID NO 95
<211> LENGTH: 1746
<212> TYPE: DNA
<213> ORGANISM: Homo sapiens
<220> FEATURE:
<221> NAME/KEY: CDS
<222> LOCATION: (1)..(1746)

<400> SEQUENCE: 95 cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt gca gcc tct gga ttc tcc ttc agt agc tat      96
Ser Leu Arg Leu Ser Cys Ala Ala Ser Gly Phe Ser Phe Ser Ser Tyr
            20                  25                  30 gct atg cac tgg gtc cgc cag gct cca ggc aag ggg ctg gag tgg gtg     144
Ala Met His Trp Val Arg Gln Ala Pro Gly Lys Gly Leu Glu Trp Val
        35                  40                  45 gca gtt ata tca tat ggt gga agc aaa aaa tac tac gca gac tcc gtg     192
Ala Val Ile Ser Tyr Gly Gly Ser Lys Lys Tyr Tyr Ala Asp Ser Val
    50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                85                  90                  95 gcg aga atg ggg tat tac gat att ttg act ggt ccc ttt gac tac tgg     336
Ala Arg Met Gly Tyr Tyr Asp Ile Leu Thr Gly Pro Phe Asp Tyr Trp
            100                 105                 110 ggc cag gga acc ctg gtc acc gtc tcc tca gcc tcc act aaa gga cct     384
Gly Gln Gly Thr Leu Val Thr Val Ser Ser Ala Ser Thr Lys Gly Pro
        115                 120                 125 agc gtg ttt ccg cta gcc ccc tgt tca aga agc aca agc gag tca acc     432
Ser Val Phe Pro Leu Ala Pro Cys Ser Arg Ser Thr Ser Glu Ser Thr
    130                 135                 140 gcc gca ctg gga tgc ctg gtg aag gac tac ttc cct gag cca gtc aca     480
Ala Ala Leu Gly Cys Leu Val Lys Asp Tyr Phe Pro Glu Pro Val Thr
145                 150                 155                 160 gtg tcc tgg aac tct gga gcc ctg aca tct ggc gtc cac act ttt ccc     528
Val Ser Trp Asn Ser Gly Ala Leu Thr Ser Gly Val His Thr Phe Pro
                165                 170                 175 gct gtg ctg cag agc tcc gga ctg tac agc ctg tct agt gtg gtc acc     576
Ala Val Leu Gln Ser Ser Gly Leu Tyr Ser Leu Ser Ser Val Val Thr
            180                 185                 190 gtg cct tca agc tcc ctg ggc act aag acc tat aca tgc aac gtg gac     624
Val Pro Ser Ser Ser Leu Gly Thr Lys Thr Tyr Thr Cys Asn Val Asp
        195                 200                 205 cat aaa cca tcc aat aca aag gtc gat aaa cga gtg ggt ggc ggg ggt     672
His Lys Pro Ser Asn Thr Lys Val Asp Lys Arg Val Gly Gly Gly Gly
    210                 215                 220 tcg ggt gga gga ggt tct cag gtg cag ctg gtg cag agc gga gcc gaa     720
Ser Gly Gly Gly Gly Ser Gln Val Gln Leu Val Gln Ser Gly Ala Glu
225                 230                 235                 240 gtg aag aaa cct ggc gcc agc gtg aag gtg tcc tgc aag gcc agc ggc     768
Val Lys Lys Pro Gly Ala Ser Val Lys Val Ser Cys Lys Ala Ser Gly
                245                 250                 255
```

```
tac acc ttc aac gag tac acc atg cac tgg gtg aag cag gcc ccc ggc      816
Tyr Thr Phe Asn Glu Tyr Thr Met His Trp Val Lys Gln Ala Pro Gly
            260             265             270 cag aga ctg gaa tgg atg ggc ggc atc aac ccc aat agc gga ggc gtg      864
Gln Arg Leu Glu Trp Met Gly Gly Ile Asn Pro Asn Ser Gly Gly Val
        275             280             285 agc tac aac cag aac ttc aag ggc aag gcc acc ctg acc gtc gac aca      912
Ser Tyr Asn Gln Asn Phe Lys Gly Lys Ala Thr Leu Thr Val Asp Thr
    290             295             300 agc gcc agc acc gcc tac atg gaa ctg agc agc ctg aga agc gag gac      960
Ser Ala Ser Thr Ala Tyr Met Glu Leu Ser Ser Leu Arg Ser Glu Asp
305             310             315             320 acc gcc gtg tac tac tgc gcc aga ggc ggc gac ggc tac tac acc aac     1008
Thr Ala Val Tyr Tyr Cys Ala Arg Gly Gly Asp Gly Tyr Tyr Thr Asn
            325             330             335 tac ttc gac atc gac tac tgg ggc cag ggc acc acc gtg acc gtg tcc     1056
Tyr Phe Asp Ile Asp Tyr Trp Gly Gln Gly Thr Thr Val Thr Val Ser
        340             345             350 agc gag tct aag tac gga cca cct tgc cca cca tgt cca gct cct gag     1104
Ser Glu Ser Lys Tyr Gly Pro Pro Cys Pro Pro Cys Pro Ala Pro Glu
    355             360             365 ttc ctg gga gga cct tcc gtg ttc ctg ttt cct cca aag cca aaa gac     1152
Phe Leu Gly Gly Pro Ser Val Phe Leu Phe Pro Pro Lys Pro Lys Asp
370             375             380 act ctg atg atc tcc aga act cca gag gtc acc tgc gtg gtc gtg gac     1200
Thr Leu Met Ile Ser Arg Thr Pro Glu Val Thr Cys Val Val Val Asp
385             390             395             400 gtg tct cag gag gat ccc gaa gtc cag ttc aac tgg tac gtg gat ggg     1248
Val Ser Gln Glu Asp Pro Glu Val Gln Phe Asn Trp Tyr Val Asp Gly
            405             410             415 gtc gaa gtg cac aat gcc aag acc aaa ccc agg gag gaa cag ttt aac     1296
Val Glu Val His Asn Ala Lys Thr Lys Pro Arg Glu Glu Gln Phe Asn
        420             425             430 agc act tac cgc gtc gtg tcc gtc ctg acc gtg ctg cat cag gat tgg     1344
Ser Thr Tyr Arg Val Val Ser Val Leu Thr Val Leu His Gln Asp Trp
    435             440             445 ctg aac ggg aag gag tat aag tgc aaa gtg agt aat aag gga ctg cct     1392
Leu Asn Gly Lys Glu Tyr Lys Cys Lys Val Ser Asn Lys Gly Leu Pro
450             455             460 tct agt atc gag aaa aca att tcc aag gca aaa ggc cag cca cgg gaa     1440
Ser Ser Ile Glu Lys Thr Ile Ser Lys Ala Lys Gly Gln Pro Arg Glu
465             470             475             480 ccc cag gtg tac act ctg ccc cct agt cag gag gaa atg acc aag aac     1488
Pro Gln Val Tyr Thr Leu Pro Pro Ser Gln Glu Glu Met Thr Lys Asn
            485             490             495 cag gtc tca ctg aca tgt ctg gtg aaa ggc ttc tat ccc tca gat atc     1536
Gln Val Ser Leu Thr Cys Leu Val Lys Gly Phe Tyr Pro Ser Asp Ile
        500             505             510 gcc gtg gag tgg gaa agc aat ggg cag cct gag aac aat tac aag acc     1584
Ala Val Glu Trp Glu Ser Asn Gly Gln Pro Glu Asn Asn Tyr Lys Thr
    515             520             525 aca cca ccc gtg ctg gac agt gat ggg tca ttc ttt ctg tat tct cgg     1632
Thr Pro Pro Val Leu Asp Ser Asp Gly Ser Phe Phe Leu Tyr Ser Arg
530             535             540 ctg acc gtg gat aaa agt aga tgg cag gaa gga aat gtc ttt tca tgc     1680
Leu Thr Val Asp Lys Ser Arg Trp Gln Glu Gly Asn Val Phe Ser Cys
545             550             555             560 agc gtg atg cac gaa gca ctg cac aat cat tac act cag aag tcc ctg     1728
Ser Val Met His Glu Ala Leu His Asn His Tyr Thr Gln Lys Ser Leu
            565             570             575
```

```
tca ctg tcc ctg ggc aaa                                              1746
Ser Leu Ser Leu Gly Lys
            580
```

<210> SEQ ID NO 96
<211> LENGTH: 582
<212> TYPE: PRT
<213> ORGANISM: Homo sapiens

<400> SEQUENCE: 96

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Gly Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Gly Gly Gly Gly
    210                 215                 220

Ser Gly Gly Gly Gly Ser Gln Val Gln Leu Val Gln Ser Gly Ala Glu
225                 230                 235                 240

Val Lys Lys Pro Gly Ala Ser Val Lys Val Ser Cys Lys Ala Ser Gly
                245                 250                 255

Tyr Thr Phe Asn Glu Tyr Thr Met His Trp Val Lys Gln Ala Pro Gly
            260                 265                 270

Gln Arg Leu Glu Trp Met Gly Gly Ile Asn Pro Asn Ser Gly Gly Val
        275                 280                 285

Ser Tyr Asn Gln Asn Phe Lys Gly Lys Ala Thr Leu Thr Val Asp Thr
    290                 295                 300

Ser Ala Ser Thr Ala Tyr Met Glu Leu Ser Ser Leu Arg Ser Glu Asp
305                 310                 315                 320

Thr Ala Val Tyr Tyr Cys Ala Arg Gly Gly Asp Gly Tyr Tyr Thr Asn
                325                 330                 335

Tyr Phe Asp Ile Asp Tyr Trp Gly Gln Gly Thr Thr Val Thr Val Ser
            340                 345                 350
```

```
Ser Glu Ser Lys Tyr Gly Pro Pro Cys Pro Pro Cys Pro Ala Pro Glu
            355                 360                 365

Phe Leu Gly Gly Pro Ser Val Phe Leu Phe Pro Pro Lys Pro Lys Asp
        370                 375                 380

Thr Leu Met Ile Ser Arg Thr Pro Glu Val Thr Cys Val Val Val Asp
385                 390                 395                 400

Val Ser Gln Glu Asp Pro Glu Val Gln Phe Asn Trp Tyr Val Asp Gly
                405                 410                 415

Val Glu Val His Asn Ala Lys Thr Lys Pro Arg Glu Glu Gln Phe Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Gly Leu Pro
    450                 455                 460

Ser Ser Ile Glu Lys Thr Ile Ser Lys Ala Lys Gly Gln Pro Arg Glu
465                 470                 475                 480

Pro Gln Val Tyr Thr Leu Pro Pro Ser Gln Glu Glu Met Thr Lys Asn
                485                 490                 495

Gln Val Ser Leu Thr Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
        515                 520                 525

Thr Pro Pro Val Leu Asp Ser Asp Gly Ser Phe Phe Leu Tyr Ser Arg
    530                 535                 540

Leu Thr Val Asp Lys Ser Arg Trp Gln Glu Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Leu Gly Lys
            580

<210> SEQ ID NO 97
<211> LENGTH: 1746
<212> TYPE: DNA
<213> ORGANISM: Homo sapiens
<220> FEATURE:
<221> NAME/KEY: CDS
<222> LOCATION: (1)..(1746)

<400> SEQUENCE: 97 cag gtg cag ctg gtg cag agc gga gcc gaa gtg aag aaa cct ggc gcc      48
Gln Val Gln Leu Val Gln Ser Gly Ala Glu Val Lys Lys Pro Gly Ala
1               5                   10                  15 agc gtg aag gtg tcc tgc aag gcc agc ggc tac acc ttc aac gag tac      96
Ser Val Lys Val Ser Cys Lys Ala Ser Gly Tyr Thr Phe Asn Glu Tyr
            20                  25                  30 acc atg cac tgg gtg aag cag gcc ccc ggc cag aga ctg gaa tgg atg     144
Thr Met His Trp Val Lys Gln Ala Pro Gly Gln Arg Leu Glu Trp Met
        35                  40                  45 ggc ggc atc aac ccc aat agc gga ggc gtg agc tac aac cag aac ttc     192
Gly Gly Ile Asn Pro Asn Ser Gly Gly Val Ser Tyr Asn Gln Asn Phe
    50                  55                  60 aag ggc aag gcc acc ctg acc gtc gac aca agc gcc agc acc gcc tac     240
Lys Gly Lys Ala Thr Leu Thr Val Asp Thr Ser Ala Ser Thr Ala Tyr
65                  70                  75                  80 atg gaa ctg agc agc ctg aga agc gag gac acc gcc gtg tac tac tgc     288
Met Glu Leu Ser Ser Leu Arg Ser Glu Asp Thr Ala Val Tyr Tyr Cys
                85                  90                  95
```

| | | | | | | | | | | | | | | | | |
|---|---|---|---|---|---|---|---|---|---|---|---|---|---|---|---|---|
| gcc | aga | ggc | ggc | gac | ggc | tac | tac | acc | aac | tac | ttc | gac | atc | gac | tac | 336 |
| Ala | Arg | Gly | Gly | Asp | Gly | Tyr | Tyr | Thr | Asn | Tyr | Phe | Asp | Ile | Asp | Tyr | |
| | | | 100 | | | | 105 | | | | | 110 | | | | |

```
gcc aga ggc ggc gac ggc tac tac acc aac tac ttc gac atc gac tac      336
Ala Arg Gly Gly Asp Gly Tyr Tyr Thr Asn Tyr Phe Asp Ile Asp Tyr
            100                 105                 110 tgg ggc cag ggc acc acc gtg acc gtg tcc agc gcc tcc act aaa gga      384
Trp Gly Gln Gly Thr Thr Val Thr Val Ser Ser Ala Ser Thr Lys Gly
        115                 120                 125 cct agc gtg ttt ccg cta gcc ccc tgt tca aga agc aca agc gag tca      432
Pro Ser Val Phe Pro Leu Ala Pro Cys Ser Arg Ser Thr Ser Glu Ser
130                 135                 140 acc gcc gca ctg gga tgc ctg gtg aag gac tac ttc cct gag cca gtc      480
Thr Ala Ala Leu Gly Cys Leu Val Lys Asp Tyr Phe Pro Glu Pro Val
145                 150                 155                 160 aca gtg tcc tgg aac tct gga gcc ctg aca tct ggc gtc cac act ttt      528
Thr Val Ser Trp Asn Ser Gly Ala Leu Thr Ser Gly Val His Thr Phe
                165                 170                 175 ccc gct gtg ctg cag agc tcc gga ctg tac agc ctg tct agt gtg gtc      576
Pro Ala Val Leu Gln Ser Ser Gly Leu Tyr Ser Leu Ser Ser Val Val
                180                 185                 190 acc gtg cct tca agc tcc ctg ggc act aag acc tat aca tgc aac gtg      624
Thr Val Pro Ser Ser Ser Leu Gly Thr Lys Thr Tyr Thr Cys Asn Val
            195                 200                 205 gac cat aaa cca tcc aat aca aag gtc gat aaa cga gtg ggt ggc ggg      672
Asp His Lys Pro Ser Asn Thr Lys Val Asp Lys Arg Val Gly Gly Gly
210                 215                 220 ggt tcg ggt gga gga ggt tct cag gtg cag ctg gtg gag tct ggg gga      720
Gly Ser Gly Gly Gly Gly Ser Gln Val Gln Leu Val Glu Ser Gly Gly
225                 230                 235                 240 ggc gtg gtc cag cct ggg agg tcc ctg aga ctc tcc tgt gca gcc tct      768
Gly Val Val Gln Pro Gly Arg Ser Leu Arg Leu Ser Cys Ala Ala Ser
                245                 250                 255 gga ttc tcc ttc agt agc tat gct atg cac tgg gtc cgc cag gct cca      816
Gly Phe Ser Phe Ser Ser Tyr Ala Met His Trp Val Arg Gln Ala Pro
                260                 265                 270 ggc aag ggg ctg gag tgg gtg gca gtt ata tca tat ggt gga agc aaa      864
Gly Lys Gly Leu Glu Trp Val Ala Val Ile Ser Tyr Gly Gly Ser Lys
            275                 280                 285 aaa tac tac gca gac tcc gtg aag ggc cga ttc acc atc tcc aga gac      912
Lys Tyr Tyr Ala Asp Ser Val Lys Gly Arg Phe Thr Ile Ser Arg Asp
290                 295                 300 aat tcc aag aac acg ctg tat ctg caa atg aac agc ctg aga gct gag      960
Asn Ser Lys Asn Thr Leu Tyr Leu Gln Met Asn Ser Leu Arg Ala Glu
305                 310                 315                 320 gac acg gct gtg tat tac tgt gcg aga atg ggg tat tac gat att ttg     1008
Asp Thr Ala Val Tyr Tyr Cys Ala Arg Met Gly Tyr Tyr Asp Ile Leu
                325                 330                 335 act ggt ccc ttt gac tac tgg ggc cag gga acc ctg gtc acc gtc tcc     1056
Thr Gly Pro Phe Asp Tyr Trp Gly Gln Gly Thr Leu Val Thr Val Ser
                340                 345                 350 tca gag tct aag tac gga cca cct tgc cca cca tgt cca gct cct gag     1104
Ser Glu Ser Lys Tyr Gly Pro Pro Cys Pro Pro Cys Pro Ala Pro Glu
            355                 360                 365 ttc ctg gga gga cct tcc gtc ttc ctg ttt cct cca aag cca aaa gac     1152
Phe Leu Gly Gly Pro Ser Val Phe Leu Phe Pro Pro Lys Pro Lys Asp
370                 375                 380 act ctg atg atc tcc aga act cca gag gtc acc tgc gtg gtc gtg gac     1200
Thr Leu Met Ile Ser Arg Thr Pro Glu Val Thr Cys Val Val Val Asp
385                 390                 395                 400 gtg tct cag gag gat ccc gaa gtc cag ttc aac tgg tac gtg gat ggg     1248
Val Ser Gln Glu Asp Pro Glu Val Gln Phe Asn Trp Tyr Val Asp Gly
```

```
                    405                 410                 415
gtc gaa gtg cac aat gcc aag acc aaa ccc agg gag gaa cag ttt aac    1296
Val Glu Val His Asn Ala Lys Thr Lys Pro Arg Glu Glu Gln Phe Asn
            420                 425                 430 agc act tac cgc gtc gtg tcc gtc ctg acc gtg ctg cat cag gat tgg    1344
Ser Thr Tyr Arg Val Val Ser Val Leu Thr Val Leu His Gln Asp Trp
        435                 440                 445 ctg aac ggg aag gag tat aag tgc aaa gtg agt aat aag gga ctg cct    1392
Leu Asn Gly Lys Glu Tyr Lys Cys Lys Val Ser Asn Lys Gly Leu Pro
    450                 455                 460 tct agt atc gag aaa aca att tcc aag gca aaa ggc agc cca cgg gaa    1440
Ser Ser Ile Glu Lys Thr Ile Ser Lys Ala Lys Gly Gln Pro Arg Glu
465                 470                 475                 480 ccc cag gtg tac act ctg ccc cct agt cag gag gaa atg acc aag aac    1488
Pro Gln Val Tyr Thr Leu Pro Pro Ser Gln Glu Glu Met Thr Lys Asn
                485                 490                 495 cag gtc tca ctg aca tgt ctg gtg aaa ggc ttc tat ccc tca gat atc    1536
Gln Val Ser Leu Thr Cys Leu Val Lys Gly Phe Tyr Pro Ser Asp Ile
            500                 505                 510 gcc gtg gag tgg gaa agc aat ggg cag cct gag aac aat tac aag acc    1584
Ala Val Glu Trp Glu Ser Asn Gly Gln Pro Glu Asn Asn Tyr Lys Thr
        515                 520                 525 aca cca ccc gtg ctg gac agt gat ggg tca ttc ttt ctg tat tct cgg    1632
Thr Pro Pro Val Leu Asp Ser Asp Gly Ser Phe Phe Leu Tyr Ser Arg
    530                 535                 540 ctg acc gtg gat aaa agt aga tgg cag gaa gga aat gtc ttt tca tgc    1680
Leu Thr Val Asp Lys Ser Arg Trp Gln Glu Gly Asn Val Phe Ser Cys
545                 550                 555                 560 agc gtg atg cac gaa gca ctg cac aat cat tac act cag aag tcc ctg    1728
Ser Val Met His Glu Ala Leu His Asn His Tyr Thr Gln Lys Ser Leu
                565                 570                 575 tca ctg tcc ctg ggc aaa                                            1746
Ser Leu Ser Leu Gly Lys
            580

<210> SEQ ID NO 98
<211> LENGTH: 582
<212> TYPE: PRT
<213> ORGANISM: Homo sapiens

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ala Pro Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
```

```
                130               135               140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Lys Thr Tyr Thr Cys Asn Val
                195                 200                 205
Asp His Lys Pro Ser Asn Thr Lys Val Asp Lys Arg Val Gly Gly Gly
                210                 215                 220
Gly Ser Gly Gly Gly Ser Gln Val Gln Leu Val Glu Ser Gly Gly
225                 230                 235                 240
Gly Val Val Gln Pro Gly Arg Ser Leu Arg Leu Ser Cys Ala Ala Ser
                245                 250                 255
Gly Phe Ser Phe Ser Ser Tyr Ala Met His Trp Val Arg Gln Ala Pro
                260                 265                 270
Gly Lys Gly Leu Glu Trp Val Ala Val Ile Ser Tyr Gly Gly Ser Lys
                275                 280                 285
Lys Tyr Tyr Ala Asp Ser Val Lys Gly Arg Phe Thr Ile Ser Arg Asp
                290                 295                 300
Asn Ser Lys Asn Thr Leu Tyr Leu Gln Met Asn Ser Leu Arg Ala Glu
305                 310                 315                 320
Asp Thr Ala Val Tyr Tyr Cys Ala Arg Met Gly Tyr Tyr Asp Ile Leu
                325                 330                 335
Thr Gly Pro Phe Asp Tyr Trp Gly Gln Gly Thr Leu Val Thr Val Ser
                340                 345                 350
Ser Glu Ser Lys Tyr Gly Pro Pro Cys Pro Pro Cys Pro Ala Pro Glu
                355                 360                 365
Phe Leu Gly Gly Pro Ser Val Phe Leu Phe Pro Pro Lys Pro Lys Asp
                370                 375                 380
Thr Leu Met Ile Ser Arg Thr Pro Glu Val Thr Cys Val Val Val Asp
385                 390                 395                 400
Val Ser Gln Glu Asp Pro Glu Val Gln Phe Asn Trp Tyr Val Asp Gly
                405                 410                 415
Val Glu Val His Asn Ala Lys Thr Lys Pro Arg Glu Glu Gln Phe Asn
                420                 425                 430
Ser Thr Tyr Arg Val Val Ser Val Leu Thr Val Leu His Gln Asp Trp
                435                 440                 445
Leu Asn Gly Lys Glu Tyr Lys Cys Lys Val Ser Asn Lys Gly Leu Pro
450                 455                 460
Ser Ser Ile Glu Lys Thr Ile Ser Lys Ala Lys Gly Gln Pro Arg Glu
465                 470                 475                 480
Pro Gln Val Tyr Thr Leu Pro Pro Ser Gln Glu Glu Met Thr Lys Asn
                485                 490                 495
Gln Val Ser Leu Thr Cys Leu Val Lys Gly Phe Tyr Pro Ser Asp Ile
                500                 505                 510
Ala Val Glu Trp Glu Ser Asn Gly Gln Pro Glu Asn Asn Tyr Lys Thr
                515                 520                 525
Thr Pro Pro Val Leu Asp Ser Asp Gly Ser Phe Phe Leu Tyr Ser Arg
                530                 535                 540
Leu Thr Val Asp Lys Ser Arg Trp Gln Glu Gly Asn Val Phe Ser Cys
545                 550                 555                 560
```

```
Ser Val Met His Glu Ala Leu His Asn His Tyr Thr Gln Lys Ser Leu
            565                 570                 575
Ser Leu Ser Leu Gly Lys
            580

<210> SEQ ID NO 99
<211> LENGTH: 1767
<212> TYPE: DNA
<213> ORGANISM: Homo sapiens
<220> FEATURE:
<221> NAME/KEY: CDS
<222> LOCATION: (1)..(1767)

<400> SEQUENCE: 99 cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt gca gcc tct gga ttc tcc ttc agt agc tat      96
Ser Leu Arg Leu Ser Cys Ala Ala Ser Gly Phe Ser Phe Ser Ser Tyr
            20                  25                  30 gct atg cac tgg gtc cgc cag gct cca ggc aag ggg ctg gag tgg gtg     144
Ala Met His Trp Val Arg Gln Ala Pro Gly Lys Gly Leu Glu Trp Val
        35                  40                  45 gca gtt ata tca tat ggt gga agc aaa aaa tac tac gca gac tcc gtg     192
Ala Val Ile Ser Tyr Gly Gly Ser Lys Lys Tyr Tyr Ala Asp Ser Val
    50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                85                  90                  95 gcg aga atg ggg tat tac gat att ttg act ggt ccc ttt gac tac tgg     336
Ala Arg Met Gly Tyr Tyr Asp Ile Leu Thr Gly Pro Phe Asp Tyr Trp
            100                 105                 110 ggc cag gga acc ctg gtc acc gtc tcc tca gcc tct acc aag ggc ccc     384
Gly Gln Gly Thr Leu Val Thr Val Ser Ser Ala Ser Thr Lys Gly Pro
        115                 120                 125 agc gtg ttc cct ctg gcc ccc agc agc aag agc aca agc gga ggc aca     432
Ser Val Phe Pro Leu Ala Pro Ser Ser Lys Ser Thr Ser Gly Gly Thr
    130                 135                 140 gcc gcc ctg ggc tgc ctg gtg aag gac tac ttc ccc gag ccc gtg aca     480
Ala Ala Leu Gly Cys Leu Val Lys Asp Tyr Phe Pro Glu Pro Val Thr
145                 150                 155                 160 gtg tcc tgg aac agc gga gcc ctg acc agc ggc gtg cac acc ttt cca     528
Val Ser Trp Asn Ser Gly Ala Leu Thr Ser Gly Val His Thr Phe Pro
                165                 170                 175 gcc gtg ctg cag agc agc ggc ctg tac agc ctg agc agc gtg gtg acc     576
Ala Val Leu Gln Ser Ser Gly Leu Tyr Ser Leu Ser Ser Val Val Thr
            180                 185                 190 gtg cct agc agc agc ctg ggc acc cag acc tac atc tgc aac gtg aac     624
Val Pro Ser Ser Ser Leu Gly Thr Gln Thr Tyr Ile Cys Asn Val Asn
        195                 200                 205 cac aag ccc agc aac acc aag gtg gac aag aag gtg gag ccc aag agc     672
His Lys Pro Ser Asn Thr Lys Val Asp Lys Lys Val Glu Pro Lys Ser
    210                 215                 220 tgc agc agc gct tcc acc aag ggc cca tcg cag gtg cag ctg gtg cag     720
Cys Ser Ser Ala Ser Thr Lys Gly Pro Ser Gln Val Gln Leu Val Gln
225                 230                 235                 240 agc gga gcc gaa gtg aag aaa cct ggc gcc agc gtg aag gtg tcc tgc     768
```

```
Ser Gly Ala Glu Val Lys Lys Pro Gly Ala Ser Val Lys Val Ser Cys
                245                 250                 255 aag gcc agc ggc tac acc ttc aac gag tac acc atg cac tgg gtg aag      816
Lys Ala Ser Gly Tyr Thr Phe Asn Glu Tyr Thr Met His Trp Val Lys
                260                 265                 270 cag gcc ccc ggc cag aga ctg gaa tgg atg ggc ggc atc aac ccc aat      864
Gln Ala Pro Gly Gln Arg Leu Glu Trp Met Gly Gly Ile Asn Pro Asn
            275                 280                 285 agc gga ggc gtg agc tac aac cag aac ttc aag ggc aag gcc acc ctg      912
Ser Gly Gly Val Ser Tyr Asn Gln Asn Phe Lys Gly Lys Ala Thr Leu
        290                 295                 300 acc gtc gac aca agc gcc agc acc gcc tac atg gaa ctg agc agc ctg      960
Thr Val Asp Thr Ser Ala Ser Thr Ala Tyr Met Glu Leu Ser Ser Leu
305                 310                 315                 320 aga agc gag gac acc gcc gtg tac tac tgc gcc aga ggc ggc gac ggc     1008
Arg Ser Glu Asp Thr Ala Val Tyr Tyr Cys Ala Arg Gly Gly Asp Gly
                325                 330                 335 tac tac acc aac tac ttc gac atc gac tac tgg ggc cag ggc acc acc     1056
Tyr Tyr Thr Asn Tyr Phe Asp Ile Asp Tyr Trp Gly Gln Gly Thr Thr
            340                 345                 350 gtg acc gtg tcc agc gag ccc aag agc agc gac aag acc cac acc tgt     1104
Val Thr Val Ser Ser Glu Pro Lys Ser Ser Asp Lys Thr His Thr Cys
        355                 360                 365 ccc cct tgt cct gcc cct gaa gcc gaa ggc gcg cct tcc gtg ttc ctg     1152
Pro Pro Cys Pro Ala Pro Glu Ala Glu Gly Ala Pro Ser Val Phe Leu
370                 375                 380 ttc ccc cca aag ccc aag gac acc ctg atg atc agc cgg acc ccc gaa     1200
Phe Pro Pro Lys Pro Lys Asp Thr Leu Met Ile Ser Arg Thr Pro Glu
385                 390                 395                 400 gtg acc tgc gtg gtg gtg gac gtg tcc cac gag gac cct gaa gtg aag     1248
Val Thr Cys Val Val Val Asp Val Ser His Glu Asp Pro Glu Val Lys
                405                 410                 415 ttc aat tgg tac gtg gac ggc gtg gag gtg cac aac gcc aag acc aag     1296
Phe Asn Trp Tyr Val Asp Gly Val Glu Val His Asn Ala Lys Thr Lys
            420                 425                 430 ccc cgg gag gaa cag tac aac agc acc tac cgg gtg gtg tcc gtg ctg     1344
Pro Arg Glu Glu Gln Tyr Asn Ser Thr Tyr Arg Val Val Ser Val Leu
        435                 440                 445 acc gtg ctg cac cag gac tgg ctg aac ggc aaa gag tac aag tgc aag     1392
Thr Val Leu His Gln Asp Trp Leu Asn Gly Lys Glu Tyr Lys Cys Lys
450                 455                 460 gtc tcc aac aag gcc ctg ccc agc agc atc gag aaa acc atc agc aag     1440
Val Ser Asn Lys Ala Leu Pro Ser Ser Ile Glu Lys Thr Ile Ser Lys
465                 470                 475                 480 gcc aag ggc cag ccc aga gaa ccc cag gtg tac acc ctg ccc cct agc     1488
Ala Lys Gly Gln Pro Arg Glu Pro Gln Val Tyr Thr Leu Pro Pro Ser
                485                 490                 495 agg gac gag ctg acc aag aac cag gtg tcc ctg acc tgt ctg gtg aag     1536
Arg Asp Glu Leu Thr Lys Asn Gln Val Ser Leu Thr Cys Leu Val Lys
            500                 505                 510 ggc ttc tac ccc agc gat atc gcc gtg gag tgg gag agc aac ggc cag     1584
Gly Phe Tyr Pro Ser Asp Ile Ala Val Glu Trp Glu Ser Asn Gly Gln
        515                 520                 525 ccc gaa aac aac tac aag acc acc ccc cct gtg ctg gac agc gac ggc     1632
Pro Glu Asn Asn Tyr Lys Thr Thr Pro Pro Val Leu Asp Ser Asp Gly
530                 535                 540 agc ttc ttc ctg tac tcc aaa ctg acc gtg gac aag agc cgg tgg cag     1680
Ser Phe Phe Leu Tyr Ser Lys Leu Thr Val Asp Lys Ser Arg Trp Gln
545                 550                 555                 560
```

-continued

| | | | | | | | | | | | | |
|---|---|---|---|---|---|---|---|---|---|---|---|---|
| cag | ggc | aac | gtg | ttc | agc | tgc | agc | gtg | atg | cac | gag | gcc | ctg | cac | aac | 1728 |
| Gln | Gly | Asn | Val | Phe | Ser | Cys | Ser | Val | Met | His | Glu | Ala | Leu | His | Asn |
| | | | 565 | | | | | 570 | | | | | 575 | | |

| cac | tac | acc | cag | aag | tcc | ctg | agc | ctg | agc | ccc | ggc | aag | 1767 |
| His | Tyr | Thr | Gln | Lys | Ser | Leu | Ser | Leu | Ser | Pro | Gly | Lys |
| | | | 580 | | | | | 585 | | | | |

<210> SEQ ID NO 100
<211> LENGTH: 589
<212> TYPE: PRT
<213> ORGANISM: Homo sapiens

<400> SEQUENCE: 100

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Gly Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Tyr Tyr Asp Ile Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Ser Ser Ala Ser Thr Lys Gly Pro Ser Gln Val Gln Leu Val Gln
225                 230                 235                 240

Ser Gly Ala Glu Val Lys Lys Pro Gly Ala Ser Val Lys Val Ser Cys
                245                 250                 255

Lys Ala Ser Gly Tyr Thr Phe Asn Glu Tyr Thr Met His Trp Val Lys
            260                 265                 270

Gln Ala Pro Gly Gln Arg Leu Glu Trp Met Gly Gly Ile Asn Pro Asn
        275                 280                 285

Ser Gly Gly Val Ser Tyr Asn Gln Asn Phe Lys Gly Lys Ala Thr Leu
    290                 295                 300

Thr Val Asp Thr Ser Ala Ser Thr Ala Tyr Met Glu Leu Ser Ser Leu
305                 310                 315                 320

Arg Ser Glu Asp Thr Ala Val Tyr Tyr Cys Ala Arg Gly Gly Asp Gly
                325                 330                 335

```
Tyr Tyr Thr Asn Tyr Phe Asp Ile Asp Tyr Trp Gly Gln Gly Thr Thr
            340                 345                 350

Val Thr Val Ser Ser Glu Pro Lys Ser Ser Asp Lys Thr His Thr Cys
        355                 360                 365

Pro Pro Cys Pro Ala Pro Glu Ala Glu Gly Ala Pro Ser Val Phe Leu
    370                 375                 380

Phe Pro Pro Lys Pro Lys Asp Thr Leu Met Ile Ser Arg Thr Pro Glu
385                 390                 395                 400

Val Thr Cys Val Val Val Asp Val Ser His Glu Asp Pro Glu Val Lys
                405                 410                 415

Phe Asn Trp Tyr Val Asp Gly Val Glu Val His Asn Ala Lys Thr Lys
            420                 425                 430

Pro Arg Glu Glu Gln Tyr Asn Ser Thr Tyr Arg Val Val Ser Val Leu
        435                 440                 445

Thr Val Leu His Gln Asp Trp Leu Asn Gly Lys Glu Tyr Lys Cys Lys
    450                 455                 460

Val Ser Asn Lys Ala Leu Pro Ser Ser Ile Glu Lys Thr Ile Ser Lys
465                 470                 475                 480

Ala Lys Gly Gln Pro Arg Glu Pro Gln Val Tyr Thr Leu Pro Pro Ser
                485                 490                 495

Arg Asp Glu Leu Thr Lys Asn Gln Val Ser Leu Thr Cys Leu Val Lys
            500                 505                 510

Gly Phe Tyr Pro Ser Asp Ile Ala Val Glu Trp Glu Ser Asn Gly Gln
        515                 520                 525

Pro Glu Asn Asn Tyr Lys Thr Thr Pro Pro Val Leu Asp Ser Asp Gly
    530                 535                 540

Ser Phe Phe Leu Tyr Ser Lys Leu Thr Val Asp Lys Ser Arg Trp Gln
545                 550                 555                 560

Gln Gly Asn Val Phe Ser Cys Ser Val Met His Glu Ala Leu His Asn
                565                 570                 575

His Tyr Thr Gln Lys Ser Leu Ser Leu Ser Pro Gly Lys
            580                 585

<210> SEQ ID NO 101
<211> LENGTH: 981
<212> TYPE: DNA
<213> ORGANISM: Homo sapiens
<220> FEATURE:
<221> NAME/KEY: CDS
<222> LOCATION: (1)..(981)

<400> SEQUENCE: 101 gaa att gtg ttg acg cag tct cca ggc acc ctg tct ttg tct cca ggg    48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc    96
Glu Arg Ala Thr Leu Ser Cys Arg Ala Ser Gln Ser Val Ser Ser Ser
            20                  25                  30 tac tta gcc tgg tat cag cag aaa cct ggc cag gct ccc agg ctc ctc   144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt   192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag   240
Gly Ser Gly Ser Gly Thr Asp Phe Thr Leu Thr Ile Ser Arg Leu Glu
65                  70                  75                  80
```

| | | |
|---|---|---|
| cct gaa gat ttt gca gtg tat tac tgt cag cag tat ggt agc tca tac<br>Pro Glu Asp Phe Ala Val Tyr Tyr Cys Gln Gln Tyr Gly Ser Ser Tyr<br>                      85                           90                        95 | | 288 |
| act ttt ggc cag ggg acc aag ctg gag atc aaa cgg acc gtg gcc gct<br>Thr Phe Gly Gln Gly Thr Lys Leu Glu Ile Lys Arg Thr Val Ala Ala<br>                100                        105                    110 | | 336 |
| ccc agc gtg ttc atc ttc cca ccc agc gac gag cag ctg aag tcc ggt<br>Pro Ser Val Phe Ile Phe Pro Pro Ser Asp Glu Gln Leu Lys Ser Gly<br>           115                        120                      125 | | 384 |
| acc gcc agc gtg gtg tgc ctg ctg aac aac ttc tac ccg cgg gag gcc<br>Thr Ala Ser Val Val Cys Leu Leu Asn Asn Phe Tyr Pro Arg Glu Ala<br>130                        135                      140 | | 432 |
| aag gtg cag tgg aag gtg gac aac gcc ctg cag agc ggc aac tcc cag<br>Lys Val Gln Trp Lys Val Asp Asn Ala Leu Gln Ser Gly Asn Ser Gln<br>145                        150                      155                    160 | | 480 |
| gaa agc gtc acc gag cag gac agc aag gac tcc acc tac agc ctg agc<br>Glu Ser Val Thr Glu Gln Asp Ser Lys Asp Ser Thr Tyr Ser Leu Ser<br>                    165                        170                    175 | | 528 |
| agc acc ctg acc ctg agc aag gcc gac tac gag aag cac aag gtg tac<br>Ser Thr Leu Thr Leu Ser Lys Ala Asp Tyr Glu Lys His Lys Val Tyr<br>           180                        185                      190 | | 576 |
| gcc tgc gaa gtg acc cac cag ggc ctg tcc agc ccc gtg acc aag agc<br>Ala Cys Glu Val Thr His Gln Gly Leu Ser Ser Pro Val Thr Lys Ser<br>           195                        200                    205 | | 624 |
| ttc aac cgg ggc gag tgt cga act gtg gct gca cca tct gac atc cag<br>Phe Asn Arg Gly Glu Cys Arg Thr Val Ala Ala Pro Ser Asp Ile Gln<br>          210                        215                    220 | | 672 |
| atg acc cag tcc ccc tcc tcc ctg tcc gcc tcc gtg ggc gac aga gtg<br>Met Thr Gln Ser Pro Ser Ser Leu Ser Ala Ser Val Gly Asp Arg Val<br>225                        230                      235                    240 | | 720 |
| acc atc acc tgc tcc gcc tcc agc tcc gtg aac tac atg cac tgg tat<br>Thr Ile Thr Cys Ser Ala Ser Ser Ser Val Asn Tyr Met His Trp Tyr<br>                    245                        250                    255 | | 768 |
| cag cag aaa cct ggc aag gtg ccc aag ctg ctg atc tac gac acc tcc<br>Gln Gln Lys Pro Gly Lys Val Pro Lys Leu Leu Ile Tyr Asp Thr Ser<br>          260                        265                      270 | | 816 |
| aag ctg gcc tcc ggc gtg cct tcc cgg ttc tcc ggc tcc ggc tct ggc<br>Lys Leu Ala Ser Gly Val Pro Ser Arg Phe Ser Gly Ser Gly Ser Gly<br>           275                        280                    285 | | 864 |
| acc gac ttc acc ctg acc atc tcc agc ctg cag cct gag gac gtg gcc<br>Thr Asp Phe Thr Leu Thr Ile Ser Ser Leu Gln Pro Glu Asp Val Ala<br>          290                        295                    300 | | 912 |
| acc tac tac tgc cag cag tgg aac tcc cac cct ctg acc ttc gga cag<br>Thr Tyr Tyr Cys Gln Gln Trp Asn Ser His Pro Leu Thr Phe Gly Gln<br>305                        310                      315                    320 | | 960 |
| ggc acc aag ctg gag atc aaa<br>Gly Thr Lys Leu Glu Ile Lys<br>          325 | | 981 |

<210> SEQ ID NO 102
<211> LENGTH: 327
<212> TYPE: PRT
<213> ORGANISM: Homo sapiens

<400> SEQUENCE: 102

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu

```
            35                  40                  45
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Thr Val Ala Ala Pro Ser Asp Ile Gln
210                 215                 220

Met Thr Gln Ser Pro Ser Ser Leu Ser Ala Ser Val Gly Asp Arg Val
225                 230                 235                 240

Thr Ile Thr Cys Ser Ala Ser Ser Ser Val Asn Tyr Met His Trp Tyr
                245                 250                 255

Gln Gln Lys Pro Gly Lys Val Pro Lys Leu Leu Ile Tyr Asp Thr Ser
            260                 265                 270

Lys Leu Ala Ser Gly Val Pro Ser Arg Phe Ser Gly Ser Gly Ser Gly
        275                 280                 285

Thr Asp Phe Thr Leu Thr Ile Ser Ser Leu Gln Pro Glu Asp Val Ala
290                 295                 300

Thr Tyr Tyr Cys Gln Gln Trp Asn Ser His Pro Leu Thr Phe Gly Gln
305                 310                 315                 320

Gly Thr Lys Leu Glu Ile Lys
                325

<210> SEQ ID NO 103
<211> LENGTH: 1767
<212> TYPE: DNA
<213> ORGANISM: Homo sapiens
<220> FEATURE:
<221> NAME/KEY: CDS
<222> LOCATION: (1)..(1767)

<400> SEQUENCE: 103 cag gtg cag ctg gtg cag agc gga gcc gaa gtg aag aaa cct ggc gcc      48
Gln Val Gln Leu Val Gln Ser Gly Ala Glu Val Lys Lys Pro Gly Ala
  1               5                  10                  15 agc gtg aag gtg tcc tgc aag gcc agc ggc tac acc ttc aac gag tac      96
Ser Val Lys Val Ser Cys Lys Ala Ser Gly Tyr Thr Phe Asn Glu Tyr
             20                  25                  30 acc atg cac tgg gtg aag cag gcc ccc ggc cag aga ctg gaa tgg atg     144
Thr Met His Trp Val Lys Gln Ala Pro Gly Gln Arg Leu Glu Trp Met
         35                  40                  45
```

|   |   |
|---|---|
| ggc ggc atc aac ccc aat agc gga ggc gtg agc tac aac cag aac ttc<br>Gly Gly Ile Asn Pro Asn Ser Gly Gly Val Ser Tyr Asn Gln Asn Phe<br>50                        55                        60 | 192 |
| aag ggc aag gcc acc ctg acc gtc gac aca agc gcc agc acc gcc tac<br>Lys Gly Lys Ala Thr Leu Thr Val Asp Thr Ser Ala Ser Thr Ala Tyr<br>65                       70                     75                   80 | 240 |
| atg gaa ctg agc agc ctg aga agc gag gac acc gcc gtg tac tac tgc<br>Met Glu Leu Ser Ser Leu Arg Ser Glu Asp Thr Ala Val Tyr Tyr Cys<br>                    85                     90                     95 | 288 |
| gcc aga ggc ggc gac ggc tac tac acc aac tac ttc gac atc gac tac<br>Ala Arg Gly Gly Asp Gly Tyr Tyr Thr Asn Tyr Phe Asp Ile Asp Tyr<br>        100                      105                   110 | 336 |
| tgg ggc cag ggc acc acc gtg acc gtg tcc agc gcc tct acc aag ggc<br>Trp Gly Gln Gly Thr Thr Val Thr Val Ser Ser Ala Ser Thr Lys Gly<br>        115                      120                   125 | 384 |
| ccc agc gtg ttc cct ctg gcc ccc agc agc aag agc aca agc gga ggc<br>Pro Ser Val Phe Pro Leu Ala Pro Ser Ser Lys Ser Thr Ser Gly Gly<br>130                       135                    140 | 432 |
| aca gcc gcc ctg ggc tgc ctg gtg aag gac tac ttc ccc gag ccc gtg<br>Thr Ala Ala Leu Gly Cys Leu Val Lys Asp Tyr Phe Pro Glu Pro Val<br>145                       150                    155                   160 | 480 |
| aca gtg tcc tgg aac agc gga gcc ctg acc agc ggc gtg cac acc ttt<br>Thr Val Ser Trp Asn Ser Gly Ala Leu Thr Ser Gly Val His Thr Phe<br>                  165                     170                   175 | 528 |
| cca gcc gtg ctg cag agc agc ggc ctg tac agc ctg agc agc gtg gtg<br>Pro Ala Val Leu Gln Ser Ser Gly Leu Tyr Ser Leu Ser Ser Val Val<br>        180                      185                   190 | 576 |
| acc gtg cct agc agc agc ctg ggc acc cag acc tac atc tgc aac gtg<br>Thr Val Pro Ser Ser Ser Leu Gly Thr Gln Thr Tyr Ile Cys Asn Val<br>               195                     200                   205 | 624 |
| aac cac aag ccc agc aac acc aag gtg gac aag aag gtg gag ccc aag<br>Asn His Lys Pro Ser Asn Thr Lys Val Asp Lys Lys Val Glu Pro Lys<br>210                       215                    220 | 672 |
| agc tgc agc agc gct tcc acc aag ggc cca tcg cag gtg cag ctg gtg<br>Ser Cys Ser Ser Ala Ser Thr Lys Gly Pro Ser Gln Val Gln Leu Val<br>225                       230                    235                   240 | 720 |
| gag tct ggg gga ggc gtg gtc cag cct ggg agg tcc ctg aga ctc tcc<br>Glu Ser Gly Gly Gly Val Val Gln Pro Gly Arg Ser Leu Arg Leu Ser<br>                  245                     250                   255 | 768 |
| tgt gca gcc tct gga ttc tcc ttc agt agc tat gct atg cac tgg gtc<br>Cys Ala Ala Ser Gly Phe Ser Phe Ser Ser Tyr Ala Met His Trp Val<br>        260                      265                   270 | 816 |
| cgc cag gct cca ggc aag ggg ctg gag tgg gtg gca gtt ata tca tat<br>Arg Gln Ala Pro Gly Lys Gly Leu Glu Trp Val Ala Val Ile Ser Tyr<br>        275                      280                   285 | 864 |
| ggt gga agc aaa aaa tac tac gca gac tcc gtg aag ggc cga ttc acc<br>Gly Gly Ser Lys Lys Tyr Tyr Ala Asp Ser Val Lys Gly Arg Phe Thr<br>290                       295                    300 | 912 |
| atc tcc aga gac aat tcc aag aac acg ctg tat ctg caa atg aac agc<br>Ile Ser Arg Asp Asn Ser Lys Asn Thr Leu Tyr Leu Gln Met Asn Ser<br>305                       310                    315                   320 | 960 |
| ctg aga gct gag gac acg gct gtg tat tac tgt gcg aga atg ggg tat<br>Leu Arg Ala Glu Asp Thr Ala Val Tyr Tyr Cys Ala Arg Met Gly Tyr<br>                  325                     330                   335 | 1008 |
| tac gat att ttg act ggt ccc ttt gac tac tgg ggc cag gga acc ctg<br>Tyr Asp Ile Leu Thr Gly Pro Phe Asp Tyr Trp Gly Gln Gly Thr Leu<br>        340                      345                   350 | 1056 |
| gtc acc gtc tcc tca gag ccc aag agc agc gac aag acc cac acc tgt<br>Val Thr Val Ser Ser Glu Pro Lys Ser Ser Asp Lys Thr His Thr Cys<br>        355                      360                   365 | 1104 |

```
ccc cct tgt cct gcc cct gaa gcc gaa ggc gcg cct tcc gtg ttc ctg      1152
Pro Pro Cys Pro Ala Pro Glu Ala Glu Gly Ala Pro Ser Val Phe Leu
    370             375                 380 ttc ccc cca aag ccc aag gac acc ctg atg atc agc cgg acc ccc gaa      1200
Phe Pro Pro Lys Pro Lys Asp Thr Leu Met Ile Ser Arg Thr Pro Glu
385             390                 395                 400 gtg acc tgc gtg gtg gtg gac gtg tcc cac gag gac cct gaa gtg aag      1248
Val Thr Cys Val Val Val Asp Val Ser His Glu Asp Pro Glu Val Lys
                405                 410                 415 ttc aat tgg tac gtg gac ggc gtg gag gtg cac aac gcc aag acc aag      1296
Phe Asn Trp Tyr Val Asp Gly Val Glu Val His Asn Ala Lys Thr Lys
            420                 425                 430 ccc cgg gag gaa cag tac aac agc acc tac cgg gtg gtg tcc gtg ctg      1344
Pro Arg Glu Glu Gln Tyr Asn Ser Thr Tyr Arg Val Val Ser Val Leu
        435                 440                 445 acc gtg ctg cac cag gac tgg ctg aac ggc aaa gag tac aag tgc aag      1392
Thr Val Leu His Gln Asp Trp Leu Asn Gly Lys Glu Tyr Lys Cys Lys
    450                 455                 460 gtc tcc aac aag gcc ctg ccc agc agc atc gag aaa acc atc agc aag      1440
Val Ser Asn Lys Ala Leu Pro Ser Ser Ile Glu Lys Thr Ile Ser Lys
465                 470                 475                 480 gcc aag ggc cag ccc aga gaa ccc cag gtg tac acc ctg ccc cct agc      1488
Ala Lys Gly Gln Pro Arg Glu Pro Gln Val Tyr Thr Leu Pro Pro Ser
                485                 490                 495 agg gac gag ctg acc aag aac cag gtg tcc ctg acc tgt ctg gtg aag      1536
Arg Asp Glu Leu Thr Lys Asn Gln Val Ser Leu Thr Cys Leu Val Lys
            500                 505                 510 ggc ttc tac ccc agc gat atc gcc gtg gag tgg gag agc aac ggc cag      1584
Gly Phe Tyr Pro Ser Asp Ile Ala Val Glu Trp Glu Ser Asn Gly Gln
        515                 520                 525 ccc gaa aac aac tac aag acc acc ccc cct gtg ctg gac agc gac ggc      1632
Pro Glu Asn Asn Tyr Lys Thr Thr Pro Pro Val Leu Asp Ser Asp Gly
    530                 535                 540 agc ttc ttc ctg tac tcc aaa ctg acc gtg gac aag agc cgg tgg cag      1680
Ser Phe Phe Leu Tyr Ser Lys Leu Thr Val Asp Lys Ser Arg Trp Gln
545                 550                 555                 560 cag ggc aac gtg ttc agc tgc agc gtg atg cac gag gcc ctg cac aac      1728
Gln Gly Asn Val Phe Ser Cys Ser Val Met His Glu Ala Leu His Asn
                565                 570                 575 cac tac acc cag aag tcc ctg agc ctg agc ccc ggc aag                  1767
His Tyr Thr Gln Lys Ser Leu Ser Leu Ser Pro Gly Lys
            580                 585

<210> SEQ ID NO 104
<211> LENGTH: 589
<212> TYPE: PRT
<213> ORGANISM: Homo sapiens

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Glu Tyr
            20                  25                  30

Thr Met His Trp Val Lys Gln Ala Pro Gly Gln Arg Leu Glu Trp Met
        35                  40                  45

Gly Gly Ile Asn Pro Asn Ser Gly Gly Val Ser Tyr Asn Gln Asn Phe
    50                  55                  60

Lys Gly Lys Ala Thr Leu Thr Val Asp Thr Ser Ala Ser Thr Ala Tyr
65                  70                  75                  80
```

-continued

```
Met Glu Leu Ser Ser Leu Arg Ser Glu Asp Thr Ala Val Tyr Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Ser Ser Ala Ser Thr Lys Gly Pro Ser Gln Val Gln Leu Val
225                 230                 235                 240

Glu Ser Gly Gly Gly Val Val Gln Pro Gly Arg Ser Leu Arg Leu Ser
                245                 250                 255

Cys Ala Ala Ser Gly Phe Ser Phe Ser Ser Tyr Ala Met His Trp Val
                260                 265                 270

Arg Gln Ala Pro Gly Lys Gly Leu Glu Trp Val Ala Val Ile Ser Tyr
            275                 280                 285

Gly Gly Ser Lys Lys Tyr Ala Asp Ser Val Lys Gly Arg Phe Thr
            290                 295                 300

Ile Ser Arg Asp Asn Ser Lys Asn Thr Leu Tyr Leu Gln Met Asn Ser
305                 310                 315                 320

Leu Arg Ala Glu Asp Thr Ala Val Tyr Tyr Cys Ala Arg Met Gly Tyr
                325                 330                 335

Tyr Asp Ile Leu Thr Gly Pro Phe Asp Tyr Trp Gly Gln Gly Thr Leu
            340                 345                 350

Val Thr Val Ser Ser Glu Pro Lys Ser Ser Asp Lys Thr His Thr Cys
            355                 360                 365

Pro Pro Cys Pro Ala Pro Glu Ala Glu Gly Ala Pro Ser Val Phe Leu
            370                 375                 380

Phe Pro Pro Lys Pro Lys Asp Thr Leu Met Ile Ser Arg Thr Pro Glu
385                 390                 395                 400

Val Thr Cys Val Val Val Asp Val Ser His Glu Asp Pro Glu Val Lys
                405                 410                 415

Phe Asn Trp Tyr Val Asp Gly Val Glu Val His Asn Ala Lys Thr Lys
            420                 425                 430

Pro Arg Glu Glu Gln Tyr Asn Ser Thr Tyr Arg Val Val Ser Val Leu
            435                 440                 445

Thr Val Leu His Gln Asp Trp Leu Asn Gly Lys Glu Tyr Lys Cys Lys
450                 455                 460

Val Ser Asn Lys Ala Leu Pro Ser Ser Ile Glu Lys Thr Ile Ser Lys
465                 470                 475                 480

Ala Lys Gly Gln Pro Arg Glu Pro Gln Val Tyr Thr Leu Pro Pro Ser
            485                 490                 495
```

```
Arg Asp Glu Leu Thr Lys Asn Gln Val Ser Leu Thr Cys Leu Val Lys
            500                 505                 510
Gly Phe Tyr Pro Ser Asp Ile Ala Val Glu Trp Glu Ser Asn Gly Gln
            515                 520                 525
Pro Glu Asn Asn Tyr Lys Thr Thr Pro Pro Val Leu Asp Ser Asp Gly
            530                 535                 540
Ser Phe Phe Leu Tyr Ser Lys Leu Thr Val Asp Lys Ser Arg Trp Gln
545                 550                 555                 560
Gln Gly Asn Val Phe Ser Cys Ser Val Met His Glu Ala Leu His Asn
                565                 570                 575
His Tyr Thr Gln Lys Ser Leu Ser Leu Ser Pro Gly Lys
            580                 585

<210> SEQ ID NO 105
<211> LENGTH: 981
<212> TYPE: DNA
<213> ORGANISM: Homo sapiens
<220> FEATURE:
<221> NAME/KEY: CDS
<222> LOCATION: (1)..(981)

<400> SEQUENCE: 105 gac atc cag atg acc cag tcc ccc tcc tcc ctg tcc gcc tcc gtg ggc      48
Asp Ile Gln Met Thr Gln Ser Pro Ser Ser Leu Ser Ala Ser Val Gly
1               5                   10                  15 gac aga gtg acc atc acc tgc tcc gcc tcc agc tcc gtg aac tac atg      96
Asp Arg Val Thr Ile Thr Cys Ser Ala Ser Ser Ser Val Asn Tyr Met
            20                  25                  30 cac tgg tat cag cag aaa cct ggc aag gtg ccc aag ctg ctg atc tac     144
His Trp Tyr Gln Gln Lys Pro Gly Lys Val Pro Lys Leu Leu Ile Tyr
        35                  40                  45 gac acc tcc aag ctg gcc tcc ggc gtg cct tcc cgg ttc tcc ggc tcc     192
Asp Thr Ser Lys Leu Ala Ser Gly Val Pro Ser Arg Phe Ser Gly Ser
    50                  55                  60 ggc tct ggc acc gac ttc acc ctg acc atc tcc agc ctg cag cct gag     240
Gly Ser Gly Thr Asp Phe Thr Leu Thr Ile Ser Ser Leu Gln Pro Glu
65                  70                  75                  80 gac gtg gcc acc tac tac tgc cag cag tgg aac tcc cac cct ctg acc     288
Asp Val Ala Thr Tyr Tyr Cys Gln Gln Trp Asn Ser His Pro Leu Thr
                85                  90                  95 ttc gga cag ggc acc aag ctg gag atc aaa cgg acc gtg gcc gct ccc     336
Phe Gly Gln Gly Thr Lys Leu Glu Ile Lys Arg Thr Val Ala Ala Pro
            100                 105                 110 agc gtg ttc atc ttc cca ccc agc gac gag cag ctg aag tcc ggt acc     384
Ser Val Phe Ile Phe Pro Pro Ser Asp Glu Gln Leu Lys Ser Gly Thr
        115                 120                 125 gcc agc gtg gtg tgc ctg ctg aac aac ttc tac ccg cgg gag gcc aag     432
Ala Ser Val Val Cys Leu Leu Asn Asn Phe Tyr Pro Arg Glu Ala Lys
    130                 135                 140 gtg cag tgg aag gtg gac aac gcc ctg cag agc ggc aac tcc cag gaa     480
Val Gln Trp Lys Val Asp Asn Ala Leu Gln Ser Gly Asn Ser Gln Glu
145                 150                 155                 160 agc gtc acc gag cag gac agc aag gac tcc acc tac agc ctg agc agc     528
Ser Val Thr Glu Gln Asp Ser Lys Asp Ser Thr Tyr Ser Leu Ser Ser
                165                 170                 175 acc ctg acc ctg agc aag gcc gac tac gag aag cac aag gtg tac gcc     576
Thr Leu Thr Leu Ser Lys Ala Asp Tyr Glu Lys His Lys Val Tyr Ala
            180                 185                 190 tgc gaa gtg acc cac cag ggc ctg tcc agc ccc gtg acc aag agc ttc     624
Cys Glu Val Thr His Gln Gly Leu Ser Ser Pro Val Thr Lys Ser Phe
```

| | | | | | | | | | | | | | | | |
|---|---|---|---|---|---|---|---|---|---|---|---|---|---|---|---|
| | | 195 | | | | 200 | | | | | 205 | | | | |
| aac | cgg | ggc | gag | tgt | cga | act | gtg | gct | gca | cca | tct | gaa | att | gtg | ttg | 672 |
| Asn | Arg | Gly | Glu | Cys | Arg | Thr | Val | Ala | Ala | Pro | Ser | Glu | Ile | Val | Leu |
| | 210 | | | | 215 | | | | | 220 | | | | | |
| acg | cag | tct | cca | ggc | acc | ctg | tct | ttg | tct | cca | ggg | gaa | aga | gcc | acc | 720 |
| Thr | Gln | Ser | Pro | Gly | Thr | Leu | Ser | Leu | Ser | Pro | Gly | Glu | Arg | Ala | Thr |
| 225 | | | | | 230 | | | | | 235 | | | | | 240 |
| ctc | tcc | tgc | agg | gcc | agt | cag | agt | gtt | agc | agc | agc | tac | tta | gcc | tgg | 768 |
| Leu | Ser | Cys | Arg | Ala | Ser | Gln | Ser | Val | Ser | Ser | Ser | Tyr | Leu | Ala | Trp |
| | | | 245 | | | | | 250 | | | | | 255 | | |
| tat | cag | cag | aaa | cct | ggc | cag | gct | ccc | agg | ctc | ctc | atc | tat | ggt | gca | 816 |
| Tyr | Gln | Gln | Lys | Pro | Gly | Gln | Ala | Pro | Arg | Leu | Leu | Ile | Tyr | Gly | Ala |
| | | 260 | | | | | 265 | | | | | 270 | | | |
| tcc | agc | agg | gcc | act | ggc | atc | cca | gac | agg | ttc | agt | ggc | agt | ggg | tct | 864 |
| Ser | Ser | Arg | Ala | Thr | Gly | Ile | Pro | Asp | Arg | Phe | Ser | Gly | Ser | Gly | Ser |
| | 275 | | | | | 280 | | | | | 285 | | | | |
| ggg | aca | gac | ttc | act | ctc | acc | atc | agc | aga | ctg | gag | cct | gaa | gat | ttt | 912 |
| Gly | Thr | Asp | Phe | Thr | Leu | Thr | Ile | Ser | Arg | Leu | Glu | Pro | Glu | Asp | Phe |
| 290 | | | | | 295 | | | | | 300 | | | | | |
| gca | gtg | tat | tac | tgt | cag | cag | tat | ggt | agc | tca | tac | act | ttt | ggc | cag | 960 |
| Ala | Val | Tyr | Tyr | Cys | Gln | Gln | Tyr | Gly | Ser | Ser | Tyr | Thr | Phe | Gly | Gln |
| 305 | | | | 310 | | | | | 315 | | | | | | 320 |
| ggg | acc | aag | ctg | gag | atc | aaa | | | | | | | | | | 981 |
| Gly | Thr | Lys | Leu | Glu | Ile | Lys |
| | | | 325 | | | |

<210> SEQ ID NO 106
<211> LENGTH: 327
<212> TYPE: PRT
<213> ORGANISM: Homo sapiens

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Asn Tyr Met
            20                  25                  30

His Trp Tyr Gln Gln Lys Pro Gly Lys Val Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Gln Trp Asn Ser His Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe

|   |   |   |   |   | 195 |   |   |   |   | 200 |   |   |   |   | 205 |   |   |
|---|---|---|---|---|-----|---|---|---|---|-----|---|---|---|---|-----|---|---|

Asn Arg Gly Glu Cys Arg Thr Val Ala Ala Pro Ser Glu Ile Val Leu
    210                  215                220

Thr Gln Ser Pro Gly Thr Leu Ser Leu Ser Pro Gly Glu Arg Ala Thr
225                230                235              240

Leu Ser Cys Arg Ala Ser Gln Ser Val Ser Ser Tyr Leu Ala Trp
                245                250              255

Tyr Gln Gln Lys Pro Gly Gln Ala Pro Arg Leu Leu Ile Tyr Gly Ala
            260                265              270

Ser Ser Arg Ala Thr Gly Ile Pro Asp Arg Phe Ser Gly Ser Gly Ser
        275                280              285

Gly Thr Asp Phe Thr Leu Thr Ile Ser Arg Leu Glu Pro Glu Asp Phe
        290                295              300

Ala Val Tyr Tyr Cys Gln Gln Tyr Gly Ser Ser Tyr Thr Phe Gly Gln
305                310                315              320

Gly Thr Lys Leu Glu Ile Lys
        325

<210> SEQ ID NO 107
<211> LENGTH: 1350
<212> TYPE: DNA
<213> ORGANISM: Homo sapiens
<220> FEATURE:
<221> NAME/KEY: CDS
<222> LOCATION: (1)..(1350)

<400> SEQUENCE: 107

```
gag gag cag ctg gtg cag tct gga gca gag gtg aaa aag ccc ggg gag      48
Glu Glu Gln Leu Val Gln Ser Gly Ala Glu Val Lys Lys Pro Gly Glu
1               5                   10                  15 tct ctg aag atc tcc tgt aag ggt tct gga ttc agc ttt gac agc tac      96
Ser Leu Lys Ile Ser Cys Lys Gly Ser Gly Phe Ser Phe Asp Ser Tyr
            20                  25                  30 tgg atc ggc tgg gtg cgc cag ctg ccc ggg aaa ggc ctg gag tgg atg     144
Trp Ile Gly Trp Val Arg Gln Leu Pro Gly Lys Gly Leu Glu Trp Met
        35                  40                  45 ggg atc atc ttg cct ggt aac tct gat acc aga tac agc ccg tcc ttc     192
Gly Ile Ile Leu Pro Gly Asn Ser Asp Thr Arg Tyr Ser Pro Ser Phe
    50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
65                  70                  75                  80 ctg cag tgg agc agc ctg gag gcc tcg gac acc gcc atg tat tat tgt     288
Leu Gln Trp Ser Ser Leu Glu Ala Ser Asp Thr Ala Met Tyr Tyr Cys
                85                  90                  95 gcg aga cag gcc tat tac gat ctt ttg act ggt ccc ttt gac tac tgg     336
Ala Arg Gln Ala Tyr Tyr Asp Leu Leu Thr Gly Pro Phe Asp Tyr Trp
            100                 105                 110 ggc cag gga acc ctg gtc acc gtc tcc tca gct agc acc aag ggc cca     384
Gly Gln Gly Thr Leu Val Thr Val Ser Ser Ala Ser Thr Lys Gly Pro
        115                 120                 125 tcc gtc ttc ccc ctg gcg ccc tgc tcc agg agc acc tcc gag agc aca     432
Ser Val Phe Pro Leu Ala Pro Cys Ser Arg Ser Thr Ser Glu Ser Thr
    130                 135                 140 gcc gcc ctg ggc tgc ctg gtc aag gac tac ttc ccc gaa ccg gtg acg     480
Ala Ala Leu Gly Cys Leu Val Lys Asp Tyr Phe Pro Glu Pro Val Thr
145                 150                 155                 160 gtg tcg tgg aac tca ggc gcc ctg acc agc ggc gtg cac acc ttc ccg     528
Val Ser Trp Asn Ser Gly Ala Leu Thr Ser Gly Val His Thr Phe Pro
```

-continued

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     |     |     | 165 |     |     |     |     | 170 |     |     |     |     | 175 |     |     |
| gct | gtc | cta | cag | tcc | tca | gga | ctc | tac | tcc | ctc | agc | agc | gtg | gtg | acc | 576 |
| Ala | Val | Leu | Gln | Ser | Ser | Gly | Leu | Tyr | Ser | Leu | Ser | Ser | Val | Val | Thr |     |
|     |     |     | 180 |     |     |     |     | 185 |     |     |     |     | 190 |     |     |     |
| gtg | ccc | tcc | agc | agc | ttg | ggc | acg | aag | acc | tac | acc | tgc | aac | gta | gat | 624 |
| Val | Pro | Ser | Ser | Ser | Leu | Gly | Thr | Lys | Thr | Tyr | Thr | Cys | Asn | Val | Asp |     |
|     |     | 195 |     |     |     |     | 200 |     |     |     |     | 205 |     |     |     |     |
| cac | aag | ccc | agc | aac | acc | aag | gtg | gac | aag | aga | gtt | gag | tcc | aaa | tat | 672 |
| His | Lys | Pro | Ser | Asn | Thr | Lys | Val | Asp | Lys | Arg | Val | Glu | Ser | Lys | Tyr |     |
| 210 |     |     |     |     | 215 |     |     |     |     | 220 |     |     |     |     |     |     |
| ggt | ccc | cca | tgc | cca | cca | tgc | cca | gca | cct | gag | ttc | ctg | ggg | gga | cca | 720 |
| Gly | Pro | Pro | Cys | Pro | Pro | Cys | Pro | Ala | Pro | Glu | Phe | Leu | Gly | Gly | Pro |     |
| 225 |     |     |     | 230 |     |     |     |     | 235 |     |     |     |     | 240 |     |     |
| tca | gtc | ttc | ctg | ttc | ccc | cca | aaa | ccc | aag | gac | act | ctc | atg | atc | tcc | 768 |
| Ser | Val | Phe | Leu | Phe | Pro | Pro | Lys | Pro | Lys | Asp | Thr | Leu | Met | Ile | Ser |     |
|     |     |     |     | 245 |     |     |     |     | 250 |     |     |     |     | 255 |     |     |
| cgg | acc | cct | gag | gtc | acg | tgc | gtg | gtg | gtg | gac | gtg | agc | cag | gaa | gac | 816 |
| Arg | Thr | Pro | Glu | Val | Thr | Cys | Val | Val | Val | Asp | Val | Ser | Gln | Glu | Asp |     |
|     |     |     | 260 |     |     |     |     | 265 |     |     |     |     | 270 |     |     |     |
| ccc | gag | gtc | cag | ttc | aac | tgg | tac | gtg | gat | ggc | gtg | gag | gtg | cat | aat | 864 |
| Pro | Glu | Val | Gln | Phe | Asn | Trp | Tyr | Val | Asp | Gly | Val | Glu | Val | His | Asn |     |
|     |     | 275 |     |     |     |     | 280 |     |     |     |     | 285 |     |     |     |     |
| gcc | aag | aca | aag | ccg | cgg | gag | gag | cag | ttc | aac | agc | acg | tac | cgt | gtg | 912 |
| Ala | Lys | Thr | Lys | Pro | Arg | Glu | Glu | Gln | Phe | Asn | Ser | Thr | Tyr | Arg | Val |     |
|     | 290 |     |     |     |     | 295 |     |     |     |     | 300 |     |     |     |     |     |
| gtc | agc | gtc | ctc | acc | gtc | ctg | cac | cag | gac | tgg | ctg | aac | ggc | aag | gag | 960 |
| Val | Ser | Val | Leu | Thr | Val | Leu | His | Gln | Asp | Trp | Leu | Asn | Gly | Lys | Glu |     |
| 305 |     |     |     |     | 310 |     |     |     |     | 315 |     |     |     |     | 320 |     |
| tac | aag | tgc | aag | gtc | tcc | aac | aaa | ggc | ctc | ccg | tcc | tcc | atc | gag | aaa | 1008 |
| Tyr | Lys | Cys | Lys | Val | Ser | Asn | Lys | Gly | Leu | Pro | Ser | Ser | Ile | Glu | Lys |     |
|     |     |     |     | 325 |     |     |     |     | 330 |     |     |     |     | 335 |     |     |
| acc | atc | tcc | aaa | gcc | aaa | ggg | cag | ccc | cga | gag | cca | cag | gtg | tac | acc | 1056 |
| Thr | Ile | Ser | Lys | Ala | Lys | Gly | Gln | Pro | Arg | Glu | Pro | Gln | Val | Tyr | Thr |     |
|     |     |     | 340 |     |     |     |     | 345 |     |     |     |     | 350 |     |     |     |
| ctg | ccc | cca | tcc | cag | gag | gag | atg | acc | aag | aac | cag | gtc | agc | ctg | acc | 1104 |
| Leu | Pro | Pro | Ser | Gln | Glu | Glu | Met | Thr | Lys | Asn | Gln | Val | Ser | Leu | Thr |     |
|     |     | 355 |     |     |     |     | 360 |     |     |     |     | 365 |     |     |     |     |
| tgc | ctg | gtc | aaa | ggc | ttc | tac | ccc | agc | gac | atc | gcc | gtg | gag | tgg | gag | 1152 |
| Cys | Leu | Val | Lys | Gly | Phe | Tyr | Pro | Ser | Asp | Ile | Ala | Val | Glu | Trp | Glu |     |
| 370 |     |     |     |     | 375 |     |     |     |     | 380 |     |     |     |     |     |     |
| agc | aat | ggg | cag | ccg | gag | aac | aac | tac | aag | acc | acg | cct | ccc | gtg | ctg | 1200 |
| Ser | Asn | Gly | Gln | Pro | Glu | Asn | Asn | Tyr | Lys | Thr | Thr | Pro | Pro | Val | Leu |     |
| 385 |     |     |     | 390 |     |     |     |     | 395 |     |     |     |     | 400 |     |     |
| gac | tcc | gac | ggc | tcc | ttc | ttc | ctc | tac | agc | agg | cta | acc | gtg | gac | aag | 1248 |
| Asp | Ser | Asp | Gly | Ser | Phe | Phe | Leu | Tyr | Ser | Arg | Leu | Thr | Val | Asp | Lys |     |
|     |     |     | 405 |     |     |     |     | 410 |     |     |     |     | 415 |     |     |     |
| agc | agg | tgg | cag | gag | ggg | aat | gtc | ttc | tca | tgc | tcc | gtg | atg | cat | gag | 1296 |
| Ser | Arg | Trp | Gln | Glu | Gly | Asn | Val | Phe | Ser | Cys | Ser | Val | Met | His | Glu |     |
|     |     |     | 420 |     |     |     |     | 425 |     |     |     |     | 430 |     |     |     |
| gct | ctg | cac | aac | cac | tac | aca | cag | aag | agc | ctc | tcc | ctg | tct | ctg | ggt | 1344 |
| Ala | Leu | His | Asn | His | Tyr | Thr | Gln | Lys | Ser | Leu | Ser | Leu | Ser | Leu | Gly |     |
|     |     | 435 |     |     |     |     | 440 |     |     |     |     | 445 |     |     |     |     |
| aaa | tga |     |     |     |     |     |     |     |     |     |     |     |     |     |     | 1350 |
| Lys |     |     |     |     |     |     |     |     |     |     |     |     |     |     |     |     |

<210> SEQ ID NO 108
<211> LENGTH: 449
<212> TYPE: PRT
<213> ORGANISM: Homo sapiens

```
<400> SEQUENCE: 108

Glu Glu Gln Leu Val Gln Ser Gly Ala Glu Val Lys Lys Pro Gly Glu
1               5                   10                  15

Ser Leu Lys Ile Ser Cys Lys Gly Ser Gly Phe Ser Phe Asp Ser Tyr
            20                  25                  30

Trp Ile Gly Trp Val Arg Gln Leu Pro Gly Lys Gly Leu Glu Trp Met
        35                  40                  45

Gly Ile Ile Leu Pro Gly Asn Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Glu Ala Ser Asp Thr Ala Met Tyr Tyr Cys
                85                  90                  95

Ala Arg Gln Ala Tyr Tyr Asp Leu Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415
```

```
Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 109
<211> LENGTH: 645
<212> TYPE: DNA
<213> ORGANISM: Homo sapiens
<220> FEATURE:
<221> NAME/KEY: CDS
<222> LOCATION: (1)..(645)

<400> SEQUENCE: 109 gaa att gtg ttg acg cag tct cca ggc acc ctg tct ttg tct cca ggg     48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc     96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt    192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag    240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca cct    288
Pro Glu Asp Phe Ala Val Tyr Tyr Cys Gln Gln Tyr Gly Ser Ser Pro
                85                  90                  95 act ttc ggc gga ggg acc aag gtg gag atc aaa cgt acg gtg gct gca    336
Thr Phe Gly Gly Gly Thr Lys Val Glu Ile Lys Arg Thr Val Ala Ala
            100                 105                 110 cca tct gtc ttc atc ttc ccg cca tct gat gag cag ttg aaa tct gga    384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc    432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag    480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc    528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac    576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc    624
Ala Cys Glu Val Thr His Gln Gly Leu Ser Ser Pro Val Thr Lys Ser
        195                 200                 205 ttc aac agg gga gag tgt tag                                        645
Phe Asn Arg Gly Glu Cys
    210

<210> SEQ ID NO 110
<211> LENGTH: 214
```

<212> TYPE: PRT
<213> ORGANISM: Homo sapiens

<400> SEQUENCE: 110

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 111
<211> LENGTH: 1770
<212> TYPE: DNA
<213> ORGANISM: Homo sapiens
<220> FEATURE:
<221> NAME/KEY: CDS
<222> LOCATION: (1)..(1770)

<400> SEQUENCE: 111

```
gag gaa cag ctg gtc cag agc gga gct gag gtg aaa aaa cca ggg gaa      48
Glu Glu Gln Leu Val Gln Ser Gly Ala Glu Val Lys Lys Pro Gly Glu
1               5                   10                  15 tct ctg aag atc agt tgt aaa ggt tct ggc ttc agt ttt gac tca tat      96
Ser Leu Lys Ile Ser Cys Lys Gly Ser Gly Phe Ser Phe Asp Ser Tyr
            20                  25                  30 tgg att gga tgg gtg agg cag ctg cca gga aag ggg ctg gag tgg atg     144
Trp Ile Gly Trp Val Arg Gln Leu Pro Gly Lys Gly Leu Glu Trp Met
        35                  40                  45 ggt atc att ctg cca ggc aac agc gac acc cga tac tcc cct agc ttt     192
Gly Ile Ile Leu Pro Gly Asn Ser Asp Thr Arg Tyr Ser Pro Ser Phe
50                  55                  60 cag ggc cag gtg aca atc tct gct gat aag tct att agt act gcc tat     240
Gln Gly Gln Val Thr Ile Ser Ala Asp Lys Ser Ile Ser Thr Ala Tyr
65                  70                  75                  80 ctg cag tgg agt tca ctg gag gca tct gat aca gcc atg tac tat tgc     288
```

```
                Leu Gln Trp Ser Ser Leu Glu Ala Ser Asp Thr Ala Met Tyr Tyr Cys
                                85                  90                  95 gcc cga cag gct tac tat gac ctg ctg act ggt ccc ttc gat tac tgg        336
Ala Arg Gln Ala Tyr Tyr Asp Leu Leu Thr Gly Pro Phe Asp Tyr Trp
            100                 105                 110 ggt cag ggc acc ctg gtc aca gtg tcc agc gcc tct acc aag ggc ccc        384
Gly Gln Gly Thr Leu Val Thr Val Ser Ser Ala Ser Thr Lys Gly Pro
            115                 120                 125 agc gtg ttc cct ctg gcc ccc agc agc aag agc aca agc gga ggc aca        432
Ser Val Phe Pro Leu Ala Pro Ser Ser Lys Ser Thr Ser Gly Gly Thr
        130                 135                 140 gcc gcc ctg ggc tgc ctg gtg aag gac tac ttc ccc gag ccc gtg aca        480
Ala Ala Leu Gly Cys Leu Val Lys Asp Tyr Phe Pro Glu Pro Val Thr
145                 150                 155                 160 gtg tcc tgg aac agc gga gcc ctg acc agc ggc gtg cac acc ttt cca        528
Val Ser Trp Asn Ser Gly Ala Leu Thr Ser Gly Val His Thr Phe Pro
                165                 170                 175 gcc gtg ctg cag agc agc ggc ctg tac agc ctg agc agc gtg gtg acc        576
Ala Val Leu Gln Ser Ser Gly Leu Tyr Ser Leu Ser Ser Val Val Thr
            180                 185                 190 gtg cct agc agc agc ctg ggc acc cag acc tac atc tgc aac gtg aac        624
Val Pro Ser Ser Ser Leu Gly Thr Gln Thr Tyr Ile Cys Asn Val Asn
            195                 200                 205 cac aag ccc agc aac acc aag gtg gac aag aag gtg gag ccc aag agc        672
His Lys Pro Ser Asn Thr Lys Val Asp Lys Lys Val Glu Pro Lys Ser
210                 215                 220 tgc ggt ggc ggg ggt tcg ggt gga gga ggt tct gag gtc cag ctg caa        720
Cys Gly Gly Gly Gly Ser Gly Gly Gly Gly Ser Glu Val Gln Leu Gln
225                 230                 235                 240 cag tca gga cct gag ctg gtg aag cct ggg gct tca gtg aag ata tcc        768
Gln Ser Gly Pro Glu Leu Val Lys Pro Gly Ala Ser Val Lys Ile Ser
                245                 250                 255 tgt aag act tct gga tac aca ttc aat gaa tac acc atg cac tgg gtg        816
Cys Lys Thr Ser Gly Tyr Thr Phe Asn Glu Tyr Thr Met His Trp Val
            260                 265                 270 aag cag agc cat gga aag cgc ctt gag tgg att gga ggt att aat cct        864
Lys Gln Ser His Gly Lys Arg Leu Glu Trp Ile Gly Gly Ile Asn Pro
        275                 280                 285 aac agt ggt ggt gtt agc tac aac cag aac ttc aag ggc aag gcc aca        912
Asn Ser Gly Gly Val Ser Tyr Asn Gln Asn Phe Lys Gly Lys Ala Thr
    290                 295                 300 ttg act gta gac aag tcc tcc agc aca gcc tcc atg gag ctc cgc agc        960
Leu Thr Val Asp Lys Ser Ser Ser Thr Ala Ser Met Glu Leu Arg Ser
305                 310                 315                 320 ctg aca tct gag gat tct gca gtc ttt tac tgt gca aga ggg gga gat       1008
Leu Thr Ser Glu Asp Ser Ala Val Phe Tyr Cys Ala Arg Gly Gly Asp
                325                 330                 335 ggt tac tac acc aat tac ttt gat att gac tac tgg ggt caa gga acc       1056
Gly Tyr Tyr Thr Asn Tyr Phe Asp Ile Asp Tyr Trp Gly Gln Gly Thr
            340                 345                 350 tca gtc acc gtc tcc tca gag ccc aag agc agc gac aag acc cac acc       1104
Ser Val Thr Val Ser Ser Glu Pro Lys Ser Ser Asp Lys Thr His Thr
        355                 360                 365 tgt ccc cct tgt cct gcc cct gaa gcc gaa ggc gcg cct tcc gtg ttc       1152
Cys Pro Pro Cys Pro Ala Pro Glu Ala Glu Gly Ala Pro Ser Val Phe
370                 375                 380 ctg ttc ccc cca aag ccc aag gac acc ctg atg atc agc cgg acc ccc       1200
Leu Phe Pro Pro Lys Pro Lys Asp Thr Leu Met Ile Ser Arg Thr Pro
385                 390                 395                 400
```

-continued

| | | |
|---|---|---|
| gaa gtg acc tgc gtg gtg gtg gac gtg tcc cac gag gac cct gaa gtg<br>Glu Val Thr Cys Val Val Val Asp Val Ser His Glu Asp Pro Glu Val<br>405 410 415 | 1248 | |
| aag ttc aat tgg tac gtg gac ggc gtg gag gtg cac aac gcc aag acc<br>Lys Phe Asn Trp Tyr Val Asp Gly Val Glu Val His Asn Ala Lys Thr<br>420 425 430 | 1296 | |
| aag ccc cgg gag gaa cag tac aac agc acc tac cgg gtg gtg tcc gtg<br>Lys Pro Arg Glu Glu Gln Tyr Asn Ser Thr Tyr Arg Val Val Ser Val<br>435 440 445 | 1344 | |
| ctg acc gtg ctg cac cag gac tgg ctg aac ggc aaa gag tac aag tgc<br>Leu Thr Val Leu His Gln Asp Trp Leu Asn Gly Lys Glu Tyr Lys Cys<br>450 455 460 | 1392 | |
| aag gtc tcc aac aag gcc ctg ccc agc agc atc gag aaa acc atc agc<br>Lys Val Ser Asn Lys Ala Leu Pro Ser Ser Ile Glu Lys Thr Ile Ser<br>465 470 475 480 | 1440 | |
| aag gcc aag ggc cag ccc aga gaa ccc cag gtg tac acc ctg ccc cct<br>Lys Ala Lys Gly Gln Pro Arg Glu Pro Gln Val Tyr Thr Leu Pro Pro<br>485 490 495 | 1488 | |
| agc agg gac gag ctg acc aag aac cag gtg tcc ctg acc tgt ctg gtg<br>Ser Arg Asp Glu Leu Thr Lys Asn Gln Val Ser Leu Thr Cys Leu Val<br>500 505 510 | 1536 | |
| aag ggc ttc tac ccc agc gat atc gcc gtg gag tgg gag agc aac ggc<br>Lys Gly Phe Tyr Pro Ser Asp Ile Ala Val Glu Trp Glu Ser Asn Gly<br>515 520 525 | 1584 | |
| cag ccc gaa aac aac tac aag acc acc cct gtg ctg gac agc gac<br>Gln Pro Glu Asn Asn Tyr Lys Thr Thr Pro Pro Val Leu Asp Ser Asp<br>530 535 540 | 1632 | |
| ggc agc ttc ttc ctg tac tcc aaa ctg acc gtg gac aag agc cgg tgg<br>Gly Ser Phe Phe Leu Tyr Ser Lys Leu Thr Val Asp Lys Ser Arg Trp<br>545 550 555 560 | 1680 | |
| cag cag ggc aac gtg ttc agc tgc agc gtg atg cac gag gcc ctg cac<br>Gln Gln Gly Asn Val Phe Ser Cys Ser Val Met His Glu Ala Leu His<br>565 570 575 | 1728 | |
| aac cac tac acc cag aag tcc ctg agc ctg agc ccc ggc aag<br>Asn His Tyr Thr Gln Lys Ser Leu Ser Leu Ser Pro Gly Lys<br>580 585 590 | 1770 | |

<210> SEQ ID NO 112
<211> LENGTH: 590
<212> TYPE: PRT
<213> ORGANISM: Homo sapiens

<400> SEQUENCE: 112

Glu Glu Gln Leu Val Gln Ser Gly Ala Glu Val Lys Lys Pro Gly Glu
1               5                   10                  15

Ser Leu Lys Ile Ser Cys Lys Gly Ser Gly Phe Ser Phe Asp Ser Tyr
            20                  25                  30

Trp Ile Gly Trp Val Arg Gln Leu Pro Gly Lys Gly Leu Glu Trp Met
        35                  40                  45

Gly Ile Ile Leu Pro Gly Asn Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Glu Ala Ser Asp Thr Ala Met Tyr Tyr Cys
                85                  90                  95

Ala Arg Gln Ala Tyr Tyr Asp Leu Leu Thr Gly Pro Phe Asp Tyr Trp
            100                 105                 110

Gly Gln Gly Thr Leu Val Thr Val Ser Ser Ala Ser Thr Lys Gly Pro
        115                 120                 125

```
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
    210                 215                 220

Cys Gly Gly Gly Ser Gly Gly Gly Ser Glu Val Gln Leu Gln
225                 230                 235                 240

Gln Ser Gly Pro Glu Leu Val Lys Pro Gly Ala Ser Val Lys Ile Ser
                    245                 250                 255

Cys Lys Thr Ser Gly Tyr Thr Phe Asn Glu Tyr Thr Met His Trp Val
                260                 265                 270

Lys Gln Ser His Gly Lys Arg Leu Glu Trp Ile Gly Gly Ile Asn Pro
    275                 280                 285

Asn Ser Gly Gly Val Ser Tyr Asn Gln Asn Phe Lys Gly Lys Ala Thr
    290                 295                 300

Leu Thr Val Asp Lys Ser Ser Ser Thr Ala Ser Met Glu Leu Arg Ser
305                 310                 315                 320

Leu Thr Ser Glu Asp Ser Ala Val Phe Tyr Cys Ala Arg Gly Gly Asp
                325                 330                 335

Gly Tyr Tyr Thr Asn Tyr Phe Asp Ile Asp Tyr Trp Gly Gln Gly Thr
                340                 345                 350

Ser Val Thr Val Ser Ser Glu Pro Lys Ser Ser Asp Lys Thr His Thr
                355                 360                 365

Cys Pro Pro Cys Pro Ala Pro Glu Ala Glu Gly Ala Pro Ser Val Phe
    370                 375                 380

Leu Phe Pro Pro Lys Pro Lys Asp Thr Leu Met Ile Ser Arg Thr Pro
385                 390                 395                 400

Glu Val Thr Cys Val Val Val Asp Val Ser His Glu Asp Pro Glu Val
                405                 410                 415

Lys Phe Asn Trp Tyr Val Asp Gly Val Glu Val His Asn Ala Lys Thr
                420                 425                 430

Lys Pro Arg Glu Glu Gln Tyr Asn Ser Thr Tyr Arg Val Val Ser Val
    435                 440                 445

Leu Thr Val Leu His Gln Asp Trp Leu Asn Gly Lys Glu Tyr Lys Cys
    450                 455                 460

Lys Val Ser Asn Lys Ala Leu Pro Ser Ser Ile Glu Lys Thr Ile Ser
465                 470                 475                 480

Lys Ala Lys Gly Gln Pro Arg Glu Pro Gln Val Tyr Thr Leu Pro Pro
                485                 490                 495

Ser Arg Asp Glu Leu Thr Lys Asn Gln Val Ser Leu Thr Cys Leu Val
                500                 505                 510

Lys Gly Phe Tyr Pro Ser Asp Ile Ala Val Glu Trp Glu Ser Asn Gly
                515                 520                 525

Gln Pro Glu Asn Asn Tyr Lys Thr Thr Pro Pro Val Leu Asp Ser Asp
    530                 535                 540
```

```
Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
            565                 570                 575

Asn His Tyr Thr Gln Lys Ser Leu Ser Leu Ser Pro Gly Lys
        580                 585                 590

<210> SEQ ID NO 113
<211> LENGTH: 990
<212> TYPE: DNA
<213> ORGANISM: Homo sapiens
<220> FEATURE:
<221> NAME/KEY: CDS
<222> LOCATION: (1)..(990)

<400> SEQUENCE: 113 gag att gtc ctg acc cag agc cct ggg aca ctg agc ctg tct cca ggc      48
Glu Ile Val Leu Thr Gln Ser Pro Gly Thr Leu Ser Leu Ser Pro Gly
1               5                   10                  15 gag agg gct act ctg tcc tgc cgg gca agt cag tca gtg tcc agc tct      96
Glu Arg Ala Thr Leu Ser Cys Arg Ala Ser Gln Ser Val Ser Ser Ser
            20                  25                  30 tac ctg gcc tgg tat cag cag aag cca ggg cag gct ccc aga ctg ctg     144
Tyr Leu Ala Trp Tyr Gln Gln Lys Pro Gly Gln Ala Pro Arg Leu Leu
        35                  40                  45 atc tac ggc gca agt tca aga gcc acc ggc atc ccc gac cgc ttc tcc     192
Ile Tyr Gly Ala Ser Ser Arg Ala Thr Gly Ile Pro Asp Arg Phe Ser
    50                  55                  60 ggt agc ggc tct gga aca gat ttt acc ctg aca atc agc cga ctg gag     240
Gly Ser Gly Ser Gly Thr Asp Phe Thr Leu Thr Ile Ser Arg Leu Glu
65                  70                  75                  80 ccc gaa gac ttc gcc gtg tac tat tgc cag cag tat ggc tcc agc cct     288
Pro Glu Asp Phe Ala Val Tyr Tyr Cys Gln Gln Tyr Gly Ser Ser Pro
                85                  90                  95 aca ttt ggc gga ggg act aag gtc gag atc aaa cgg acc gtg gcc gct     336
Thr Phe Gly Gly Gly Thr Lys Val Glu Ile Lys Arg Thr Val Ala Ala
            100                 105                 110 ccc agc gtg ttc atc ttc cca ccc agc gac gag cag ctg aag tcc ggt     384
Pro Ser Val Phe Ile Phe Pro Pro Ser Asp Glu Gln Leu Lys Ser Gly
        115                 120                 125 acc gcc agc gtg gtg tgc ctg ctg aac aac ttc tac ccg cgg gag gcc     432
Thr Ala Ser Val Val Cys Leu Leu Asn Asn Phe Tyr Pro Arg Glu Ala
    130                 135                 140 aag gtg cag tgg aag gtg gac aac gcc ctg cag agc ggc aac tcc cag     480
Lys Val Gln Trp Lys Val Asp Asn Ala Leu Gln Ser Gly Asn Ser Gln
145                 150                 155                 160 gaa agc gtc acc gag cag gac agc aag gac tcc acc tac agc ctg agc     528
Glu Ser Val Thr Glu Gln Asp Ser Lys Asp Ser Thr Tyr Ser Leu Ser
                165                 170                 175 agc acc ctg acc ctg agc aag gcc gac tac gag aag cac aag gtg tac     576
Ser Thr Leu Thr Leu Ser Lys Ala Asp Tyr Glu Lys His Lys Val Tyr
            180                 185                 190 gcc tgc gaa gtg acc cac cag ggc ctg tcc agc ccc gtg acc aag agc     624
Ala Cys Glu Val Thr His Gln Gly Leu Ser Ser Pro Val Thr Lys Ser
        195                 200                 205 ttc aac cgg ggc gag tgt ggt ggc ggg ggt tcg ggt gga gga ggt tct     672
Phe Asn Arg Gly Glu Cys Gly Gly Gly Gly Ser Gly Gly Gly Gly Ser
    210                 215                 220 caa att gtt ctc acc cag tct cca gca atc atg tct gca tct cca ggg     720
Gln Ile Val Leu Thr Gln Ser Pro Ala Ile Met Ser Ala Ser Pro Gly
225                 230                 235                 240
```

```
gag aag gtc acc atg tcc tgc agt gcc agc tca agt gta aat tac atg      768
Glu Lys Val Thr Met Ser Cys Ser Ala Ser Ser Ser Val Asn Tyr Met
            245                 250                 255 cac tgg ttc cag cag aag tca ggc acc tcc ccc aaa cga tgg att tat      816
His Trp Phe Gln Gln Lys Ser Gly Thr Ser Pro Lys Arg Trp Ile Tyr
        260                 265                 270 gac aca tcc aaa ctg gct tct gga gtc cct gct cgc ttc agt ggc agt      864
Asp Thr Ser Lys Leu Ala Ser Gly Val Pro Ala Arg Phe Ser Gly Ser
    275                 280                 285 ggg tct ggg acc tct tac tct ctc aca atc acc gac atg gag gct gag      912
Gly Ser Gly Thr Ser Tyr Ser Leu Thr Ile Thr Asp Met Glu Ala Glu
290                 295                 300 gat gct gcc act tat tac tgc cag cag tgg aat agt cac cca ctc acg      960
Asp Ala Ala Thr Tyr Tyr Cys Gln Gln Trp Asn Ser His Pro Leu Thr
305                 310                 315                 320 ttc ggt gct ggg acc aag ctg gag ctg ata                              990
Phe Gly Ala Gly Thr Lys Leu Glu Leu Ile
                325                 330

<210> SEQ ID NO 114
<211> LENGTH: 330
<212> TYPE: PRT
<213> ORGANISM: Homo sapiens

<400> SEQUENCE: 114

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gln Ile Val Leu Thr Gln Ser Pro Ala Ile Met Ser Ala Ser Pro Gly
225                 230                 235                 240

Glu Lys Val Thr Met Ser Cys Ser Ala Ser Ser Ser Val Asn Tyr Met
```

```
                245                 250                 255
His Trp Phe Gln Gln Lys Ser Gly Thr Ser Pro Lys Arg Trp Ile Tyr
            260                 265                 270

Asp Thr Ser Lys Leu Ala Ser Gly Val Pro Ala Arg Phe Ser Gly Ser
            275                 280                 285

Gly Ser Gly Thr Ser Tyr Ser Leu Thr Ile Thr Asp Met Glu Ala Glu
        290                 295                 300

Asp Ala Ala Thr Tyr Tyr Cys Gln Gln Trp Asn Ser His Pro Leu Thr
305                 310                 315                 320

Phe Gly Ala Gly Thr Lys Leu Glu Leu Ile
                325                 330

<210> SEQ ID NO 115
<211> LENGTH: 1770
<212> TYPE: DNA
<213> ORGANISM: Homo sapiens
<220> FEATURE:
<221> NAME/KEY: CDS
<222> LOCATION: (1)..(1770)

<400> SEQUENCE: 115 gag gtc cag ctg caa cag tca gga cct gag ctg gtg aag cct ggg gct        48
Glu Val Gln Leu Gln Gln Ser Gly Pro Glu Leu Val Lys Pro Gly Ala
1               5                   10                  15 tca gtg aag ata tcc tgt aag act tct gga tac aca ttc aat gaa tac        96
Ser Val Lys Ile Ser Cys Lys Thr Ser Gly Tyr Thr Phe Asn Glu Tyr
                20                  25                  30 acc atg cac tgg gtg aag cag agc cat gga aag cgc ctt gag tgg att       144
Thr Met His Trp Val Lys Gln Ser His Gly Lys Arg Leu Glu Trp Ile
            35                  40                  45 gga ggt att aat cct aac agt ggt ggt gtt agc tac aac cag aac ttc       192
Gly Gly Ile Asn Pro Asn Ser Gly Gly Val Ser Tyr Asn Gln Asn Phe
        50                  55                  60 aag ggc aag gcc aca ttg act gta gac aag tcc tcc agc aca gcc tcc       240
Lys Gly Lys Ala Thr Leu Thr Val Asp Lys Ser Ser Ser Thr Ala Ser
65                  70                  75                  80 atg gag ctc cgc agc ctg aca tct gag gat tct gca gtc ttt tac tgt       288
Met Glu Leu Arg Ser Leu Thr Ser Glu Asp Ser Ala Val Phe Tyr Cys
                85                  90                  95 gca aga ggg gga gat ggt tac tac acc aat tac ttt gat att gac tac       336
Ala Arg Gly Gly Asp Gly Tyr Tyr Thr Asn Tyr Phe Asp Ile Asp Tyr
                100                 105                 110 tgg ggt caa gga acc tca gtc acc gtc tcc tca gcc tct acc aag ggc       384
Trp Gly Gln Gly Thr Ser Val Thr Val Ser Ser Ala Ser Thr Lys Gly
            115                 120                 125 ccc agc gtg ttc cct ctg gcc ccc agc agc aag agc aca agc gga ggc       432
Pro Ser Val Phe Pro Leu Ala Pro Ser Ser Lys Ser Thr Ser Gly Gly
        130                 135                 140 aca gcc gcc ctg ggc tgc ctg gtg aag gac tac ttc ccc gag ccc gtg       480
Thr Ala Ala Leu Gly Cys Leu Val Lys Asp Tyr Phe Pro Glu Pro Val
145                 150                 155                 160 aca gtg tcc tgg aac agc gga gcc ctg acc agc ggc gtg cac acc ttt       528
Thr Val Ser Trp Asn Ser Gly Ala Leu Thr Ser Gly Val His Thr Phe
                165                 170                 175 cca gcc gtg ctg cag agc agc ggc ctg tac agc ctg agc agc gtg gtg       576
Pro Ala Val Leu Gln Ser Ser Gly Leu Tyr Ser Leu Ser Ser Val Val
            180                 185                 190 acc gtg cct agc agc agc ctg ggc acc cag acc tac atc tgc aac gtg       624
Thr Val Pro Ser Ser Ser Leu Gly Thr Gln Thr Tyr Ile Cys Asn Val
        195                 200                 205
```

```
aac cac aag ccc agc aac acc aag gtg gac aag aag gtg gag ccc aag      672
Asn His Lys Pro Ser Asn Thr Lys Val Asp Lys Lys Val Glu Pro Lys
    210             215                 220 agc tgc ggt ggc ggg ggt tcg ggt gga gga ggt tct gag gaa cag ctg      720
Ser Cys Gly Gly Gly Gly Ser Gly Gly Gly Gly Ser Glu Glu Gln Leu
225                 230                 235                 240 gtc cag agc gga gct gag gtg aag aaa cca ggg gaa tct ctg aag atc      768
Val Gln Ser Gly Ala Glu Val Lys Lys Pro Gly Glu Ser Leu Lys Ile
                245                 250                 255 agt tgt aaa ggt tct ggc ttc agt ttt gac tca tat tgg att gga tgg      816
Ser Cys Lys Gly Ser Gly Phe Ser Phe Asp Ser Tyr Trp Ile Gly Trp
            260                 265                 270 gtg agg cag ctg cca gga aag ggg ctg gag tgg atg ggt atc att ctg      864
Val Arg Gln Leu Pro Gly Lys Gly Leu Glu Trp Met Gly Ile Ile Leu
        275                 280                 285 cca ggc aac agc gac acc cga tac tcc cct agc ttt cag ggc cag gtg      912
Pro Gly Asn Ser Asp Thr Arg Tyr Ser Pro Ser Phe Gln Gly Gln Val
    290                 295                 300 aca atc tct gct gat aag tct att agt act gcc tat ctg cag tgg agt      960
Thr Ile Ser Ala Asp Lys Ser Ile Ser Thr Ala Tyr Leu Gln Trp Ser
305                 310                 315                 320 tca ctg gag gca tct gat aca gcc atg tac tat tgc gcc cga cag gct     1008
Ser Leu Glu Ala Ser Asp Thr Ala Met Tyr Tyr Cys Ala Arg Gln Ala
                325                 330                 335 tac tat gac ctg ctg act ggt ccc ttc gat tac tgg ggt cag ggc acc     1056
Tyr Tyr Asp Leu Leu Thr Gly Pro Phe Asp Tyr Trp Gly Gln Gly Thr
            340                 345                 350 ctg gtc aca gtg tcc agc gag ccc aag agc agc gac aag acc cac acc     1104
Leu Val Thr Val Ser Ser Glu Pro Lys Ser Ser Asp Lys Thr His Thr
        355                 360                 365 tgt ccc cct tgt cct gcc cct gaa gcc gaa ggc gcg cct tcc gtg ttc     1152
Cys Pro Pro Cys Pro Ala Pro Glu Ala Glu Gly Ala Pro Ser Val Phe
    370                 375                 380 ctg ttc ccc cca aag ccc aag gac acc ctg atg atc agc cgg acc ccc     1200
Leu Phe Pro Pro Lys Pro Lys Asp Thr Leu Met Ile Ser Arg Thr Pro
385                 390                 395                 400 gaa gtg acc tgc gtg gtg gtg gac gtg tcc cac gag gac cct gaa gtg     1248
Glu Val Thr Cys Val Val Val Asp Val Ser His Glu Asp Pro Glu Val
                405                 410                 415 aag ttc aat tgg tac gtg gac ggc gtg gag gtg cac aac gcc aag acc     1296
Lys Phe Asn Trp Tyr Val Asp Gly Val Glu Val His Asn Ala Lys Thr
            420                 425                 430 aag ccc cgg gag gaa cag tac aac agc acc tac cgg gtg gtg tcc gtg     1344
Lys Pro Arg Glu Glu Gln Tyr Asn Ser Thr Tyr Arg Val Val Ser Val
        435                 440                 445 ctg acc gtg ctg cac cag gac tgg ctg aac ggc aaa gag tac aag tgc     1392
Leu Thr Val Leu His Gln Asp Trp Leu Asn Gly Lys Glu Tyr Lys Cys
    450                 455                 460 aag gtc tcc aac aag gcc ctg ccc agc agc atc gag aaa acc atc agc     1440
Lys Val Ser Asn Lys Ala Leu Pro Ser Ser Ile Glu Lys Thr Ile Ser
465                 470                 475                 480 aag gcc aag ggc cag ccc aga gaa ccc cag gtg tac acc ctg ccc cct     1488
Lys Ala Lys Gly Gln Pro Arg Glu Pro Gln Val Tyr Thr Leu Pro Pro
                485                 490                 495 agc agg gac gag ctg acc aag aac cag gtg tcc ctg acc tgt ctg gtg     1536
Ser Arg Asp Glu Leu Thr Lys Asn Gln Val Ser Leu Thr Cys Leu Val
            500                 505                 510 aag ggc ttc tac ccc agc gat atc gcc gtg gag tgg gag agc aac ggc     1584
Lys Gly Phe Tyr Pro Ser Asp Ile Ala Val Glu Trp Glu Ser Asn Gly
```

-continued

```
                515                 520                 525
cag ccc gaa aac aac tac aag acc acc ccc cct gtg ctg gac agc gac       1632
Gln Pro Glu Asn Asn Tyr Lys Thr Thr Pro Pro Val Leu Asp Ser Asp
    530                 535                 540 ggc agc ttc ttc ctg tac tcc aaa ctg acc gtg gac aag agc cgg tgg       1680
Gly Ser Phe Phe Leu Tyr Ser Lys Leu Thr Val Asp Lys Ser Arg Trp
545                 550                 555                 560 cag cag ggc aac gtg ttc agc tgc agc gtg atg cac gag gcc ctg cac       1728
Gln Gln Gly Asn Val Phe Ser Cys Ser Val Met His Glu Ala Leu His
            565                 570                 575 aac cac tac acc cag aag tcc ctg agc ctg agc ccc ggc aag               1770
Asn His Tyr Thr Gln Lys Ser Leu Ser Leu Ser Pro Gly Lys
        580                 585                 590
```

<210> SEQ ID NO 116
<211> LENGTH: 590
<212> TYPE: PRT
<213> ORGANISM: Homo sapiens

<400> SEQUENCE: 116

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Asn Glu Tyr
            20                  25                  30

Thr Met His Trp Val Lys Gln Ser His Gly Lys Arg Leu Glu Trp Ile
        35                  40                  45

Gly Gly Ile Asn Pro Asn Ser Gly Val Ser Tyr Asn Gln Asn Phe
    50                  55                  60

Lys Gly Lys Ala Thr Leu Thr Val Asp Lys Ser Ser Thr Ala Ser
65                  70                  75                  80

Met Glu Leu Arg Ser Leu Thr Ser Glu Asp Ser Ala Val Phe Tyr Cys
                85                  90                  95

Ala Arg Gly Gly Asp Gly Tyr Tyr Thr Asn Tyr Phe Asp Ile Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Gly Gly Gly Ser Gly Gly Gly Ser Glu Glu Gln Leu
225                 230                 235                 240

Val Gln Ser Gly Ala Glu Val Lys Lys Pro Gly Glu Ser Leu Lys Ile
                245                 250                 255

Ser Cys Lys Gly Ser Gly Phe Ser Phe Asp Ser Tyr Trp Ile Gly Trp
            260                 265                 270

Val Arg Gln Leu Pro Gly Lys Gly Leu Glu Trp Met Gly Ile Ile Leu
        275                 280                 285
```

```
Pro Gly Asn Ser Asp Thr Arg Tyr Ser Pro Ser Phe Gln Gly Gln Val
    290                 295                 300

Thr Ile Ser Ala Asp Lys Ser Ile Ser Thr Ala Tyr Leu Gln Trp Ser
305                 310                 315                 320

Ser Leu Glu Ala Ser Asp Thr Ala Met Tyr Tyr Cys Ala Arg Gln Ala
                325                 330                 335

Tyr Tyr Asp Leu Leu Thr Gly Pro Phe Asp Tyr Trp Gly Gln Gly Thr
            340                 345                 350

Leu Val Thr Val Ser Ser Glu Pro Lys Ser Ser Asp Lys Thr His Thr
        355                 360                 365

Cys Pro Pro Cys Pro Ala Pro Glu Ala Glu Gly Ala Pro Ser Val Phe
    370                 375                 380

Leu Phe Pro Pro Lys Pro Lys Asp Thr Leu Met Ile Ser Arg Thr Pro
385                 390                 395                 400

Glu Val Thr Cys Val Val Val Asp Val Ser His Glu Asp Pro Glu Val
                405                 410                 415

Lys Phe Asn Trp Tyr Val Asp Gly Val Glu Val His Asn Ala Lys Thr
            420                 425                 430

Lys Pro Arg Glu Glu Gln Tyr Asn Ser Thr Tyr Arg Val Val Ser Val
        435                 440                 445

Leu Thr Val Leu His Gln Asp Trp Leu Asn Gly Lys Glu Tyr Lys Cys
    450                 455                 460

Lys Val Ser Asn Lys Ala Leu Pro Ser Ser Ile Glu Lys Thr Ile Ser
465                 470                 475                 480

Lys Ala Lys Gly Gln Pro Arg Glu Pro Gln Val Tyr Thr Leu Pro Pro
                485                 490                 495

Ser Arg Asp Glu Leu Thr Lys Asn Gln Val Ser Leu Thr Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
    530                 535                 540

Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys
            580                 585                 590

<210> SEQ ID NO 117
<211> LENGTH: 990
<212> TYPE: DNA
<213> ORGANISM: Homo sapiens
<220> FEATURE:
<221> NAME/KEY: CDS
<222> LOCATION: (1)..(990)

<400> SEQUENCE: 117 caa att gtt ctc acc cag tct cca gca atc atg tct gca tct ccc ggg    48
Gln Ile Val Leu Thr Gln Ser Pro Ala Ile Met Ser Ala Ser Pro Gly
1               5                   10                  15 gag aag gtc acc atg tcc tgc agt gcc agc tca agt gta aat tac atg    96
Glu Lys Val Thr Met Ser Cys Ser Ala Ser Ser Ser Val Asn Tyr Met
            20                  25                  30 cac tgg ttc cag cag aag tca ggc acc tcc ccc aaa cga tgg att tat   144
His Trp Phe Gln Gln Lys Ser Gly Thr Ser Pro Lys Arg Trp Ile Tyr
```

```
                35                  40                  45
gac aca tcc aaa ctg gct tct gga gtc cct gct cgc ttc agt ggc agt        192
Asp Thr Ser Lys Leu Ala Ser Gly Val Pro Ala Arg Phe Ser Gly Ser
     50                  55                  60 ggg tct ggg acc tct tac tct ctc aca atc acc gac atg gag gct gag        240
Gly Ser Gly Thr Ser Tyr Ser Leu Thr Ile Thr Asp Met Glu Ala Glu
 65                  70                  75                  80 gat gct gcc act tat tac tgc cag cag tgg aat agt cac cca ctc acg        288
Asp Ala Ala Thr Tyr Tyr Cys Gln Gln Trp Asn Ser His Pro Leu Thr
                 85                  90                  95 ttc ggt gct ggg acc aag ctg gag ctg ata cgg acc gtg gcc gct ccc        336
Phe Gly Ala Gly Thr Lys Leu Glu Leu Ile Arg Thr Val Ala Ala Pro
            100                 105                 110 agc gtg ttc atc ttc cca ccc agc gac gag cag ctg aag tcc ggt acc        384
Ser Val Phe Ile Phe Pro Pro Ser Asp Glu Gln Leu Lys Ser Gly Thr
        115                 120                 125 gcc agc gtg gtg tgc ctg ctg aac aac ttc tac ccg cgg gag gcc aag        432
Ala Ser Val Val Cys Leu Leu Asn Asn Phe Tyr Pro Arg Glu Ala Lys
130                 135                 140 gtg cag tgg aag gtg gac aac gcc ctg cag agc ggc aac tcc cag gaa        480
Val Gln Trp Lys Val Asp Asn Ala Leu Gln Ser Gly Asn Ser Gln Glu
145                 150                 155                 160 agc gtc acc gag cag gac agc aag gac tcc acc tac agc ctg agc agc        528
Ser Val Thr Glu Gln Asp Ser Lys Asp Ser Thr Tyr Ser Leu Ser Ser
                165                 170                 175 acc ctg acc ctg agc aag gcc gac tac gag aag cac aag gtg tac gcc        576
Thr Leu Thr Leu Ser Lys Ala Asp Tyr Glu Lys His Lys Val Tyr Ala
            180                 185                 190 tgc gaa gtg acc cac cag ggc ctg tcc agc ccc gtg acc aag agc ttc        624
Cys Glu Val Thr His Gln Gly Leu Ser Ser Pro Val Thr Lys Ser Phe
        195                 200                 205 aac cgg ggc gag tgt ggt ggc ggg ggt tcg ggt gga gga ggt tct gag        672
Asn Arg Gly Glu Cys Gly Gly Gly Gly Ser Gly Gly Gly Gly Ser Glu
    210                 215                 220 att gtc ctg acc cag agc cct ggg aca ctg agc ctg tct cca ggc gag        720
Ile Val Leu Thr Gln Ser Pro Gly Thr Leu Ser Leu Ser Pro Gly Glu
225                 230                 235                 240 agg gct act ctg tcc tgc cgg gca agt cag tca gtg tcc agc tct tac        768
Arg Ala Thr Leu Ser Cys Arg Ala Ser Gln Ser Val Ser Ser Ser Tyr
                245                 250                 255 ctg gcc tgg tat cag cag aag cca ggg cag gct ccc aga ctg ctg atc        816
Leu Ala Trp Tyr Gln Gln Lys Pro Gly Gln Ala Pro Arg Leu Leu Ile
            260                 265                 270 tac ggc gca agt tca aga gcc acc ggc atc ccc gac cgc ttc tcc ggt        864
Tyr Gly Ala Ser Ser Arg Ala Thr Gly Ile Pro Asp Arg Phe Ser Gly
        275                 280                 285 agc ggc tct gga aca gat ttt acc ctg aca atc agc cga ctg gag ccc        912
Ser Gly Ser Gly Thr Asp Phe Thr Leu Thr Ile Ser Arg Leu Glu Pro
    290                 295                 300 gaa gac ttc gcc gtg tac tat tgc cag cag tat ggc tcc agc cct aca        960
Glu Asp Phe Ala Val Tyr Tyr Cys Gln Gln Tyr Gly Ser Ser Pro Thr
305                 310                 315                 320 ttt ggc gga ggg act aag gtc gag atc aaa                                990
Phe Gly Gly Gly Thr Lys Val Glu Ile Lys
                325                 330

<210> SEQ ID NO 118
<211> LENGTH: 330
<212> TYPE: PRT
<213> ORGANISM: Homo sapiens
```

<400> SEQUENCE: 118

Gln Ile Val Leu Thr Gln Ser Pro Ala Ile Met Ser Ala Ser Pro Gly
1               5                   10                  15

Glu Lys Val Thr Met Ser Cys Ser Ala Ser Ser Val Asn Tyr Met
            20                  25                  30

His Trp Phe Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Thr Asp Met Glu Ala Glu
65                  70                  75                  80

Asp Ala Ala Thr Tyr Tyr Cys Gln Gln Trp Asn Ser His Pro Leu Thr
                85                  90                  95

Phe Gly Ala Gly Thr Lys Leu Glu Leu Ile Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser Gly Gly Gly Ser Glu
    210                 215                 220

Ile Val Leu Thr Gln Ser Pro Gly Thr Leu Ser Leu Ser Pro Gly Glu
225                 230                 235                 240

Arg Ala Thr Leu Ser Cys Arg Ala Ser Gln Ser Val Ser Ser Ser Tyr
                245                 250                 255

Leu Ala Trp Tyr Gln Gln Lys Pro Gly Gln Ala Pro Arg Leu Leu Ile
            260                 265                 270

Tyr Gly Ala Ser Ser Arg Ala Thr Gly Ile Pro Asp Arg Phe Ser Gly
        275                 280                 285

Ser Gly Ser Gly Thr Asp Phe Thr Leu Thr Ile Ser Arg Leu Glu Pro
    290                 295                 300

Glu Asp Phe Ala Val Tyr Tyr Cys Gln Gln Tyr Gly Ser Ser Pro Thr
305                 310                 315                 320

Phe Gly Gly Gly Thr Lys Val Glu Ile Lys
                325                 330

<210> SEQ ID NO 119
<211> LENGTH: 1776
<212> TYPE: DNA
<213> ORGANISM: Homo sapiens
<220> FEATURE:
<221> NAME/KEY: CDS
<222> LOCATION: (1)..(1776)

<400> SEQUENCE: 119 cag atc cag ttg gtg cag tct gga cct gag ctg aag aag cct gga gag    48
Gln Ile Gln Leu Val Gln Ser Gly Pro Glu Leu Lys Lys Pro Gly Glu

```
                1               5                     10                      15
       aca gtc gag atc tcc tgc aag gct tct ggt tat acc ttc aca gac tat        96
       Thr Val Glu Ile Ser Cys Lys Ala Ser Gly Tyr Thr Phe Thr Asp Tyr
                        20                    25                  30 tta ata ttc tgg gtg aag cag gct cca gga aag ggt tta aac tgg atg       144
       Leu Ile Phe Trp Val Lys Gln Ala Pro Gly Lys Gly Leu Asn Trp Met
                    35                    40                  45 ggc tgg ata aac act gag act gtt gag cct aca tat gca gat gac ttc       192
       Gly Trp Ile Asn Thr Glu Thr Val Glu Pro Thr Tyr Ala Asp Asp Phe
               50                    55                  60 aag gga cga ttt gcc ttc tct ttg gaa acc tct gcc agc act gcc cat       240
       Lys Gly Arg Phe Ala Phe Ser Leu Glu Thr Ser Ala Ser Thr Ala His
       65                    70                  75                      80 ttg ctg atc aac aac ctc aaa aaa gag gac acg tct aca tac ttc tgt       288
       Leu Leu Ile Asn Asn Leu Lys Lys Glu Asp Thr Ser Thr Tyr Phe Cys
                            85                  90                  95 gca aga gtc cct cac ctc ggg ccc tat tat tat gct atg gac tac tgg       336
       Ala Arg Val Pro His Leu Gly Pro Tyr Tyr Tyr Ala Met Asp Tyr Trp
                        100                 105                 110 ggt caa gga acc tca gtc acc gtc tct tca gcc tct acc aag ggc ccc       384
       Gly Gln Gly Thr Ser Val Thr Val Ser Ser Ala Ser Thr Lys Gly Pro
                    115                 120                 125 agc gtg ttc cct ctg gcc ccc agc agc aag agc aca agc gga ggc aca       432
       Ser Val Phe Pro Leu Ala Pro Ser Ser Lys Ser Thr Ser Gly Gly Thr
               130                 135                 140 gcc gcc ctg ggc tgc ctg gtg aag gac tac ttc ccc gag ccc gtg aca       480
       Ala Ala Leu Gly Cys Leu Val Lys Asp Tyr Phe Pro Glu Pro Val Thr
       145                 150                 155                     160 gtg tcc tgg aac agc gga gcc ctg acc agc ggc gtg cac acc ttt cca       528
       Val Ser Trp Asn Ser Gly Ala Leu Thr Ser Gly Val His Thr Phe Pro
                            165                 170                 175 gcc gtg ctg cag agc agc ggc ctg tac agc ctg agc agc gtg gtg acc       576
       Ala Val Leu Gln Ser Ser Gly Leu Tyr Ser Leu Ser Ser Val Val Thr
                        180                 185                 190 gtg cct agc agc agc ctg ggc acc cag acc tac atc tgc aac gtg aac       624
       Val Pro Ser Ser Ser Leu Gly Thr Gln Thr Tyr Ile Cys Asn Val Asn
                    195                 200                 205 cac aag ccc agc aac acc aag gtg gac aag aag gtg gag ccc aag agc       672
       His Lys Pro Ser Asn Thr Lys Val Asp Lys Lys Val Glu Pro Lys Ser
               210                 215                 220 tgc ggt ggc ggg ggt tcg ggt gga gga ggt tct cag gtt act ctg aaa       720
       Cys Gly Gly Gly Gly Ser Gly Gly Gly Gly Ser Gln Val Thr Leu Lys
       225                 230                 235                     240 gag tct ggc cct ggg ata ttg cag ccc tcc cag acc ctc agt ctg act       768
       Glu Ser Gly Pro Gly Ile Leu Gln Pro Ser Gln Thr Leu Ser Leu Thr
                            245                 250                 255 tgt tct ttc tct ggg ttt tca ctg agc act tct ggt atg ggt gta ggc       816
       Cys Ser Phe Ser Gly Phe Ser Leu Ser Thr Ser Gly Met Gly Val Gly
                        260                 265                 270 tgg att cgt cag cct tca ggg aag ggt ctg gag tgg ctg gca aac att       864
       Trp Ile Arg Gln Pro Ser Gly Lys Gly Leu Glu Trp Leu Ala Asn Ile
                    275                 280                 285 tgg tgg gat gat gac aag cgc tat aac cca gcc ctg aag agc cga ctg       912
       Trp Trp Asp Asp Asp Lys Arg Tyr Asn Pro Ala Leu Lys Ser Arg Leu
               290                 295                 300 aca atc tcc aag gac acc tcc agc aac cag gtt ttc ctc aag att gcc       960
       Thr Ile Ser Lys Asp Thr Ser Ser Asn Gln Val Phe Leu Lys Ile Ala
       305                 310                 315                     320 agt gtg gac act gca gat act gcc aca tac tac tgt gct cga ata gac      1008
       Ser Val Asp Thr Ala Asp Thr Ala Thr Tyr Tyr Cys Ala Arg Ile Asp
```

```
                Ser Val Asp Thr Ala Asp Thr Ala Thr Tyr Tyr Cys Ala Arg Ile Asp
                                325                 330                 335 tat gat tac gac agg ggg gcc tac cat gtt atg gac tac tgg ggt caa             1056
Tyr Asp Tyr Asp Arg Gly Ala Tyr His Val Met Asp Tyr Trp Gly Gln
                340                 345                 350 ggc acc tca gtc acc gtc tcc tca gag ccc aag agc agc gac aag acc             1104
Gly Thr Ser Val Thr Val Ser Ser Glu Pro Lys Ser Ser Asp Lys Thr
                355                 360                 365 cac acc tgt ccc cct tgt cct gcc cct gaa gcc gaa ggc gcg cct tcc             1152
His Thr Cys Pro Pro Cys Pro Ala Pro Glu Ala Glu Gly Ala Pro Ser
370                 375                 380 gtg ttc ctg ttc ccc cca aag ccc aag gac acc ctg atg atc agc cgg             1200
Val Phe Leu Phe Pro Pro Lys Pro Lys Asp Thr Leu Met Ile Ser Arg
385                 390                 395                 400 acc ccc gaa gtg acc tgc gtg gtg gtg gac gtg tcc cac gag gac cct             1248
Thr Pro Glu Val Thr Cys Val Val Val Asp Val Ser His Glu Asp Pro
                405                 410                 415 gaa gtg aag ttc aat tgg tac gtg gac ggc gtg gag gtg cac aac gcc             1296
Glu Val Lys Phe Asn Trp Tyr Val Asp Gly Val Glu Val His Asn Ala
                420                 425                 430 aag acc aag ccc cgg gag gaa cag tac aac agc acc tac cgg gtg gtg             1344
Lys Thr Lys Pro Arg Glu Glu Gln Tyr Asn Ser Thr Tyr Arg Val Val
                435                 440                 445 tcc gtg ctg acc gtg ctg cac cag gac tgg ctg aac ggc aaa gag tac             1392
Ser Val Leu Thr Val Leu His Gln Asp Trp Leu Asn Gly Lys Glu Tyr
450                 455                 460 aag tgc aag gtc tcc aac aag gcc ctg ccc agc agc atc gag aaa acc             1440
Lys Cys Lys Val Ser Asn Lys Ala Leu Pro Ser Ser Ile Glu Lys Thr
465                 470                 475                 480 atc agc aag gcc aag ggc cag ccc aga gaa ccc cag gtg tac acc ctg             1488
Ile Ser Lys Ala Lys Gly Gln Pro Arg Glu Pro Gln Val Tyr Thr Leu
                485                 490                 495 ccc cct agc agg gac gag ctg acc aag aac cag gtg tcc ctg acc tgt             1536
Pro Pro Ser Arg Asp Glu Leu Thr Lys Asn Gln Val Ser Leu Thr Cys
                500                 505                 510 ctg gtg aag ggc ttc tac ccc agc gat atc gcc gtg gag tgg gag agc             1584
Leu Val Lys Gly Phe Tyr Pro Ser Asp Ile Ala Val Glu Trp Glu Ser
                515                 520                 525 aac ggc cag ccc gaa aac aac tac aag acc acc ccc cct gtg ctg gac             1632
Asn Gly Gln Pro Glu Asn Asn Tyr Lys Thr Thr Pro Pro Val Leu Asp
530                 535                 540 agc gac ggc agc ttc ttc ctg tac tcc aaa ctg acc gtg gac aag agc             1680
Ser Asp Gly Ser Phe Phe Leu Tyr Ser Lys Leu Thr Val Asp Lys Ser
545                 550                 555                 560 cgg tgg cag cag ggc aac gtg ttc agc tgc agc gtg atg cac gag gcc             1728
Arg Trp Gln Gln Gly Asn Val Phe Ser Cys Ser Val Met His Glu Ala
                565                 570                 575 ctg cac aac cac tac acc cag aag tcc ctg agc ctg agc ccc ggc aag             1776
Leu His Asn His Tyr Thr Gln Lys Ser Leu Ser Leu Ser Pro Gly Lys
                580                 585                 590

<210> SEQ ID NO 120
<211> LENGTH: 592
<212> TYPE: PRT
<213> ORGANISM: Homo sapiens

<400> SEQUENCE: 120

Gln Ile Gln Leu Val Gln Ser Gly Pro Glu Leu Lys Lys Pro Gly Glu
1               5                   10                  15

Thr Val Glu Ile Ser Cys Lys Ala Ser Gly Tyr Thr Phe Thr Asp Tyr
```

-continued

```
            20                  25                  30
Leu Ile Phe Trp Val Lys Gln Ala Pro Gly Lys Gly Leu Asn Trp Met
        35                  40                  45
Gly Trp Ile Asn Thr Glu Thr Val Glu Pro Thr Tyr Ala Asp Asp Phe
 50                  55                  60
Lys Gly Arg Phe Ala Phe Ser Leu Glu Thr Ser Ala Ser Thr Ala His
 65                  70                  75                  80
Leu Leu Ile Asn Asn Leu Lys Lys Glu Asp Thr Ser Thr Tyr Phe Cys
                85                  90                  95
Ala Arg Val Pro His Leu Gly Pro Tyr Tyr Ala Met Asp Tyr Trp
            100                 105                 110
Gly Gln Gly Thr Ser Val Thr Val Ser Ser Ala Ser Thr Lys Gly Pro
            115                 120                 125
Ser Val Phe Pro Leu Ala Pro Ser Ser Lys Ser Thr Ser Gly Gly Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Lys Val Glu Pro Lys Ser
    210                 215                 220
Cys Gly Gly Gly Gly Ser Gly Gly Gly Gly Ser Gln Val Thr Leu Lys
225                 230                 235                 240
Glu Ser Gly Pro Gly Ile Leu Gln Pro Ser Gln Thr Leu Ser Leu Thr
                245                 250                 255
Cys Ser Phe Ser Gly Phe Ser Leu Ser Thr Ser Gly Met Gly Val Gly
            260                 265                 270
Trp Ile Arg Gln Pro Ser Gly Lys Gly Leu Glu Trp Leu Ala Asn Ile
        275                 280                 285
Trp Trp Asp Asp Asp Lys Arg Tyr Asn Pro Ala Leu Lys Ser Arg Leu
        290                 295                 300
Thr Ile Ser Lys Asp Thr Ser Ser Asn Gln Val Phe Leu Lys Ile Ala
305                 310                 315                 320
Ser Val Asp Thr Ala Asp Thr Ala Thr Tyr Tyr Cys Ala Arg Ile Asp
                325                 330                 335
Tyr Asp Tyr Asp Arg Gly Ala Tyr His Val Met Asp Tyr Trp Gly Gln
            340                 345                 350
Gly Thr Ser Val Thr Val Ser Ser Glu Pro Lys Ser Ser Asp Lys Thr
            355                 360                 365
His Thr Cys Pro Pro Cys Pro Ala Pro Glu Ala Glu Gly Ala Pro Ser
    370                 375                 380
Val Phe Leu Phe Pro Pro Lys Pro Lys Asp Thr Leu Met Ile Ser Arg
385                 390                 395                 400
Thr Pro Glu Val Thr Cys Val Val Val Asp Val Ser His Glu Asp Pro
                405                 410                 415
Glu Val Lys Phe Asn Trp Tyr Val Asp Gly Val Glu Val His Asn Ala
            420                 425                 430
Lys Thr Lys Pro Arg Glu Glu Gln Tyr Asn Ser Thr Tyr Arg Val Val
            435                 440                 445
```

Ser Val Leu Thr Val Leu His Gln Asp Trp Leu Asn Gly Lys Glu Tyr
    450                 455                 460

Lys Cys Lys Val Ser Asn Lys Ala Leu Pro Ser Ser Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590

<210> SEQ ID NO 121
<211> LENGTH: 1005
<212> TYPE: DNA
<213> ORGANISM: Homo sapiens
<220> FEATURE:
<221> NAME/KEY: CDS
<222> LOCATION: (1)..(1005)

<400> SEQUENCE: 121

```
gac att gtg ctg aaa cag tct cct gct tcc tta ggt gtg gct ctg ggg      48
Asp Ile Val Leu Lys Gln Ser Pro Ala Ser Leu Gly Val Ala Leu Gly
1               5                   10                  15 cag agg gcc acc atc tca tgc agg gcc agc aaa agt gtc agt aca tct      96
Gln Arg Ala Thr Ile Ser Cys Arg Ala Ser Lys Ser Val Ser Thr Ser
            20                  25                  30 gac ttt agt tat atg cac tgg tat caa cag aaa cca ggg cag cca ccc     144
Asp Phe Ser Tyr Met His Trp Tyr Gln Gln Lys Pro Gly Gln Pro Pro
        35                  40                  45 gaa ctc ctc atc tac ctt gca tcc aac ctc gaa tct ggg gtc cct gcc     192
Glu Leu Leu Ile Tyr Leu Ala Ser Asn Leu Glu Ser Gly Val Pro Ala
    50                  55                  60 agg ttc agt ggc agt ggg tct ggg aca gac ttc acc ctc aac atc cat     240
Arg Phe Ser Gly Ser Gly Ser Gly Thr Asp Phe Thr Leu Asn Ile His
65                  70                  75                  80 cct gtg gag gag gag gat gct gca acc tat tac tgt cag cac agt agg     288
Pro Val Glu Glu Glu Asp Ala Ala Thr Tyr Tyr Cys Gln His Ser Arg
                85                  90                  95 gaa ttt cct ccc aca ttc ggt gct ggg acc aaa ctg gag ctg aaa cgg     336
Glu Phe Pro Pro Thr Phe Gly Ala Gly Thr Lys Leu Glu Leu Lys Arg
            100                 105                 110 acc gtg gcc gct ccc agc gtg ttc atc ttc cca ccc agc gac gag cag     384
Thr Val Ala Ala Pro Ser Val Phe Ile Phe Pro Pro Ser Asp Glu Gln
        115                 120                 125 ctg aag tcc ggt acc gcc agc gtg gtg tgc ctg ctg aac aac ttc tac     432
Leu Lys Ser Gly Thr Ala Ser Val Val Cys Leu Leu Asn Asn Phe Tyr
    130                 135                 140 ccg cgg gag gcc aag gtg cag tgg aag gtg gac aac gcc ctg cag agc     480
Pro Arg Glu Ala Lys Val Gln Trp Lys Val Asp Asn Ala Leu Gln Ser
145                 150                 155                 160
```

```
ggc aac tcc cag gaa agc gtc acc gag cag gac agc aag gac tcc acc       528
Gly Asn Ser Gln Glu Ser Val Thr Glu Gln Asp Ser Lys Asp Ser Thr
            165                 170                 175 tac agc ctg agc agc acc ctg acc ctg agc aag gcc gac tac gag aag       576
Tyr Ser Leu Ser Ser Thr Leu Thr Leu Ser Lys Ala Asp Tyr Glu Lys
        180                 185                 190 cac aag gtg tac gcc tgc gaa gtg acc cac cag ggc ctg tcc agc ccc       624
His Lys Val Tyr Ala Cys Glu Val Thr His Gln Gly Leu Ser Ser Pro
    195                 200                 205 gtg acc aag agc ttc aac cgg ggc gag tgt ggt ggc ggg ggt tcg ggt       672
Val Thr Lys Ser Phe Asn Arg Gly Glu Cys Gly Gly Gly Gly Ser Gly
210                 215                 220 gga ggt ggt tct gac atc cag atg act cag tct cca gcc tcc cta tct      720
Gly Gly Gly Ser Asp Ile Gln Met Thr Gln Ser Pro Ala Ser Leu Ser
225                 230                 235                 240 gta tct gtg gga gaa act gtc acc atc aca tgt cgg aca agt gag aat      768
Val Ser Val Gly Glu Thr Val Thr Ile Thr Cys Arg Thr Ser Glu Asn
            245                 250                 255 att ttc agt aat tta gca tgg tat caa cag aaa cag gga aaa tct ccc      816
Ile Phe Ser Asn Leu Ala Trp Tyr Gln Gln Lys Gln Gly Lys Ser Pro
        260                 265                 270 cag ctc ctg gtc tat gat gca aca aac tta gca gat ggt gtt cca tca      864
Gln Leu Leu Val Tyr Asp Ala Thr Asn Leu Ala Asp Gly Val Pro Ser
    275                 280                 285 agg ttc agt ggc agt gga tca ggc aca cag tat tcc ctc aag atc aac      912
Arg Phe Ser Gly Ser Gly Ser Gly Thr Gln Tyr Ser Leu Lys Ile Asn
290                 295                 300 agc ctg cag tct gaa gat ttt ggg act tat tac tgt caa cat ttt tgg      960
Ser Leu Gln Ser Glu Asp Phe Gly Thr Tyr Tyr Cys Gln His Phe Trp
305                 310                 315                 320 tat act ccg tgg acg ttc ggt gga ggc acc aag ctg gaa atc aaa         1005
Tyr Thr Pro Trp Thr Phe Gly Gly Gly Thr Lys Leu Glu Ile Lys
            325                 330                 335

<210> SEQ ID NO 122
<211> LENGTH: 335
<212> TYPE: PRT
<213> ORGANISM: Homo sapiens

<400> SEQUENCE: 122

Asp Ile Val Leu Lys Gln Ser Pro Ala Ser Leu Gly Val Ala Leu Gly
1               5                   10                  15

Gln Arg Ala Thr Ile Ser Cys Arg Ala Ser Lys Ser Val Ser Thr Ser
            20                  25                  30

Asp Phe Ser Tyr Met His Trp Tyr Gln Gln Lys Pro Gly Gln Pro Pro
        35                  40                  45

Glu Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Pro Thr Phe Gly Ala Gly Thr Lys Leu Glu Leu Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Gly
210                 215                 220

Gly Gly Gly Ser Asp Ile Gln Met Thr Gln Ser Pro Ala Ser Leu Ser
225                 230                 235                 240

Val Ser Val Gly Glu Thr Val Thr Ile Thr Cys Arg Thr Ser Glu Asn
            245                 250                 255

Ile Phe Ser Asn Leu Ala Trp Tyr Gln Gln Lys Gln Gly Lys Ser Pro
            260                 265                 270

Gln Leu Leu Val Tyr Asp Ala Thr Asn Leu Ala Asp Gly Val Pro Ser
        275                 280                 285

Arg Phe Ser Gly Ser Gly Ser Gly Thr Gln Tyr Ser Leu Lys Ile Asn
    290                 295                 300

Ser Leu Gln Ser Glu Asp Phe Gly Thr Tyr Tyr Cys Gln His Phe Trp
305                 310                 315                 320

Tyr Thr Pro Trp Thr Phe Gly Gly Gly Thr Lys Leu Glu Ile Lys
            325                 330                 335

<210> SEQ ID NO 123
<211> LENGTH: 1737
<212> TYPE: DNA
<213> ORGANISM: Homo sapiens
<220> FEATURE:
<221> NAME/KEY: CDS
<222> LOCATION: (1)..(1737)

<400> SEQUENCE: 123 gaa gtg cag ctg gtg gag tct ggg gga ggc tta gtg aag cct gga ggg      48
Glu Val Gln Leu Val Glu Ser Gly Gly Gly Leu Val Lys Pro Gly Gly
1               5                   10                  15 tcc ctg aaa ctc tcc tgt gca gcc tct gga ttc gct ttc agt agc tat      96
Ser Leu Lys Leu Ser Cys Ala Ala Ser Gly Phe Ala Phe Ser Ser Tyr
            20                  25                  30 gcc atg tct tgg gtt cgc cag agt ccg gaa aag agg ctg gag tgg gtc     144
Ala Met Ser Trp Val Arg Gln Ser Pro Glu Lys Arg Leu Glu Trp Val
        35                  40                  45 gca acc att agc agt ggt ggt cat tac acc ttc tat cca gac agt gtg     192
Ala Thr Ile Ser Ser Gly Gly His Tyr Thr Phe Tyr Pro Asp Ser Val
    50                  55                  60 aag ggt cgc ttc acc atc tcc aga gac aat gcc aag aac acc ctg tac     240
Lys Gly Arg Phe Thr Ile Ser Arg Asp Asn Ala Lys Asn Thr Leu Tyr
65                  70                  75                  80 ctg caa atg agc agt ctg agg tct gag gac acg gcc att tat tac tgt     288
Leu Gln Met Ser Ser Leu Arg Ser Glu Asp Thr Ala Ile Tyr Tyr Cys
                85                  90                  95 gca aga cgt tac tat gct ctg gac tac tgg ggt caa gga acc tca gtc     336
Ala Arg Arg Tyr Tyr Ala Leu Asp Tyr Trp Gly Gln Gly Thr Ser Val
            100                 105                 110 acc gtc tcc tca gcc tct acc aag ggc ccc agc gtg ttc cct ctg gcc     384
Thr Val Ser Ser Ala Ser Thr Lys Gly Pro Ser Val Phe Pro Leu Ala
        115                 120                 125
```

-continued

| | | |
|---|---|---|
| ccc agc agc aag agc aca agc gga ggc aca gcc gcc ctg ggc tgc ctg<br>Pro Ser Ser Lys Ser Thr Ser Gly Gly Thr Ala Ala Leu Gly Cys Leu<br>130                       135                   140 | 432 |

```
ccc agc agc aag agc aca agc gga ggc aca gcc gcc ctg ggc tgc ctg      432
Pro Ser Ser Lys Ser Thr Ser Gly Gly Thr Ala Ala Leu Gly Cys Leu
            130             135             140 gtg aag gac tac ttc ccc gag ccc gtg aca gtg tcc tgg aac agc gga      480
Val Lys Asp Tyr Phe Pro Glu Pro Val Thr Val Ser Trp Asn Ser Gly
145             150             155             160 gcc ctg acc agc ggc gtg cac acc ttt cca gcc gtg ctg cag agc agc      528
Ala Leu Thr Ser Gly Val His Thr Phe Pro Ala Val Leu Gln Ser Ser
                165             170             175 ggc ctg tac agc ctg agc agc gtg gtg acc gtg cct agc agc agc ctg      576
Gly Leu Tyr Ser Leu Ser Ser Val Val Thr Val Pro Ser Ser Ser Leu
            180             185             190 ggc acc cag acc tac atc tgc aac gtg aac cac aag ccc agc aac acc      624
Gly Thr Gln Thr Tyr Ile Cys Asn Val Asn His Lys Pro Ser Asn Thr
        195             200             205 aag gtg gac aag aag gtg gag ccc aag agc tgc ggt ggc ggg ggt tcg      672
Lys Val Asp Lys Lys Val Glu Pro Lys Ser Cys Gly Gly Gly Gly Ser
210             215             220 ggt gga gga ggt tct gag gtc cag ctg cag cag tct gga cct gag cta      720
Gly Gly Gly Gly Ser Glu Val Gln Leu Gln Gln Ser Gly Pro Glu Leu
225             230             235             240 gtg aag act ggg gct tca gtg aag ata tcc tgc aag gct tct ggt tat      768
Val Lys Thr Gly Ala Ser Val Lys Ile Ser Cys Lys Ala Ser Gly Tyr
            245             250             255 tca ttc att aat cac tac atg aac tgg gtc aag cag agc cgt gga aag      816
Ser Phe Ile Asn His Tyr Met Asn Trp Val Lys Gln Ser Arg Gly Lys
                260             265             270 agc ctt gag tgg att gga tat gtt agt tgt tac aat ggt gct act ggc      864
Ser Leu Glu Trp Ile Gly Tyr Val Ser Cys Tyr Asn Gly Ala Thr Gly
            275             280             285 tac aac cag aag ttt aag gac aag gcc aca ttt act gta gac aca tcc      912
Tyr Asn Gln Lys Phe Lys Asp Lys Ala Thr Phe Thr Val Asp Thr Ser
        290             295             300 tcc agc aca gcc tac atg cag ttc aac aac ctg aca tct gaa gac tct      960
Ser Ser Thr Ala Tyr Met Gln Phe Asn Asn Leu Thr Ser Glu Asp Ser
305             310             315             320 gcg gtc tac tat tgt gca cga aga ggg ttt atg gag gct atg gac tac     1008
Ala Val Tyr Tyr Cys Ala Arg Arg Gly Phe Met Glu Ala Met Asp Tyr
            325             330             335 tgg ggt caa gga acc tca gtc acc gtc tcc tca gag ccc aag agc agc     1056
Trp Gly Gln Gly Thr Ser Val Thr Val Ser Ser Glu Pro Lys Ser Ser
                340             345             350 gac aag acc cac acc tgt ccc cct tgt cct gcc cct gaa gcc gaa ggc     1104
Asp Lys Thr His Thr Cys Pro Pro Cys Pro Ala Pro Glu Ala Glu Gly
            355             360             365 gcg cct tcc gtg ttc ctg ttc ccc cca aag ccc aag gac acc ctg atg     1152
Ala Pro Ser Val Phe Leu Phe Pro Pro Lys Pro Lys Asp Thr Leu Met
370             375             380 atc agc cgg acc ccc gaa gtg acc tgc gtg gtg gtg gac gtg tcc cac     1200
Ile Ser Arg Thr Pro Glu Val Thr Cys Val Val Val Asp Val Ser His
385             390             395             400 gag gac cct gaa gtg aag ttc aat tgg tac gtg gac ggc gtg gag gtg     1248
Glu Asp Pro Glu Val Lys Phe Asn Trp Tyr Val Asp Gly Val Glu Val
            405             410             415 cac aac gcc aag acc aag ccc cgg gag gaa cag tac aac agc acc tac     1296
His Asn Ala Lys Thr Lys Pro Arg Glu Glu Gln Tyr Asn Ser Thr Tyr
                420             425             430 cgg gtg gtg tcc gtg ctg acc gtg ctg cac cag gac tgg ctg aac ggc     1344
Arg Val Val Ser Val Leu Thr Val Leu His Gln Asp Trp Leu Asn Gly
            435             440             445
```

```
aaa gag tac aag tgc aag gtc tcc aac aag gcc ctg ccc agc agc atc      1392
Lys Glu Tyr Lys Cys Lys Val Ser Asn Lys Ala Leu Pro Ser Ser Ile
    450                 455                 460 gag aaa acc atc agc aag gcc aag ggc cag ccc aga gaa ccc cag gtg      1440
Glu Lys Thr Ile Ser Lys Ala Lys Gly Gln Pro Arg Glu Pro Gln Val
465                 470                 475                 480 tac acc ctg ccc cct agc agg gac gag ctg acc aag aac cag gtg tcc      1488
Tyr Thr Leu Pro Pro Ser Arg Asp Glu Leu Thr Lys Asn Gln Val Ser
                485                 490                 495 ctg acc tgt ctg gtg aag ggc ttc tac ccc agc gat atc gcc gtg gag      1536
Leu Thr Cys Leu Val Lys Gly Phe Tyr Pro Ser Asp Ile Ala Val Glu
            500                 505                 510 tgg gag agc aac ggc cag ccc gaa aac aac tac aag acc acc ccc cct      1584
Trp Glu Ser Asn Gly Gln Pro Glu Asn Asn Tyr Lys Thr Thr Pro Pro
        515                 520                 525 gtg ctg gac agc gac ggc agc ttc ttc ctg tac tcc aaa ctg acc gtg      1632
Val Leu Asp Ser Asp Gly Ser Phe Phe Leu Tyr Ser Lys Leu Thr Val
    530                 535                 540 gac aag agc cgg tgg cag cag ggc aac gtg ttc agc tgc agc gtg atg      1680
Asp Lys Ser Arg Trp Gln Gln Gly Asn Val Phe Ser Cys Ser Val Met
545                 550                 555                 560 cac gag gcc ctg cac aac cac tac acc cag aag tcc ctg agc ctg agc      1728
His Glu Ala Leu His Asn His Tyr Thr Gln Lys Ser Leu Ser Leu Ser
                565                 570                 575 ccc ggc aag                                                          1737
Pro Gly Lys <210> SEQ ID NO 124
<211> LENGTH: 579
<212> TYPE: PRT
<213> ORGANISM: Homo sapiens

<400> SEQUENCE: 124

Glu Val Gln Leu Val Glu Ser Gly Gly Leu Val Lys Pro Gly Gly
1               5                   10                  15

Ser Leu Lys Leu Ser Cys Ala Ala Ser Gly Phe Ala Phe Ser Ser Tyr
                20                  25                  30

Ala Met Ser Trp Val Arg Gln Ser Pro Glu Lys Arg Leu Glu Trp Val
            35                  40                  45

Ala Thr Ile Ser Ser Gly Gly His Tyr Thr Phe Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Ile Tyr Tyr Cys
                85                  90                  95

Ala Arg Arg Tyr Tyr Ala Leu Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Lys Val Glu Pro Lys Ser Cys Gly Gly Gly Gly Ser
            210                 215                 220

Gly Gly Gly Gly Ser Glu Val Gln Leu Gln Gln Ser Gly Pro Glu Leu
225                 230                 235                 240

Val Lys Thr Gly Ala Ser Val Lys Ile Ser Cys Lys Ala Ser Gly Tyr
            245                 250                 255

Ser Phe Ile Asn His Tyr Met Asn Trp Val Lys Gln Ser Arg Gly Lys
            260                 265                 270

Ser Leu Glu Trp Ile Gly Tyr Val Ser Cys Tyr Asn Gly Ala Thr Gly
            275                 280                 285

Tyr Asn Gln Lys Phe Lys Asp Lys Ala Thr Phe Thr Val Asp Thr Ser
            290                 295                 300

Ser Ser Thr Ala Tyr Met Gln Phe Asn Asn Leu Thr Ser Glu Asp Ser
305                 310                 315                 320

Ala Val Tyr Tyr Cys Ala Arg Arg Gly Phe Met Glu Ala Met Asp Tyr
            325                 330                 335

Trp Gly Gln Gly Thr Ser Val Thr Val Ser Ser Glu Pro Lys Ser Ser
            340                 345                 350

Asp Lys Thr His Thr Cys Pro Pro Cys Pro Ala Pro Glu Ala Glu Gly
            355                 360                 365

Ala Pro Ser Val Phe Leu Phe Pro Pro Lys Pro Lys Asp Thr Leu Met
370                 375                 380

Ile Ser Arg Thr Pro Glu Val Thr Cys Val Val Val Asp Val Ser His
385                 390                 395                 400

Glu Asp Pro Glu Val Lys Phe Asn Trp Tyr Val Asp Gly Val Glu Val
            405                 410                 415

His Asn Ala Lys Thr Lys Pro Arg Glu Glu Gln Tyr Asn Ser Thr Tyr
            420                 425                 430

Arg Val Val Ser Val Leu Thr Val Leu His Gln Asp Trp Leu Asn Gly
            435                 440                 445

Lys Glu Tyr Lys Cys Lys Val Ser Asn Lys Ala Leu Pro Ser Ser Ile
            450                 455                 460

Glu Lys Thr Ile Ser Lys Ala Lys Gly Gln Pro Arg Glu Pro Gln Val
465                 470                 475                 480

Tyr Thr Leu Pro Pro Ser Arg Asp Glu Leu Thr Lys Asn Gln Val Ser
            485                 490                 495

Leu Thr Cys Leu Val Lys Gly Phe Tyr Pro Ser Asp Ile Ala Val Glu
            500                 505                 510

Trp Glu Ser Asn Gly Gln Pro Glu Asn Asn Tyr Lys Thr Thr Pro Pro
            515                 520                 525

Val Leu Asp Ser Asp Gly Ser Phe Phe Leu Tyr Ser Lys Leu Thr Val
            530                 535                 540

Asp Lys Ser Arg Trp Gln Gln Gly Asn Val Phe Ser Cys Ser Val Met
545                 550                 555                 560

His Glu Ala Leu His Asn His Tyr Thr Gln Lys Ser Leu Ser Leu Ser
            565                 570                 575

Pro Gly Lys

<210> SEQ ID NO 125
<211> LENGTH: 1008
<212> TYPE: DNA

```
<213> ORGANISM: Homo sapiens
<220> FEATURE:
<221> NAME/KEY: CDS
<222> LOCATION: (1)..(1008)

<400> SEQUENCE: 125 gac att gtg atg acc cag tct caa aaa ttc atg tcc aca tca cta gga      48
Asp Ile Val Met Thr Gln Ser Gln Lys Phe Met Ser Thr Ser Leu Gly
1               5                   10                  15 gac agg gtc agc gtc tcc tgc aag gcc agt cag aat gtg ctt act aat      96
Asp Arg Val Ser Val Ser Cys Lys Ala Ser Gln Asn Val Leu Thr Asn
            20                  25                  30 gta gcc tgg tat caa caa aaa cca ggg caa tct cct aaa act ctg att     144
Val Ala Trp Tyr Gln Gln Lys Pro Gly Gln Ser Pro Lys Thr Leu Ile
        35                  40                  45 tat tcg gca tcc tac cgg tac agt gga gtc cct gat cgc ttc aca ggc     192
Tyr Ser Ala Ser Tyr Arg Tyr Ser Gly Val Pro Asp Arg Phe Thr Gly
    50                  55                  60 agt gga tct ggg aca gat ttc act ctc acc atc agc att gtt cag tct     240
Ser Gly Ser Gly Thr Asp Phe Thr Leu Thr Ile Ser Ile Val Gln Ser
65                  70                  75                  80 gaa gac ttg gca gag tat ttc tgt caa caa tat aac atc tat ccg tgg     288
Glu Asp Leu Ala Glu Tyr Phe Cys Gln Gln Tyr Asn Ile Tyr Pro Trp
                85                  90                  95 acg ttc ggt gga ggc acc aag ctg gaa atc aaa cgg acc gtg gcc gct     336
Thr Phe Gly Gly Gly Thr Lys Leu Glu Ile Lys Arg Thr Val Ala Ala
            100                 105                 110 ccc agc gtg ttc atc ttc cca ccc agc gac gag cag ctg aag tcc ggt     384
Pro Ser Val Phe Ile Phe Pro Pro Ser Asp Glu Gln Leu Lys Ser Gly
        115                 120                 125 acc gcc agc gtg gtg tgc ctg ctg aac aac ttc tac ccg cgg gag gcc     432
Thr Ala Ser Val Val Cys Leu Leu Asn Asn Phe Tyr Pro Arg Glu Ala
    130                 135                 140 aag gtg cag tgg aag gtg gac aac gcc ctg cag agc ggc aac tcc cag     480
Lys Val Gln Trp Lys Val Asp Asn Ala Leu Gln Ser Gly Asn Ser Gln
145                 150                 155                 160 gaa agc gtc acc gag cag gac agc aag gac tcc acc tac agc ctg agc     528
Glu Ser Val Thr Glu Gln Asp Ser Lys Asp Ser Thr Tyr Ser Leu Ser
                165                 170                 175 agc acc ctg acc ctg agc aag gcc gac tac gag aag cac aag gtg tac     576
Ser Thr Leu Thr Leu Ser Lys Ala Asp Tyr Glu Lys His Lys Val Tyr
            180                 185                 190 gcc tgc gaa gtg acc cac cag ggc ctg tcc agc ccc gtg acc aag agc     624
Ala Cys Glu Val Thr His Gln Gly Leu Ser Ser Pro Val Thr Lys Ser
        195                 200                 205 ttc aac cgg ggc gag tgt ggt ggc ggg ggt tcg ggt gga gga ggt tct     672
Phe Asn Arg Gly Glu Cys Gly Gly Gly Gly Ser Gly Gly Gly Gly Ser
    210                 215                 220 gac att gtg atg aca cag tct cca ttc tcc ctg act gtg aca gta gga     720
Asp Ile Val Met Thr Gln Ser Pro Phe Ser Leu Thr Val Thr Val Gly
225                 230                 235                 240 gag aag gtc act atg agc tgc aaa tcc agt cag agt ctg ctc aac agt     768
Glu Lys Val Thr Met Ser Cys Lys Ser Ser Gln Ser Leu Leu Asn Ser
                245                 250                 255 aga acc cga aag aac tac ttg gct tgg tac cag cag aaa cca ggg cag     816
Arg Thr Arg Lys Asn Tyr Leu Ala Trp Tyr Gln Gln Lys Pro Gly Gln
            260                 265                 270 tct cct aaa ctt ctg atc tat tgg gca tcc act agg gaa tct ggg gtc     864
Ser Pro Lys Leu Leu Ile Tyr Trp Ala Ser Thr Arg Glu Ser Gly Val
        275                 280                 285
```

| | | | | | | | | | | | | | | | | |
|---|---|---|---|---|---|---|---|---|---|---|---|---|---|---|---|---|
| cct | gat | cgc | ttc | aca | ggc | agt | gga | tct | ggg | aca | gat | ttc | act | ctc | acc | 912 |
| Pro | Asp | Arg | Phe | Thr | Gly | Ser | Gly | Ser | Gly | Thr | Asp | Phe | Thr | Leu | Thr | |
| 290 | | | | | 295 | | | | | 300 | | | | | | |
| atc | agc | agt | gtg | cag | gct | gaa | gac | ctg | gca | gtt | tat | tac | tgc | aag | caa | 960 |
| Ile | Ser | Ser | Val | Gln | Ala | Glu | Asp | Leu | Ala | Val | Tyr | Tyr | Cys | Lys | Gln | |
| 305 | | | | 310 | | | | | 315 | | | | | 320 | | |
| tct | tat | aat | ctt | tat | acg | ttc | gga | ggg | ggg | acc | aag | ctg | gaa | ata | aaa | 1008 |
| Ser | Tyr | Asn | Leu | Tyr | Thr | Phe | Gly | Gly | Gly | Thr | Lys | Leu | Glu | Ile | Lys | |
| | | | | 325 | | | | 330 | | | | | | 335 | | |

<210> SEQ ID NO 126
<211> LENGTH: 336
<212> TYPE: PRT
<213> ORGANISM: Homo sapiens

<400> SEQUENCE: 126

Asp Ile Val Met Thr Gln Ser Gln Lys Phe Met Ser Thr Ser Leu Gly
1               5                   10                  15

Asp Arg Val Ser Val Ser Cys Lys Ala Ser Gln Asn Val Leu Thr Asn
            20                  25                  30

Val Ala Trp Tyr Gln Gln Lys Pro Gly Gln Ser Pro Lys Thr Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ile Val Gln Ser
65                  70                  75                  80

Glu Asp Leu Ala Glu Tyr Phe Cys Gln Gln Tyr Asn Ile Tyr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Asp Ile Val Met Thr Gln Ser Pro Phe Ser Leu Thr Val Thr Val Gly
225                 230                 235                 240

Glu Lys Val Thr Met Ser Cys Lys Ser Ser Gln Ser Leu Leu Asn Ser
                245                 250                 255

Arg Thr Arg Lys Asn Tyr Leu Ala Trp Tyr Gln Gln Lys Pro Gly Gln
            260                 265                 270

Ser Pro Lys Leu Leu Ile Tyr Trp Ala Ser Thr Arg Glu Ser Gly Val
        275                 280                 285

Pro Asp Arg Phe Thr Gly Ser Gly Ser Gly Thr Asp Phe Thr Leu Thr
    290                 295                 300

Ile Ser Ser Val Gln Ala Glu Asp Leu Ala Val Tyr Tyr Cys Lys Gln
305                 310                 315                 320

-continued

```
Ser Tyr Asn Leu Tyr Thr Phe Gly Gly Gly Thr Lys Leu Glu Ile Lys
            325                 330                 335

<210> SEQ ID NO 127
<211> LENGTH: 329
<212> TYPE: PRT
<213> ORGANISM: Homo sapiens
<220> FEATURE:
<221> NAME/KEY: VARIANT
<222> LOCATION: (97)..(97)
<223> OTHER INFORMATION: allotype variance
<220> FEATURE:
<221> NAME/KEY: MOD_RES
<222> LOCATION: (117)..(117)
<223> OTHER INFORMATION: L117A
<220> FEATURE:
<221> NAME/KEY: MOD_RES
<222> LOCATION: (118)..(118)
<223> OTHER INFORMATION: L118E
<220> FEATURE:
<221> NAME/KEY: MOD_RES
<222> LOCATION: (120)..(120)
<223> OTHER INFORMATION: G120A
<220> FEATURE:
<221> NAME/KEY: MOD_RES
<222> LOCATION: (213)..(213)
<223> OTHER INFORMATION: A213S
<220> FEATURE:
<221> NAME/KEY: MOD_RES
<222> LOCATION: (214)..(214)
<223> OTHER INFORMATION: P214S
<220> FEATURE:
<221> NAME/KEY: VARIANT
<222> LOCATION: (239)..(239)
<223> OTHER INFORMATION: allotype variance
<220> FEATURE:
<221> NAME/KEY: VARIANT
<222> LOCATION: (241)..(241)
<223> OTHER INFORMATION: allotype variance

<400> SEQUENCE: 127

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ser Ser Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 128
<211> LENGTH: 330
<212> TYPE: PRT
<213> ORGANISM: Homo sapiens
<220> FEATURE:
<221> NAME/KEY: VARIANT
<222> LOCATION: (97)..(97)
<223> OTHER INFORMATION: allotype variance
<220> FEATURE:
<221> NAME/KEY: MOD_RES
<222> LOCATION: (117)..(117)
<223> OTHER INFORMATION: L117A
<220> FEATURE:
<221> NAME/KEY: MOD_RES
<222> LOCATION: (118)..(118)
<223> OTHER INFORMATION: L117E
<220> FEATURE:
<221> NAME/KEY: MOD_RES
<222> LOCATION: (120)..(120)
<223> OTHER INFORMATION: G120A
<220> FEATURE:
<221> NAME/KEY: MOD_RES
<222> LOCATION: (213)..(213)
<223> OTHER INFORMATION: A213S
<220> FEATURE:
<221> NAME/KEY: MOD_RES
<222> LOCATION: (214)..(214)
<223> OTHER INFORMATION: P214S
<220> FEATURE:
<221> NAME/KEY: VARIANT
<222> LOCATION: (239)..(239)
<223> OTHER INFORMATION: allotype variance
<220> FEATURE:
<221> NAME/KEY: VARIANT
<222> LOCATION: (241)..(241)
<223> OTHER INFORMATION: allotype variance

<400> SEQUENCE: 128

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60
```

```
Leu Ser Ser Val Val Thr Val Pro Ser Ser Leu Gly Thr Gln Thr
65                  70              75                  80

Tyr Ile Cys Asn Val Asn His Lys Pro Ser Asn Thr Lys Val Asp Lys
            85              90                  95

Arg Val Glu Pro Lys Ser Cys Asp Lys Thr His Thr Cys Pro Pro Cys
            100             105             110

Pro Ala Pro Glu Ala Glu Gly Ala Pro Ser Val Phe Leu Phe Pro Pro
            115             120             125

Lys Pro Lys Asp Thr Leu Met Ile Ser Arg Thr Pro Glu Val Thr Cys
130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ser Ser Ile Glu Lys Thr Ile Ser Lys Ala Lys Gly
            210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
            290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```

METHODS OF TREATMENT USING IL-23P19 MONOCLONAL ANTIBODIES

CROSS-REFERENCE TO RELATED APPLICATIONS

The present application is a divisional of U.S. patent application Ser. No. 15/620,358, filed Jun. 12, 2017, now U.S. Pat. No. 10,358,489, which is a divisional of U.S. patent application Ser. No. 14/402,322, filed Nov. 20, 2014, now U.S. Pat. No. 9,708,401, which is the National Stage filed under 35 U.S.C. § 371 of PCT Application No. PCT/US2013/041928, filed May 21, 2013, which claims benefit of U.S. Patent Application Ser. No. 61/787,890, filed Mar. 15, 2013, U.S. Patent Application Ser. No. 61/784,600, filed Mar. 14, 2013, and U.S. Patent Application Ser. No. 61/650,286, filed May 22, 2012, all of which are herein incorporated by reference in their entirety.

BACKGROUND OF THE INVENTION

Cytokines are soluble, small proteins that mediate a variety of biological effects, including the induction of immune cell proliferation, development, differentiation, and/or migration, as well as the regulation of the growth and differentiation of many cell types (see, for example, Arai et al., *Annu. Rev. Biochem.* 59:783 (1990); Mosmann, *Curr. Opin. Immunol.* 3:311 (1991); Paul et al., *Cell,* 76:241 (1994)). Cytokine-induced immune functions can also include an inflammatory response, characterized by a systemic or local accumulation of immune cells. Although they do have host-protective effects, these immune responses can produce pathological consequences when the response involves excessive and/or chronic inflammation, as in autoimmune disorders (such as multiple sclerosis) and cancer/neoplastic diseases (Oppenheim et al., eds., *Cytokine Reference,* Academic Press, San Diego, Calif. (2001); von Andrian et al., *New Engl. J. Med.,* 343:1020 (2000); Davidson et al., *New Engl. J. Med.,* 345:340 (2001); Lu et al., *Mol. Cancer Res.,* 4:221 (2006); Dalgleish et al., *Cancer Treat Res.,* 130:1 (2006)).

IL-17A, IL-17F and IL-23 are cytokines involved in inflammation. IL-17A induces the production of inflammatory cytokines such as IL-1β, TNF-α, IL-6, and IL-23 by synovial fibroblasts, monocytes, and macrophages, all of which promote inflammation and Th17 development. IL-17A also induces an array of chemokines, including CXCL-1, CXCL-2, CXCL-5, CXCL-8, CCL-2, and CCL-20, leading to recruitment of T cells, B cells, monocytes, and neutrophils. Lundy, S. K., *Arthritis Res. Ther.,* 9:202 (2007). IL-17F shares the greatest homology (55%) with IL-17A and is also a proinflammatory cytokine. Both IL-17A and IL-17F are produced by Th17 cells, whereas the other IL-17 family members, IL-17B, IL-17C, and IL-17D, are produced by non-T cell sources. IL-17A and IL-17F can exist as IL-17A homodimers and IL-17F homodimers or as IL-17A/F heterodimers. Liang, S. C. et al., *J. Immunol.,* 179:7791-7799 (2007). IL-17A is increased in rheumatoid arthritis sera and synovial fluid, and is present in the T-cell rich areas of the synovium. Shahrara, S., *Arthritis Res. Ther.,* 10:R93 (2005). IL-17A can also orchestrate bone and cartilage damage. An effective blockade of IL-17 will need to neutralize IL-17A homodimers, IL-17F homodimers and IL-17A/F heterodimers.

IL-23 is a type-1 heterodimer, comprising a 19 kilodalton (kD) fourfold helical core α subunit (IL-23p19), disulfide linked to an additional 40 kD distinct β subunit (IL-12p40). IL-23 is a key cytokine in bridging the innate and adaptive arms of the immune response; it is produced early in response to an antigen challenge, and is essential for driving early local immune responses. Furthermore, IL-23 plays a central role in the activation of NK cells, the enhancement of T cell proliferation and the regulation of antibody production. IL-23 also regulates pro-inflammatory cytokines (e.g., IFN-γ), which are important in cell-mediated immunity against intracellular pathogens. Recent reports have indicated that in humans increased amounts of IL-23 have been associated with several autoimmune diseases including rheumatoid arthritis (RA), Lyme arthritis, inflammatory bowel disease (IBD), Crohn's disease (CD), psoriasis and multiple sclerosis (MS). IL-23p19 knock-out mice were resistant to autoimmune encephalomyelitis (EAE), collagen-induced arthritis (CIA) and central nervous system autoimmune induction. IL-23 is not essential for the development of human Th17 cells, but appears to be required for their survival and/or expansion. Paradowska-Gorycka, A., *Scandinavian Journal of Immunology,* 71:134-145 (2010). Genetic studies revealed an association between IL-23 receptor genes and susceptibility to several autoimmune diseases including CD, RA and Graves' ophthalmopathy. The IL-23-Th17 axis is crucial to autoimmune disease development. Leng et al., *Archives of Medical Research,* 41:221-225 (2010).

The demonstrated activities of IL-17A, IL-17F and IL-23p19 in mediating and promoting several autoimmune diseases illustrate the clinical potential of, and need for, molecules which can antagonize these targets. The present invention, as set forth herein, meets these and other needs.

DETAILED DESCRIPTION OF THE INVENTION

Figure 1:
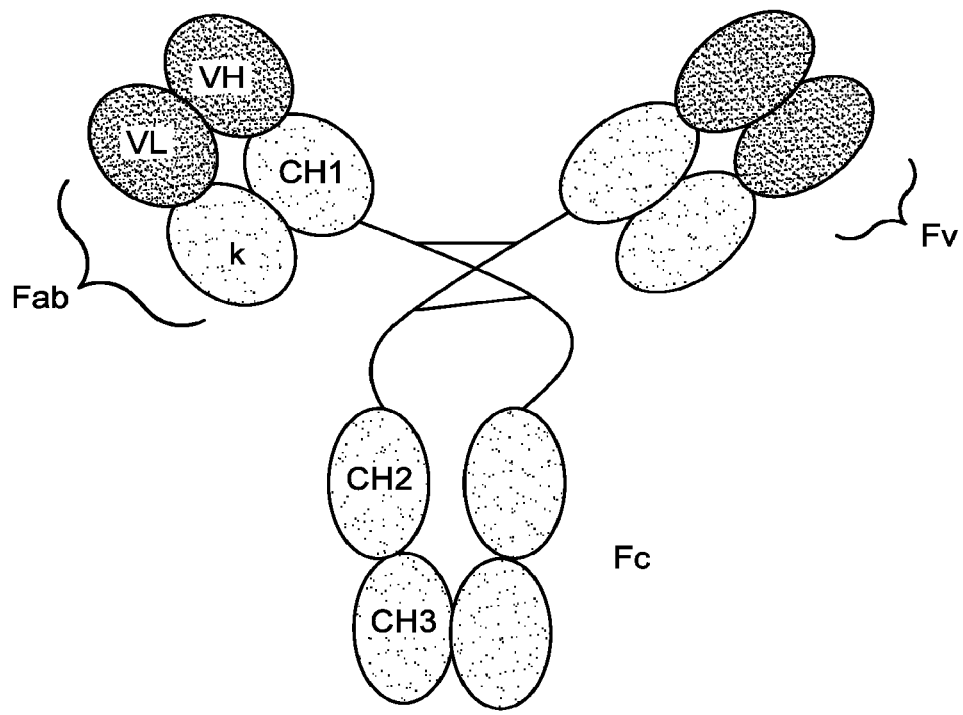
FIG. 1 is a schematic illustration of a whole antibody and its modular components.

The present invention provides, in one embodiment, bispecific antibodies comprising an IL-17A/F binding entity that binds to IL-17A and IL-17F and an IL-23 binding entity that binds to IL-23 via p19. The invention also includes isolated nucleic acids encoding the heavy chains and light chains of the bispecific antibodies of the invention, as well as vectors comprising the nucleic acids, host cells comprising the vectors, and methods of making and using the bispecific antibodies.

In other embodiments, the present invention provides compositions comprising the bispecific antibodies and kits comprising the bispecific antibodies, as well as articles of manufacture comprising the bispecific antibodies.

The bispecific antibodies of the present invention are useful for the inhibition of proinflammatory cytokines, e.g., IL-17A, IL-17F and IL-23p19. The antibodies can be used to reduce, limit, neutralize, or block the proinflammatory effects of the IL-17A homodimer, the IL-17F homodimer, or the IL-17A/F heterodimer. Likewise, the antibodies can be used to reduce, limit, neutralize, or block the pro-cancerous effects of the IL-17A homodimer, the IL-17F homodimer, or the IL-17A/F heterodimer. In such cases, the anti-IL-23p19 portion of the antibody is used to reduce, limit, neutralize, or block production of new T cells that would produce IL-17A and/or IL-17F, including homodimers and heterodimers. The bispecific antibodies described herein can be used to treat inflammatory disorders and autoimmune diseases, such as multiple sclerosis (e.g., relapsing-remitting multiple sclerosis, secondary-progressive multiple sclerosis, primary-progressive multiple sclerosis and progressive-relapsing multiple sclerosis), inflammatory bowel disease, psoriasis, systemic sclerosis, systemic lupus erythematosus, antineutrophil cytoplasmic antibodies (ANCA)-associated vasculitis (AAV) and giant cell arteritis. The bispecific antibodies described herein can also be used to treat cancer, including angiogenesis. For instance, the bispecific antibodies as described herein can be used to treat multiple-myeloma-induced lytic bone disease (Sotomayor, E. M., *Blood,* 116 (18):3380-3382 (2010)).

In the description that follows, a number of terms are used extensively. The following definitions are provided to facilitate understanding of the invention.

Unless otherwise specified, "a", "an", "the", and "at least one" are used interchangeably and mean one or more than one.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. Thus, as used herein, the term "antibody" or "antibody peptide(s)" refers to an intact antibody, or an antigen-binding fragment thereof that competes with the intact antibody for specific binding and includes chimeric, humanized, fully human, and bispecific antibodies. In certain embodiments, antigen-binding fragments are produced, for example, by recombinant DNA techniques. In additional embodiments, antigen-binding fragments are produced by enzymatic or chemical cleavage of intact antibodies. Antigen-binding fragments include, but are not limited to, Fab, Fab', $F(ab)^2$, $F(ab')^2$, Fv, and single-chain antibodies.

The term "isolated antibody" as used herein refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "agonist" refers to any compound including a protein, polypeptide, peptide, antibody, antibody fragment, large molecule, or small molecule (less than 10 kD), that increases the activity, activation or function of another molecule.

The term "antagonist" refers to any compound including a protein, polypeptide, peptide, antibody, antibody fragment, large molecule, or small molecule (less than 10 kD), that decreases the activity, activation or function of another molecule.

The term "bind(ing) of a polypeptide" includes, but is not limited to, the binding of a ligand polypeptide of the present invention to a receptor; the binding of a receptor polypeptide of the present invention to a ligand; the binding of an antibody of the present invention to an antigen or epitope; the binding of an antigen or epitope of the present invention to an antibody; the binding of an antibody of the present invention to an anti-idiotypic antibody; the binding of an anti-idiotypic antibody of the present invention to a ligand; the binding of an anti-idiotypic antibody of the present invention to a receptor; the binding of an anti-anti-idiotypic antibody of the present invention to a ligand, receptor or antibody, etc.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai et al., *Clin. Exp. Immunol.*, 79:315-321 (1990); Kostelny et al., *J. Immunol.*, 148:1547-1553 (1992).

As used herein, the term "epitope" refers to the portion of an antigen to which an antibody specifically binds. Thus, the term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. More specifically, the term "IL-17 epitope", "IL-23 epitope" and/or "IL-23/p19 epitope" as used herein refers to a portion of the corresponding polypeptide having antigenic or immunogenic activity in an animal, preferably in a mammal, and most preferably in a mouse or a human. An epitope having immunogenic activity is a portion of, for example, an IL-17A or IL-17F or IL-23/p19 polypeptide that elicits an antibody response in an animal. An epitope having antigenic activity is a portion of, for example, an IL-17A or IL-17F or IL-23/p19 polypeptide to which an antibody immunospecifically binds as determined by any method well known in the art, for example, by immunoassays, protease digest, crystallography or H/D-Exchange. Antigenic epitopes need not necessarily be immunogenic. Such epitopes can be linear in nature or can be a discontinuous epitope. Thus, as used herein, the term "conformational epitope" refers to a discontinuous epitope formed by a spatial relationship between amino acids of an antigen other than an unbroken series of amino acids.

As used herein, the term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or about 214 amino acids) are encoded by a variable region gene at the NH2-terminus (about 110 amino acids) and a kappa or lambda constant region gene at the COOH-terminus. Full-length immunoglobulin "heavy chains" (about 50 Kd or about 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG (such as IgG1, IgG2, IgG3 and IgG4), IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd Edition, Raven Press, NY (1989)), Chapter 7 (incorporated by reference in its entirety for all purposes).

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" (Kabat et al., *Sequences of Proteins of Immunological Interest*, 5th Edition, Public Health Service, National Institutes of Health, Bethesda, Md. (1991)) and/or those residues from a "hypervariable loop" (Chothia et al., *J. Mol. Biol.* 196: 901-917 (1987)) (both of which are incorporated herein by reference). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen. Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. Further, one or more residues in the human framework region may be back mutated to the parental sequence to retain optimal antigen-binding affinity and specificity. In this way, certain framework residues from the non-human parent antibody are retained in the humanized antibody in order to retain the binding properties of the parent antibody while minimizing its immunogenicity. The term "human framework region" as used herein includes regions with such back mutations. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

The term "humanized" immunoglobulin refers to an immunoglobulin comprising a human framework region and one or more CDR's from a non-human, e.g., mouse, rat or rabbit, immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's and possibly a few back-mutated amino acid residues in the framework region (e.g., 1-15 residues), are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

As used herein, the term "human antibody" includes an antibody that has an amino acid sequence of a human immunoglobulin and includes antibodies isolated from human immunoglobulin libraries or from animals transgenic for one or more human immunoglobulin and that do not express endogenous immunoglobulins, as described, for example, by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable and/or constant region. Changes in the constant region will, in general, be made in order to improve or alter characteristics, such as complement fixation, interaction with membranes and other effector functions. Changes in the variable region will be made in order to improve the antigen binding characteristics.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a $F(ab')_2$ molecule.

A "$F(ab')_2$ fragment" contains two light chains and two heavy chains containing a portion of the constant region between the $C_{H1}$ and $C_{H2}$ domains, such that an interchain disulfide bond is formed between two heavy chains.

A "Fv fragment" contains the variable regions from both heavy and light chains but lacks the constant regions.

A "single domain antibody" is an antibody fragment consisting of a single domain Fv unit, e.g., $V_H$ or $V_L$. Like a whole antibody, it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain). The first single-domain antibodies were engineered from heavy-chain antibodies found in camelids. Although most research into single-domain antibodies is currently based on heavy chain variable domains, light chain variable domains and nanobodies derived from light chains have also been shown to bind specifically to target epitopes.

The term "monoclonal antibody" or "mAb" or "MAb" or "Mab" or "mab" as used herein is not limited to antibodies produced through hybridoma technology. The term "monoclonal antibody" or "mAb" or "MAb" or "Mab" or "mab" refer to an antibody that is derived from a single clone, including any eukaryotic, prokaryotic, or phage clone, and not the method by which it is produced.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids", which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.*, 7:551 (1993)), cyclic AMP response elements (CREs), serum response elements (SREs; Treisman, *Seminars in Cancer Biol.*, 1:47 (1990)), glucocorticoid response elements (GREs), and binding sites for other transcription factors, such as CRE/ATF (O'Reilly et al., *J. Biol. Chem.*, 267:19938 (1992)), AP2 (Ye et al., *J. Biol. Chem.*, 269:25728 (1994)), SP1, cAMP response element binding protein (CREB; Loeken, *Gene Expr.*, 3:253 (1993)) and octamer factors (see, in general, Watson et al., eds., *Molecular Biology of the Gene,* 4th Edition, The Benjamin/Cummings Publishing Company, Inc. (1987), and Lemaigre et al., *Biochem. J.*, 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific", "tissue-specific", or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces an antagonist of the present invention from an expression vector. In contrast, such an antagonist can be produced by a cell that is a "natural source" of said antagonist, and that lacks an expression vector.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "fusion protein" is a hybrid protein expressed by a nucleic acid molecule comprising nucleotide sequences of at least two genes. For example, a fusion protein can comprise at least part of a IL-17RA polypeptide fused with a polypeptide that binds an affinity matrix. Such a fusion protein provides a means to isolate large quantities of IL-17A using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "expression" refers to the biosynthesis of a gene product. For example, in the case of a structural gene, expression involves transcription of the structural gene into mRNA and the translation of mRNA into one or more polypeptides.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.*, 4:1075 (1985); Nilsson et al., *Methods Enzymol.*, 198:3 (1991)), glutathione S transferase (Smith et al., *Gene*, 67:31 (1988)), Glu-Glu affinity tag (Grussenmeyer et al., *Proc. Natl. Acad. Sci. USA*, 82:7952 (1985)), substance P, FLAG® peptide (Hopp et al., *Biotechnology*, 6:1204 (1988)), streptavidin binding peptide, or other antigenic epitope or binding domain. See, in general, Ford et al., *Protein Expression and Purification*, 2:95 (1991). DNA molecules encoding affinity tags are available from commercial suppliers (e.g., Pharmacia Biotech, Piscataway, N.J.).

An "IL-17A binding entity" is a binding entity, such as an antibody, that specifically binds to IL-17A in its homodimeric form (IL-17A/IL-17A) and in its heterodimeric form (IL-17A/IL-17F).

An "IL-17F binding entity" is a binding entity, such as an antibody, that specifically binds to IL-17F in its homodimeric form (IL-17F/IL-17F) and in its heterodimeric form (IL-17A/IL-17F).

An "IL-17A/F binding entity" is a binding entity, such as an antibody, that specifically binds to IL-17A and IL-17F by recognizing and binding to the same or similar epitope, e.g., continuous or discontinuous epitope, shared by IL-17A and IL-17F. The IL-17A/F binding entity binds to the IL-17A homodimer, IL-17F homodimer and IL-17A/IL-17F heterodimer.

One problem is that IL-17A, IL-17F and IL-23p19 are overexpressed in and implicated in the cause and/or sustainability of several inflammatory and/or autoimmune disorders. One solution several embodiments of the present invention provide is to inhibit or reduce the ability of these cytokines to cell-signal by administering a bispecific antibody which binds to each cytokine and inhibits or reduces each cytokine, e.g., homodimeric or heterodimeric form, from signaling through their cognate receptor.

Another problem is that in creating a bispecific IL-17A/F and IL-23p19 bispecific antibody, e.g, biAb3, difficulties were encountered to generate a bispecific antibody which had high affinity to IL-17A and was an effective neutralizer, e.g., IC50, of IL-17A. The mouse parent antibody (e.g, chimeric 339.15, 339.15.3.5, 339.15.5.3 or 339.15.3.6) as shown in Table 1 had an IL-17A/F IC50 of 0.30 nM and an IL-17F IC50 of 0.26 nM, but only had an IL-17A IC50 of 11 nM. The antibodies ability to inhibit or neutralize IL-17A from signaling needed to be enhanced. As shown in Table 3, mouse parent chimeric 339.15 and humanized parent 339.134 had a similar binding affinity towards IL-17A. Furthermore, as shown in Table 8, humanized parent 339.134 ability to inhibit IL-17A (IC50 of 1.3 nM) was still significantly reduced as compared to its ability to inhibit IL-17A/F (IC50 of 0.27 nM) and IL-17F (IC50 of 0.24 nM). This problem was surprisingly overcome by utilizing the light chain of the IL-23p19 antibody of biAb3 (SEQ ID NO:17). When the IL-23p19 light chain was paired with the humanized heavy chain of 339.134, the resulting monoclonal antibody significantly increased its ability to inhibit IL-17A from signaling (see Table 9) and significantly increased its affinity for IL-17A (see Table 10). The critical residue in the now shared IL-23p19/IL-17A/F light chain of, for example, biAb3, that may have provided this enhanced affinity and neutralization ability may be Y108 or Tyr108 of SEQ ID NO:2 as evidence by the X-ray crystallography and alanine mutant studies of Example 9.

In one embodiment, the present invention provides bispecific antibodies, antibodies and antigen-binding fragments thereof. The bispecific antibodies of the invention comprise an IL-17A binding entity that binds to IL-17A and an IL-23 binding entity that binds to IL-23 via p19. In another aspect, the bispecific antibodies of the invention comprise an IL-17F binding entity that binds to IL-17F and a IL-23 binding entity that binds to IL-23 via p19. In another aspect, the bispecific antibodies of the invention comprise an IL-17A/F binding entity that binds to IL-17A and IL-17F and a IL-23 binding entity that binds to IL-23 via p19. The binding entity that binds to IL-23 via p19 is referred to hereinafter as a binding entity that binds to IL-23 or an "IL-23 binding entity". The polynucleotide sequence of the human IL-17A is shown in SEQ ID NO:1 and the corresponding polypeptide sequence is shown in SEQ ID NO:2. The signal sequence of the IL-17A polypeptide is amino acid residues 1-23 of SEQ ID NO:2. Thus, amino acid residues 24-155 of SEQ ID NO:2 constitute the mature IL-17A polypeptide. Antibodies (and antigen-binding fragments thereof) and bispecific antibodies disclosed herein that bind to IL-17A bind to the mature IL-17A polypeptide (amino acid residues 24-155 of SEQ ID NO:2). The polynucleotide sequence of the human IL-17F is shown in SEQ ID NO:3 and the corresponding polypeptide sequence is shown in SEQ ID NO:4. The signal sequence of the IL-17F polypeptide is amino acid residues 1-30 of SEQ ID NO:4. Thus, amino acid residues 31-163 of SEQ ID NO:4 constitute the mature IL-17F polypeptide. Antibodies (and antigen-binding fragments thereof) and bispecific antibodies disclosed herein that bind to IL-17F bind to the mature IL-17F polypeptide (amino acid residues 31-163 of SEQ ID NO:4). The polynucleotide sequence of the human p19 subunit of IL-23 is shown in SEQ ID NO:5 and the corresponding polypeptide sequence is shown in SEQ ID NO:6. The signal sequence of the IL-23p19 polypeptide is amino acid residues 1-19 of SEQ ID NO:6. Thus, amino acid residues 20-189 of SEQ ID NO:6 constitute the mature IL-23p19 polypeptide. Antibodies (and antigen-binding fragments thereof) and bispecific antibodies disclosed herein that bind to IL-23p19 bind to the mature IL-23p19 polypeptide (amino acid residues 20-189 of SEQ ID NO:6).

In one aspect of the invention, the IL-17A/F binding entity comprises an antibody, i.e., two pairs of immunoglobulin chains, each pair having one light and one heavy chain, and the IL-23 binding entity comprises two Fab fragments each comprising a light chain and the $C_{H1}$ and variable regions of a heavy chain, and the Fab fragments of the IL-23 binding entity are linked to the C-termini of the heavy chains (Fc) of the IL-17A/F binding entity. This bispecific antibody format is referred to herein as biAbFabL (see FIG. 2). In another embodiment, each of the light chain and the $C_{H1}$ and variable regions of the heavy chain comprising the Fab fragments of the IL-23 binding entity are linked to the N-termini of the light chains and heavy chains, respectively, of the IL-17A/F binding entity. This bispecific antibody format is referred to herein as taFab (see FIG. 3).

In another aspect of the invention, the IL-23 binding entity comprises an antibody, i.e., two pairs of immunoglobulin chains, each pair having one light and one heavy chain, and the IL-17A/F binding entity comprises two Fab fragments each comprising a light chain and the $C_{H1}$ and variable regions of a heavy chain, and the Fab fragments of the IL-17A/F binding entity are linked to the C-termini of the heavy chains (Fc) of the IL-23 binding entity. This bispecific antibody format is referred to herein as biAbFabL (See FIG. 2). In another embodiment, each of the light chain and the $C_{H1}$ and variable regions of the heavy chain comprising the Fab fragments of the IL-17A/F binding entity are linked to the N-termini of the light chain and heavy chain, respectively, of the IL-23 binding entity. This bispecific antibody format is referred to herein as taFab (see FIG. 3).

In another aspect of the invention, the IL-23 binding entity comprises a light chain and an IL-23 heavy chain and the IL-17A/F binding entity comprises a light chain and an IL-17A/F heavy chain. This bispecific antibody resembles a traditional antibody except that it comprises two different heavy chains that associate through an electrostatic complementarity association in the $C_{H3}$ regions. It utilizes a common light chain. This bispecific antibody format is referred to herein as Heterodimeric Fc (see FIG. 4).

Figure 5:
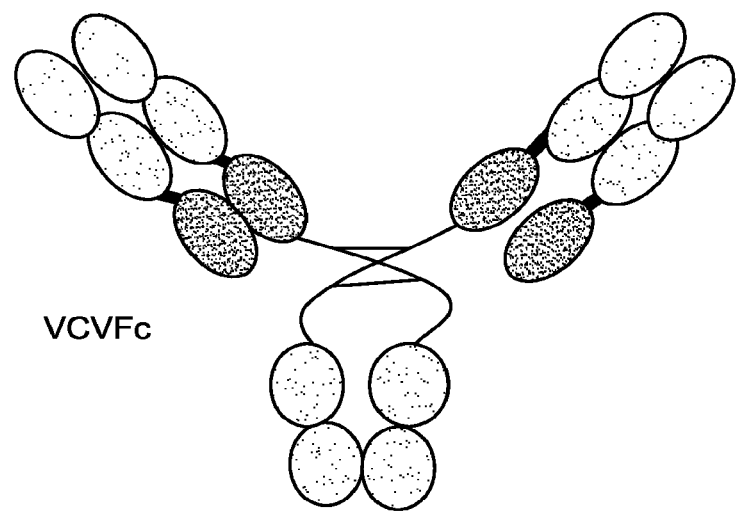
FIG. 5 depicts a model of a bispecific antibody designated VCVFc which contains a whole antibody with a Fv unit of the second arm of the bispecific antibody inserted between the Fab region and the hinge via linkers.

In another embodiment, the present invention provides bispecific antibodies comprising a first binding entity comprising an antibody, i.e., two pairs of immunoglobulin chains, each pair having one light chain and one heavy chain, and a second binding entity comprising an Fv unit, i.e., the variable domains from a heavy and a light chain, and in which the second binding entity comprising the Fv unit is positioned between the Fab region and the hinge of the first binding entity as shown in FIG. 5. The Fv unit is linked to the Fab region of the first binding entity by linker molecules. More specifically, the Fv unit comprises a variable light domain which is linked to the light chain constant region of the Fab fragment, and a variable heavy domain which is linked to the $C_{H1}$ region of the Fab fragment. This bispecific antibody format is referred to herein as VCVFc. The first binding entity and second binding entity of a VCVFc do not have to share a common light chain, while the first binding entity and second binding entity of a biAbFabL do have to share a common light chain. In one aspect of this embodiment of the invention, the first binding entity specifically binds a lymphocyte antigen, cytokine, cytokine receptor, growth factor, growth factor receptor, interleukin (e.g., IL-17A, IL-17F, IL-17A/F and IL-23) or interleukin receptor and the second binding entity specifically binds a lymphocyte antigen, cytokine, cytokine receptor, growth factor, growth factor receptor, interleukin (e.g., IL-17A, IL-17F, IL-17A/F and IL-23) or interleukin receptor. In another aspect of this embodiment of the invention, the first binding entity is an IL-17A/F binding entity and the second binding entity is an IL-23 binding entity. In another aspect of this embodiment of the invention, the first binding entity is an IL-23 binding entity and the second binding entity is an IL-17A/F binding entity.

Figure 6:
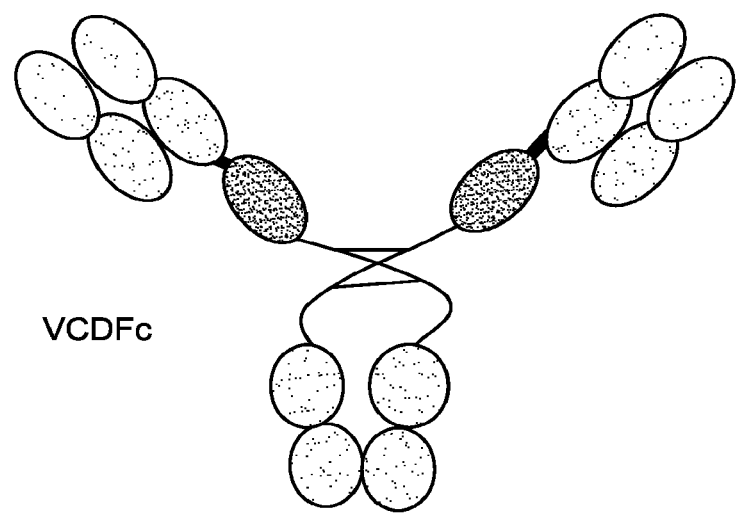
FIG. 6 depicts a model of a bispecific antibody designated VCDFc which contains a whole antibody with a single domain antibody for the second arm of the bispecific antibody inserted between the Fab region and the hinge via linkers.

In another embodiment, the present invention provides bispecific antibodies comprising a first binding entity comprising an antibody, i.e., two pairs of immunoglobulin chains, each pair having one light chain and one heavy chain, and a second binding entity comprising a single domain antibody. This bispecific antibody format is referred to herein as VCDFc. An illustration of a VCDFc bispecific antibody is shown in FIG. 6. The second binding entity comprising the single domain antibody is positioned between the Fab region, more specifically the $C_{H1}$ region of the Fab fragment, and the hinge of the first binding entity. The single domain antibody is linked to the $C_{H1}$ region of the Fab of the first binding entity by linker molecules (for example, but not limited to, 10mer $G_4S$, which is represented by the equation $(G_4S)_2$, or SSASTKGPS (SEQ ID NO:86)). In one aspect of this embodiment of the invention, the first binding entity specifically binds a lymphocyte antigen, cytokine, cytokine receptor, growth factor, growth factor receptor, interleukin (e.g., IL-17A, IL-17F, IL-17A/F and IL-23) or interleukin receptor and the second binding entity specifically binds a lymphocyte antigen, cytokine, cytokine receptor, growth factor, growth factor receptor, interleukin (e.g., IL-17A, IL-17F, IL-17A/F and IL-23) or interleukin receptor. In one aspect of this embodiment of the invention, the first binding entity is an IL-23 binding entity and the second binding entity is an IL-17A/F binding entity. In another aspect of this embodiment of the invention, the first binding entity is an IL-17A/F binding entity and the second binding entity is an IL-23 binding entity.

The amino acid sequences of the binding entities are preferably based upon the sequences of human and/or humanized monoclonal antibodies against a lymphocyte antigen, cytokine, cytokine receptor, growth factor, growth factor receptor, interleukin (e.g., IL-17A, IL-17F, IL-17A/F and IL-23) or interleukin receptor.

In one embodiment of the foregoing aspects of the invention, the light chains of the IL-17A/F binding entity and the IL-23 binding entity of the bispecific antibody each comprise a variable domain comprising a CDR1 having the amino acid sequence of SEQ ID NO:22, a CDR2 having the amino acid sequence of SEQ ID NO:23, and a CDR3 having the sequence of SEQ ID NO:24. In another embodiment, the light chains of the IL-17A/F binding entity and the IL-23 binding entity each comprise a variable domain comprising the amino acid sequence of SEQ ID NO:9. In another embodiment, the light chains of the IL-17A/F binding entity and the IL-23 binding entity each comprise a constant domain comprising the amino acid sequence of SEQ ID NO:10. In another embodiment, the light chains of the IL-17A/F binding entity and the IL-23 binding entity each comprise a variable domain comprising the amino acid sequence of SEQ ID NO:9 and a constant domain comprising the amino acid sequence of SEQ ID NO:10.

In another embodiment of the foregoing aspects of the invention, the heavy chain of the IL-17A/F binding entity of the bispecific antibody comprises a variable domain comprising a CDR1 having the amino acid sequence of SEQ ID NO:25, a CDR2 having the amino acid sequence of SEQ ID NO:26, and a CDR3 having the amino acid sequence of SEQ ID NO:27. In another embodiment, the heavy chain of the IL-17A/F binding entity comprises a variable domain comprising the amino acid sequence of SEQ ID NO:13. In another embodiment, when the IL-17A/F binding entity comprises an antibody, the heavy chain constant domain comprises the amino acid sequence of SEQ ID NO:8, SEQ ID NO:11, SEQ ID NO:127 or SEQ ID NO:128. In another embodiment, when the IL-17A/F binding entity comprises a Fab fragment, the $C_{H1}$ region of the heavy chain comprises the amino acid sequence of SEQ ID NO:14 or SEQ ID NO:15.

In another embodiment of the foregoing aspects of the invention, the IL-17A/F binding entity of the bispecific antibody comprises a heavy chain variable domain having at least 90%, at least 91%, at least 92%, at least 93%, at least 94%, at least 95%, at least 96%, at least 97%, at least 98%, at least 99% sequence identity with the amino acid sequence of SEQ ID NO:13. Optionally, all of the substitutions, additions or deletions are within the framework region of the heavy chain variable domain. Optionally, the IL-17A/F binding entity of the bispecific antibody comprises a heavy chain variable domain having at least 90%, at least 91%, at least 92%, at least 93%, at least 94%, at least 95%, at least 96%, at least 97%, at least 98%, at least 99% sequence identity with the amino acid sequence of SEQ ID NO:13, wherein the variable domain comprises a CDR1 having the amino acid sequence of SEQ ID NO:25, a CDR2 having the amino acid sequence of SEQ ID NO:26, and a CDR3 having the amino acid sequence of SEQ ID NO:27. Optionally, the heavy chain variable domain comprises the amino acid sequence of SEQ ID NO:13. Optionally, the three IL-17A/F heavy chain variable domain CDRs include a CDR1 region comprising an amino acid sequence having at least 90%, at least 91%, at least 92%, at least 93%, at least 94%, at least 95%, at least 96%, at least 97%, at least 98%, at least 99% sequence identity with the amino acid sequence of SEQ ID NO:25; a CDR2 region comprising an amino acid sequence having at least 90%, at least 91%, at least 92%, at least 93%, at least 94%, at least 95%, at least 96%, at least 97%, at least 98%, at least 99% sequence identity with the amino acid sequence of SEQ ID NO:26; and a CDR3 region comprising an amino acid sequence having at least 90%, at least 91%, at least 92%, at least 93%, at least 94%, at least 95%, at least 96%, at least 97%, at least 98%, at least 99% sequence identity with the amino acid sequence of SEQ ID NO:27. Optionally, the IL-17A/F heavy chain variable domain CDR1 has the amino acid sequence of SEQ ID NO:25; the heavy chain variable domain CDR2 has the amino acid sequence of SEQ ID NO:26; and the heavy chain variable domain CDR3 has the amino acid sequence of SEQ ID NO:27. The IL-17A/F and/or IL-23p19 binding entity comprises a light chain variable domain having at least 90%, at least 91%, at least 92%, at least 93%, at least 94%, at least 95%, at least 96%, at least 97%, at least 98%, at least 99% sequence identity with the amino acid sequence of SEQ ID NO:9. Optionally, all of the substitutions, additions or deletions are within the framework region of the light chain variable domain. Optionally, the IL-17A/F and/or IL-23p19 binding entity of the bispecific antibody comprises a light chain variable domain having at least 90%, at least 91%, at least 92%, at least 93%, at least 94%, at least 95%, at least 96%, at least 97%, at least 98%, at least 99% sequence identity with the amino acid sequence of SEQ ID NO:9, wherein the variable domain comprises a CDR1 having the amino acid sequence of SEQ ID NO:22, a CDR2 having the amino acid sequence of SEQ ID NO:23, and a CDR3 having the amino acid sequence of SEQ ID NO:24. Optionally, the light chain variable domain comprises the amino acid sequence of SEQ ID NO:9. Optionally, the three IL-17A/F and/or IL-23p19 light chain variable domain CDRs include a CDR1 region comprising an amino acid sequence having at least 90%, at least 91%, at least 92%, at least 93%, at least 94%, at least 95%, at least 96%, at least 97%, at least 98%, at least 99% sequence identity with the amino acid sequence of SEQ ID NO:22; a CDR2 region comprising an amino acid sequence having at least 90%, at least 91%, at least 92%, at least 93%, at least 94%, at least 95%, at least 96%, at least 97%, at least 98%, at least 99% sequence identity with the amino acid sequence of SEQ ID NO:23; and a CDR3 region comprising an amino acid sequence having at least 90%, at least 91%, at least 92%, at least 93%, at least 94%, at least 95%, at least 96%, at least 97%, at least 98%, at least 99% sequence identity with the amino acid sequence of SEQ ID NO:24. Optionally, the IL-17A/F and/or IL-23p19 light chain variable domain CDR1 has the amino acid sequence of SEQ ID NO:22; the IL-17A/F and/or IL-23p19 light chain variable domain CDR2 has the amino acid sequence of SEQ ID NO:23; and the IL-17A/F and/or IL-23p19 light chain variable domain CDR3 has the amino acid sequence of SEQ ID NO:24. The IL-23p19 binding entity comprises a heavy chain variable domain having at least 90%, at least 91%, at least 92%, at least 93%, at least 94%, at least 95%, at least 96%, at least 97%, at least 98%, at least 99% sequence identity with the amino acid sequence of SEQ ID NO:7. Optionally, all of the substitutions, additions or deletions are within the framework region of the IL-23p19 heavy chain variable domain. Optionally, the IL-23p19 binding entity of the bispecific antibody comprises a heavy chain variable domain having at least 90%, at least 91%, at least 92%, at least 93%, at least 94%, at least 95%, at least 96%, at least 97%, at least 98%, at least 99% sequence identity with the amino acid sequence of SEQ ID NO:7, wherein the variable domain comprises a CDR1 having the amino acid sequence of SEQ ID NO:19, a CDR2 having the amino acid sequence of SEQ ID NO:20, and a CDR3 having the amino acid sequence of SEQ ID NO:21. Optionally, the IL-23p19 heavy chain variable domain comprises the amino acid sequence of SEQ ID NO:7. Optionally, the three IL-23p19 heavy chain variable domain CDRs include a CDR1 region comprising an amino acid sequence having at least 90%, at least 91%, at least 92%, at least 93%, at least 94%, at least 95%, at least 96%, at least 97%, at least 98%, at least 99% sequence identity with the amino acid sequence of SEQ ID NO:19; a CDR2 region comprising an amino acid sequence having at least 90%, at least 91%, at least 92%, at least 93%, at least 94%, at least 95%, at least 96%, at least 97%, at least 98%, at least 99% sequence identity with the amino acid sequence of SEQ ID NO:20; and a CDR3 region comprising an amino acid sequence having at least 90%, at least 91%, at least 92%, at least 93%, at least 94%, at least 95%, at least 96%, at least 97%, at least 98%, at least 99% sequence identity with the amino acid sequence of SEQ ID NO:21. Optionally, the IL-23p19 heavy chain variable domain CDR1 has the amino acid sequence of SEQ ID NO:19; the heavy chain variable domain CDR2 has the amino acid sequence of SEQ ID NO:20; and the heavy chain variable domain CDR3 has the amino acid sequence of SEQ ID NO:21.

In another embodiment of the foregoing aspects of the invention, the heavy chain of the IL-23 binding entity of the bispecific antibody comprises a variable domain comprising a CDR1 having the amino acid sequence of SEQ ID NO:19, a CDR2 having the amino acid sequence of SEQ ID NO:20, and a CDR3 having the amino acid sequence of SEQ ID NO:21. In another embodiment, the heavy chain of the IL-23 binding entity comprises a variable domain comprising the amino acid sequence of SEQ ID NO:7. In another embodiment, when the IL-23 binding entity comprises an antibody, the heavy chain constant domain comprises the amino acid sequence of SEQ ID NO:8, SEQ ID NO:11, SEQ ID NO:127 or SEQ ID NO:128. In some embodiments, the C-terminal lysine of SEQ ID NO:8 has been cleaved, and so the heavy chain constant domain comprises the amino acid sequence of residues 1-326 of SEQ ID NO:8. In another embodiment, when the IL-23 binding entity comprises a Fab fragment, the $C_{H1}$ region of the heavy chain comprises the amino acid sequence of SEQ ID NO:14 or SEQ ID NO:15.

In another embodiment of the foregoing aspects of the invention, when the IL-23 binding entity or IL-17A/F binding entity of the bispecific antibody is an Fv unit, the variable domain of the light chain comprises a CDR1 having the amino acid sequence of SEQ ID NO:22, a CDR2 having the amino acid sequence of SEQ ID NO:23, and a CDR3 having the sequence of SEQ ID NO:24. In another embodiment, the light chains of the IL-17A/F binding entity and the IL-23 binding entity each comprise a variable domain comprising the amino acid sequence of SEQ ID NO:9.

In another embodiment of the foregoing aspects of the invention, when the IL-17A/F binding entity of the bispecific antibody is an Fv unit, the variable domain of the heavy chain comprises a CDR1 having the amino acid sequence of SEQ ID NO:25, a CDR2 having the amino acid sequence of SEQ ID NO:26, and a CDR3 having the amino acid sequence of SEQ ID NO:27. In another embodiment, the heavy chain of the IL-17A/F binding entity comprises a variable domain comprising the amino acid sequence of SEQ ID NO:13.

In another embodiment of the foregoing aspects of the invention, when the IL-23 binding entity of the bispecific antibody is an Fv unit, the variable domain of the heavy chain comprises a CDR1 having the amino acid sequence of SEQ ID NO:19, a CDR2 having the amino acid sequence of SEQ ID NO:20, and a CDR3 having the amino acid sequence of SEQ ID NO:21. In another embodiment, the heavy chain of the IL-23 binding entity comprises a variable domain comprising the amino acid sequence of SEQ ID NO:7.

Figure 2:
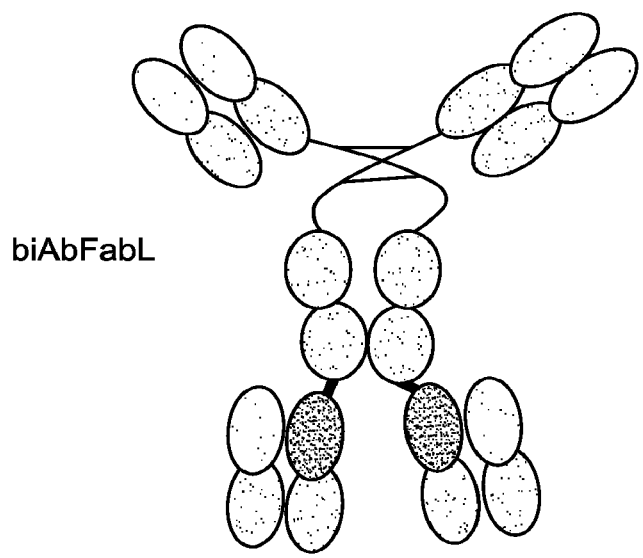
FIG. 2 depicts a model of a bispecific antibody designated biAbFabL which contains a whole antibody with a C-terminal Fab unit of the second arm of the bispecific antibody attached via a linker, and which utilizes a common light chain.

In another embodiment of the foregoing aspects of the invention, the Fab fragments of the IL-23 binding entity of the bispecific antibody are linked to the C-termini of the heavy chains (Fc) of the IL-17A/F binding entity, or the Fab fragments of the IL-17A/F binding entity are linked, for example, to the C-termini of the heavy chains (Fc) of the IL-23 binding entity by a linker molecule (see, for example, FIG. 2). In another embodiment, each of the light chain and the $C_{H1}$ and variable regions of the heavy chain comprising the Fab fragments of the IL-23 binding entity are linked to the N-termini of the light chain and heavy chain, respectively, of the IL-17A/F binding entity, or each of the light chain and the $C_{H1}$ and variable regions of the heavy chain comprising the Fab fragments of the IL-17A/F binding entity are linked to the N-termini of the light chain and heavy chain, respectively, of the IL-23 binding entity by a linker molecule (see, for example, FIG. 3). In another embodiment of the VCVFc bispecific antibody, each of the light chain variable region and the heavy chain variable region of the Fv unit comprising the second binding entity are linked to each of the light chain constant region and the $C_{H1}$ region, respectively, of the Fab fragment of the first binding entity by a linker molecule (see FIG. 5). Suitable linker molecules are known in the art and include, for example, short polypeptides. A suitable linker may include a short polypeptide, which contains glycine, which confers flexibility, and serine or threonine, which confer solubility. A suitable linker may comprise $Gly_4Ser_1$ units. For example, the linker may be $(Gly_4Ser_1)_x$, wherein x is 1, 2, or 3. Optionally, the linker polypeptide has the amino acid sequence of SEQ ID NO:12. In another embodiment of the VCVFc bispecific antibodies, the linker for the light chain has the amino acid sequence of SEQ ID NO:85 and the linker for the heavy chain has the amino acid sequence of SEQ ID NO:86.

In another embodiment of the foregoing aspects of the invention, the bispecific antibody comprises a pair of heavy chains each comprising the amino acid sequence of SEQ ID NO:16, SEQ ID NO:18, SEQ ID NO:28, SEQ ID NO:29, SEQ ID NO:74, or SEQ ID NO:84 and a pair of light chains each comprising the amino acid sequence of SEQ ID NO:17.

In a preferred embodiment, the bispecific antibody comprises a pair of heavy chains comprising the amino acid sequence of SEQ ID NO:74 and a pair of light chains each comprising the amino acid sequence of SEQ ID NO:17.

In another embodiment of the foregoing aspects of the invention, an IL-17A/F antibody (or an antigen-binding fragment thereof) or the IL-17A/F binding entity of the bispecific antibody, such as a biAbFabL (see FIG. 2), a taFab (see FIG. 3), a heterodimeric Fc (see FIG. 4), a VCVFc (see FIG. 5) or a VCDFc (see FIG. 6) binds (a) an IL-17A homodimer with a binding affinity ($K_{D1}$) of at least $1\times10^{-9}$ M, at least $5\times10^{-9}$ M, at least $1\times10^{-10}$ M, at least $5\times10^{-10}$ M, at least $8\times10^{-10}$ M or at least at least $1\times10^{-11}$ M; (b) an IL-17F homodimer with a binding affinity ($K_{D1}$) of at least $1\times10^{-9}$ M, at least $5\times10^{-9}$ M, at least $1\times10^{-10}$ M, at least $2\times10^{-10}$ M, at least $3\times10^{-10}$ M, at least $4\times10^{-10}$ M, at least $5\times10^{-10}$ M or at least $1\times10^{-11}$ M; and/or (c) an IL-17A/F heterodimer with a binding affinity ($K_{D1}$) of at least $1\times10^{-8}$ M, at least $5\times10^{-8}$ M, at least $1\times10^{-9}$ M, at least $2\times10^{-9}$ M, at least $3\times10^{-9}$ M, at least $4\times10^{-9}$ M, at least $5\times10^{-9}$ M, at least $6\times10^{-9}$ M, at least $7\times10^{-9}$ M, at least $9\times10^{-9}$ M, at least $1\times10^{-10}$ M or at least $5\times10^{-10}$ M, wherein the binding affinity is measured by surface plasmon resonance, such as Biacore.

In another embodiment of the foregoing aspects of the invention, an IL-23p19 antibody (or an antigen-binding fragment thereof) or the IL-23p19 binding entity of the bispecific antibody, such as a biAbFabL (see FIG. 2), a taFab (see FIG. 3), a heterodimeric Fc (see FIG. 4), a VCVFc (see FIG. 5) or a VCDFc (see FIG. 6) binds IL-23p19 with a binding affinity ($K_{D1}$) of at least $1\times10^{-9}$ M, at least $5\times10^{-9}$ M, at least $1\times10^{-10}$ M, at least $2\times10^{-10}$ M, at least $3\times10^{-10}$ M, at least $4\times10^{-10}$ M, at least $5\times10^{-10}$, at least $6\times10^{-10}$, at least $7\times10^{-10}$, at least $8\times10^{-10}$ or at least $9\times10^{-10}$, at least $1\times10^{-11}$, wherein the binding affinity is measured by surface plasmon resonance, such as Biacore.

In another embodiment of the foregoing aspects of the invention, the IL-17A/F binding entity of the bispecific antibody, such as a biAbFabL (see FIG. 2), a taFab (see FIG. 3), a heterodimeric Fc (see FIG. 4), a VCVFc (see FIG. 5) or a VCDFc (see FIG. 6) binds (a) an IL-17A homodimer with a binding affinity ($K_{D1}$) of at least $1\times10^{-9}$ M, at least $5\times10^{-9}$ M, at least $1\times10^{-10}$ M, at least $5\times10^{-10}$ M, at least $8\times10^{-10}$ M or at least at least $1\times10^{-11}$ M; (b) an IL-17F homodimer with a binding affinity ($K_{D1}$) of at least $1\times10^{-9}$ M, at least $5\times10^{-9}$ M, at least $1\times10^{-10}$ M, at least $2\times10^{-10}$ M, at least $3\times10^{-10}$ M, at least $4\times10^{-10}$ M, at least $5\times10^{-10}$ M or at least $1\times10^{-11}$ M; and/or (c) an IL-17A/F heterodimer with a binding affinity ($K_{D1}$) of at least $1\times10^{-8}$ M, at least $5\times10^{-8}$ M, at least $1\times10^{-9}$ M, at least $2\times10^{-9}$ M, at least $3\times10^{-9}$ M, at least $4\times10^{-9}$ M, at least $5\times10^{-9}$ M, at least $6\times10^{-9}$ M, at least $7\times10^{-9}$ M, at least $9\times10^{-9}$ M, at least $1\times10^{-10}$ M or at least $5\times10^{-10}$ M; and the IL-23p19 binding entity of the bispecific antibody binds IL-23p19 with a binding affinity ($K_{D1}$) of at least $1\times10^{-9}$ M, at least $5\times10^{-9}$ M, at least $1\times10^{-10}$ M, at least $2\times10^{-10}$ M, at least $3\times10^{-10}$ M, at least $4\times10^{-10}$ M, at least $5\times10^{-10}$, at least $6\times10^{-10}$, at least $7\times10^{-10}$, at least $8\times10^{-10}$ or at least $9\times10^{-10}$, at least $1\times10^{-11}$, wherein the binding affinity is measured by surface plasmon resonance, such as Biacore.

In another embodiment of the foregoing aspects of the invention, an IL-17A/F antibody (or an antigen-binding fragment thereof) or the IL-17A/F binding entity of the bispecific antibody neutralizes or inhibits (a) IL-17A induction of G-CSF in primary human small airway epithelial cells (SAEC) with an $IC_{50}$ of 0.5 pm or less; (b) IL-17F induction G-CSF in primary human small airway epithelial cells (SAEC) with an $IC_{50}$ of 2.0 nM or less, 1.5 nM or less, 1.4 nM or less, 1.3 nM or less, 1.2 nM or less, 1.1 nM or less, or 1.0 nM or less; and/or (c) IL-17A/F induction G-CSF in primary human small airway epithelial cells (SAEC) with an $IC_{50}$ of 1.3 nM or less, 1.2 nM or less, 1.1 nM or less, 1.0 nM or less, 0.9 nM or less, 0.8 nM or less, 0.7 nM or less, 0.6 nM or less, or 0.5 nM or less.

In another embodiment of the foregoing aspects of the invention, an IL-17A/F antibody (or an antigen-binding fragment thereof) or the IL-17A/F binding entity of the bispecific antibody neutralizes or inhibits (a) IL-17A induction of IL-6 in human primary fibroblast cells (HFFF) with an $IC_{50}$ of 0.5 nM or less, 0.4 nM or less, 0.3 nM or less, 0.2 nM or less, 0.1 nM or less, 0.09 nM or less, 0.08 nM or less, 0.07 nM or less, 0.06 nM or less, 0.05 nM or less, 0.04 nM or less, 0.03 nM or less, 0.02 nM or less, or 0.01 nM or less; (b) IL-17F induction of IL-6 in human primary fibroblast cells (HFFF) with an $IC_{50}$ of 30 nM or less, 28 nM or less, 26 nM or less, 25 nM or less, 22 nM or less, 20 nM or less, 19 nM or less, 18 nM or less, 17 nM or less, 16 nM or less, 15 nM or less, 14 nM or less, 13 nM or less, 12 nM or less, 11 nM or less, or 10 nM or less; and/or (c) IL-17A/F induction of IL-6 in human primary fibroblast cells (HFFF) with an $IC_{50}$ of 30 nM or less, 28 nM or less, 26 nM or less, 22 nM or less, 20 nM or less, 18 nM or less, 17 nM or less, 16 nM or less, 15 nM or less, 14 nM or less, 13 nM or less, 12 nM or less, 11 nM or less, 10 nM or less, 9.5 nM or less, 9.4 nM or less, 9.3 nM or less, 9.2 nM or less, 9.1 nM or less, or 9.0 nM or less.

In another embodiment of the foregoing aspects of the invention, an IL-23p19 antibody (or an antigen-binding fragment thereof) or the IL-23p19 binding entity of the bispecific antibody neutralizes or inhibits (a) IL-23 induced IL-17A and IL-17F production in murine splenocytes with an $IC_{50}$ of 0.5 nM or less, 0.4 nM or less, 0.3 nM or less, 0.2 nM or less, 0.1 nM or less, 0.09 nM or less, 0.08 nM or less, 0.07 nM or less, or 0.06 nM or less.

In another embodiment of the foregoing aspects of the invention, an IL-23p19 antibody (or an antigen-binding fragment thereof) or the IL-23p19 binding entity of the bispecific antibody neutralizes or inhibits IL-23 induced STAT3 phosphorylation in activated primary human T cells with an $IC_{50}$ of 0.1 nM or less, 0.2 nM or less, 0.3 nM or less, 0.4 nM or less, 0.5 nM or less, 0.8 nM or less, 0.9 nM or less, 0.01 nM or less, 0.02 nM or less, 0.03 nM or less, 0.04 nM or less, or 0.05 nM or less.

In another embodiment of the foregoing aspects of the invention, the IL-17A/F binding entity of the bispecific antibody, such as a biAbFabL (see FIG. 2), a taFab (see FIG. 3), a heterodimeric Fc (see FIG. 4), a VCVFc (see FIG. 5) or a VCDFc (see FIG. 6) binds (a) an IL-17A homodimer with a binding affinity ($K_{D1}$) of at least $1 \times 10^{-9}$ M, at least $5 \times 10^{-9}$ M, at least $1 \times 10^{-10}$ M, at least $5 \times 10^{-10}$ M, at least $8 \times 10^{-10}$ M or at least at least $1 \times 10^{-11}$ M; (b) an IL-17F homodimer with a binding affinity ($K_{D1}$) of at least $1 \times 10^{-9}$ M, at least $5 \times 10^{-9}$ M, at least $1 \times 10^{-10}$ M, at least $2 \times 10^{-10}$ M, at least $3 \times 10^{-10}$ M, at least $4 \times 10^{-10}$ M, at least $5 \times 10^{-10}$ M or at least $1 \times 10^{-11}$ M; and/or (c) an IL-17A/F heterodimer with a binding affinity ($K_{D1}$) of at least $1 \times 10^{-8}$ M, at least $5 \times 10^{-8}$ M, at least $1 \times 10^{-9}$ M, at least $2 \times 10^{-9}$ M, at least $3 \times 10^{-9}$ M, at least $4 \times 10^{-9}$ M, at least $5 \times 10^{-9}$ M, at least $6 \times 10^{-9}$ M, at least $7 \times 10^{-9}$ M, at least $9 \times 10^{-9}$ M, at least $1 \times 10^{-10}$ M or at least $5 \times 10^{-10}$ M. Optionally, the IL-23p19 binding entity of the bispecific antibody binds IL-23p19 with a binding affinity ($K_{D1}$) of at least $1 \times 10^{-9}$ M, at least $5 \times 10^{-9}$ M, at least $1 \times 10^{-10}$ M, at least $2 \times 10^{-10}$ M, at least $3 \times 10^{-10}$ M, at least $4 \times 10^{-10}$ M, at least $5 \times 10^{-10}$, at least $6 \times 10^{-10}$, at least $7 \times 10^{-10}$, at least $8 \times 10^{-10}$ or at least $9 \times 10^{-10}$, at least $1 \times 10^{-11}$, wherein the binding affinity is measured by surface plasmon resonance, such as Biacore. Optionally, the IL-17A/F binding entity of the bispecific antibody neutralizes or inhibits (a) IL-17A induction of G-CSF in primary human small airway epithelial cells (SAEC) with an $IC_{50}$ of 0.5 pm or less; (b) IL-17F induction G-CSF in primary human small airway epithelial cells (SAEC) with an $IC_{50}$ of 2.0 nM or less, 1.5 nM or less, 1.4 nM or less, 1.3 nM or less, 1.2 nM or less, 1.1 nM or less, or 1.0 nM or less; and/or (c) IL-17A/F induction G-CSF in primary human small airway epithelial cells (SAEC) with an $IC_{50}$ of 1.3 nM or less, 1.2 nM or less, 1.1 nM or less, 1.0 nM or less, 0.9 nM or less, 0.8 nM or less, 0.7 nM or less, 0.6 nM or less, or 0.5 nM or less. Optionally, the IL-17A/F binding entity of the bispecific antibody neutralizes or inhibits (a) IL-17A induction of IL-6 in human primary fibroblast cells (HFFF) with an $IC_{50}$ of 0.5 nM or less, 0.4 nM or less, 0.3 nM or less, 0.2 nM or less, 0.1 nM or less, 0.09 nM or less, 0.08 nM or less, 0.07 nM or less, 0.06 nM or less, 0.05 nM or less, 0.04 nM or less, 0.03 nM or less, 0.02 nM or less, or 0.01 nM or less; (b) IL-17F induction of IL-6 in human primary fibroblast cells (HFFF) with an $IC_{50}$ of 30 nM or less, 28 nM or less, 26 nM or less, 25 nM or less, 22 nM or less, 20 nM or less, 19 nM or less, 18 nM or less, 17 nM or less, 16 nM or less, 15 nM or less, 14 nM or less, 13 nM or less, 12 nM or less, 11 nM or less, or 10 nM or less; and/or (c) IL-17A/F induction of IL-6 in human primary fibroblast cells (HFFF) with an $IC_{50}$ of 30 nM or less, 28 nM or less, 26 nM or less, 22 nM or less, 20 nM or less, 18 nM or less, 17 nM or less, 16 nM or less, 15 nM or less, 14 nM or less, 13 nM or less, 12 nM or less, 11 nM or less, 10 nM or less, 9.5 nM or less, 9.4 nM or less, 9.3 nM or less, 9.2 nM or less, 9.1 nM or less, or 9.0 nM or less. Optionally, the IL-23p19 binding entity of the bispecific antibody neutralizes or inhibits IL-23 induced STAT3 phosphorylation in activated primary human T cells with an $IC_{50}$ of 0.1 nM or less, 0.2 nM or less, 0.3 nM or less, 0.4 nM or less, 0.5 nM or less, 0.8 nM or less, 0.9 nM or less, 0.01 nM or less, 0.02 nM or less, 0.03 nM or less, 0.04 nM or less, or 0.05 nM or less.

In another embodiment of the foregoing aspects of the invention, the bispecific antibody comprises a pair of heavy chains comprising the amino acid sequence of SEQ ID NO:28 and a pair of light chains comprising the amino acid sequence of SEQ ID NO:17 is referred to herein as "biAb1", "bAb1" or "23/17bAb1". A bispecific antibody comprising a pair of heavy chains each comprising the amino acid sequence of SEQ ID NO:18 and a pair of light chains each comprising the amino acid sequence of SEQ ID NO:17 is referred to herein as "biAb2", "bAb2" or "23/17bAb2". A bispecific antibody comprising a pair of heavy chains each comprising the amino acid sequence of SEQ ID NO:74 and a pair of light chains each comprising the amino acid sequence of SEQ ID NO:17 is referred to herein as "biAb3", "bAb3" or "23/17bAb3". A bispecific antibody comprising a pair of heavy chains comprising the amino acid sequence of SEQ ID NO:29 and a pair of light chains each comprising the amino acid sequence of SEQ ID NO:17 is referred to herein as "biAb4", "bAb4" or "23/17bAb4".

In another embodiment of the foregoing aspects of the invention, the bispecific antibody comprises a pair of heavy chains each comprising the amino acid sequence of SEQ ID NO:77 and a pair of light chains each comprising the amino acid sequence of SEQ ID NO:79 and is referred to herein as "taFab1".

In another embodiment of the foregoing aspects of the invention, the bispecific antibody comprises an IL-23 heavy chain comprising the amino acid sequence of SEQ ID NO:63, an IL-17A/F heavy chain comprising the amino acid sequence of SEQ ID NO:65, and a pair of light chains each comprising the sequence of SEQ ID NO:17, and is referred to herein as "hetero1". In another embodiment, the bispecific antibody comprises an IL-23 heavy chain comprising the amino acid sequence of SEQ ID NO:61, an IL-17A/F heavy chain comprising the amino acid sequence of SEQ ID NO:81, and a pair of light chains each comprising the sequence of SEQ ID NO:17, and is referred to herein as "hetero2".

In another embodiment of the foregoing aspects of the invention, the bispecific antibody in the VCVFc format, see FIG. 5, has a pair of heavy chains each comprising the amino acid sequence of SEQ ID NO:88 and a pair of light chains each comprising the amino acid sequence of SEQ ID NO:90, or a pair of heavy chains each comprising the amino acid sequence of SEQ ID NO:92 and a pair of light chains each comprising the amino acid sequence of SEQ ID NO:94, or a pair of heavy chains each comprising the amino acid sequence of SEQ ID NO:96 and a pair of light chains each comprising the amino acid sequence of SEQ ID NO:90, or a pair of heavy chains each comprising the amino acid sequence of SEQ ID NO:98 and a pair of light chains each comprising the amino acid sequence of SEQ ID NO:94, or a pair of heavy chains each comprising the amino acid sequence of SEQ ID NO:100 and a pair of light chains each comprising the amino acid sequence of SEQ ID NO:102, or a pair of heavy chains each comprising the amino acid sequence of SEQ ID NO:104 and a pair of light chains each comprising the amino acid sequence of SEQ ID NO:106, or a pair of heavy chains each comprising the amino acid sequence of SEQ ID NO:112 and a pair of light chains each comprising the amino acid sequence of SEQ ID NO:114, or a pair of heavy chains each comprising the amino acid sequence of SEQ ID NO:116 and a pair of light chains each comprising the amino acid sequence of SEQ ID NO:118.

In another embodiment of the foregoing aspects of the invention, an isolated monoclonal antibody or antigen-binding fragment thereof that specifically binds to IL-17A (SEQ ID NO:2) and IL-17F (SEQ ID NO:4) comprising a heavy chain variable domain and a light chain variable domain, wherein the heavy chain variable domain comprises the amino acid residues of SEQ ID NO:13 and a light chain variable domain comprises the amino acid residues of SEQ ID NO:9. Optionally, the monoclonal antibody comprises a human constant region, e.g., IgG1, IgG2, IgG3 or IgG4. The IgG4 human constant region may have a Serine to Proline mutation at position 241 according to Kabat. Optionally, the heavy chain comprises the amino acid residues of SEQ ID NOs:16, 18, 28, 29 or 74. Optionally, the light chain comprises the amino acid residues of SEQ ID NO:17. Optionally, the heavy chain comprises the amino acid residues of SEQ ID NOs:16, 18, 28, 29 or 74, and the light chain comprises the amino acid residues of SEQ ID NO:17. Optionally, a bispecific antibody comprises the monoclonal antibody.

Heavy chain and light chain constant regions include, IgG1.1 (SEQ ID NO:11, which may be encoded by SEQ ID NO:82), IgG1.1f without a C-terminal Lysine (SEQ ID NO:127), IgG1.1f with a C-terminal Lysine (SEQ ID NO:128), human kappa constant region (SEQ ID NO:10, which may be encoded by SEQ ID NO:83), or IgG4.1 (SEQ ID NO:8). The IgG4 heavy chain constant domain may include a variant of wild-type IgG4 that has a mutation in the hinge region, S228P (EU index numbering system) or S241P (Kabat numbering system). Changing the serine at 241 (Kabat) to proline (found at that position in IgG1 and IgG2) in a mouse/human chimeric heavy chain leads to the production of a homogeneous antibody and abolishes the heterogeneity. Further, the variant IgG4 has significantly extended serum half-life and shows an improved tissue distribution compared to the original chimeric IgG4. Angal et al., Molecular Immunology, 30(1):105-108 (1993); Schuurman et al., Molecular Immunology, 38:1-8 (2001); Lewis et al., Molecular Immunology, 46:3488-3494 (2009).

In another embodiment of the foregoing aspects of the invention, an isolated monoclonal antibody or antigen-binding fragment thereof that specifically binds to IL-23p19 (SEQ ID NO:6) comprising a heavy chain variable domain and a light chain variable domain, wherein the heavy chain variable domain comprises the amino acid residues of SEQ ID NO:7, and wherein the light chain variable domain comprises the amino acid residues of SEQ ID NO:9. Optionally, the monoclonal antibody comprises a human constant region, e.g., IgG1, IgG2, IgG3 or IgG4. Optionally, the IgG4 human constant region has a Serine to Proline mutation at position 241 according to Kabat. Optionally, the heavy chain comprises the amino acid residues of SEQ ID NOs:16, 18, 28, 29 or 74. Optionally, the light chain comprises the amino acid residues of SEQ ID NO:17. Optionally, the heavy chain comprises the amino acid residues of SEQ ID NOs:16, 18, 28, 29 or 74, and the light chain comprises the amino acid residues of SEQ ID NO:17. Optionally, a bispecific antibody comprises the monoclonal antibody.

In another embodiment of the foregoing aspects of the invention, the antibody, bispecific antibody, or antigen-binding fragment thereof, specifically binds IL-23p19, wherein the antibody or antigen-binding fragment binds a discontinuous epitope on IL-23p19 comprising a first epitope and a second epitope, wherein the first epitope consists of at least one amino acid of amino acid residues 33-59 of SEQ ID NO:6 and the second epitope consists of at least one amino acid of amino acid residues 89-125 of SEQ ID NO:6. Optionally, the antibody, bispecific antibody, or antigen-binding fragment thereof binds to at least amino acid residue 54 of SEQ ID NO:6 of the first epitope. Optionally, the antibody, bispecific antibody, or antigen-binding fragment thereof binds to at least amino acid residue 55 of SEQ ID NO:6 of the first epitope. Optionally, the antibody, bispecific antibody, or antigen-binding fragment thereof binds to at least amino acid residues 54 and 55 of SEQ ID NO:6 of the first epitope. Optionally, the antibody, bispecific antibody, or antigen-binding fragment thereof binds to at least amino acid residue 116 of SEQ ID NO:6 of the second epitope. Optionally, the antibody, bispecific antibody, or antigen-binding fragment thereof binds to at least amino acid residues 54 and 55 of SEQ ID NO:6 of the first epitope, and to least amino acid residue 116 of SEQ ID NO:6 of the second epitope.

In another embodiment of the foregoing aspects of the invention, the antibody, bispecific antibody, or antigen-binding fragment thereof specifically binds IL-23p19, wherein the antibody or antigen-binding fragment binds a discontinuous epitope on IL-23p19 comprising a first epitope and a second epitope, wherein the antibody or antigen-binding fragment binds to at least amino acid residues 54 and 55 of SEQ ID NO:6 of the first epitope, and to least amino acid residue 116 of SEQ ID NO:6 of the second epitope.

In another embodiment of the foregoing aspects of the invention, an IL-17A/F binding entity specifically binds IL-17A (IL-17A/IL-17A homodimer and IL-17A/IL-17F heterodimer) at an epitope comprising at least amino acid residue 108 (Tyr) of SEQ ID NO:2, wherein the IL-17A/F binding entity is a monoclonal antibody or antigen-binding fragment thereof. Optionally, the epitope on IL-17A is determined by alanine mutagenesis and/or X-ray crystallography. The epitope on which the IL-17A/F binding entity binds IL-17A may be a continuous or a discontinuous epitope.

In another embodiment of the foregoing aspects of the invention, the IL-17A/F cross-reactive monoclonal antibody or antigen-binding fragment thereof binds IL-17A at an epitope comprising at least amino acid residue 108 (Tyr) of SEQ ID NO:2. Optionally, the epitope on IL-17A is determined by alanine mutagenesis and/or X-ray crystallography. The epitope on which the IL-17A/F cross-reactive monoclonal antibody or antigen-binding fragment thereof binds IL-17A may be a continuous or a discontinuous epitope.

The bispecific antibodies of the invention may be used alone or as immunoconjugates with a cytotoxic agent. In some embodiments, the agent is a chemotherapeutic agent. In some embodiments, the agent is a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, abrin, modified *Pseudomonas* enterotoxin A, *Pseudomonas* exotoxin, calicheamicin, adriamycin, 5-fluorouracil, diphtheria toxin, and the like. Methods of conjugation of antibodies to such agents are known in the literature, and include direct and indirect conjugation.

Suitable detectable molecules may be directly or indirectly attached to the antibodies of the present invention. Suitable detectable molecules include radionuclides, enzymes, substrates, cofactors, inhibitors, fluorescent markers, chemiluminescent markers, magnetic particles and the like. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

The bispecific antibodies, antibodies and antigen-binding fragments of the invention also include derivatives that are modified, e.g., by the covalent attachment of any type of molecule to the antibody such that covalent attachment does not prevent the antibody from binding to its epitope. Examples of suitable derivatives include, but are not limited to fucosylated antibodies, glycosylated antibodies, acetylated antibodies, pegylated antibodies, phosphorylated antibodies, and amidated antibodies. The antibodies and derivatives thereof of the invention may themselves by derivatized by known protecting/blocking groups, proteolytic cleavage, linkage to a cellular ligand or other proteins, and the like. In some embodiments of the invention, at least one heavy chain of the antibody is fucosylated. In some embodiments, the fucosylation is N-linked. In some preferred embodiments, at least one heavy chain of the antibody comprises a fucosylated, N-linked oligosaccharide.

The bispecific antibodies, antibodies and antigen-binding fragments of the invention include variants having single or multiple amino acid substitutions, deletions, additions, or replacements that retain the biological properties (e.g., block the binding of IL-17A or IL-17F and/or IL-23 to their respective receptors, inhibit the biological activity of IL-17A or IL-17F and IL-23) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In another embodiment, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art.

The invention also includes isolated nucleic acids encoding the bispecific antibodies of the invention, which includes, for instance, the light chain, light chain variable region, light chain constant region, heavy chain, heavy chain variable region, heavy chain constant region, linkers, and any and all components and combinations thereof of the bispecific antibodies disclosed herein. Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG® software program. Nucleic acids of the invention also include complementary nucleic acids. In some instances, the sequences will be fully complementary (no mismatches) when aligned. In other instances, there may be up to about a 20% mismatch in the sequences. In some embodiments of the invention are provided nucleic acids encoding both a heavy chain and a light chain of an antibody of the invention.

Nucleic acids of the invention can be cloned into a vector, such as a plasmid, cosmid, bacmid, phage, artificial chromosome (BAC, YAC) or virus, into which another genetic sequence or element (either DNA or RNA) may be inserted so as to bring about the replication of the attached sequence or element. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfection, for example.

Thus in another embodiment, the present invention provides an expression vector comprising the following operably linked elements: a transcription promoter; a nucleic acid molecule encoding the heavy chain of a bispecific antibody of the invention; and a transcription terminator. In another embodiment, the present invention provides an expression vector comprising the following operably linked elements; a transcription promoter; a nucleic acid molecule encoding the light chain of a bispecific antibody of the invention; and a transcription terminator. Recombinant host cells comprising such vectors and expressing the heavy and light chains are also provided.

In another embodiment, the present invention provides an expression vector comprising the following operably linked elements; a transcription promoter; a first nucleic acid molecule encoding the heavy chain of a bispecific antibody, antibody or antigen-binding fragment of the invention; a second nucleic acid molecule encoding the light chain of a bispecific antibody, antibody or antigen-binding fragment of the invention; and a transcription terminator. In another embodiment, the present invention provides an expression vector comprising the following operably linked elements; a first transcription promoter; a first nucleic acid molecule encoding the heavy chain of a bispecific antibody, antibody or antigen-binding fragment of the invention; a first transcription terminator; a second transcription promoter a second nucleic acid molecule encoding the light chain of a bispecific antibody, antibody or antigen-binding fragment of the invention; and a second transcription terminator. Recombinant host cells comprising such vectors and expressing the heavy and light chains are also provided.

Antibody-producing cells containing a nucleic acid encoding the heavy chain and a nucleic acid encoding the light chain of the bispecific antibodies, antibodies or antigen-binding fragments of the invention can be used to produce the bispecific antibodies, antibodies or antigen-binding fragments in accordance with techniques known in the art. The present invention, in one embodiment, provides a method of producing a bispecific antibody, antibody or antigen-binding fragment of the invention comprising culturing a recombinant host cell expressing the heavy and light chains and isolating the bispecific antibody, antibody or antigen-binding fragment produced by the cell.

The recombinant host cell may be a prokaryotic cell, for example a *E. coli* cell, or a eukaryotic cell, for example a mammalian cell or a yeast cell. Yeast cells include *Saccharomyces cerevisiae, Schizosaccharomyces pombe*, and *Pichia pastoris* cells. Mammalian cells include VERO, HeLa, Chinese hamster Ovary (CHO), W138, baby hamster kidney (BHK), COS-7, MDCK, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK31 cells, mouse sertoli cells, human cervical carcinoma cells, buffalo rat liver cells, human lung cells, human liver cells, mouse mammary tumor cells, TRI cells, MRC 5 cells, and FS4 cells. Antibody-producing cells of the invention also include any insect expression cell line known, such as for example, *Spodoptera frugiperda* cells. In a preferred embodiment, the cells are mammalian cells. In another preferred embodiment, the mammalian cells are CHO cells.

The antibody-producing cells preferably are substantially free of IL-17A, IL-17F and IL-23 binding competitors. In preferred embodiments, the antibody-producing cells comprise less than about 10%, preferably less than about 5%, more preferably less than about 1%, more preferably less than about 0.5%, more preferably less than about 0.1%, and most preferably 0% by weight IL-17A, IL-17F, or IL-23 binding competitors. In some embodiments, the antibodies produced by the antibody-producing cells are substantially free of IL-17A, IL-17F, and IL-23 competitors. In preferred embodiments, antibodies produced by the antibody-producing cells comprise less than about 10%, preferably less than about 5%, more preferably less than about 1%, more preferably less than about 0.5%, more preferably less than about 0.1%, and most preferably 0% by weight both IL-17 and IL-23 binding competitors.

Methods of antibody purification are known in the art. In some embodiments of the invention, methods for antibody purification include filtration, affinity column chromatography, cation exchange chromatography, anion exchange chromatography, and concentration. The filtration step preferably comprises ultrafiltration, and more preferably ultrafiltration and diafiltration. Filtration is preferably performed at least about 5-50 times, more preferably 10 to 30 times, and most preferably 14 to 27 times. Affinity column chromatography, may be performed using, for example, PROSEP® Affinity Chromatography (Millipore, Billerica, Mass.). In a preferred embodiment, the affinity chromatography step comprises PROSEP®-vA column chromatography. Eluate may be washed in a solvent detergent. Cation exchange chromatography may include, for example, SP-Sepharose Cation Exchange Chromatography. Anion exchange chromatography may include, for example but not limited to, Q-Sepharose Fast Flow Anion Exchange. The anion exchange step is preferably non-binding, thereby allowing removal of contaminants including DNA and BSA. The antibody product is preferably nanofiltered, for example, using a Pall DV 20 Nanofilter. The antibody product may be concentrated, for example, using ultrafiltration and diafiltration. The method may further comprise a step of size exclusion chromatography to remove aggregates.

The bispecific antibodies, antibodies or antigen-binding fragments may also be produced by other methods known in the art, for example by chemical coupling of antibodies and antibody fragments.

The bispecific antibodies, antibodies or antigen-binding fragments of the present invention are useful, for example, for the inhibition of proinflammatory cytokines, such as IL-17A, IL-17F and IL-23/p19. The antibodies can be used to reduce, limit, neutralize, or block the proinflammatory effects of the IL-17A homodimer, the IL-17F homodimer, and/or the IL-17A/F heterodimer. Likewise, the antibodies can be used to reduce, limit, neutralize, or block the pro-cancerous effects of the IL-17A homodimer, the IL-17F homodimer, or the IL-17A/F heterodimer. In such cases, the anti-IL-23p19 portion of the antibody is used to reduce, limit, neutralize, or block production of new T cells that would produce IL-17A and/or IL-17F, including homodimers and heterodimers. The bispecific antibodies, antibodies or antigen-binding fragments described herein can be used to treat inflammatory disorders and autoimmune diseases, such as multiple sclerosis (e.g., relapsing-remitting multiple sclerosis, secondary-progressive multiple sclerosis, primary-progressive multiple sclerosis and progressive-relapsing multiple sclerosis), cystic fibrosis, inflammatory bowel disease, psoriasis, systemic sclerosis, systemic lupus erythematosus, lupus nephritis, IgA nephropathy, diabetic kidney disease, minimal change disease (lipoid nephrosis), focal segmental glomerulosclerosis (FSGS), nephrogenic systemic fibrosis (NSF), nephrogenic fibrosing dermopathy, fibrosing cholestatic hepatitis, eosinophilic fasciitis (Shulman's syndrome), scleromyxedema (popular mucinosis), scleroderma, lichen sclerosusetatrophicus, POEMs syndrome (Crow-Fukase syndrome, Takatsuki disease or PEP syndrome), nephrotic syndrome, graft-versus-host-disease (GVHD), graft-versus-host-disease (GVHD) (from a transplant, such as blood, bone marrow, kidney, pancreas, liver, orthotopic liver, lung, heart, intestine, small intestine, large intestine, thymus, allogeneic stem cell, reduced-intensity allogeneic, bone, tendon, cornea, skin, heart valves, veins, arteries, blood vessels, stomach and testis), antineutrophil cytoplasmic antibodies (ANCA)-associated vasculitis (AAV), giant cell arteritis and multiple-myeloma-induced lytic bone disease. The bispecific antibodies, antibodies or antigen-binding fragments described herein can also be used to treat cancer, including angiogenesis.

The bispecific antibodies, antibodies or antigen-binding fragments of the present invention inhibit the activity of IL-17A and/or IL-17F and IL-23 (via the p19 subunit), and thus, inhibit the production, maintenance, and activity of new and existing IL-17A and IL-17F and IL-17-producing T cells (Th17). The invention further concerns the use of the bispecific antibodies, antibodies or antigen-binding fragments of the present invention in the treatment of inflammatory diseases characterized by the presence of elevated levels of IL-17A, IL-17F, and/or IL-23, and in the treatment of cancers characterized by the presence of elevated levels of IL-17A, IL-17F, and/or IL-23.

The bispecific antibodies, antibodies or antigen-binding fragments of the present invention may block, inhibit, reduce, antagonize or neutralize the activity of IL-17A, IL-17F, (including both homodimers and the heterodimer), and IL-23/p19 thus are advantageous over therapies that target only one or two of these three cytokines.

The antibodies, e.g., bispecific antibodies, of the invention are thus useful to:

(1) Block, inhibit, reduce, antagonize or neutralize signaling via IL-17A or IL-17F and IL-23 in the treatment of cancer, acute inflammation, and chronic inflammatory diseases such as inflammatory bowel disease (IBD), Crohn's disease, ulcerative colitis, irritable bowel syndrome (IBS), cystic fibrosis, chronic colitis, Sjögren's syndrome, splenomegaly, inflammation in chronic kidney disease (CKD), psoriasis, psoriatic arthritis, rheumatoid arthritis, and other diseases associated with the induction of acute-phase response.

(2) Block, inhibit, reduce, antagonize or neutralize signaling via IL-17A or IL-17F or IL-23 in the treatment of autoimmune diseases such as insulin-dependent diabetes mellitus (IDDM), multiple sclerosis (MS) (e.g., relapsing-remitting multiple sclerosis, secondary-progressive multiple sclerosis, primary-progressive multiple sclerosis and progressive-relapsing multiple sclerosis), systemic Lupus erythematosus (SLE), myasthenia gravis, rheumatoid arthritis, Sjögren's syndrome, IBS and IBD to prevent or inhibit signaling in immune cells (e.g., lymphocytes, monocytes, leukocytes) via their receptors (e.g., IL-23Rα, IL-12Rβ1, IL-17RA and IL-17RC). Blocking, inhibiting, reducing, or antagonizing signaling via IL-23Rα, IL-12Rβ1, IL-17RA and IL-17RC, using the antibodies of the present invention, also benefits diseases of the pancreas, kidney, pituitary and neuronal cells and may be used to treat IDDM, non-insulin dependent diabetes mellitus (NIDDM), pancreatitis, and pancreatic carcinoma.

For example, the bispecific antibodies, antibodies or antigen-binding fragments of the present invention are useful in therapeutic treatment of inflammatory diseases, particularly as antagonists to IL-17A, IL-17F, and IL-23/p19, in the treatment of inflammatory diseases such as multiple sclerosis (MS) (e.g., relapsing-remitting multiple sclerosis, secondary-progressive multiple sclerosis, primary-progressive multiple sclerosis and progressive-relapsing multiple sclerosis), inflammatory bowel disease (IBD), and cancer. These antagonists are capable of binding, blocking, inhibiting, reducing, antagonizing or neutralizing IL-17A, IL-17F, their homodimers and heterodimers, and IL-23 (via p19) (either individually or together) in the treatment of atopic and contact dermatitis, systemic sclerosis, systemic lupus erythematosus (SLE), antineutrophil cytoplasmic antibodies (ANCA)-associated vasculitis (AAV), giant cell arteritis, multiple sclerosis (MS) (e.g., relapsing-remitting multiple sclerosis, secondary-progressive multiple sclerosis, primary-progressive multiple sclerosis and progressive-relapsing multiple sclerosis), colitis, endotoxemia, arthritis, rheumatoid arthritis (RA), Sjögren's syndrome, psoriatic arthritis, adult respiratory disease (ARD), septic shock, multiple organ failure, inflammatory lung injury such as idiopathic pulmonary fibrosis, asthma, chronic obstructive pulmonary disease (COPD), airway hyper-responsiveness, chronic bronchitis, allergic asthma, psoriasis, eczema, IBS and inflammatory bowel disease (IBD) such as ulcerative colitis and Crohn's disease, *Helicobacter pylori* infection, lupus nephritis, IgA nephropathy, diabetic kidney disease, minimal change disease (lipoid nephrosis), focal segmental glomerulosclerosis (FSGS), nephrogenic systemic fibrosis (NSF), nephrogenic fibrosing dermopathy, fibrosing cholestatic hepatitis, eosinophilic fasciitis (Shulman's syndrome), scleromyxedema (popular mucinosis), scleroderma, lichen sclerosusetatrophicus, POEMs syndrome (Crow-Fukase syndrome, Takatsuki disease or PEP syndrome), nephrotic syndrome, transplant rejection, graft-versus-host-disease (GVHD), graft-versus-host-disease (GVHD) (from a transplant, such as blood, bone marrow, kidney, pancreas, liver, orthotopic liver, lung, heart, intestine, small intestine, large intestine, thymus, allogeneic stem cell, reduced-intensity allogeneic, bone, tendon, cornea, skin, heart valves, veins, arteries, blood vessels, stomach and testis), intraabdominal adhesions and/or abscesses as results of peritoneal inflammation (e.g., from infection, injury, etc.), nephrotic syndrome, cystic fibrosis (Tan, H.-L. et al., *American Journal of Respiratory and Critical Care Medicine*, 184(2):252-258 (2011)), lytic bone disease (e.g., multiple-myeloma-induced lytic bone disease) (Sotomayor, E. M., *Blood*, 116(18):3380-3382 (2010)), organ allograft rejection, streptococcal cell wall (SCW)-induced arthritis, osteoarthritis, gingivitis/periodontitis, herpetic stromal keratitis, restenosis, Kawasaki disease, age-related macular degeneration (AMD; e.g., wet form of AMD and dry form of AMD) (Wei, L. et al., *Cell Reports*, 2:1151-1158 (Nov. 29, 2012), immune mediated renal diseases, liver fibrosis (Meng, F. et al., *Gastroenterology*, 143:765-776 (2012), pulmonary fibrosis (Meng, F. et al., *Gastroenterology*, 143:765-776 (2012), hepatobiliary diseases, myocarditis (Ding, H.-S., *Mol. Biol. Rep.*, 39(7): 7473-7478 (Feb. 14, 2012); Valente, A. J. et al., *Cellular Signalling*, 24:560-568 (2012)), cardiac fibrosis (Valente, A. J. et al., *Cellular Signalling*, 24:560-568 (2012)), adverse myocardial remodeling (Valente, A. J. et al., *Cellular Signalling*, 24:560-568 (2012)), atherosclerosis (Ding, H.-S., *Mol. Biol. Rep.*, 39(7):7473-7478 (Feb. 14, 2012), cardiac ischemia/reperfusion injury (Ding, H.-S., *Mol. Biol. Rep.*, 39(7):7473-7478 (Feb. 14, 2012), heart failure (Ding, H.-S., *Mol. Biol. Rep.*, 39(7):7473-7478 (Feb. 14, 2012) and cancers/neoplastic diseases that are characterized by IL-17 and/or IL-23 expression, including but not limited to prostate, renal, colon, ovarian and cervical cancer, and leukemias (Tartour et al., *Cancer Res.*, 59:3698 (1999); Kato et al., *Biochem. Biophys. Res. Commun.*, 282:735 (2001); Steiner et al., *Prostate*, 56:171 (2003); Langowksi et al., *Nature*, May 10 [Epub ahead of print], (2006)).

For example, the bispecific antibodies, antibodies or antigen-binding fragments of the present invention are useful, e.g., antagonists to IL-17A, IL-17F, and IL-23/p19, in therapeutic treatment of inflammatory diseases, particularly in the treatment of Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Degos' disease, dermatomyositis-juvenile, discoid lupus (e.g., childhood discoid lupus erythematosus, generalized discoid lupus erythematosus and localized discoid lupus erythematosus), chilblain lupus erythematosus, lupus erythematosus-lichen planus overlap syndrome, lupus erythematosus panniculitis, tumid lupus erythematosus, verrucous lupus erythematosus cutaneous, systemic lupus erythematosus, subacute cutaneous lupus erythematosus, acute cutaneous lupus erythematosus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, rheumatoid arthritis (RA), Meniere's disease, mixed connective tissue disease, multiple sclerosis (MS) (e.g., relapsing-remitting multiple sclerosis, secondary-progressive multiple sclerosis, primary-progressive multiple sclerosis and progressive-relapsing multiple sclerosis), myasthenia gravis, pemacious anemia, polyarteritis nodosa, polychondritis, polyglandular syndromes, polymyalgia rheumatica, polymyositis and dermatomyositis, primary agammaglobulinemia, primary biliary cirrhosis, eczema, psoriasis, psoriatic arthritis, Raynaud's phenomena, Reiter's syndrome, adult respiratory disease (ARD), rheumatic fever, arthritis, sarcoidosis, scleroderma (e.g., progressive systemic sclerosis (PSS), also known as systemic sclerosis (SS)), Sjögren's syndrome, stiff-man syndrome, systemic lupus erythematosus (SLE), antineutrophil cytoplasmic antibodies (ANCA)-associated vasculitis (AAV), giant cell arteritis, Takayasu arteritis, temporal arteritis/giant cell arteritis, endotoxia, sepsis or septic shock, toxic shock syndrome, multiple organ failure, inflammatory lung injury such as idiopathic pulmonary fibrosis, colitis, inflammatory bowel disease (IBD) such as ulcerative colitis and Crohn's disease, irritable bowel syndrome (IBS), uveitis, vitiligo, Wegener's granulomatosis, Alzheimer's disease, atopic allergy, allergy, asthma, bronchial asthma, chronic obstructive pulmonary disease (COPD), airway hyper-responsiveness, allergic asthma, glomerulonephritis, hemolytic anemias, *Helicobacter pylori* infection, intraabdominal adhesions and/or abscesses as results of peritoneal inflammation (e.g., from infection, injury, etc.), nephrotic syndrome, idiopathic demyelinating polyneuropathy, Guillain-Barre syndrome, organ allograft rejection, lupus nephritis, IgA nephropathy, diabetic kidney disease, minimal change disease (lipoid nephrosis), focal segmental glomerulosclerosis (FSGS), nephrogenic systemic fibrosis (NSF), nephrogenic fibrosing dermopathy, fibrosing cholestatic hepatitis, eosinophilic fasciitis (Shulman's syndrome), scleromyxedema (popular mucinosis), scleroderma, lichen sclerosusetatrophicus, POEMs syndrome (Crow-Fukase syndrome, Takatsuki disease or PEP syndrome), nephrotic syndrome, graft-versus-host-disease (GVHD), graft-versus-host-disease (GVHD) (from a transplant, such as blood, bone marrow, kidney, pancreas, liver, orthotopic liver, lung, heart, intestine, small intestine, large intestine, thymus, allogeneic stem cell, reduced-intensity allogeneic, bone, tendon, cornea, skin, heart valves, veins, arteries, blood vessels, stomach and testis), lytic bone disease (e.g., multiple myeloma-induced lytice bone disease), cystic fibrosis, age-related mascular degeneration (AMD; e.g., wet AMD and dry AMD), liver fibrosis, pulmonary fibrosis, atherosclerosis, cardiac ischemia/reperfusion injury, heart failure, myocarditis, cardiac fibrosis, adverse myocardial remodeling, diabetic retinopathy and ventilator induced lung injury.

Accordingly, in one embodiment, the present invention provides a method of inhibiting one or more of proinflammatory cytokines, e.g., IL-17A, IL-17F and IL-23, in a mammal in need of such treatment comprising administering a therapeutically effective amount of a bispecific antibody, antibody or antigen-binding fragment to a mammal in need of such treatment. In a preferred embodiment, the mammal is a human. The method may be used to treat a disorder characterized by elevated expression of IL-17A, IL-17F, or IL-23. The bispecific antibody, antibody or antigen-binding fragment may be administered with another pharmaceutical agent, either in the same formulation or separately.

In another embodiment, the present invention provides a method of treating an immune related disorder in a mammal in need thereof, comprising administering to the mammal a therapeutically effective amount of an IL-17A/F polypeptide, an agonist thereof, or an antagonist (such as an IL-17A/F binding entity which includes an IL-17A/F cross-reactive antibody) thereto. In a preferred aspect, the immune related disorder is selected form the group consisting of: systemic lupus erythematosis (SLE), rheumatoid arthritis (RA), osteoarthritis, juvenile chronic arthritis, spondyloarthropathies, systemic sclerosis, idiopathic inflammatory myopathies, Sjögren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis (MS) (e.g., relapsing-remitting multiple sclerosis, secondary-progressive multiple sclerosis, primary-progressive multiple sclerosis and progressive-relapsing multiple sclerosis), idiopathic demyelinating polyneuropathy or Guillain-Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease (IBD), Crohn's disease, ulcerative colitis, gluten-sensitive enteropathy, and Whipple's disease, autoimmune or immune-mediated skin diseases including bullous skin diseases, erythema multiforme and contact dermatitis, antineutrophil cytoplasmic antibodies (ANCA)-associated vasculitis (AAV), giant cell arteritis, psoriasis, psoriatic arthritis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, lupus nephritis, IgA nephropathy, diabetic kidney disease, minimal change disease (lipoid nephrosis), focal segmental glomerulosclerosis (FSGS), nephrogenic systemic fibrosis (NSF), nephrogenic fibrosing dermopathy, fibrosing cholestatic hepatitis, eosinophilic fasciitis (Shulman's syndrome), scleromyxedema (popular mucinosis), scleroderma, lichen sclerosusetatrophicus, POEMs syndrome (Crow-Fukase syndrome, Takatsuki disease or PEP syndrome), nephrotic syndrome, graft-versus-host-disease (GVHD), graft-versus-host-disease (GVHD) (from a transplant, such as blood, bone marrow, kidney, pancreas, liver, orthotopic liver, lung, heart, intestine, small intestine, large intestine, thymus, allogeneic stem cell, reduced-intensity allogeneic, bone, tendon, cornea, skin, heart valves, veins, arteries, blood vessels, stomach and testis), lytic bone disease (e.g., multiple myeloma-induced lytice bone disease), cystic fibrosis, age-related mascular degeneration (AMD; e.g., wet AMD and dry AMD), liver fibrosis, pulmonary fibrosis, atherosclerosis, cardiac ischemia/reperfusion injury, heart failure, myocarditis, cardiac fibrosis, adverse myocardial remodeling, transplantation associated diseases including graft rejection and graft-versus-host-disease.

In another embodiment, the present invention provides a method for inhibiting inflammation in a mammal in need of such treatment comprising administering a therapeutically effective amount of a bispecific antibody, antibody or antigen-binding fragment of the invention to a mammal in need of such treatment. In a preferred embodiment, the mammal is a human. The inflammation may be associated with a disease selected from the group consisting of multiple sclerosis (MS) (e.g., relapsing-remitting multiple sclerosis, secondary-progressive multiple sclerosis, primary-progressive multiple sclerosis and progressive-relapsing multiple sclerosis), chronic inflammation, Sjögren's syndrome, autoimmune diabetes, rheumatoid arthritis (RA) and other arthritic conditions, asthma, systemic sclerosis, atopic dermatitis, antineutrophil cytoplasmic antibodies (ANCA)-associated vasculitis (AAV), giant cell arteritis, systemic lupus erythematosus (SLE), Degos' disease, dermatomyositis-juvenile, discoid lupus (e.g., childhood discoid lupus erythematosus, generalized discoid lupus erythematosus and localized discoid lupus erythematosus), chilblain lupus erythematosus, lupus erythematosus-lichen planus overlap syndrome, lupus erythematosus panniculitis, tumid lupus erythematosus, verrucous lupus erythematosus cutaneous, systemic lupus erythematosus, subacute cutaneous lupus erythematosus, acute cutaneous lupus erythematosus, essential mixed cryoglobulinemia, fibromyalgia-fibromyositis, Graves' disease, lytic bone disease (e.g., multiple myeloma-induced lytice bone disease), cystic fibrosis, age-related mascular degeneration (AMD; e.g., wet AMD and dry AMD), liver fibrosis, pulmonary fibrosis, atherosclerosis, cardiac ischemia/reperfusion injury, heart failure, myocarditis, cardiac fibrosis, adverse myocardial remodeling, Guillain-Barre syndrome, Hashimoto's thyroiditis, psoriasis, psoritic arthritis, Crohn's Disease, ulcerative colitis, irritable bowel syndrome (IBS), inflammatory bowel disease (IBD), lupus nephritis, IgA nephropathy, diabetic kidney disease, minimal change disease (lipoid nephrosis), focal segmental glomerulosclerosis (FSGS), nephrogenic systemic fibrosis (NSF), nephrogenic fibrosing dermopathy, fibrosing cholestatic hepatitis, eosinophilic fasciitis (Shulman's syndrome), scleromyxedema (popular mucinosis), scleroderma, lichen sclerosusetatrophicus, POEMs syndrome (Crow-Fukase syndrome, Takatsuki disease or PEP syndrome), nephrotic syndrome, graft-versus-host-disease (GVHD), graft-versus-host-disease (GVHD) (from a transplant, such as blood, bone marrow, kidney, pancreas, liver, orthotopic liver, lung, heart, intestine, small intestine, large intestine, thymus, allogeneic stem cell, reduced-intensity allogeneic, bone, tendon, cornea, skin, heart valves, veins, arteries, blood vessels, stomach and testis). The bispecific antibody, antibody or antigen-binding fragment made be administered with another pharmaceutical agent, for example an anti-inflammatory agent, either in the same formulation or separately.

In another embodiment, the present invention provides a composition comprising an antibody, e.g., a bispecific antibody, as described herein and a pharmaceutically acceptable carrier. A pharmaceutical composition comprising an antibody, e.g., a bispecific antibody, of the invention can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro, ed., *Remington's Pharmaceutical Sciences,* 19th Edition, Mack Publishing Company (1995).

For pharmaceutical use, an antibody, e.g., a bispecific antibody, of the present invention are formulated for parenteral, particularly intravenous or subcutaneous, delivery according to conventional methods. Intravenous administration may be by bolus injection, controlled release, e.g., using mini-pumps or other appropriate technology, or by infusion over a typical period of one to several hours. In general, pharmaceutical formulations will include an antibody, e.g., a bispecific antibody, of the invention in combination with a pharmaceutically acceptable carrier, such as saline, buffered saline, 5% dextrose in water or the like. Formulations may further include one or more excipients, preservatives, solubilizers, buffering agents, albumin to prevent protein loss on vial surfaces, etc. When utilizing such a combination therapy, the antibodies, which include bispecific antibodies, may be combined in a single formulation or may be administered in separate formulations. Methods of formulation are well known in the art and are disclosed, for example, in Gennaro, ed., *Remington's Pharmaceutical Sciences,* Mack Publishing Co., Easton Pa. (1990), which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. More commonly, the antibodies will be administered over one week or less, often over a period of one to three days. Generally, the dosage of administered antibodies will vary depending upon such factors as the patient's age, weight, height, sex, general medical condition and previous medical history. Typically, it is desirable to provide the recipient with a dosage of antibodies which is in the range of from about 1 pg/kg to 10 mg/kg (amount of agent/body weight of patient), although a lower or higher dosage also may be administered as circumstances dictate.

Administration of an antibody, e.g., bispecific antibody, of the invention to a subject can be intravenous, intraarterial, intraperitoneal, intramuscular, subcutaneous, intrapleural, intrathecal, by perfusion through a regional catheter, or by direct intralesional injection. When administering therapeutic antibodies by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase et al., "Oral Delivery of Microencapsulated Proteins", in Sanders et al., eds., *Protein Delivery: Physical Systems*, pp. 255-288, Plenum Press (1997)). The feasibility of an intranasal delivery is exemplified by such a mode of insulin administration (see, for example, Hinchcliffe et al., *Adv. Drug Deliv. Rev.*, 35:199 (1999)). Dry or liquid particles comprising antibodies of the invention can be prepared and inhaled with the aid of dry-powder dispersers, liquid aerosol generators, or nebulizers (e.g., Pettit et al., *TIBTECH*, 16:343 (1998); Patton et al., *Adv. Drug Deliv. Rev.*, 35:235 (1999)). This approach is illustrated by the AERX® diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science*, 269:850 (1995)). Transdermal delivery using electroporation provides another means to administer a molecule having IL-17 and IL-23/p19 binding activity (Potts et al., *Pharm. Biotechnol.*, 10:213 (1997)).

For purposes of therapy, compositions comprising an antibody, e.g., a bispecific antibody, of the invention and a pharmaceutically acceptable carrier are administered to a patient in a therapeutically effective amount. A combination of an antibody, e.g., a bispecific antibody, of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response. Effective treatment may be assessed in a variety of ways. In one embodiment, effective treatment is determined by reduced inflammation. In other embodiments, effective treatment is marked by inhibition of inflammation. In still other embodiments, effective therapy is measured by increased well-being of the patient including such signs as weight gain, regained strength, decreased pain, thriving, and subjective indications from the patient of better health.

A pharmaceutical composition comprising an antibody, e.g., a bispecific antibody, of the invention can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.*, 10:239 (1997); Ranade, "Implants in Drug Delivery", in Ranade et al., eds., *Drug Delivery Systems*, pp. 95-123, CRC Press (1995); Bremer et al., "Protein Delivery with Infusion Pumps", in Sanders et al., eds., *Protein Delivery: Physical Systems*, pp. 239-254, Plenum Press (1997); Yewey et al., "Delivery of Proteins from a Controlled Release Injectable Implant", in Sanders et al., eds., *Protein Delivery: Physical Systems*, pp. 93-117, Plenum Press (1997).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.*, 12(Suppl. 1):S61 (1993), *Kim, Drugs*, 46:618 (1993), and Ranade, "Site-Specific Drug Delivery Using Liposomes as Carriers", in Ranade et al., eds., *Drug Delivery Systems*, pp. 3-24, CRC Press (1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes in Cell Biology and Pharmacology*, John Libbey (1987), and Ostro et al., *American J Hosp. Pharm.*, 46:1576 (1989)). Moreover, it is possible to control the therapeutic availability of the encapsulated agent by varying liposome size, the number of bilayers, lipid composition, as well as the charge and surface characteristics of the liposomes.

Liposomes can absorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.*, 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta*, 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta*, 1068:133 (1991); Allen et al., *Biochim. Biophys. Acta*, 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., *Japanese Patent No.* 04-244,018; Kato et al., *Biol. Pharm. Bull.*, 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.*, 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato et al., *Crit. Rev. Ther. Drug Carrier Syst.*, 14:287 (1997); Murahashi et al., *Biol. Pharm. Bull.*, 20:259 (1997)). Similarly, Wu et al., *Hepatology*, 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.,* 20:259 (1997)). Polyaconitylated human serum albumin liposomes provide another approach for targeting liposomes to liver cells (Kamps et al., *Proc. Nat'l Acad. Sci. USA,* 94:11681 (1997)). Moreover, Geho et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.,* 32:99 (1998)). After plasma elimination of free antibody, streptavidin-conjugated liposomes are administered. In another approach, targeting antibodies are directly attached to liposomes (Harasym et al., *Adv. Drug Deliv. Rev.,* 32:99 (1998)).

Antibodies can be encapsulated within liposomes using standard techniques of protein microencapsulation (see, for example, Anderson et al., *Infect. Immun.,* 31:1099 (1981), Anderson et al., *Cancer Res.,* 50:1853 (1990), and Cohen et al., *Biochim. Biophys. Acta,* 1063:95 (1991), Alving et al. "Preparation and Use of Liposomes in Immunological Studies", in Gregoriadis, ed., *Liposome Technology,* 2nd Edition, Vol. III, p. 317, CRC Press (1993), Wassef et al., *Meth. Enzymol.,* 149:124 (1987)). As noted above, therapeutically useful liposomes may contain a variety of components. For example, liposomes may comprise lipid derivatives of poly(ethylene glycol) (Allen et al., *Biochim. Biophys. Acta,* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly(ortho esters), nonbiodegradable ethylvinyl acetate polymers, in which proteins are entrapped in the polymer (Gombotz et al., *Bioconjugate Chem.,* 6:332 (1995); Ranade, "Role of Polymers in Drug Delivery", in Ranade et al., eds., *Drug Delivery Systems,* pp. 51-93, CRC Press (1995); Roskos et al., "Degradable Controlled Release Systems Useful for Protein Delivery", in Sanders et al., eds., *Protein Delivery: Physical Systems,* pp. 45-92, Plenum Press (1997); Bartus et al., *Science,* 281:1161 (1998); Putney et al., *Nature Biotechnology,* 16:153 (1998); Putney, *Curr. Opin. Chem. Biol.,* 2:548 (1998)). Polyethylene glycol (PEG)-coated nanospheres can also provide carriers for intravenous administration of therapeutic proteins (see, for example, Gref et al., *Pharm. Biotechnol.,* 10:167 (1996).

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, an antibody, e.g., a bispecific antibody, of the invention is administered in combination therapy, i.e., combined with other agents, e.g., therapeutic agents, that are useful for treating pathological conditions or disorders, such as autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more an antibodies, e.g., bispecific antibodies, of the invention coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more antibodies, e.g., bispecific antibodies, described herein may be used in combination with two or more of the therapeutic agents described herein. Such combination therapies may advantageously utilize lower dosages of the administered therapeutic agents, thus avoiding possible toxicities or complications associated with the various monotherapies.

Preferred therapeutic agents used in combination with an antibody, e.g., bispecific antibody, of the invention are those agents that interfere at different stages in an inflammatory response. In one embodiment, one or more antibodies, e.g., bispecific antibodies, described herein may be coformulated with, and/or coadministered with, one or more additional agents such as other cytokine or growth factor antagonists (e.g., soluble receptors, peptide inhibitors, small molecules, ligand fusions); or antibodies or antigen binding fragments thereof that bind to other targets (e.g., antibodies that bind to other cytokines or growth factors, their receptors, or other cell surface molecules); and anti-inflammatory cytokines or agonists thereof. Nonlimiting examples of the agents that can be used in combination with the antibodies described herein, include, but are not limited to, antagonists of one or more interleukins (ILs) or their receptors, e.g., antagonists of IL-1, IL-2, IL-6, IL-7, IL-8, IL-12, IL-13, IL-15, IL-16, IL-18, IL-20, IL-21, IL-22 and IL-31; antagonists of cytokines or growth factors or their receptors, such as tumor necrosis factor (TNF), LT, EMAP-II, GM-CSF, FGF and PDGF. Antibodies of the invention can also be combined with inhibitors of, e.g., antibodies to, cell surface molecules such as CD2, CD3, CD4, CD8, CD20 (e.g., the CD20 inhibitor rituximab (RITUXAN®)), CD25, CD28, CD30, CD40, CD45, CD69, CD80 (B7.1), CD86 (B7.2), CD90, or their ligands, including CD154 (gp39 or CD40L), or LFA-1/ICAM-1 and VLA-4/VCAM-1 (Yusuf-Makagiansar et al., *Med. Res. Rev.,* 22:146-167 (2002)). Preferred antagonists that can be used in combination with one or more antibodies, e.g., bispecific antibodies, described herein include antagonists of IL-1, IL-6, IL-12, TNF-alpha, IL-15, IL-18, IL-20, IL-22 and IL-31.

Examples of those agents include IL-12 antagonists, such as chimeric, humanized, human or in vitro-generated antibodies (or antigen binding fragments thereof) that bind to IL-12 (preferably human IL-12), e.g., the antibody disclosed in WO 00/56772; IL-12 receptor inhibitors, e.g., antibodies to human IL-12 receptor; and soluble fragments of the IL-12 receptor, e.g., human IL-12 receptor. Examples of IL-15 antagonists include antibodies (or antigen binding fragments thereof) against IL-15 or its receptor, e.g., chimeric, humanized, human or in vitro-generated antibodies to human IL-15 or its receptor, soluble fragments of the IL-15 receptor, and IL-15-binding proteins. Examples of IL-18 antagonists include antibodies, e.g., chimeric, humanized, human or in vitro-generated antibodies (or antigen binding fragments thereof), to human IL-18, soluble fragments of the IL-18 receptor, and IL-18 binding proteins (IL-18BP). Examples of IL-1 antagonists include Interleukin-1-converting enzyme (ICE) inhibitors, such as Vx740, IL-1 antagonists, e.g., IL-1 RA (anikinra, KINERET®, Amgen), sIL1RII (Immunex), and anti-IL-1 receptor antibodies (or antigen binding fragments thereof).

Examples of TNF antagonists include chimeric, humanized, human or in vitro-generated antibodies (or antigen binding fragments thereof) to TNF (e.g., human TNF-alpha), such as (HUMIRA®, D2E7, human TNF-alpha antibody), CDP-571/CDP-870/BAY-10-3356 (humanized anti-TNF-alpha antibody; Celltech/Pharmacia), cA2 (chimeric anti-TNF-alpha antibody; REMICADE®, Centocor); anti-TNF antibody fragments (e.g., CPD870); soluble fragments of the TNF receptors, e.g., p55 or p75 human TNF receptors or derivatives thereof, e.g., 75 kdTNFR-IgG (75 kD TNF receptor-IgG fusion protein, ENBREL®; Immunex), p55 kdTNFR-IgG (55 kD TNF receptor-IgG fusion protein (Lenercept)); enzyme antagonists, e.g., TNF-alpha converting enzyme (TACE) inhibitors (e.g., an alpha-sulfonyl hydroxamic acid derivative, and N-hydroxyformamide TACE inhibitor GW 3333, -005, or -022); and TNF-bp/s-TNFR (soluble TNF binding protein). Preferred TNF antagonists are soluble fragments of the TNF receptors, e.g., p55 or p75 human TNF receptors or derivatives thereof, e.g., 75 kdTNFR-IgG, and TNF-alpha converting enzyme (TACE) inhibitors.

In other embodiments, one or more antibodies, e.g., bispecific antibodies, described herein may be administered in combination with one or more of the following: IL-13 antagonists, e.g., soluble IL-13 receptors (sIL-13) and/or antibodies against IL-13; IL-2 antagonists, e.g., DAB 486-IL-2 and/or DAB 389-IL-2 (IL-2 fusion proteins, Seragen), and/or antibodies to IL-2R, e.g., anti-Tac (humanized anti-IL-2R, Protein Design Labs). Yet another combination includes one or more antibodies, e.g., bispecific antibodies, of the invention, antagonistic small molecules, and/or inhibitory antibodies in combination with nondepleting anti-CD4 inhibitors (DEC-CE9.1/SB 210396; nondepleting primatized anti-CD4 antibody; IDEC/SmithKline). Yet other preferred combinations include antagonists of the costimulatory pathway CD80 (B7.1) or CD86 (B7.2), including antibodies, soluble receptors or antagonistic ligands; as well as p-selectin glycoprotein ligand (PSGL), anti-inflammatory cytokines, e.g., IL-4 (DNAX/Schering); IL-10 (SCH 52000; recombinant IL-10 DNAX/Schering); IL-13 and TGF-beta, and agonists thereof (e.g., agonist antibodies).

In other embodiments, one or more antibodies, e.g., bispecific antibodies, of the invention can be coformulated with, and/or coadministered with, one or more anti-inflammatory drugs, immunosuppressants, or metabolic or enzymatic inhibitors. Nonlimiting examples of the drugs or inhibitors that can be used in combination with the antibodies described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such. as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl) methyl]methylamino] benzoyl]-L-glutamic acid); and inhibitors of pyrimidine biosynthesis, e.g., dihydroorotate dehydrogenase (DHODH) inhibitors. Preferred therapeutic agents for use in combination with one or more antibodies, e.g., bispecific antibodies, of the invention include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppressants, e.g., cyclosporin, tacrolimus (FK-506); and mTOR inhibitors, e.g., sirolimus (rapamycin—RAPAMUNE® or rapamycin derivatives, e.g., soluble rapamycin derivatives (e.g., ester rapamycin derivatives, e.g., CCI-779); agents which interfere with signaling by proinflammatory cytokines such as TNF-alpha or IL-1 (e.g., IRAK, NIK, IKK, p38 or MAP kinase inhibitors); COX2 inhibitors, e.g., celecoxib, rofecoxib, and variants thereof; phosphodiesterase inhibitors, e.g., R973401 (phosphodiesterase Type IV inhibitor); phospholipase inhibitors, e.g., inhibitors of cytosolic phospholipase 2 (cPLA2) (e.g., trifluoromethyl ketone analogs); inhibitors of vascular endothelial cell growth factor or growth factor receptor, e.g., VEGF inhibitor and/or VEGF-R inhibitor; and inhibitors of angiogenesis. Preferred therapeutic agents for use in combination with the antibodies of the invention are immunosuppressants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs.

Additional examples of therapeutic agents that can be combined with an antibody, e.g., bispecific antibody, of the invention include one or more of: 6-mercaptopurines (6-MP); azathioprine sulphasalazine; mesalazine; olsalazine; chloroquine/hydroxychloroquine (PLAQUENIL®); pencillamine; aurothiomalate (intramuscular and oral); azathioprine; coichicine; beta-2 adrenoreceptor agonists (salbutamol, terbutaline, salmeteral); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

Nonlimiting examples of agents for treating or preventing arthritic disorders (e.g., rheumatoid arthritis, inflammatory arthritis, rheumatoid arthritis, juvenile rheumatoid arthritis, osteoarthritis and psoriatic arthritis), with which an antibody, e.g., bispecific antibody, of the invention may be combined include one or more of the following: IL-12 antagonists as described herein; NSAIDs; CSAIDs; TNFs, e.g., TNF-alpha, antagonists as described herein; nondepleting anti-CD4 antibodies as described herein; IL-2 antagonists as described herein; anti-inflammatory cytokines, e.g., IL-4, IL-10, IL-13 and TGF-alpha, or agonists thereof; IL-1 or IL-1 receptor antagonists as described herein; phosphodiesterase inhibitors as described herein; Cox-2 inhibitors as described herein; iloprost: methotrexate; thalidomide and thalidomide-related drugs (e.g., Celgen); leflunomide; inhibitor of plasminogen activation, e.g., tranexamic acid; cytokine inhibitor, e.g., T-614; prostaglandin E1; azathioprine; an inhibitor of interleukin-1 converting enzyme (ICE); zap-70 and/or 1ck inhibitor (inhibitor of the tyrosine kinase zap-70 or 1ck); an inhibitor of vascular endothelial cell growth factor or vascular endothelial cell growth factor receptor as described herein; an inhibitor of angiogenesis as described herein; corticosteroid anti-inflammatory drugs (e.g., SB203580); TNF-convertase inhibitors; IL-11; IL-13; IL-17 inhibitors; gold; penicillamine; chloroquine; hydroxychloroquine; chlorambucil; cyclophosphamide; cyclosporine; total lymphoid irradiation; antithymocyte globulin; CD5-toxins; orally administered peptides and collagen; lobenzarit disodium; cytokine regulating agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP 10; T Cell Sciences, Inc.); prednisone; orgotein; glycosaminoglycan polysulphate; minocycline (MINOCIN®); anti-IL2R antibodies; marine and botanical lipids (fish and plant seed fatty acids); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine. Preferred combinations include one or more antibodies, e.g., bispecific antibodies, of the invention in combination with methotrexate or leflunomide, and in moderate or severe rheumatoid arthritis cases, cyclosporine.

Preferred examples of inhibitors to use in combination with one or more antibodies, e.g., bispecific antibodies, of the invention to treat arthritic disorders include TNF antagonists (e.g., chimeric, humanized, human or in vitro-generated antibodies, or antigen binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, ENBREL®), p55 kD TNF receptor-IgG fusion protein; TNF enzyme antagonists, e.g., TNF-alpha converting enzyme (TACE) inhibitors); antagonists of IL-12, IL-15, IL-18, IL-22; T cell and B cell-depleting agents (e.g., anti-CD4 or anti-CD22 antibodies); small molecule inhibitors, e.g., methotrexate and leflunomide; sirolimus (rapamycin) and analogs thereof, e.g., CCI-779; cox-2 and cPLA2 inhibitors; NSAIDs; p38 inhibitors, TPL-2, Mk-2 and NFκB inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFκB antagonists. Most preferred additional therapeutic agents that can be coadministered and/or coformulated with one or more antibodies, e.g., bispecific antibodies, of the invention include one or more of: a soluble fragment of a TNF receptor, e.g., p55 or p75 human TNF receptor or derivatives thereof, e.g., 75 kdTNFR-IgG (75 kD TNF receptor-IgG fusion protein, ENBREL®); methotrexate, leflunomide, or a sirolimus (rapamycin) or an analog thereof, e.g., CCI-779.

Nonlimiting examples of agents for treating or preventing multiple sclerosis (e.g., relapsing-remitting multiple sclerosis, secondary-progressive multiple sclerosis, primary-progressive multiple sclerosis and progressive-relapsing multiple sclerosis) with one or more antibodies, e.g., bispecific antibodies, of the invention can be combined include the following: interferons, e.g., interferon-alphala (e.g., AVONEX®, Biogen) and interferon-1b (BETASERON®, Chiron/Berlex); Copolymer 1 (Cop-1; COPAXONE®, Teva Pharmaceutical Industries, Inc.); dimethyl fumarate (e.g., BG-12; Biogen); hyperbaric oxygen; intravenous immunoglobulin; cladribine; TNF antagonists as described herein; corticosteroids; prednisolone; methylprednisolone; azathioprine; cyclophosphamide; cyclosporine; cyclosporine A; methotrexate; 4-aminopyridine; and tizanidine. Additional antagonists that can be used in combination with antibodies of the invention include antibodies to or antagonists of other human cytokines or growth factors, for example, TNF, LT, IL-1, IL-2, IL-6, EL-7, IL-8, IL-12 IL-15, IL-16, IL-18, EMAP-11, GM-CSF, FGF, and PDGF. Antibodies as described herein can be combined with antibodies to cell surface molecules such as CD2, CD3, CD4, CD8, CD25, CD28, CD30, CD40, CD45, CD69, CD80, CD86, CD90 or their ligands. One or more antibodies, e.g., bispecific antibodies, of the invention may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines as described herein, IL-1b converting enzyme inhibitors (e.g., Vx740), anti-P7s, PSGL, TACE inhibitors, T-cell signaling inhibitors such as kinase inhibitors, metalloproteinase inhibitors, sulfasalazine, azathloprine, 6-mercaptopurines, angiotensin converting enzyme inhibitors, soluble cytokine receptors and derivatives thereof, as described herein, and anti-inflammatory cytokines (e.g., IL-4, IL-10, IL-13 and TGF).

Preferred examples of therapeutic agents for multiple sclerosis (e.g., relapsing-remitting multiple sclerosis, secondary-progressive multiple sclerosis, primary-progressive multiple sclerosis and progressive-relapsing multiple sclerosis) with which the antibodies of the invention can be combined include dimethyl fumarate (e.g., BG-12; Biogen), interferon-beta, for example, IFN-beta-1a and IFN-beta-1b; COPAXONE®, corticosteroids, IL-1 inhibitors, TNF inhibitors, antibodies to CD40 ligand and CD80, IL-12 antagonists.

Nonlimiting examples of agents for treating or preventing inflammatory bowel disease (e.g., Crohn's disease, ulcerative colitis) with which an antibody, e.g., bispecific antibody, of the invention can be combined include the following: budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies (e.g., anti-IL-6 receptor antibodies and anti-IL-6 antibodies); growth factors; elastase inhibitors; pyridinyl-imidazole compounds; TNF antagonists as described herein; IL-4, IL-10, IL-13 and/or TGF.beta. cytokines or agonists thereof (e.g., agonist antibodies); IL-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of platelet activating factor (PAF); ciprofloxacin; and lignocaine.

Nonlimiting examples of agents for treating or preventing psoriasis with which an antibody, e.g., bispecific antibody, of the invention can be combined include the following: corticosteroids; vitamin $D_3$ and analogs thereof; retinoiods (e.g., soriatane); methotrexate; cyclosporine, 6-thioguanine; Accutane; hydrea; hydroxyurea; sulfasalazine; mycophenolate mofetil; azathioprine; tacrolimus; fumaric acid esters; biologics such as AMEVIVE®, ENBREL®, HUMIRA®, Raptiva and REMICADE®, Ustekinmab, and XP-828L; phototherapy; and photochemotherapy (e.g., psoralen and ultraviolet phototherapy combined).

Nonlimiting examples of agents for treating or preventing inflammatory airway/respiratory disease (e.g., chronic obstructive pulmonary disorder, asthma) with which an antibody, e.g., bispecific antibody, of the invention can be combined include the following: beta2-adrenoceptor agonists (e.g., salbutamol (albuterol USAN), levalbuterol, terbutaline, bitolterol); long-acting beta2-adrenoceptor agonists (e.g., salmeterol, formoterol, bambuterol); adrenergic agonists (e.g., inhaled epinephrine and ephedrine tablets); anticholinergic medications (e.g., ipratropium bromide); combinations of inhaled steroids and long-acting bronchodilators (e.g., fluticasone/salmeterol (ADVAIR® in the United States, and Seretide in the United Kingdom)) or. budesonide/formoterol (SYMBICORT®)); inhaled glucocorticoids (e.g., ciclesonide, beclomethasone, budesonide, flunisolide, fluticasone, mometasone, triamcinolone); leukotriene modifiers (e.g., montelukast, zafirlukast, pranlukast, and zileuton); mast cell stabilizers (e.g., cromoglicate (cromolyn), and nedocromil); antimuscarinics/anticholinergics (e.g., ipratropium, oxitropium, tiotropium); methylxanthines (e.g., theophylline, aminophylline); antihistamines; IgE blockers (e.g., Omalizumab); M.sub.3 muscarinic antagonists (anticholinergics) (e.g., ipratropium, tiotropium); cromones (e.g., chromoglicate, nedocromil); zanthines (e.g., theophylline); and TNF antagonists (e.g., infliximab, adalimumab and etanercept).

In one embodiment, an antibody, e.g., bispecific antibody, of the invention can be used in combination with one or more antibodies directed at other targets involved in regulating immune responses, e.g., transplant rejection.

Nonlimiting examples of agents for treating or preventing immune responses with which an antibody, e.g., bispecific antibody, of the invention can be combined include the following: antibodies against other cell surface molecules, including but not limited to CD25 (interleukin-2 receptor-a), CD11a (LFA-1), CD54 (ICAM-1), CD4, CD45, CD28/CTLA4 (CD80 (B7.1), e.g., CTLA4 Ig-abatacept (ORENCIA®)), ICOSL, ICOS and/or CD86 (B7.2). In yet another embodiment, an antibody of the invention is used in combination with one or more general immunosuppressive agents, such as cyclosporin A or FK506.

In other embodiments, antibodies are used as vaccine adjuvants against autoimmune disorders, inflammatory diseases, etc. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

For example, desirable vaccines for moderating responses to allergens in a vertebrate host, which contain the adjuvant combinations of this invention, include those containing an allergen or fragment thereof. Examples of such allergens are described in U.S. Pat. No. 5,830,877 and PCT Publication No. WO 99/51259, which are hereby incorporated by reference in their entireties, and include pollen, insect venoms, animal dander, fungal spores and drugs (such as penicillin). The vaccines interfere with the production of IgE antibodies, a known cause of allergic reactions. In another example, desirable vaccines for preventing or treating disease characterized by amyloid deposition in a vertebrate host, which contain the adjuvant combinations of this invention, include those containing portions of amyloid peptide protein (APP). This disease is referred to variously as Alzheimer's disease, amyloidosis or amyloidogenic disease. Thus, the vaccines of this invention include the adjuvant combinations of this invention plus Aβ peptide, as well as fragments of Aβ peptide and antibodies to Aβ peptide or fragments thereof.

In another embodiment, pharmaceutical compositions may be supplied as a kit comprising a container that comprises an antibody, bispecific antibody or antigen-binding fragment of the invention. Antibodies, e.g., bispecific antibodies, of the invention can be provided in the form of an injectable solution for single or multiple doses, or as a sterile powder that will be reconstituted before injection. Alternatively, such a kit can include a dry-powder disperser, liquid aerosol generator, or nebulizer for administration of the antibody, e.g., bispecific antibody. Such a kit may further comprise written information on indications and usage of the pharmaceutical composition. Moreover, such information may include a statement that the antibody composition is contraindicated in patients with known hypersensitivity to IL-17 and IL-23.

In a further embodiment, the invention provides an article of manufacture, comprising: (a) a composition of matter comprising an antibody, bispecific antibody or antigen-binding fragment as described herein; (b) a container containing said composition; and (c) a label affixed to said container, or a package insert included in said container referring to the use of said antibody in the treatment of an immune related disease.

In another aspect, the composition comprises a further active ingredient, which may, for example, be a further antibody or an anti-inflammatory, cytotoxic or chemotherapeutic agent. Preferably, the composition is sterile.

The antibodies, bispecific antibodies and antigen-binding fragments as described herein are also useful to prepare medicines and medicaments for the treatment of immune-related and inflammatory diseases, including for example, multiple sclerosis (MS) (e.g., relapsing-remitting multiple sclerosis, secondary-progressive multiple sclerosis, primary-progressive multiple sclerosis and progressive-relapsing multiple sclerosis), irritable bowel syndrome (IBS), inflammatory bowel disease (IBD) such as ulcerative colitis and Crohn's disease, atopic dermatitis, contact dermatitis, systemic sclerosis, systemic lupus erythematosus (SLE), antineutrophil cytoplasmic antibodies (ANCA)-associated vasculitis (AAV), giant cell arteritis, multiple sclerosis (MS), colitis, endotoxemia, arthritis, rheumatoid arthritis (RA), osteoarthritis, Sjögren's syndrome, psoriasis, psoriatic arthritis, adult respiratory disease (ARD), septic shock, multiple organ failure, inflammatory lung injury such as idiopathic pulmonary fibrosis, asthma, chronic obstructive pulmonary disease (COPD), airway hyper-responsiveness, chronic bronchitis, allergic asthma, eczema, *Helicobacter pylori* infection, intraabdominal adhesions and/or abscesses as results of peritoneal inflammation (e.g., from infection, injury, etc.), nephrotic syndrome, idiopathic demyelinating polyneuropathy, Guillain-Barre syndrome, organ allograft rejection, graft vs. host disease (GVHD), lupus nephritis, IgA nephropathy, diabetic kidney disease, minimal change disease (lipoid nephrosis), focal segmental glomerulosclerosis (FSGS), nephrogenic systemic fibrosis (NSF), nephrogenic fibrosing dermopathy, fibrosing cholestatic hepatitis, eosinophilic fasciitis (Shulman's syndrome), scleromyxedema (popular mucinosis), scleroderma, lichen sclerosusetatrophicus, POEMs syndrome (Crow-Fukase syndrome, Takatsuki disease or PEP syndrome), nephrotic syndrome, graft-versus-host-disease (GVHD), graft-versus-host-disease (GVHD) (from a transplant, such as blood, bone marrow, kidney, pancreas, liver, orthotopic liver, lung, heart, intestine, small intestine, large intestine, thymus, allogeneic stem cell, reduced-intensity allogeneic, bone, tendon, cornea, skin, heart valves, veins, arteries, blood vessels, stomach and testis), lytic bone disease (e.g., multiple myeloma-induced lytice bone disease), cystic fibrosis, age-related mascular degeneration (AMD; e.g., wet AMD and dry AMD), liver fibrosis, pulmonary fibrosis, atherosclerosis, cardiac ischemia/reperfusion injury, heart failure, myocarditis, cardiac fibrosis, adverse myocardial remodeling, transplant rejection, streptococcal cell wall (SCW)-induced arthritis, gingivitis/periodontitis, herpetic stromal keratitis, gluten-sensitive enteropathy restenosis, Kawasaki disease, and immune mediated renal diseases. In a specific aspect, such medicines and medicaments comprise a therapeutically effective amount of a bispecific antibody, antibody or antigen-binding fragment of the invention with a pharmaceutically acceptable carrier. In an embodiment, the admixture is sterile.

The complete disclosure of all patents, patent applications, and publications, and electronically available material (e.g., GENBANK® amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention is further illustrated by the following non-limiting examples.

Example 1

Humanization of a Murine Anti-Human IL-17A/F Dual Specific Antibody

Selection of Hybridoma Clones and Variable Region Identification

Recombinant human proteins IL-17A, IL-17A/F, and IL-17F were produced using an HEK293 transient expression system at ZymoGenetics Inc., a Bristol-Myers Squibb Company (Seattle, Wash., USA). BALB/c mice (Charles River Laboratories, Wilmington, Mass.) were immunized and boosted with recombinant human IL-17F conjugated to BSA followed by immunizations with recombinant human IL-17A conjugated to BSA. The mice with sera containing the highest anti-IL-17F and anti-IL-17A antibody binding activity were given a final pre-fusion boost of IL-17F. Four days later, the splenocytes and lymph node cells were fused with Ag8.653 myeloma cells to generate antibody producing hybridomas. Hybridoma culture supernatants were screened for IL-17F and IL-17A binding by plate based ELISA and IL-17F and IL-17A neutralization in the IL-17A/F cell-based assay. Hybridoma cells corresponding to the supernatant sample that bound and neutralized both IL-17F and IL-17A were cloned in order to isolate a monoclonal hybridoma, 339.15.3.5 (designated as 339.15) producing the neutralizing monoclonal antibody of interest. Hybridoma 339.15 was isotyped using the ISOSTRIP® Mouse Monoclonal Antibody Isotyping Kit (Roche, Indianapolis, Ind., USA) and RNA was isolated using the QIAGEN® RNeasy kit (Qiagen, Valencia, Calif., USA). Variable regions were cloned using the SMART RACE cDNA Amplification Kit (Clontech, Mountain View, Calif., USA), utilizing 5' RACE technology and gene specific 3' primers designed to mouse constant region sequences. Heavy and light variable region sequences were cloned using the TOPO® TA Cloning Kit for Sequencing (Invitrogen, Carlsbad, Calif., USA). Gene sequences were verified by comparing the sequence to the N-terminal amino acid sequencing performed on antibody purified from hybridoma 339.15.

Variable region sequences were cloned from 339.15.3.5, 339.15.5.3 and 339.15.3.6 and were shown to contain the exact same variable region sequences. The sequence from 339.15.3.5 was used for subsequent humanization, and the 339.15.3.6 hybridoma clone was deposited on Nov. 7, 2006, with the American Type Tissue Culture Collection (ATCC, 10801 University Blvd, Manassas, Va. 20110-2209) patent depository as original deposits under the Budapest Treaty and was given ATCC® Patent Deposit Designation PTA-7988. Hybridoma clone 339.15.3.6 (ATCC® Patent Deposit Designation PTA-7988) and 339.15.5.3 (ATCC Patent Deposit Designation PTA-7987) are also disclosed, for example, in U.S. Pat. Nos. 7,790,163, 7,910,703 and 8,333,968.

Molecular Modeling of Chimeric and Humanized Anti-Human IL-17A/F Variable Region Sequences All variable region models were constructed and viewed using the MOE Software Suite, Version 2008 (Chemical Computing Group, Montreal, Canada).

Anti-Human IL-17A/F Humanized Antibody Design

Murine complementarity determining regions (CDR) were grafted onto human germline framework sequences. The sequences were compared to germline amino acid sequences in V-Base (MRC, Center for Protein Engineering, UK). One germline gene was chosen for the variable heavy region, VH1-03. Several germline genes were chosen for the variable light region; VKVI A26, VKI A20, VKVI A14, VKIII L6, and VKI L14. The VKVI germline gene family showed the highest homology to the murine sequence, however, being an under represented germline family in the human antibody repertoire, other germline families with high homology were also considered. Murine Kabat defined CDR regions were grafted on human Kabat defined framework regions for both the heavy and light chains.

Construction, Expression, and Purification of Humanized Anti-IL-17A/F Antibodies Humanized variable region sequences were ordered from GeneART, Inc. (GeneART, Inc. Burlingame, Calif., USA). Humanized and murine variable region sequences were fused to human kappa constant region (SEQ ID NO:10) or IgG1.1 (SEQ ID NO:11), an effector minus variant of wild-type IgG1 that has mutations resulting in the reduction of Fc γ receptor I binding and ability to fix complement (Gross et al., *Immunity*, 15:289-302 (2001)), utilizing overlap PCR (Horton et al., *Gene*, 77:61-68 (1989)) and/or restriction enzyme cloning into pTT5, an HEK293-6E transient expression vector (NCR Biotechnology Research Institute, Ottawa, ON, CAN). All constructs were expressed using the mod2610 (ATGCGGCG-GAGAGGCTGGTCCTGGATCTTCCTGTTTCTGCT-GAGCGGAACAG CCGGCGTGCTGAGC, SEQ ID NO:30) signal sequence, although any nucleic acid sequence that encodes the amino acid sequence MRRRGWSWI-FLFLLSGTAGVLS (SEQ ID NO:31) may be used. The HEK293-6E suspension cells were transfected with expression constructs using polyethylenimine reagent and cultivated in F17 medium (Invitrogen, Grand Island, N.Y., USA) with the addition of 5 mM L-glutamine and 25 µg/mL G418. After 24 hours, 1/40th volume of 20% Tryptone NI (Organotechnie SAS, La Courneuve, FR) was added. At approximately 120 hours post transfection, conditioned media was harvested and passed through a 0.2 µm filter. Protein was purified from the filtered conditioned media using a combination of Mab Select SuRe Affinity Chromatography (GE Healthcare, Piscataway, N.J., USA) and SUPERDEX® 200 Size Exclusion Chromatography (GE Healthcare, Piscataway, N.J., USA). Content was estimated by absorbance at UV-A280 nm and quality evaluated by analytical size exclusion high performance liquid chromatography, SDS PAGE, and western blot.

Anti-Human IL-17A/F Humanization Panel Bioassay Activity; NIH/3T3/KZ170 NF-κB Luciferase Reporter Assay to Measure Human IL-17A, IL-17A/F, and IL-17F Activity by NF-κB Induction A murine fibroblast cell line (NIH/3T3, ATCC® #CRL-1658) was stably transfected with an NF-κB luciferase reporter designated KZ170 and cloned out. NIH/3T3/KZ170 clone 1 cells were seeded at 10,000 cells/well in plating media (DMEM plus 3% FBS, 1 mM sodium pyruvate, 2 mM L-glutamine (HyClone Laboratories, South Logan, Utah)) in 96-well, white opaque, solid bottom luciferase plates (Corning Incorporated, Corning, N.Y.) and incubated overnight at 37° C., 5% $CO_2$. The following day serial dilutions of recombinant human IL-17A, IL-17A/F, or IL-17F (ZymoGenetics, A Bristol-Myers Squibb Company, Seattle, Wash., USA) were made up in assay media (DMEM plus 0.5% BSA, 1 mM sodium pyruvate, 2 mM L-glutamine, 10 mM HEPES (HyClone Laboratories, South Logan, Utah)) and added to the plates containing the cells and incubated together at 37° C., 5% $CO_2$ for 4 hours. Additionally the assay was used to measure neutralization of human IL-17A, IL-17A/F and IL-17F activity. A half maximal concentration ($EC_{50}$, effective concentration at 50 percent) of human IL-17A, IL-17A/F or IL-17F was combined with serial dilutions of anti-human IL-17A/F antibodies described herein in assay media and added to the plates containing the cells and incubated together at 37° C., 5% $CO_2$ for 4 hours. Following incubation the media was removed and cells lysed before being read on the Berthold Centro $XS^3$ Luminometer (Berthold Technologies, Wildbad, Germany) using flash substrate (Promega Corporation, Madison, Wis.) according to manufacturer's instructions. Increases in mean fluorescence intensity (via activation of the NF-κB luciferase reporter) were indicative of a human IL-17A, IL-17A/F, IL-17F receptor-ligand interaction. Decreases in mean fluorescence intensity were indicative of neutralization of the human IL-17A, IL-17A/F, IL-17F receptor-ligand interaction. $IC_{50}$ (inhibitory concentration at 50 percent) values were calculated using GraphPad Prism 4 software (GraphPad Software, Inc., San Diego Calif.) for each anti-human IL-17A/F antibody.

Anti-Human IL-17A/F Humanization CDR Grafted and Chimeric Panel Bioassay Activity; NIH/3T3/KZ170 NF-κB Luciferase Reporter Assay Results IL-17A, IL-17A/F and IL-17F induce activation of the NF-κB luciferase reporter in a dose dependent manner with an $EC_{50}$ concentration determined to be 0.15 nM for IL-17A, 0.50 nM for IL-17A/F and 0.50 nM for IL-17F. Tables 1 and 2 present example $IC_{50}$ data for the anti-IL-17A/F antibodies described herein.

TABLE 1

| Name | VH MVC# SEQ ID NO: | VL MVC# SEQ ID NO: | IL-17A $IC_{50}$ nM | IL-17A/F $IC_{50}$ nM | IL-17F $IC_{50}$ nM |
|---|---|---|---|---|---|
| Chimeric 339.15 | Ms VH VR370 MVC823 SEQ ID NO: 32 | Ms VL VR371 MVC824 SEQ ID NO: 34 | 11 | 0.30 | 0.26 |
| 339-07 | VR370e3 VH1-03 | Ms VL MVC824 | >600 | 31 | 5.5 |

TABLE 1-continued

| Name | VH MVC# SEQ ID NO: | VL MVC# SEQ ID NO: | IL-17A $IC_{50}$ nM | IL-17A/F $IC_{50}$ nM | IL-17F $IC_{50}$ nM |
|---|---|---|---|---|---|
|  | MVC 840 SEQ ID NO: 36 | SEQ ID NO: 34 |  |  |  |
| 339-08 | Ms VH VR370 MVC823 SEQ ID NO: 32 | VR371e3 VKVI A26 MVC841 SEQ ID NO: 38 | 1.5 | 0.96 | 0.81 |
| 339-02 | Ms VH VR370 MVC823 SEQ ID NO: 32 | VR371e2 VKI A20 MVC717 SEQ ID NO: 40 | 1.1 | 0.80 | 0.79 |
| 339-01 | Ms VH VR370 MVC823 SEQ ID NO: 32 | VR371e1 VKVI A14 MVC716 SEQ ID NO: 42 | 9.6 | 0.26 | 0.20 |
| 339-09 | Ms VH VR370 MVC823 SEQ ID NO: 32 | VR371e4 VKIII L6 MVC842 SEQ ID NO: 44 | 7.2 | 0.20 | 0.21 |
| 339-32 | Ms VH VR370 MVC823 SEQ ID NO: 32 | VR371e10 VKI L14 MVC856 SEQ ID NO: 46 | 7.0 | 1.5 | 0.35 |
| 339-33 | VR370e3 VH1-03 MVC840 SEQ ID NO: 36 | VR371e3 VKVI A26 MVC841 SEQ ID NO: 38 | >600 | 9.7 | 1.7 |
| 339-126 | VR370e3 VH1-03 MVC840 SEQ ID NO: 36 | VR371e2 VKI A20 MVC717 SEQ ID NO: 40 | >600 | 24 | 1.6 |

Anti-Human IL-17A/F Humanization CDR Grafted with Framework Back Mutation Panel Bioassay Activity Table: NIH/3T3/KZ170 NF-κB Luciferase Reporter Assay Results

TABLE 2

| Name | VH MVC# SEQ ID NO: | VL MVC# SEQ ID NO: | IL-17A $IC_{50}$ nM | IL-17A/F $IC_{50}$ nM | IL-17F $IC_{50}$ nM |
|---|---|---|---|---|---|
| 339-35 | VR370e4 NKSH MVC850 SEQ ID NO: 48 | VR371e3 VKVI A26 MVC841 SEQ ID NO: 38 | >600 | 2.4 | 0.64 |
| 339-71 | VR370e41 KALV MVC869 SEQ ID NO: 50 | VR371e3 VKVI A26 MVC841 SEQ ID NO: 38 | 16 | 0.37 | 0.20 |
| 339-37 | VR370e6 SF MVC852 SEQ ID NO: 52 | VR371e3 VKVI A26 MVC841 SEQ ID NO: 38 | >600 | 20 | 3.5 |
| 339-38 | VR370e7 NKSH KALV MVC853 SEQ ID NO: 54 | VR371e3 VKVI A26 MVC841 SEQ ID NO: 38 | 8.2 | 0.27 | 0.27 |
| 339-39 | VR370e8 NKSH | VR371e3 VKVI A26 | 7.6 | 0.23 | 0.25 |

TABLE 2-continued

| Name | VH MVC# SEQ ID NO: | VL MVC# SEQ ID NO: | IL-17A IC$_{50}$ nM | IL-17A/F IC$_{50}$ nM | IL-17F IC$_{50}$ nM |
|---|---|---|---|---|---|
| | KALV SF MVC854 SEQ ID NO: 56 | MVC841 SEQ ID NO: 38 | | | |
| 339-127 | VR370e4 NKSH MVC850 SEQ ID NO: 48 | VR371e2 VKI A20 MVC717 SEQ ID NO: 40 | 190 | 3.4 | 0.50 |
| 339-128 | VR370e41 KALV MVC869 SEQ ID NO: 50 | VR371e2 VKI A20 MVC717 SEQ ID NO: 40 | 5.1 | 0.41 | 0.25 |
| 339-105 | VR370e6 SF MVC852 SEQ ID NO: 52 | VR371e2 VKI A20 MVC717 SEQ ID NO: 40 | >600 | 23 | 2.6 |
| 339-125 | VR370e7 NKSH KALV MVC853 SEQ ID NO: 54 | VR371e2 VKI A20 MVC717 SEQ ID NO: 40 | 1.5 | 0.81 | 0.83 |
| 339-104 | VR370e8 NKSH KALV SF MVC854 SEQ ID NO: 56 | VR371e2 VKI A20 MVC717 SEQ ID NO: 40 | 1.5 | 0.83 | 0.83 |
| 339-134 | VR370e96 NK KALV MVC978 SEQ ID NO: 58 | VR371e2 VKI A20 MVC717 SEQ ID NO: 40 | 1.4 | 0.26 | 0.24 |

Anti-Human IL-17A/F Humanization Panel Biacore Activity; Measurement of Binding Affinities to Human IL-17A, IL-17A/F, and IL-17F Via Surface Plasmon Resonance (Biacore)

Humanized anti-human IL-17A/F monoclonal antibodies were evaluated for their binding affinity to human IL-17A, human IL-17A/F, and human IL-17F using surface plasmon resonance.

Kinetic rate constants and equilibrium dissociation constants were measured for the interaction of the humanized anti-human IL-17A/F antibodies with human IL-17A, IL-17A/F, and IL-17F via surface plasmon resonance. The association rate constant ($k_a$ ($M^{-1}s^{-1}$)) is a value that reflects the rate of the antigen-antibody complex formation. The dissociation rate constant ($k_d$ ($s^{-1}$)) is a value that reflects the stability of this complex. By dividing the dissociation rate constant by the association rate constant ($k_d/k_a$) the equilibrium dissociation constant ($K_D$ (M)) is obtained. This value describes the binding affinity of the interaction. Antibodies with similar $K_D$ can have widely variable association and dissociation rate constants. Consequently, measuring both the $k_a$ and $k_d$ of antibodies helps to more uniquely describe the affinity of the antibody-antigen interaction.

Binding kinetics and affinity studies were performed on a BIACORE® T100 system (GE Healthcare, Piscataway, N.J.). Methods for the BIACORE® T100 were programmed using BIACORE® T100 Control Software, v 2.0. For these experiments, the humanized anti-human IL-17A/F antibodies were captured onto a CM4 sensor chip via either goat anti-human IgG Fc-gamma antibody (Jackson ImmunoResearch, West Grove, Pa.) or goat anti-mouse IgG Fc-gamma antibody (Jackson ImmunoResearch). Binding experiments with the IL-17 molecules were performed at 25° C. in a buffer of 10 mM HEPES, 150 mM NaCl, 3 mM EDTA, 0.05% Surfactant P20 (GE Healthcare), 1 mg/mL bovine serum albumin, pH 7.4.

The capture antibody, goat anti-human IgG Fc-gamma, was diluted to concentration of 20 µg/mL in 10 mM sodium acetate pH 5.0, and then covalently immobilized to all four flow cells of a CM4 sensor chip using amine coupling chemistry (EDC:NHS). After immobilization of the antibody, the remaining active sites on the flow cell were blocked with 1 M ethanolamine. A capture antibody density of approximately 5000 RU was obtained. The humanized anti-human IL-17A/F antibodies were captured onto flow cell 2, 3, or 4 of the CM4 chip at a density ranging from 60-150 RU. Capture of the test antibodies to the immobilized surface was performed at a flow rate of 10 µL/min. The BIACORE® instrument measures the mass of protein bound to the sensor chip surface, and thus, capture of the test antibody was verified for each cycle. Serial dilutions of human IL-17A, IL-17A/F, or IL-17F (ZymoGenetics, A Bristol-Myers, Squibb Company, Seattle, Wash., USA) were prepared from 100 nM-0.032 nM (1:5 serial dilutions). The serial dilutions were injected over the surface and allowed to specifically bind to the test antibody captured on the sensor chip. Duplicate injections of each antigen concentration were performed with an association time of 7 minutes and dissociation time of 15 minutes. Kinetic binding studies were performed with a flow rate of 50 µL/min. In between cycles, the flow cell was washed with 20 mM hydrochloric acid to regenerate the surface. This wash step removed both the captured test antibody and any bound antigen from the immobilized antibody surface. The test antibody was subsequently captured again in the next cycle.

Data was compiled using the BIACORE® T100 Evaluation software (version 2.0). Data was processed by subtracting reference flow cell and blank injections. Baseline stability was assessed to ensure that the regeneration step provided a consistent binding surface throughout the sequence of injections. Duplicate injection curves were checked for reproducibility. Based on the binding of the bivalent IL-17 molecules to a bivalent antibody, the bivalent analyte binding interaction model was determined to be appropriate for interactions with the IL-17 molecules. The bivalent analyte model is previously described in West, A. P. et al., *Biochemistry*, 39:9698-9708 (2000); and West, A. P. et al., *J Mol. Biol.*, 313:385-397 (2001). An affinity constant ($K_{D1}$) under the bivalent analyte model may be calculated from the ratio of rate constants ($k_{d1}/k_{a1}$) as determined by surface plasmon resonance. The reference subtracted binding curves were globally fit to the appropriate binding model with a multiple Rmax and with the RI set to zero. The data fit well to the binding models with good agreement between the experimental and theoretical binding curves. The chi$^2$ and standard errors associated the fits were low. There was no trending in the residuals.

Anti-Human IL-17A/F Humanization Panel Biacore Activity

The results of the binding experiments with human IL-17A, IL-17A/F, and IL-17F are in Tables 3, 4, and 5 respectively.

Anti-Human IL-17A/F Humanized Antibodies Binding Affinity for IL-17A

TABLE 3

| Name | $k_{a1}$ ($M^{-1}s^{-1}$) | $k_{d1}$ ($s^{-1}$) | $K_{D1}$ (M) |
|---|---|---|---|
| Mouse 339.15 | 4.E+06 | 7.E-03 | 2.E-09 |
| 339-02 | 2.E+06 | 6.E-03 | 3.E-09 |

TABLE 3-continued

| Name | $k_{a1}$ (M$^{-1}$s$^{-1}$) | $k_{d1}$ (s$^{-1}$) | $K_{D1}$ (M) |
|---|---|---|---|
| SEQ ID NO: 32 SEQ ID NO: 40 Chimeric 339.15 | 3.E+06 | 1.E−02 | 4.E−09 |
| SEQ ID NO: 32 SEQ ID NO: 34 339-38 SEQ ID NO: 54 SEQ ID NO: 38 | 4.E+06 | 5.E−03 | 1.E−9 |
| 339-125 SEQ ID NO: 54 SEQ ID NO: 40 | 2.E+06 | 3.E−03 | 1.E−9 |
| 339-134 SEQ ID NO: 58 SEQ ID NO: 40 | 2.E+06 | 3.E−03 | 1.E−9 |

Anti-IL-17A/F Humanized Antibodies Binding Affinity for IL-17A/F

TABLE 4

| Name | $k_{a1}$ (M$^{-1}$s$^{-1}$) | $k_{d1}$ (s$^{-1}$) | $K_{D1}$ (M) |
|---|---|---|---|
| Mouse 339.15 | 1.E+06 | 2.E−04 | 2.E−10 |
| 339-02 SEQ ID NO: 32 SEQ ID NO: 40 | | Not Determined | |
| Chimeric 339.15 SEQ ID NO: 32 SEQ ID NO: 33 | | Not Determined | |
| 339-38 SEQ ID NO: 54 SEQ ID NO: 40 | 1.E+06 | 4.E−04 | 4.E−10 |
| 339-125 SEQ ID NO: 54 SEQ ID NO: 40 | 2.E+06 | 6.E−04 | 3.E−10 |
| 339-134 SEQ ID NO: 58 SEQ ID NO: 40 | 2.E+06 | 5.E−04 | 2.E−10 |

Anti-IL-17A/F Humanized Antibodies Binding Affinity for IL-17F

TABLE 5

| Name | $k_{a1}$ (M$^{-1}$s$^{-1}$) | $k_{d1}$ (s$^{-1}$) | $K_{D1}$ (M) |
|---|---|---|---|
| Mouse 339.15 | 2.E+06 | 1.E−04 | 5.E−11 |
| 339-02 SEQ ID NO: 32 SEQ ID NO: 40 | 1.E+06 | 5.E−04 | 4E−10 |
| Chimeric 339.15 SEQ ID NO: 32 SEQ ID NO: 34 | 1.E+06 | 5.E−04 | 4E−10 |
| 339-38 SEQ ID NO: 54 SEQ ID NO: 40 | 2.E+06 | 6.E−04 | 3.E−10 |
| 339-125 SEQ ID NO: 54 SEQ ID NO: 40 | 2.E+06 | 2.E−04 | 1.E−10 |
| 339-134 SEQ ID NO: 58 SEQ ID NO: 40 | 2.E+06 | 2.E−04 | 1.E−10 |

Example 2

7B7 Antibody Selection and Hybridoma Generation

Figure 11:
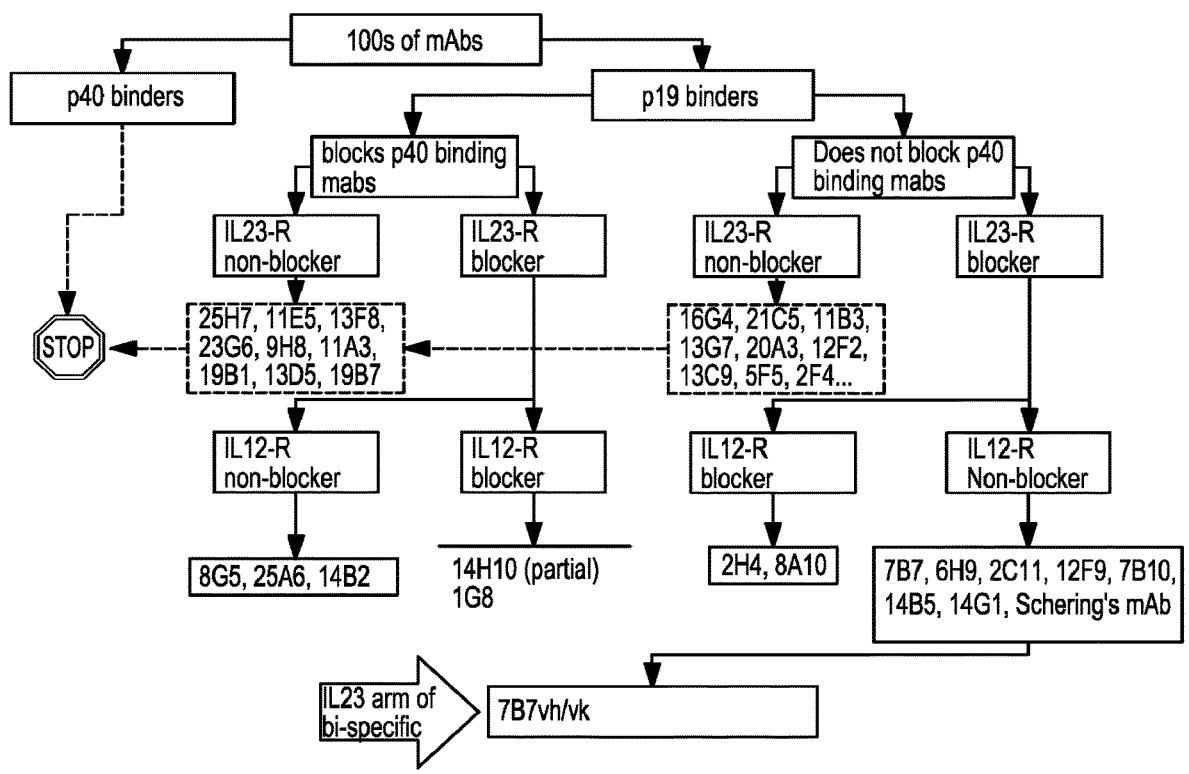
FIG. 11 schematically illustrates the process used to identify and select the 7B7 antibody (anti-IL-23p19).

Epitope Binning Approach by Surface Plasmon Resonance Technology (Using Biacore) to Group Antibodies Based on their Binding and Blocking Properties as Shown in FIG. 11.

Antibodies were grouped and selected based on their ability to:

1. Specifically bind p19 subdomain only of IL-23;
2. Specifically block only IL-23 receptor (IL-23R) and not block IL-12 receptor (IL-12R); and
3. Not compete with any antibody that could bind specifically to p40 subdomain of IL-23.

Materials such as antibodies with previously known selectivity for p19 or p40 subdomains of IL-23 and IL-23R or IL-12R were all chosen to be coated on a BIACORE® CM5 chip. The coating density varied between 500 to 8000 Resonance Units (RUs). Antibodies that were to be binned were titrated serially (1:2 or 1:3) to 8 concentrations, from starting concentrations that ranged from 10 to 100 μg/mL in a 96-well ELISA plate. To each of the well, 10 nM of IL-23 antigen was added. The antibodies on plate were allowed to form a complex with antigen and reach equilibrium overnight at 4° C. The complexes were injected over the CM5 chip at a flow rate of 20 μL/min for two minutes. The signal, as binding resonance units (RUs) at end of two minutes was noted. The antibody-antigen complex was able complete or not compete with the material that was coated on the chip. If the antibody in complex with antigen was able to compete with the material on chip, with increasing concentration of the antibody, the binding RU decreased and if it did not compete, the binding RU increased. Based on this observation, all anti-IL23 antibodies were binned according to their binding selectivities and competing abilities.

Transgenic HCo12 J/K HUMAB® Mice from the Medarex Colonies in Milpitas, Calif. were Immunized with Recombinant Human IL-23-his in RIBI Adjuvant.

Sera from immunized mice were tested for expression of IL-23 specific antibodies by a modified indirect dual ELISA. Briefly, microtiter plates (COSTAR®, 96-well flat bottom, #9018) were coated with mouse anti-his protein at 2.5 μg/ml in PBS, 50 μl/well, incubated at 4° C. overnight, and then blocked with 1% BSA in PBS. HuIL-23 at 2.5 μg/ml or HuIL-12 was added to plates for capture at 50 μl/well and incubated at room temperature for one hour. Plates were washed with PBS Tween, and dilutions of sera were added and incubated for 1 hour. The plates were washed with PBS-Tween and incubated with goat-anti-human gamma heavy chain conjugated with HRP (Jackson ImmunoResearch Cat. 109-036-098) for 1 hour. After 3× washing, the plates were developed with ABTS (Moss, CAT #ABTS-1000) substrate and OD's analyzed at 415 nm. Data were analyzed and expressed as serum titer which is defined as the highest dilution of serum which results in an antigen positive signal of at least twice background. Mouse 215094 was selected for hybridoma generation based upon relatively high titers on IL-23 with lower cross reactivity to IL-12 when compared to other mice in the cohort (see Table 6).

TABLE 6

| Serum Titers | | | |
|---|---|---|---|
| Mouse ID | Genotype | Hu IL23-his | Hu IL12-his |
| 215088 | HCo12:01[J/K] | >109, 350 | >109, 350 |
| 215090 | HCo12:01[J/K] | >109, 350 | >109, 350 |

TABLE 6-continued

Serum Titers

| Mouse ID | Genotype | Hu IL23-his | Hu IL12-his |
|---|---|---|---|
| 215092 | HCo12:01[J/K] | >109, 350 | >109, 350 |
| 215094 | HCo12:01[J/K] | >109, 350 | 12, 150 |
| 215096 | HCo12:01[J/K] | >109, 350 | 36, 450 |
| 215098 | HCo12:01[J/K] | 36, 450 | 1, 350 |
| 215089 | HCo12:01[J/K] | >109, 350 | 1, 350 |
| 215091 | HCo12:01[J/K] | >109, 350 | >109, 350 |
| 215093 | HCo12:01[J/K] | >109, 350 | 4, 050 |
| 215095 | HCo12:01[J/K] | >109, 350 | >109, 350 |
| 215097 | HCo12:01[J/K] | >109, 350 | >109, 350 |
| 215099 | HCo12:01[J/K] | 12150 | 12, 150 |

The genotype of Mouse 215094 is provided below in Table 7.

TABLE 7

Mouse 215094 Genotype

| Mouse ID | Sex | Date of birth | Genotype |
|---|---|---|---|
| 215094 | M | Oct. 11, 2009 | HCo12(15087)+^;JHD++; JKD++;KCo5(9272)+^; |

The spleen from mouse 215094 was used to generate hybridomas with mouse myeloma cells (ATCC CRL-1580) by electric field based electrofusion using a CytoPulse large chamber cell fusion electroporation device in a procedure designated fusion 2378.

Conditioned media from the resulting hybridomas were initially screened for expression of human IgG γ/κ in a standard automated assay followed by ELISA for IL-23 binding with a counter screen ELISA on IL-12 to identify specific clones as previously described. Hybridoma selection criteria for testing were samples with OD's greater than 1.5 on huIL23 plates and less than 0.15 on huIL12.

Figure 7:
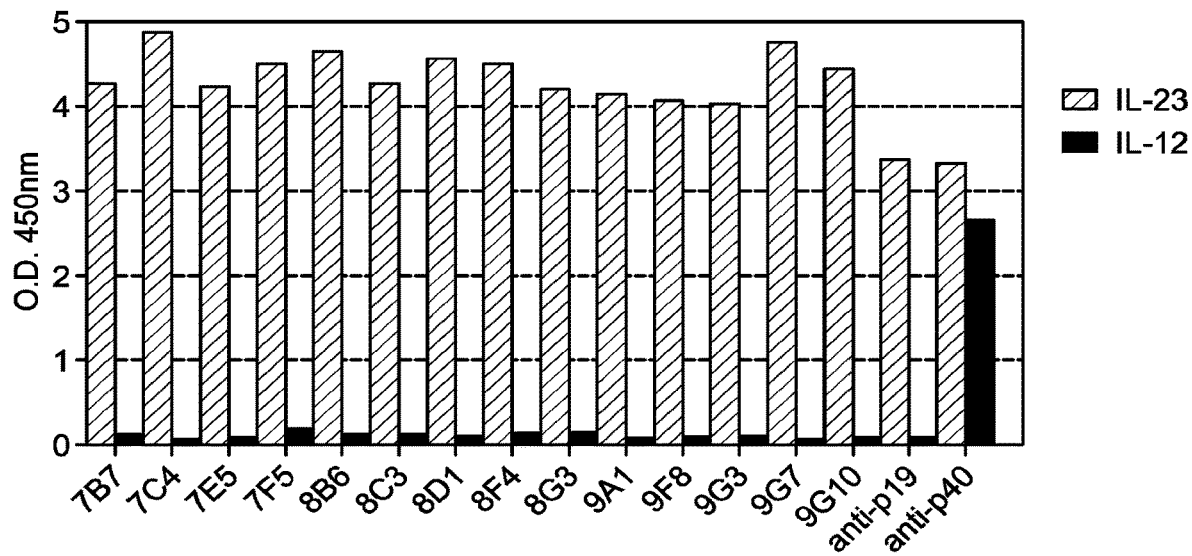
FIG. 7 illustrates the ELISA results showing strong antibody binding to IL-23p19 and lack of cross reactivity to IL-12.

Fusion 2378 generated total of 827 human IgG positive hybridomas of which, 128 were IL-23 specific. Hybridoma 7B7 was selected for further testing based on its strong binding to IL-23 and lack of cross reactivity to IL-12, when compared to anti-p19 and anti-p40 positive control antibodies; an example of hybridomas, including 7B7 selected by ELISA is given in FIG. 7. The isotype of subclone 7B7.D4 was confirmed as human IgG1, kappa by ELISA.

Figure 8:
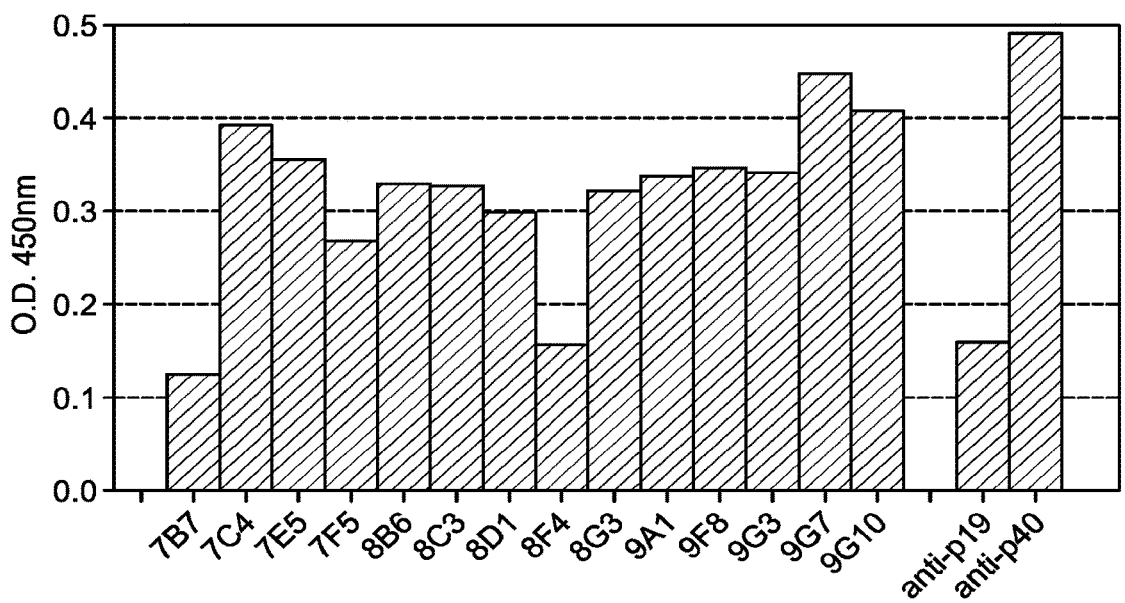
FIG. 8 illustrates the potent neutralization of IL-23 signaling as observed in the kit225 assay.
Figure 9:
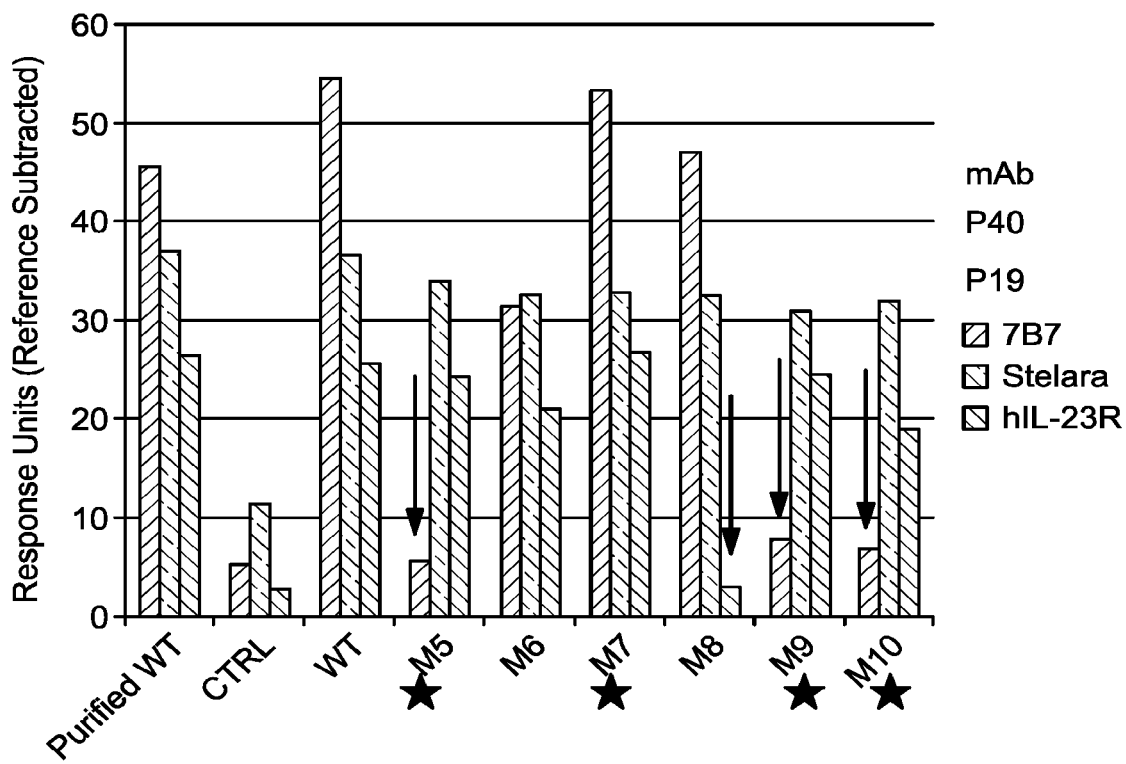
FIG. 9 shows the Biacore results of 7B7, STELARA® (ustekinumab, an anti-IL-23p40 antibody) and human IL-23 receptor ability to bind the various IL-23p19 alanine shaved mutants, wild-type and purified wild-type L-23p19 (positive control) and a negative control. 7B7 mAb binding is shown in the left column, STELARA® is shown in the center column and hIL-23R-Fc binding is shown in the right column. The four mutants shown with the star were chosen for scale-up to confirm these results.
Figure 10:
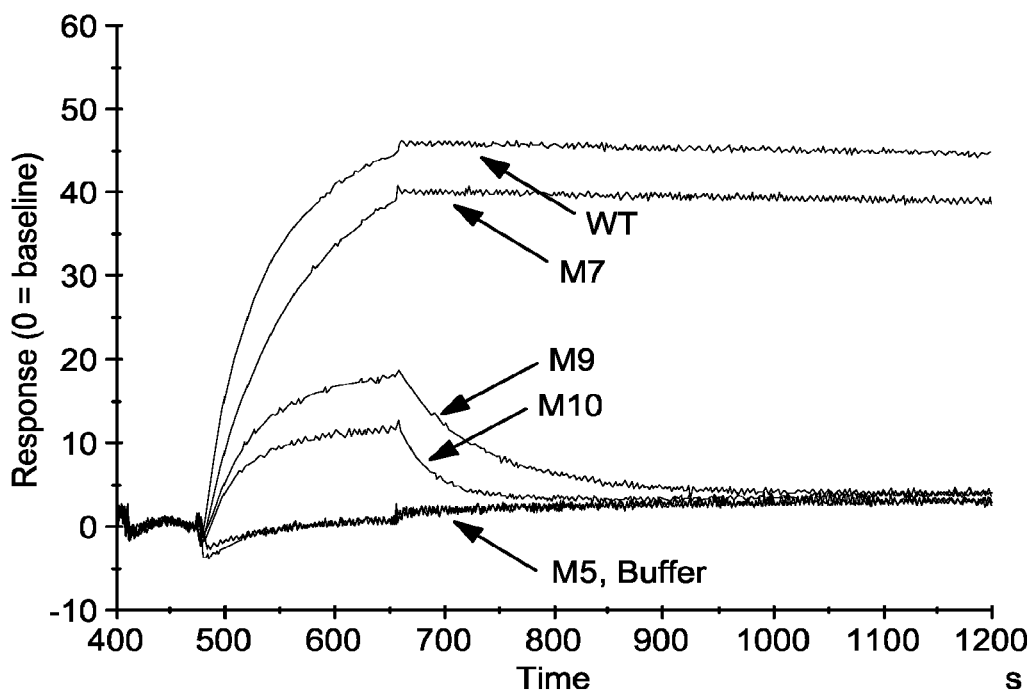
FIG. 10 shows a Biacore kinetic analysis of IL-23p19 antibody binding to the IL-23 alanine mutants.

Hybridoma conditioned medium from all IL-23p-19 specific MAbs were screened for IL-23 neutralizing activity in a cell-based assay. Kit225, a human T-cell line established from a patient with T-cell chronic lymphocytic leukemia, have been shown to respond to IL-23 with dose dependant STAT3 phosphorylation (pSTAT3). Human IL-23 at $EC_{50}$ with and without the addition of hybridoma conditioned medium or a control neutralizing anti-p19 antibody was used to stimulate cells for 15 minutes. Cells were lysed and inhibition of IL-23 dependant STAT3 phosphorylation was assessed by ELISA (Cell Signaling Technology, PATH-SCAN® Cat #7300) where reduced O.D. indicates reduced levels of pSTAT3. Hybridoma 7B7 was selected for sub-cloning and further characterization based upon the potent neutralization of IL-23 signaling observed in the Kit225 assay and as shown in FIG. 8.

Using assays similar to those described above, selective binding of IL-23 and neutralization of IL-23 signaling was demonstrated for the 7B7 subclone 1413.2378.7B7.D4.H2 which was subsequently submitted for sequencing (IL-23p19 7B7 heavy chain variable domain is shown in SEQ ID NO:7, and the light chain variable domain is shown in SEQ ID NO:9).

Example 3

Generation of Anti-Human IL-23/IL-17A/F Bispecific Antibodies

Construction and Expression of Mammalian Anti-Human IL-23/IL-17A/F Bispecific Molecules Partial or whole genes were synthesized at GeneART, Inc. (GeneART, Inc. Burlingame, Calif., USA) or GenScript (GenScript, Piscataway, N.J., USA) and inserted into pTT5, an HEK293-6E transient expression vector (NCR Biotechnology Research Institute, Ottawa, ON, Canada) via restriction enzyme cloning. MVC1059 (SEQ ID NO:62), and MVC1061 (SEQ ID NO:60) were ordered as complete constructs from GenScript (GenScript, Piscataway, N.J., USA). All constructs were expressed using the mod2610 (SEQ ID NO:30) signal sequence. The biAbFabL is a bispecific antibody which contains a whole antibody with a C-terminal Fab unit of the second arm of the bispecific attached via a linker (e.g., 10mer $G_4S$) and utilizes a common light chain (see FIG. 2). The taFab is a bispecific antibody which contains a whole antibody with an N-terminal Fab unit of the second arm of the bispecific attached via a linker, such as $(Gly_4Ser_1)_x$, wherein x is 1, 2 or 3, and the linker of SEQ ID NO:12. As with the heavy chain portion, there are two light chains for each arm of the bispecific attached via a linker, such as $(Gly_4Ser_1)_x$, wherein x is 1, 2 or 3, and the linker of SEQ ID NO:12 (see FIG. 3). The Heterodimeric Fc is a bispecific antibody that resembles a traditional antibody, however, contains two different heavy chains which associate through an electrostatic complementarity association in the $C_{H3}$ region. The Heterodimeric Fc utilizes a common light chain (see FIG. 4). Heavy chain and light chain constant regions include, IgG1.1 (SEQ ID NO:11, which may be encoded by SEQ ID NO:82), IgG1.1f without a C-terminal Lysine (SEQ ID NO:127), IgG1.1f with a C-terminal Lysine (SEQ ID NO:128), human kappa constant region (SEQ ID NO:10, which may be encoded by SEQ ID NO:83), or IgG4.1 (SEQ ID NO:8). The IgG4 heavy chain constant domain may be a variant of wild-type IgG4 that has a mutation in the hinge region, S228P (EU index numbering system) or S241P (Kabat numbering system). Changing the serine at 241 (Kabat) to proline (found at that position in IgG1 and IgG2) in a mouse/human chimeric heavy chain leads to the production of a homogeneous antibody and abolishes the heterogeneity. Further, the variant IgG4 has significantly extended serum half-life and shows an improved tissue distribution compared to the original chimeric IgG4. Angal et al., *Molecular Immunology*, 30(1):105-108 (1993); Schuurman et al., *Molecular Immunology*, 38:1-8 (2001); Lewis et al., *Molecular Immunology*, 46:3488-3494 (2009).

Transformation of electrocompetent *E. coli* host cells (DH10B) was performed using 1 µl of the yeast DNA preparation and 20 µl of *E. coli* cells. The cells were electropulsed at 2.0 kV, 25 µF, and 400 ohms. Following electroporation, 600 µl SOC (2% BACTO® Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and the cells were plated in 50 µl and 550 µl aliquots on two LB AMP plates (LB broth (Lennox), 1.8% BACTO® Agar (Difco), 100 mg/L Ampicillin).

Five colonies from each construct were subjected to sequence analysis. One clone containing the correct sequence was selected. DNA sequencing was performed using ABI PRISM® BigDye Terminator v3.1 Cycle Sequencing Kit (Applied Biosystems, Foster City, Calif.). Sequencing reactions were purified using Edge BioSystems Preforma Centriflex Gel Filtration Cartridges (Gaithersburg, Md.) and run on an Applied Biosystems 3730 DNA Analyzer (Applied Biosystems, Foster City, Calif.). Resultant sequence data was assembled and edited using SEQUENCHER® v4.6 software (GeneCodes Corporation, Ann Arbor, Mich.). One clone containing the correct sequence was selected and large-scale plasmid DNA was isolated using a commercially available kit (QIAGEN® Plasmid Mega Kit, Qiagen, Valencia, Calif.) according to manufacturer's instructions.

The HEK293-6E suspension cells were transfected with expression constructs using polyethylenimine reagent and cultivated in F17 medium (Invitrogen, Grand Island, N.Y., USA) with the addition of 5 mM L-glutamine and 25 μg/mL G418. After 24 hours, 1/40th volume of 20% Tryptone NI (Organotechnie SAS, La Courneuve, FR) was added. At approximately 120 hours post transfection, conditioned media was harvested and passed through a 0.2 μm filter. Protein was purified from the filtered conditioned media using a combination of Mab Select SuRe Affinity Chromatography (GE Healthcare, Piscataway, N.J., USA) and SUPERDEX® 200 Size Exclusion Chromatography (GE Healthcare, Piscataway, N.J., USA). Content was estimated by absorbance at UV-A280 nm and quality evaluated by analytical size exclusion high performance liquid chromatography, SDS PAGE, and western blot.

Anti-Human IL-23/IL-17A/F Bispecific Antibody Composition

Figure 3:
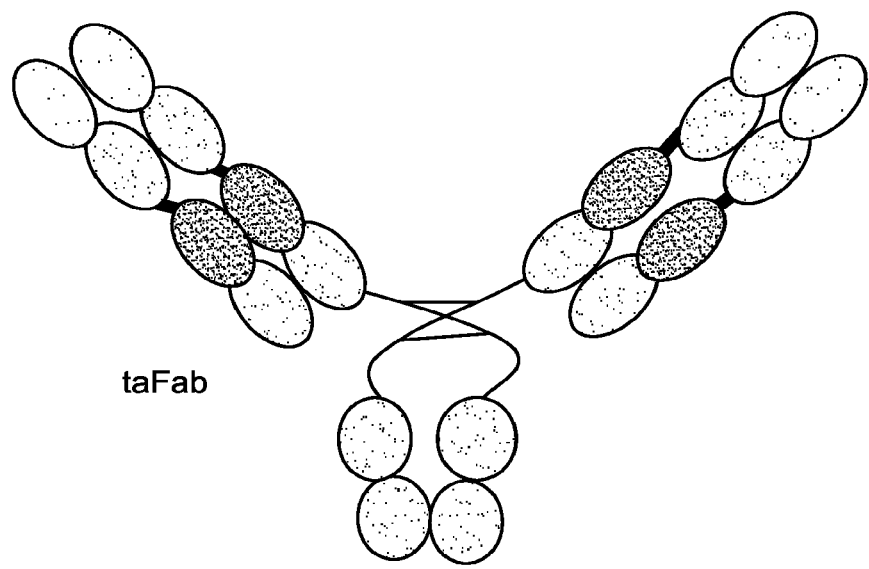
FIG. 3 depicts a model of a bispecific antibody designated taFab which contains a whole antibody with an N-terminal Fab unit of the second arm of the bispecific antibody attached via a linker. As with the heavy chain portion, there are two light chains for each arm of the bispecific attached via a linker.
Figure 4:
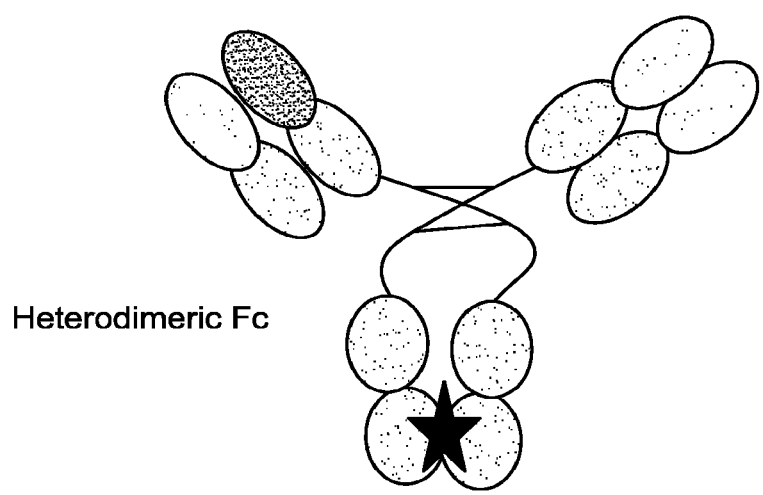
FIG. 4 depicts a model of a bispecific antibody designated Heterodimeric Fc, that resembles a traditional antibody, however, contains two different heavy chains which associate through an electrostatic complementarity association in the $C_{H3}$ region. The Heterodimeric Fc utilizes a common light chain.

A whole antibody and its modular components is depicted in FIG. 1. The biAbFabL format is depicted in FIG. 2. The taFab format is depicted in FIG. 3. The heterodimeric Fc format is depicted in FIG. 4. The VCVFc format is depicted in FIG. 5. The VCDFc format is depicted in FIG. 6.

Anti-Human IL-23/IL-17A/F Bispecific Antibodies Bioassay Activity; NIH/3T3/KZ170 NF-κB Luciferase Reporter Assay to Measure Human IL-17A, IL-17A/F, and IL-17F Activity by NF-κB Induction The material and methods for this assay are described in Example 1 hereinabove.

Anti-Human IL-23/IL-17A/F Bispecific Antibodies Bioassay Activity; Baf3/huIL-23Rα/huIL-12Rβ1 Transfectants Phospho-STAT3 Assay to Measure Human IL-23 Activity by Phospho-STAT3 Induction A murine bone marrow derived cell line (Baf3) was stably transfected with human IL-23Rα and human IL-12Rβ1 and cloned. Baf3/huIL-23Rα/huIL-12Rβ1 clone 6 cells were washed three times with assay media (RPMI 1640 plus 10% fetal bovine serum, 2 mM L-Glutamine, 1 mM Sodium Pyruvate (HyClone Laboratories, South Logan, Utah), and 2 μM β-Mercaptoethanol (Sigma-Aldrich, St. Louis, Mo.)) before being plated out at 50,000 cells/well in 96-well, round-bottom tissue culture plates. Serial dilutions of recombinant human IL-23 (ZymoGenetics, A Bristol-Myers Squibb Company, Seattle Wash., USA) were made up in assay media and added to the plates containing the cells and incubated together at 37° C., 5% $CO_2$ for 15 minutes. Additionally the assay was also used to measure neutralization of IL-23 activity. A half maximal concentration ($EC_{50}$, effective concentration at 50 percent) of IL-23 was combined with serial dilutions of anti-human IL-23/IL-17A/F antibodies described herein and incubated together at 37° C., 5% $CO_2$ for 15 minutes in assay media prior to addition to cells. Following pre-incubation, treatments were added to the plates containing the cells and incubated together at 37° C., 5% $CO_2$ for 15 minutes. Following incubation, cells were washed with ice-cold wash buffer and put on ice to stop the reaction according to manufacturer's instructions (BIO-PLEX® Cell Lysis Kit, Bio-Rad Laboratories, Hercules, Calif.). Cells were then spun down at 2000 rpm at 4° C. for 5 minutes prior to dumping the media. Fifty μL/well lysis buffer was added to each well; lysates were pipetted up and down five times while on ice, then agitated on a plate shaker for 20 minutes at 300 rpm and 4° C. Plates were centrifuged at 3200 rpm at 4° C. for 20 minutes. Supernatants were collected and transferred to a new micro titer plate for storage at −80° C.

Capture beads (BIO-PLEX® Phospho-STAT3 Assay, Bio-Rad Laboratories) were combined with 50 μL of 1:1 diluted lysates and added to a 96-well filter plate according to manufacturer's instructions (BIO-PLEX® Phosphoprotein Detection Kit, Bio-Rad Laboratories). The aluminum foil-covered plate was incubated overnight at room temperature, with shaking at 300 rpm. The plate was transferred to a microtiter vacuum apparatus and washed three times with wash buffer. After addition of 25 μL/well detection antibody, the foil-covered plate was incubated at room temperature for 30 minutes with shaking at 300 rpm. The plate was filtered and washed three times with wash buffer. Streptavidin-PE (50 μL/well) was added, and the foil-covered plate was incubated at room temperature for 15 minutes with shaking at 300 rpm. The plate was filtered and washed three times with bead resuspension buffer. After the final wash, beads were resuspended in 125 μL/well of bead suspension buffer, shaken for 30 seconds, and read on an array reader (BIO-PLEX® 100, Bio-Rad Laboratories) according to the manufacturer's instructions. Data was analyzed using analytical software (BIO-PLEX® Manager 4.1, Bio-Rad Laboratories). Increases in the level of the phosphorylated STAT3 transcription factor present in the lysates were indicative of an IL-23 receptor-ligand interaction. Decreases in the level of the phosphorylated STAT3 transcription factor present in the lysates were indicative of neutralization of the IL-23 receptor-ligand interaction. $IC_{50}$ (inhibitory concentration at 50 percent) values were calculated using GraphPad Prism 4 software (GraphPad Software, Inc., San Diego Calif.) for each anti-human IL-23/IL-17A/F antibody.

Anti-Human IL-23/IL-17A/F Bispecific Antibody Bioassay Activity; NIH/3T3/KZ170 NF-κB Luciferase Reporter Assay and Baf3/huIL-23Rα/huIL-12Rβ1 Transfectants Phospho-STAT3 Assay Results Human IL-17A, IL-17A/F and IL-17F induce activation of the NF-κB luciferase reporter in a dose dependent manner with an $EC_{50}$ concentration determined to be 0.33 nM for IL-17A, 1 nM for IL-17A/F and 1 nM for IL-17F and IL-23 induces STAT3 phosphorylation in a dose dependent manner with an $EC_{50}$ concentration determined to be 0.02 nM. The $IC_{50}$ data for the anti-human IL-23/IL-17A/F bispecific antibodies is shown below in Table 8.

Anti-Human IL-23/17A/F Bispecific Antibody Table

TABLE 8

| Name | Heavy Chain MVC# SEQ ID NO: | Light Chain MVC# SEQ ID NO: | IL-17A $IC_{50}$ nM | IL-17A/F $IC_{50}$ nM | IL-17F $IC_{50}$ nM | IL-23 $IC_{50}$ nM |
|---|---|---|---|---|---|---|
| 339-134 mAb IgG1.1 | MVC978 SEQ ID NO: 64 | MVC717 SEQ ID NO: 66 | 1.3 | 0.27 | 0.24 | Not Done |

TABLE 8-continued

| Name | Heavy Chain MVC# SEQ ID NO: | Light Chain MVC# SEQ ID NO: | IL-17A $IC_{50}$ nM | IL-17A/F $IC_{50}$ nM | IL-17F $IC_{50}$ nM | IL-23 $IC_{50}$ nM |
|---|---|---|---|---|---|---|
| IL23.6 (7B7) mAb IgG1.1 | MVC1003 SEQ ID NO: 68 | MVC1002 SEQ ID NO: 17* | Not Done | Not Done | Not Done | 0.014 |
| 23/17bAb1 IgG1.1 | MVC1006 SEQ ID NO: 28* | MVC1002 SEQ ID NO: 17* | 0.064 | 0.76 | 0.96 | 0.015 |
| 23/17bAb2 IgG1.1 | MVC1007 SEQ ID NO: 18* | MVC1002 SEQ ID NO: 17* | 0.052 | 0.43 | 0.44 | 0.041 |
| 23/17bAb3 IgG4.1 | MVC1036 SEQ ID NO: 74 | MVC1002 SEQ ID NO: 17* | 0.022 | 0.20 | 0.23 | 0.012 |
| 23/17bAb4 IgG4.1 | MVC1037 SEQ ID NO: 29* | MVC1002 SEQ ID NO: 17* | 0.035 | 0.18 | 0.87 | 0.048 |
| 23/17taFab1 IgG1.1 | MVC1008 SEQ ID NO: 76 | MVC1009 SEQ ID NO: 78 | 1.5 | 3.9 | 2.3 | 0.018 |
| 23/17hetero1 IgG1.1 | MVC1059 SEQ ID NO: 62 MVC1060 SEQ ID NO: 64 | MVC1002 SEQ ID NO: 17* | 0.34 | 0.78 | 0.33 | 0.060 |
| 23/17hetero2 IgG1.1 | MVC1061 SEQ ID NO: 60 MVC1062 SEQ ID NO: 80 | MVC1002 SEQ ID NO: 17* | 0.71 | 2.33 | 0.96 | 0.055 |

*The amino acid sequence of SEQ ID NO: 17 may be encoded by the sequence of SEQ ID NO: 70; the amino acid sequence of SEQ ID NO: 28 may be encoded by the sequence of SEQ ID NO: 71; the amino acid sequence of SEQ ID NO: 18 may be encoded by the sequence of SEQ ID NO: 72; the amino acid sequence of SEQ ID NO: 29 may be encoded by the sequence of SEQ ID NO: 75.

Anti-Human IL-23/IL-17A/F Bispecific Antibodies Bioassay Activity; Primary Human SAEC Assay to Measure Human IL-17A, IL-17AF, and IL-17F Activity by G-CSF Induction Primary human small airway epithelial cells (SAEC) were seeded at 8,000 cells/well in Small Airway Epithelial Growth Medium (SAGM) (cells and media: Lonza, Walkersville, Md.) in 96-well flat bottom tissue culture plates (Corning Incorporated, Corning, N.Y.) and incubated overnight at 37° C., 5% $CO_2$. The following day serial dilutions of human IL-17A, IL-17A/F, or IL-17F (ZymoGenetics, A Bristol-Myers Squibb Company, Seattle, Wash., USA) were made up in SAGM media and added to the plates containing the cells and incubated together at 37° C., 5% $CO_2$ for 24 hours. Additionally the assay was used to measure neutralization of IL-17A, IL-17A/F and IL-17F activity. A half maximal concentration ($EC_{50}$, effective concentration at 50 percent) of IL-17A, IL-17A/F or IL-17F was combined with serial dilutions of anti-human IL-23/IL-17A/F bispecific antibodies described herein in SAGM media and added to the plates containing the cells and incubated together at 37° C., 5% $CO_2$ for 24 hours. After incubation the supernatants were spun down, collected and frozen at −80° C. until ready to process. Human G-CSF protein levels in the supernatants were measured using a commercial bead based human G-CSF cytokine ELISA according to manufactures instructions (Procarta/Affymetrix, Santa Clara, Calif.). Increases in human G-CSF levels in the supernatant were indicative of a human IL-17A, IL-17A/F, IL-17F receptor-ligand interaction. Decreases in human G-CSF levels in the supernatant were indicative of neutralization of the human IL-17A, IL-17A/F, IL-17F receptor-ligand interaction. $IC_{50}$ (inhibitory concentration at 50 percent) values were calculated using GraphPad Prism 4 software (GraphPad Software, Inc., San Diego Calif.) for each anti-human IL-23/IL-17A/F bispecific antibody.

Anti-Human IL-23/IL-17A/F Bispecific Antibodies Bioassay Activity; Primary Human SAEC Assay Results Human IL-17A, IL-17A/F and IL-17F induce human G-CSF production in a dose dependent manner with an $EC_{50}$ concentration determined to be 0.03 nM for IL-17A, 3 nM for IL-17A/F and 3 nM for IL-17F. Bispecific antibodies tested include 23/17bAb1 (SEQ ID NO:28 and SEQ ID NO:17), 23/17bAb2 (SEQ ID NO:18 and SEQ ID NO:17), 23/17bAb3 (SEQ ID NO:74 and SEQ ID NO:17), 23/17bAb4 (SEQ ID NO:29 and SEQ ID NO:17). The humanized anti-human IL-17A/F antibody 339-134 mAb (SEQ ID NO:65 and SEQ ID NO:67) was also tested. The $IC_{50}$ data for the anti-human IL-23/IL-17A/F bispecific antibodies is shown below in Table 9. This data indicates that the anti-IL-23/IL-17A/F bispecific antibodies inhibit human IL-17A, IL-17A/F, IL-17F mediated IL-6 production were equally potent.

Anti-Human IL-23/IL-17A/F Bispecific Antibodies Bioassay Activity; Primary Human Fibroblast Assay to Measure Human IL-17A, IL-17A/F, and IL-17F Activity by IL-6 Induction A primary human fibroblast cell line (HFFF2, Cat #86031405, Health Protection Agency Culture Collections, Porton Down Salisbury, UK) was seeded at 5,000 cells/well in assay media (DMEM plus 10% FBS and 2 mM L-glutamine (HyClone Laboratories, South Logan, Utah)) in 96-well flat bottom plates (Corning Incorporated, Corning, N.Y.) and incubated overnight at 37° C., 5% $CO_2$. The following day serial dilutions of recombinant human IL-17A, IL-17AF, or IL-17F (ZymoGenetics, A Bristol-Myers Squibb Company, Seattle, Wash. 98117) were made up in assay media and added to the plates containing the cells and incubated together at 37° C., 5% $CO_2$ for 24 hours. Additionally the assay was used to measure neutralization of human IL-17A, IL-17A/F and IL-17F activity. A half maximal concentration ($EC_{50}$, effective concentration at 50 percent) of human IL-17A, IL-17A/F or IL-17F was combined with serial dilutions of anti-human IL-23/IL-17A/F antibodies described herein in assay media and added to the plates containing the cells and incubated together at 37° C., 5% $CO_2$ for 24 hours. After incubation the supernatants were spun down, collected and frozen at −80° C. until ready to process. Human IL-6 protein levels in the supernatants were measured using a commercial bead based human IL-6 cytokine ELISA according to manufactures instructions (Bio-Rad Laboratories, Hercules, Calif.). Increases in human IL-6 levels in the supernatant were indicative of a human IL-17A, IL-17A/F, IL-17F receptor-ligand interaction. Decreases in human IL-6 levels in the supernatant were indicative of neutralization of the human IL-17A, IL-17A/F, IL-17F receptor-ligand interaction. $IC_{50}$ (inhibitory concentration at 50 percent) values were calculated using GraphPad Prism 4 software (GraphPad Software, Inc., San Diego Calif.) for each anti-human IL-23/IL-17A/F bispecific antibody.

Anti-Human IL-23/IL-17A/F Bispecific Antibodies Bioassay Activity; Primary Human Fibroblast Assay Results Human IL-17A, IL-17A/F and IL-17F induce human IL-6 production in a dose dependent manner with an $EC_{50}$ concentration determined to be 0.08 nM for IL-17A, 25 nM for IL-17AF and 25 nM for IL-17F. Bispecific antibodies tested include 23/17bAb1 (SEQ ID NO:28 and SEQ ID NO:17), 23/17bAb2 (SEQ ID NO:18 and SEQ ID NO:17), 23/17bAb3 (SEQ ID NO:74 and SEQ ID NO:17), 23/17bAb4 (SEQ ID NO:29 and SEQ ID NO:17). Humanized anti-human IL-17A/F antibody 339-134 mAb (SEQ ID NO:64 and SEQ ID NO:66) was also tested. The $IC_{50}$ data for the anti-human IL-23/IL-17A/F bispecific antibodies is shown below in Table 9. These data indicate that the anti-human IL-23/IL-17A/F bispecific antibodies inhibit human IL-17A, IL-17A/F, IL-17F mediated IL-6 production were equally potent.

Anti-Human IL-23/IL-17A/F Bispecific Antibodies Bioassay Activity; Murine Splenocyte Assay to Measure Human IL-23 Activity by Murine IL-17A and IL-17F Induction A single cell suspension of murine splenocytes was prepared from whole spleens harvested from BALB/c mice. After red blood cell lysis with ACK buffer (0.010 M $KHCO_3$, 0.0001 M EDTA, 0.150 M $NH_4Cl$, pH 7.2) splenocytes were washed and resuspended in assay media (RPMI 1640 plus 10% FBS, non-essential amino acids, 1 mM Sodium Pyruvate, 2 mM L-glutamine, 10 mM HEPES, 100 units/mL Pen/Strep (HyClone Laboratories, South Logan, Utah), 50 µM 2-mercaptoethanol (Sigma-Aldrich, St. Louis, Mo.), and 50 ng/ml human IL-2 (R&D Systems, Minneapolis, Minn.)). Splenocytes were seeded at 500,000 cells per well in 96-well round bottom plates. Serial dilutions of recombinant human IL-23 (BDC 50220AN087 heterodimer material) were made up in assay media and added to the plates containing the cells and incubated together at 37° C., 5% $CO_2$ for 24 hours. Additionally the assay was also used to measure neutralization of human IL-23 activity. A half maximal concentration ($EC_{50}$, effective concentration at 50 percent) of human IL-23 was combined with serial dilutions of anti-human IL-23/IL-17A/F bispecific antibodies described herein and incubated together at 37° C., 5% $CO_2$ for 15 minutes in assay media prior to addition to cells. Following pre-incubation, treatments were added to the plates containing the cells and incubated together at 37° C., 5% $CO_2$ for 24 hours. After incubation the supernatants were spun down, collected and frozen at −80° C. until ready to process. The protein levels of murine IL-17A and IL-17F in the supernatants were measured using commercial plate based murine IL-17A and IL-17F ELISA's according to manufacturer's instructions (eBiosciences, San Diego, Calif.). Increases in murine IL-17A and IL-17F levels in the supernatant were indicative of an IL-23 receptor-ligand interaction. Decreases in murine IL-17A and IL-17F levels in the supernatant were indicative of neutralization of the IL-23 receptor-ligand interaction. $IC_{50}$ (inhibitory concentration at 50 percent) values were calculated using GraphPad Prism 4 software (GraphPad Software, Inc., San Diego Calif.) for each anti-human IL-23/IL-17A/F bispecific antibody.

Anti-Human IL-23/IL-17A/F Bispecific Antibodies Bioassay Activity; Murine Splenocyte Assay Results Human IL-23 induced murine IL-17A and IL-17F in a dose dependent manner with an $EC_{50}$ concentration determined to be 0.01 nM. Bispecific antibodies tested include 23/17bAb1 (SEQ ID NO:28 and SEQ ID NO:17), 23/17bAb2 (SEQ ID NO:18 and SEQ ID NO:17), 23/17bAb3 (SEQ ID NO:74 and SEQ ID NO:17), 23/17bAb4 (SEQ ID NO:29 and SEQ ID NO:17). The anti-human IL-23.6 (7B7) mAb (SEQ ID NO:68 and SEQ ID NO:17) was also tested. The $IC_{50}$ data for the anti-human IL-23/IL-17A/F bispecific antibodies is shown below in Table 9. This data indicates that the anti-human IL-23/IL-17A/F bispecific antibodies inhibit human IL-23 induced murine IL-17A and IL-17F production.

Anti-Human IL-23/IL-17A/F Bispecific Antibodies Bioassay Activity; Primary Human T Cell Phospho-STAT3 Assay to Measure Human IL-23 Activity by Phospho-STAT3 Induction Leukopheresis PBMC: Normal human donors (ZymoGenetics' normal donor pool) were selected at random and were voluntarily apheresed at the FHCRC (Seattle, Wash.). The leukopheresis PBMC were delivered to ZymoGenetics in a sterile blood-collection bag. The cells were poured into a sterile 500 mL plastic bottle, diluted to 400 mL with room temperature PBS plus 1 mM EDTA (HyClone Laboratories, South Logan, Utah) and transferred to 250 mL conical tubes. The 250 mL tubes were centrifuged at 1500 rpm for 10 minutes to pellet the cells. The cell supernatant was then removed and discarded. The cell pellets were then combined and suspended in 400 mL PBS plus 1 mM EDTA. The cell suspension (25 mL/tube) was overlaid onto FICOLL® (20 mL/tube) in 50 mL conical tubes (total of 16 tubes). The tubes were centrifuged at 2000 rpm for 20 minutes at room temperature. The interface layer ("buffy coat") containing the white blood cells and residual platelets was collected, pooled and washed repeatedly with PBS plus 1 mM EDTA until the majority of the platelets had been removed. The white blood cells were then suspended in 100 mL of ice-cold Cryopreservation medium (70% RPMI 1640, 20% FCS, 10% DMSO (HyClone Laboratories)) and distributed into sterile cryovials (1 mL cells/vial). The cryovials placed in a −80° C. freezer for 24 hours before transfer to a liquid-nitrogen freezer. The white blood-cell yield from a typical apheresis is $0.5$-$1.0 \times 10^{10}$ cells. Apheresis cells processed in this manner contain T cells, B cells, NK cells, monocytes and dendritic cells.

Preparation of Activated T Cells:

T cells must be activated in order to express the IL-12 receptor and be able to respond to IL-12 and IL-23. Cryopreserved leukopheresis PBMC were thawed, transferred to a sterile 50 mL conical tube, and washed with 50 mL of warm assay media (RPMI 1640 plus 10% FBS (HyClone Laboratories)) and incubated in a 37° C. water bath for 1 hour to allow the cells to recover. The cells were then centrifuged and the cell-supernatant discarded. The cell pellet was resuspended in assay media and distributed into sterile 162 cm² tissue culture flasks at $2 \times 10^7$ cells per flask in 90 mL assay media containing 5 µg/mL PHA-M (Roche, Basel, Switzerland). The cells were then cultured at 37° C. in a humidified incubator for a total of 5 days. The cells were "rested" by harvesting on the afternoon of day 4, replacing the culture medium with fresh assay media without PHA and returning to the incubator for the remainder of the 5 day culture period.

Phospho-STAT3 Assay:

Activated human T cells were harvested on day 5 of culture and resuspended in fresh assay media and were plated out at $2 \times 10^5$ cells/well in U-bottom 96-well plates. Serial dilutions of recombinant human IL-23 (BDC 50220AN087 heterodimer material) were made up in assay media and added to the plates containing the cells and incubated together at 37° C., 5% $CO_2$ for 15 minutes. Additionally the assay was also used to measure neutralization of IL-23 activity. A half maximal concentration ($EC_{50}$, effective concentration at 50 percent) of IL-23 was combined with serial dilutions of anti-human IL-23/IL-17AF antibodies described herein and incubated together at 37° C., 5% $CO_2$ for 15 minutes in assay media prior to addition to cells. Following pre-incubation, treatments were added to the plates containing the cells and incubated together at 37° C., 5% $CO_2$ for 15 minutes. Following incubation, cells were washed with ice-cold wash buffer and put on ice to stop the reaction according to manufacturer's instructions (BIO-PLEX® Cell Lysis Kit, Bio-Rad Laboratories, Hercules, Calif.). Cells were then spun down at 2000 rpm at 4° C. for 5 minutes prior to dumping the media. Fifty μL/well lysis buffer was added to each well; lysates were pipetted up and down five times while on ice, then agitated on a plate shaker for 20 minutes at 300 rpm and 4° C. Plates were centrifuged at 3200 rpm at 4° C. for 20 minutes. Supernatants were collected and transferred to a new micro titer plate for storage at −80° C.

Capture beads (BIO-PLEX® Phospho-STAT3 Assay, Bio-Rad Laboratories) were combined with 50 μL of 1:1 diluted lysates and added to a 96-well filter plate according to manufacturer's instructions (BIO-PLEX® Phosphoprotein Detection Kit, Bio-Rad Laboratories). The aluminum foil-covered plate was incubated overnight at room temperature, with shaking at 300 rpm. The plate was transferred to a microtiter vacuum apparatus and washed three times with wash buffer. After addition of 25 μL/well detection antibody, the foil-covered plate was incubated at room temperature for 30 minutes with shaking at 300 rpm. The plate was filtered and washed three times with wash buffer. Streptavidin-PE (50 μL/well) was added, and the foil-covered plate was incubated at room temperature for 15 minutes with shaking at 300 rpm. The plate was filtered and washed three times with bead resuspension buffer. After the final wash, beads were resuspended in 125 μL/well of bead suspension buffer, shaken for 30 seconds, and read on an array reader (BIO-PLEX® 100, Bio-Rad Laboratories) according to the manufacturer's instructions. Data was analyzed using analytical software (BIO-PLEX® Manager 4.1, Bio-Rad Laboratories). Increases in the level of the phosphorylated STAT3 transcription factor present in the lysates were indicative of an IL-23 receptor-ligand interaction. Decreases in the level of the phosphorylated STAT3 transcription factor present in the lysates were indicative of neutralization of the IL-23 receptor-ligand interaction. $IC_{50}$ (inhibitory concentration at 50 percent) values were calculated using GraphPad Prism 4 software (GraphPad Software, Inc., San Diego Calif.) for each anti-human IL-23/IL-17A/F bispecific antibody.

Anti-Human IL-23/IL-17A/F Bispecific Antibodies Bioassay Activity; Primary Human T Cell Phospho-STAT3 Assay Results Human IL-23 induces STAT3 phosphorylation in a dose dependent manner with an $EC_{50}$ concentration determined to be 0.02 nM. Bispecific antibodies tested include 23/17bAb1 (SEQ ID NO:28 and SEQ ID NO:17), 23/17bAb2 (SEQ ID NO:18 and SEQ ID NO:17), 23/17bAb3 (SEQ ID NO:74 and SEQ ID NO:17), 23/17bAb4 (SEQ ID NO:29 and SEQ ID NO:17). The anti-human IL-23.6 (7B7) mAb (SEQ ID NO:68 and SEQ ID NO:17) was also tested. The $IC_{50}$ data for the anti-human IL-23/IL-17A/F antibodies is shown below in Table 9.

Anti-Human IL-23/IL-17A/F Bispecific Antibody Bioassay Activity; Primary Human SAEC Assay, Primary Human Fibroblast Assay, Murine Splenocyte Assay and Primary Human T Cell Phospho-STAT3 Assay Results

TABLE 9

| Profile | | 23/17bAb1 IgG1.1 SEQ ID NO: 28 SEQ ID NO: 17 | 23/17bAb2 IgG1.1 SEQ ID NO: 18 SEQ ID NO: 17 | 23/17bAb3 IgG4.1 SEQ ID NO: 74 SEQ ID NO: 17 | 23/17bAb4 IgG4.1 SEQ ID NO: 29 SEQ ID NO: 17 | 339-134 mAbIgG1.1 SEQ ID NO: 64 SEQ ID NO: 66 | IL23.6(7B7) mAbIgG1.1 SEQ ID NO: 68 SEQ ID NO: 17 |
|---|---|---|---|---|---|---|---|
| Cellular Potency Hu. primary epithelial cells (SAEC) $IC_{50}$ | IL-17A $EC_{50}$ = 0.03 nM | <0.5 pM | <0.5 pM | <0.5 pM | ≤0.5 pM | 0.5 nM | Not Done |
| | IL-17AF $EC_{50}$ = 3 nM | 1.4 nM | 1.3 nM | 0.5 nM | 1.4 nM | 1.3 nM | Not Done |
| | IL-17F $EC_{50}$ = 3 nM | 0.8 nM | 1.6 nM | 1.0 nM | 1.3 nM | 1.1 nM | Not Done |
| Cellular Potency Hu. primary fibroblast cells (HFFF) $IC_{50}$ | IL-17A $EC_{50}$ = 0.08 nM | 0.07 nM | 0.07 nM | 0.03 nM | 0.1 nM | 0.9 nM | Not Done |
| | IL-17AF $EC_{50}$ = 25 nM | 17 nM | 12 nM | 9.4 nM | 9.1 nM | 13 nM | Not Done |
| | IL-17F $EC_{50}$ = 25 nM | 19 nM | 15 nM | 10 nM | 12 nM | 15 nM | Not Done |
| Cellular potency Murine splenocyte assay $IC_{50}$ | IL-23 $EC_{50}$ = 0.01 nM | 0.1 nM | 0.06 nM | 0.1 nM | 0.08 nM | Not Done | 0.09 nM |
| Cellular potency Primary T cell assay $IC_{50}$ | IL-23 $EC_{50}$ = 0.02 nM | 0.04 nM | 0.05 nM | 0.04 nM | 0.1 nM | Not Done | 0.04 nM |

Anti-Human IL-23/IL-17A/F Bispecific Antibodies Co-Binding Activity; Primary Human Fibroblast Assay to measure the inhibition of human IL-17A, IL-7A/F, or IL-F while simultaneously bound to human IL-23. The Primary Human T Cell Phospho-STAT3 Assay to measure the inhibition of human IL-23 while simultaneously bound to human IL-17A, IL-7A/F, or IL-17F.

The primary human fibroblast assay was run in the presence of excess amounts of IL-23 at 30 nM. The primary human T cell phospho-STAT3 assay was run in the presence of excess amounts of IL-17A, IL-17A/F, IL-17F at 30 nM.

Anti-Human IL-23/IL-17A/F Bispecific Antibodies Bioassay Co-Binding Results

Bispecific antibodies tested include 23/17bAb1 (SEQ ID NO:28 and SEQ ID NO:17), 23/17bAb2 (SEQ ID NO:18 and SEQ ID NO:17), 23/17bAb3 (SEQ ID NO:74 and SEQ ID NO:17), 23/17bAb4 (SEQ ID NO:29 and SEQ ID NO:17), and 23/17taFab1 (SEQ ID NO:76 and SEQ ID NO:78). The anti-human IL-23/IL-17A/F bispecific antibodies when examined in the presence of human IL-23 did not interfere with human IL-17A, IL-17A/F, IL-17F inhibition. The anti-human IL-23/IL-17A/F bispecific antibodies when examined in the presence of human IL-17A, IL-17A/F, IL-17F did not interfere with human IL-23 inhibition.

Measurement of Binding Affinities of Anti-Human IL-23/IL-17A/F Bispecific Antibodies to Human IL-17A, IL-17A/F, IL-17F, and Human IL-23 Via Surface Plasmon Resonance (Biacore)

Anti-human IL-23/IL-17A/F bispecific antibodies were evaluated for their binding affinity to human IL-17A, human IL-17A/F, human IL-17F, and human IL-23 using surface plasmon resonance.

Kinetic rate constants and equilibrium dissociation constants were measured for the interaction of the anti-human IL-23/IL-17A/F bispecific antibodies with human IL-17A, IL-17A/F, IL-17F, and human IL-23 via surface plasmon resonance. The association rate constant ($k_a$ ($M^{-1}s^{-1}$)) is a value that reflects the rate of the antigen-antibody complex formation. The dissociation rate constant ($k_d$ ($s^{-1}$)) is a value that reflects the stability of this complex. By dividing the dissociation rate constant by the association rate constant ($k_d/k_a$) the equilibrium dissociation constant ($K_D$ (M)) is obtained. This value describes the binding affinity of the interaction. Antibodies with similar $K_D$ can have widely variable association and dissociation rate constants. Consequently, measuring both the $k_a$ and $k_d$ of antibodies helps to more uniquely describe the affinity of the antibody-antigen interaction.

Binding kinetics and affinity studies were performed on a BIACORE® T100 system (GE Healthcare, Piscataway, N.J.). Methods for the BIACORE® T100 were programmed using BIACORE® T100 Control Software, v 2.0. For these experiments, the monoclonal and bispecific antibodies were captured onto a CM4 sensor chip via goat anti-human IgG Fc-gamma antibody (Jackson ImmunoResearch, West Grove, Pa.). Binding experiments with the human IL-17 molecules were performed at 25° C. in a buffer of 10 mM HEPES, 150 mM NaCl, 3 mM EDTA, 0.05% Surfactant P20 (GE Healthcare), 1 mg/mL bovine serum albumin, pH 7.4. Binding experiments with the IL-23/IL-12B heterodimer were performed at 25° C. in a buffer of 10 mM HEPES, 500 mM NaCl, 3 mM EDTA, 0.05% Surfactant P20 (Biacore), 1 mg/mL bovine serum albumin, pH 7.4.

The capture antibody, goat anti-human IgG Fc-gamma, was diluted to concentration of 20 µg/mL in 10 mM sodium acetate pH 5.0, and then covalently immobilized to all four flow cells of a CM4 sensor chip using amine coupling chemistry (EDC:NHS). After immobilization of the antibody, the remaining active sites on the flow cell were blocked with 1 M ethanolamine. A capture antibody density of approximately 5000 RU was obtained. The anti-human IL-23/IL-17A/F antibodies were captured onto flow cell 2, 3, or 4 of the CM4 chip at a density ranging from 60-150 RU. Capture of the test antibodies to the immobilized surface was performed at a flow rate of 10 µL/min. The BIACORE® instrument measures the mass of protein bound to the sensor chip surface, and thus, capture of the test antibody was verified for each cycle. Serial dilutions of human recombinant IL-17A, IL-17A/F, or IL-17F (ZymoGenetics, A Bristol-Myers Squibb Company, Seattle, Wash., USA) were prepared from 100 nM-0.032 nM (1:5 serial dilutions), while serial dilutions of human recombinant IL-23 (ZymoGenetics, A Bristol-Myers Squibb Company, Seattle, Wash., USA) were prepared from 200 nM-0.064 nM (1:5 serial dilutions). The serial dilutions were injected over the surface and allowed to specifically bind to the test antibody captured on the sensor chip. Duplicate injections of each antigen concentration were performed with an association time of 7 minutes and dissociation time of 15 minutes. Kinetic binding studies were performed with a flow rate of 50 µL/min. In between cycles, the flow cell was washed with 20 mM hydrochloric acid to regenerate the surface. This wash step removed both the captured test antibody and any bound antigen from the immobilized antibody surface. The test antibody was subsequently captured again in the next cycle.

Data was compiled using the BIACORE® T100 Evaluation software (version 2.0). Data was processed by subtracting reference flow cell and blank injections. Baseline stability was assessed to ensure that the regeneration step provided a consistent binding surface throughout the sequence of injections. Duplicate injection curves were checked for reproducibility. Based on the binding of the bivalent IL-17 molecules to a bivalent antibody, the bivalent analyte binding interaction model was determined to be appropriate for interactions with the IL-17 molecules. Based on the binding of the IL-23/IL-12B heterodimer to a bivalent antibody, the 1:1 binding interaction model was determined to be appropriate for interactions with the IL-23 molecule. The reference subtracted binding curves were globally fit to the appropriate binding model with a multiple Rmax and with the RI set to zero. The data fit well to the binding models with good agreement between the experimental and theoretical binding curves. The chi$^2$ and standard errors associated the fits were low. There was no trending in the residuals.

Anti-Human IL-23/IL-17A/F Bispecific Antibodies Biacore Activity

The results of the binding experiments with human IL-17A, IL-17A/F, and IL-17F are shown in Tables 10, 11, and 12, respectively. The results of the binding experiments with the human IL-23/IL-12B heterodimer are shown in Table 13.

Anti-Human IL-23/IL-17A/F Bispecific Antibodies Binding Affinity for IL-17A

TABLE 10

| Bispecific Antibody | $k_{a1}$ ($M^{-1}s^{-1}$) | $k_{d1}$ ($s^{-1}$) | $K_{D1}$ (M) |
|---|---|---|---|
| 23/17bAb1 IgG1.1 SEQ ID NO: 28 SEQ ID NO: 17 | 2.E+05 | 6.E−05 | 3.E−10 |
| 23/17bAb2 IgG1.1 SEQ ID NO: 18 SEQ ID NO: 17 | 5.E+05 | 4.E−04 | 8.E−10 |
| 23/17bAb3 IgG4.1 SEQ ID NO: 74 SEQ ID NO: 17 | 4.E+05 | 5.E−05 | 1.E−10 |
| 23/17bAb4 IgG4.1 SEQ ID NO: 29 SEQ ID NO: 17 | 5.E+05 | 3.E−04 | 6.E−10 |
| 23/17taFab1 IgG1.1 SEQ ID NO: 76 SEQ ID NO: 78 | 3.E+05 | 2.E−03 | 7.E−9 |

Anti-Human IL-23/IL-17A/F Bispecific Antibodies Binding Affinity for IL-17A/F

TABLE 11

| Bispecific Antibody | $k_{a1}$ (M$^{-1}$s$^{-1}$) | $k_{d1}$ (s$^{-1}$) | $K_{D1}$ (M) |
|---|---|---|---|
| 23/17bAb1 IgG1.1 SEQ ID NO: 28 SEQ ID NO: 17 | 2.E+05 | 9.E−05 | 4.E−10 |
| 23/17bAb2 IgG1.1 SEQ ID NO: 18 SEQ ID NO: 17 | 4.E+05 | 7.E−04 | 2.E−9 |
| 23/17bAb3 IgG4.1 SEQ ID NO: 74 SEQ ID NO: 17 | 2.E+05 | 2.E−04 | 1.E−9 |
| 23/17bAb4 IgG4.1 SEQ ID NO: 29 SEQ ID NO: 17 | 3.E+05 | 1.E−03 | 3.E−9 |
| 23/17taFab1 IgG1.1 SEQ ID NO: 76 SEQ ID NO: 78 | 1.E+05 | 5.E−04 | 5.E−9 |

Anti-Human IL-23/IL-17A/F Bispecific Antibodies Binding Affinity for IL-17F

TABLE 12

| Bispecific Antibody | $k_{a1}$ (M$^{-1}$s$^{-1}$) | $k_{d1}$ (s$^{-1}$) | $K_{D1}$ (M) |
|---|---|---|---|
| 23/17bAb1 IgG1.1 SEQ ID NO: 28 SEQ ID NO: 17 | 8.E+05 | 3.E−04 | 4.E−10 |
| 23/17bAb2 IgG1.1 SEQ ID NO: 18 SEQ ID NO: 17 | 3.E+06 | 7.E−04 | 2.E−10 |
| 23/17bAb3 IgG4.1 SEQ ID NO: 74 SEQ ID NO: 17 | 6.E+05 | 2.E−04 | 3.E−10 |
| 23/17bAb4 IgG4.1 SEQ ID NO: 29 SEQ ID NO: 17 | 2.E+06 | 7.E−04 | 4.E−10 |
| 23/17taFab1 IgG1.1 SEQ ID NO: 76 SEQ ID NO: 78 | 3.E+05 | 7.E−04 | 2.E−9 |

Anti-Human IL-23/IL-17A/F Bispecific Antibodies Binding Affinity for IL23/IL-12B

TABLE 13

| Antibody or Bispecific Antibody | $k_{a1}$ (M$^{-1}$s$^{-1}$) | $k_{d1}$ (s$^{-1}$) | $K_{D1}$ (M) |
|---|---|---|---|
| 7B7Mab SEQ ID NO: 68 SEQ ID NO: 17 | 3.E+05 | 2.E−04 | 7.E−10 |
| 23/17bAb1 IgG1.1 SEQ ID NO: 28 SEQ ID NO: 17 | 4.E+05 | 2.E−04 | 5.E−10 |
| 23/17bAb2 IgG1.1 SEQ ID NO: 18 SEQ ID NO: 17 | 2.E+05 | 8.E−05 | 4.E−10 |
| 23/17bAb3 IgG4.1 SEQ ID NO: 74 SEQ ID NO: 17 | 4.E+05 | 2.E−04 | 5.E−10 |
| 23/17bAb4 IgG4.1 SEQ ID NO: 29 SEQ ID NO: 17 | 7.E+04 | 7.E−05 | 1.E−9 |
| 23/17taFab1 IgG1.1 SEQ ID NO: 76 SEQ ID NO: 78 | 3.E+05 | 2.E−04 | 7.E−10 |

Simultaneous Co-Binding of IL-17A/F and IL-23 to the Anti-Human IL-23/IL-17A/F Bispecific Antibodies Via Surface Plasmon Resonance (Biacore)

Anti-Human IL-23/IL-17A/F bispecific antibodies were evaluated via surface plasmon resonance for ability to simultaneously co-bind both IL-23 and IL-17A/F.

For co-binding experiments in the first orientation, the human IL-17 molecules were covalently immobilized to flow cells 2-4 of a CM5 sensor chip using amine coupling chemistry (EDC:NHS). After immobilization, the remaining active sites on the flow cells were blocked with 1 M ethanolamine. Human IL-17A, IL-17A/F, and IL-17F (ZymoGenetics, A Bristol-Myers Squibb Company, Seattle, Wash., USA) were immobilized onto flow cells 2, 3, or 4 respectively. The immobilization levels of these molecules ranged from 4500-5200 RU. Flow cell 1 was used as the reference surface. The bispecific antibodies were subsequently diluted to either 25 or 50 µg/mL, flowed over the surface, and captured onto flow cells 2-4 of the sensor chip. Following capture of the bispecific antibody, the IL-23/IL-12B heterodimer (ZymoGenetics, A Bristol-Myers Squibb Company, Seattle, Wash., USA) was diluted to 500 nM and flowed over the surface to demonstrate co-binding. Binding studies were performed with a flow rate of 10 µL/min, an association time of 10 minutes, and a dissociation time of 5 minutes.

For co-binding experiments in the second orientation, a mouse anti-human IL-12 (p40/p70) monoclonal antibody (BD Pharmingen, San Jose, Calif.) was covalently immobilized onto flow cells 1-4 of a CM5 sensor chip using amine coupling chemistry (EDC:NHS). After immobilization, the remaining active sites on the flow cells were blocked with 1 M ethanolamine. The human IL-23/IL-12B heterodimer (ZymoGenetics, A Bristol-Myers Squibb Company, Seattle, Wash., USA) was diluted to 500 nM and captured onto flow cells 1-4 via the IL-12B subunit. The capture level of the IL-23/IL-12B was approximately 4000 RU. The bispecific antibodies were subsequently diluted to either 25 or 50 µg/mL, flowed over the surface, and captured via the human IL-23 subunit onto flow cells 2-4 of the sensor chip. Flow cell 1 was used as the reference surface. Following capture of the bispecific antibody, human IL-17A, IL-17A/F, and IL-17F (ZymoGenetics, A Bristol-Myers Squibb Company, Seattle, Wash., USA) were diluted to 500 nM and flowed over the surface to demonstrate co-binding. Binding studies were performed with a flow rate of 10 µL/min, an association time of 10 minutes, and a dissociation time of 5 minutes.

All binding experiments were performed at 25° C. in a buffer of 10 mM HEPES, 500 mM NaCl, 3 mM EDTA, 0.05% Surfactant P20 (GE Healthcare), 1 mg/mL bovine serum albumin, pH 7.4. Between cycles, the flow cell was washed with 20 mM hydrochloric acid to regenerate the surface. This wash step removed both the captured test antibody and any bound antigen from the chip surface. Data was compiled using BIACORE® T100 Evaluation software (version 2.0). Data was processed by subtracting reference flow cell and blank injections. Baseline stability was assessed to ensure that the regeneration step provided a consistent binding surface throughout the sequence of injections.

Simultaneous Co-binding of IL-17A/F and IL-23 to the Anti-Human IL-23/IL-17A/F Bispecific Antibodies Via Surface Plasmon Resonance (Biacore) Results Bispecific antibodies tested include 23/17bAb1 (SEQ ID NO:28 and SEQ ID NO:17), 23/17bAb2 (SEQ ID NO:18 and SEQ ID NO:17), 23/17bAb3 (SEQ ID NO:74 and SEQ ID NO:17), 23/17bAb4 (SEQ ID NO:29 and SEQ ID NO:17), and 23/17taFab1 (SEQ ID NO:76 and SEQ ID NO:78). All bispecific antibodies were able to simultaneously co-bind both human IL-23 and human IL-17A/F, demonstrating that both arms of the bispecific antibodies were functional.

Demonstration of IL-17A/F Specific Binding of the Anti-Human IL-23/IL-17A/F Bispecific Antibodies Via Surface Plasmon Resonance (Biacore)

Anti-Human IL-23/IL-17A/F bispecific antibodies were evaluated via surface plasmon resonance for lack of cross reactivity to human IL-17B, human IL-17C, human IL-17D, and human IL-17E (ZymoGenetics, A Bristol-Myers Squibb Company, Seattle, Wash., USA).

Binding studies were performed on a BIACORE® T100 (GE Healthcare, Piscataway, N.J.). Methods were programmed using BIACORE® T100 Control Software, v 2.0. Goat anti-human IgG Fc-gamma specific antibody (Jackson ImmunoResearch, West Grove, Pa.) was covalently immobilized to flow cells 1-3 of a CM4 sensor chip using amine coupling chemistry (EDC:NHS). The purified bispecific antibodies were subsequently captured onto either flow cell 2 or flow cell 3 of the sensor chip at a density of approximately 150 RU. Flow cell 1 was used as the reference surface.

Human IL-17B, IL-17C, IL-17D, and IL-17E (ZymoGenetics, A Bristol-Myers Squibb Company, Seattle, Wash., USA) were injected over the captured antibody surface (flow cell 2) and the reference flow cell (flow cell 1) at concentrations of 500, 100, 20, and 4 nM. As a positive control for this set of experiments, human IL-23 (ZymoGenetics, A Bristol-Myers Squibb Company, Seattle, Wash., USA) was injected at concentrations of 100, 20, 4 and 0.8 nM. Binding studies were performed with a flow rate of 50 µL/min, an association time of 5 minutes, and a dissociation time of 5 minutes. All binding experiments were performed at 25° C. in a buffer of 10 mM HEPES, 500 mM NaCl, 3 mM EDTA, 0.05% Surfactant P20 (GE Healthcare), 1 mg/mL bovine serum albumin, pH 7.4. Between cycles, the flow cell was washed with 20 mM hydrochloric acid to regenerate the surface. This wash step removed both the captured test antibody and any bound antigen from the chip surface. Data was compiled using BIACORE® T100 Evaluation software (version 2.0). Data was processed by subtracting reference flow cell and blank injections. Baseline stability was assessed to ensure that the regeneration step provided a consistent binding surface throughout the sequence of injections.

Demonstration of IL-17A/F Specific Binding of the Anti-Human IL-23/IL-17A/F Bispecific Antibodies Via Surface Plasmon Resonance (Biacore) Results No binding of human IL-17B, IL-17C, IL-17D, or IL17E to the bispecific antibodies was observed. Bispecific antibodies tested include 23/17bAb1 (SEQ ID NO:28 and SEQ ID NO:17), 23/17bAb2 (SEQ ID NO:18 and SEQ ID NO:17), 23/17bAb3 (SEQ ID NO:74 and SEQ ID NO:17), 23/17bAb4 (SEQ ID NO:29 and SEQ ID NO:17). In contrast, the IL-23 positive control demonstrated a dose dependent binding that was consistent with the previous studies.

Example 4

Anti-Human IL-23/17A/F bAbs Prevent Human IL-17A, F and AF-Mediated Increases in Serum Concentrations of Murine KC (CXCL1) in Mice IL-17A, F and AF are able to induce the production of a number of downstream factors that in turn play a role in host defense, but also contribute to disease pathology, especially when produced at abnormally high levels or under chronic conditions. One of these downstream mediators is CXCL1 (also known as GRO-α in human, or KC in mice), a chemokine that has important neutrophil chemoattractant activity and plays a role in inflammation. The ability of anti-human IL23/17A/F bispecific antibodies (bAbs) to reduce IL-17A, F and AF-mediated increases in GRO-α in mice was evaluated in order to show that the bAbs would be efficacious against IL-17-induced activities in an in vivo setting and thus that the bAbs would be useful in treating human diseases in which IL-17A, F or AF play a role. However, because these bAbs do not cross react with mouse IL-17A, F or AF, it was necessary to deliver human (h) IL-17A, F or AF to mice to induce the production of GRO-α (or in the case of mice, induce the production of KC, which is the murine analogue of GRO-α) which could then be neutralized in the presence of the anti-human IL23/17A/F bAbs.

For these experiments, female BALB/c mice (age 7-9 wk) were used. At time 18 hours, the mice received an intraperitoneal (i.p.) injection of either the vehicle (PBS) or a dose of one of the anti-human IL-23/17A/F bAbs as shown in Table 14 and 15, in the left-hand column. At time 0, they received a subcutaneous (s.c.) injection of one of the following recombinant human proteins: 0.175 mg/kg hIL-17A, 0.9 mg/kg hIL-17F or 0.5 mg/kg hIL17AF. Control mice received a s.c. injection of the vehicle (PBS) instead of one of the hIL-17 proteins. Two hours later, the mice were bled via the retro-orbital sinus under isoflurane gas anesthesia, serum was collected following centrifugation of the blood, and the serum was then stored at 80° C. until analyzed for serum KC concentrations using a commercial ELISA as per the manufacturer's instructions (Quantikine Mouse CXCL1/KC Immunoassay, R&D Systems, Inc., Minneapolis, Minn.).

As shown in Table 14 and 15, mice treated with the bAbs showed a dose-dependent increase in the inhibition of hIL-17A, F or AF-induced serum KC (CXCL1) concentrations indicating that the bAbs were efficacious in reducing the activities mediated by these IL-17 ligands. CXCL1 is just one example of a biological readout in response to IL-17A, F or AF; there are numerous other important downstream readouts that also play a role in diseases in which IL-17A, F or AF play a role that could be used as endpoint measurement.

TABLE 14

Percent Inhibition of Human IL-17A or F-mediated Increases in Serum Concentrations of Murine KC by i.p. bAbs, Relative to the Concentrations of Vehicle-Treated Mice (n = 3-4 per Group)

| | % Inhibition of IL-17A-Mediated Serum KC Levels | % Inhibition of IL-17F-Mediated Serum KC Levels |
|---|---|---|
| Vehicle (PBS) | 0 | 0 |
| 1 mg/kg bAb1 | 81 | 76 |
| 5 mg/kg bAb1 | 90 | 88 |
| 12 mg/kg bAb1 | 100 | 97 |
| 1 mg/kg bAb2 | 91 | 68 |
| 5 mg/kg bAb2 | 93 | 83 |
| 12 mg/kg bAb2 | 84 | 90 |
| 1 mg/kg bAb3 | 78 | 95 |
| 5 mg/kg bAb3 | 94 | 89 |
| 12 mg/kg bAb3 | 93 | 90 |
| 1 mg/kg bAb4 | 94 | 51 |
| 5 mg/kg bAb4 | 87 | 89 |
| 12 mg/kg bAb4 | 94 | 92 |

TABLE 15

Percent Inhibition of Human IL-17AF-mediated Increases in Serum Concentrations of Murine KC (pg/mL) by i.p. bAbs, Relative to the Concentrations of Vehicle-Treated Mice (n = 4 per Group)

| | % Inhibition of IL-17AF-Mediated Serum KC Levels |
|---|---|
| Vehicle (PBS) | 0 |
| 0.3 mg/kg bAb1 | 55 |
| 10 mg/kg bAb1 | 100 |
| 0.3 mg/kg bAb2 | 40 |
| 10 mg/kg bAb2 | 90 |
| 0.3 mg/kg bAb3 | 70 |
| 10 mg/kg bAb3 | 96 |
| 0.3 mg/kg bAb4 | 10 |
| 10 mg/kg bAb4 | 72 |

Example 5

Anti-Human IL-23/17A/F bAbs Prevent Human IL-23-Mediated Increases in Serum Concentrations of Mouse IL-17AF and F in Mice IL-23 is able to induce the differentiation of Th17 cells which in turn, can lead to the production of IL-17A, IL-17F and IL-17AF. These cytokines are implicated in a number of diseases and therapeutics that can inhibit IL-23 and IL-17A, F and AF would be efficacious in the treatment of these diseases. The ability of anti-human IL23/17A/F bispecific antibodies (bAbs) to reduce IL-23-mediated increases in IL-17A, F and AF in mice was evaluated in order to show that the bAbs would be efficacious against IL-23-induced activities in an in vivo setting, and thus that the bAbs would be useful in treating human diseases in which IL-23 and Th17 cells play a role. However, because these bAbs do not cross react with mouse IL-23 it was necessary to deliver human (h) IL-23 to mice to induce the production of mouse IL-17 F and AF which could then be neutralized in the presence of the anti-human IL23/17A/F bAbs. Concentrations of mouse IL-17A were too low to accurately measure in the mouse serum but the trends were expected to be similar as compared to the trends observed for serum IL-17F and AF.

For these experiments, female C57BL/6 mice (age 7-9 wk) were used. At 10:30 am on day 1, they each received 5 micrograms of mouse (m) IL-2 via an intra-peritoneal (i.p.) injection. At 8:30 am on day 2, the mice received an i.p. injection of either the vehicle (PBS) or a dose of one of the anti-human IL-23/17A/F bAbs as shown in Table 16, in the left-hand column. At 11 am on day 2 the mice each received 5 micrograms of mIL-2 and 10 micrograms of hIL-23, and at 5:20 pm on day 2, the mice received 10 micrograms each of mIL-2 and hIL-23 via i.p. injections. At 9:30 am on day 3, each of the mice received another 5 micrograms of mIL-2 and 10 micrograms of hIL-23 by i.p. injection. At 4:30 pm on day 3, the mice were bled via the retro-orbital sinus under isoflurane gas anesthesia, serum was collected following centrifugation of the blood, and the serum stored at −80° C. until analyzed for serum concentrations of mouse IL-17F and AF using ELISAs and luminex assays that specifically measured these components.

As shown in Table 16, mice treated with the bAbs showed a dose-dependent increase in the inhibition of hIL-23 induced serum concentrations of mouse 17F or AF indicating that the bAbs were efficacious in reducing the activities mediated by hIL-23.

TABLE 16

Percent Inhibition of Human IL-23 Mediated Increases in Serum Concentrations of Mouse IL-17F or AF by i.p. bAbs, Relative to the Concentrations of Vehicle-Treated Mice (n = 3 per Group)

| | % Inhibition of IL-23-Mediated Serum mIL-17F Levels | % Inhibition of IL-23-Mediated Serum mIL-17AF Levels |
|---|---|---|
| Vehicle (PBS) | 0 | 0 |
| 1 mg/kg bAb1 | 49 | 22 |
| 5 mg/kg bAb1 | 99 | 94 |
| 12 mg/kg bAb1 | 96 | 94 |
| 1 mg/kg bAb2 | 21 | 17 |
| 5 mg/kg bAb2 | 82 | 71 |
| 12 mg/kg bAb2 | 67 | 97 |
| 1 mg/kg bAb3 | 0 | 45 |
| 5 mg/kg bAb3 | 38 | 91 |
| 12 mg/kg bAb3 | 65 | 95 |
| 1 mg/kg bAb4 | 0 | 62 |
| 5 mg/kg bAb4 | 27 | 74 |
| 12 mg/kg bAb4 | 49 | 97 |

Example 6

VCVFc Bispecific Antibodies

Construction and Expression of Mammalian VCVFc Bispecific Molecules

Whole genes were synthesized at GenScript (GenScript, Piscataway, N.J., USA) and inserted into pTT5, an HEK293-6E transient expression vector (NCR Biotechnology Research Institute, Ottawa, ON, CAN) via restriction enzyme cloning. Most constructs were expressed using the mod2610 (SEQ ID NO:30) signal sequence. The VCVFc is a bispecific antibody which contains a whole antibody with a Fv unit of the second arm of the bispecific inserted between the Fab region and the hinge via a linker (for example, but not limited to, 10mer $G_4S$ for either chain, or RTVAAPS (SEQ ID NO:85) for the light chain and SSAS-TKGPS (SEQ ID NO:86) for the heavy chain). An illustration of a VCVFc bispecific antibody is shown in FIG. 5.

The HEK293-6E suspension cells were transfected with expression constructs using polyethylenimine reagent and cultivated in F17 medium (Invitrogen, Grand Island, N.Y., USA) with the addition of 5 mM L-glutamine and 25 μg/mL G418. After 24 hours, 1/40th volume of 20% Tryptone N1

(Organotechnie SAS, La Courneuve, FR) was added. At approximately 120 hours post transfection, conditioned media was harvested and passed through a 0.2 µm filter. Protein was purified from the filtered conditioned media using a combination of Mab Select SuRe Affinity Chromatography (GE Healthcare, Piscataway, N.J., USA) and SUPERDEX® 200 Size Exclusion Chromatography (GE Healthcare, Piscataway, N.J., USA). Content was estimated by absorbance at UV-A280 nm and quality evaluated by analytical size exclusion high performance liquid chromatography, SDS PAGE, and western blot.

IL-23/IL-17A/F VCVFc Bispecific Antibodies Bioassay Activity; NIH/3T3/KZ70 NF-κB Luciferase Reporter Assay to Measure Human IL-17A, IL-17A/F, and IL-17F Activity by NF-κB Induction The bioassay was performed as described in Example 1 hereinabove.

IL-23/IL-17A/F VCVFc Bispecific Antibodies Bioassay Activity; Baf3/huIL-23Rα/huIL-12Rβ1 Transfectants Phospho-STAT3 Assay to Measure Human IL-23 Activity by Phospho-STAT3 Induction The bioassay was performed as described in Example 3 hereinabove.

PDGF-C/PDGF-D VCVFc Bispecific Antibodies Bioassay Activity; Normal Human Lung Fibroblasts (NHLF) Proliferation Assay to Measure Human PDGF-C and PDGF-D Mitogenic Activity A primary normal human lung fibroblast cell line (NHLF, CC-2512, Lonza, Walkersville, Md.) was seeded at 1,000 cells/well in growth media (FGM-2 BulletKit, Lonza, Walkersville, Md.) and incubated overnight at 37° C., 5% $CO_2$. The following day media was removed and serial dilutions of recombinant human PDGF-C and PDGF-D (ZymoGenetics) were made up in assay media (FBM plus 0.1% BSA, Lonza, Walkersville, Md.) and added to the plates containing the cells and incubated together at 37° C., 5% $CO_2$ for 48 hours. Additionally the assay was used to measure neutralization PDGF-C and PDGF-D activity. A sub maximal concentration of PDGF-C or PDGF-D was combined with serial dilutions of anti-human PDGF-C/D or anti-human PDGFRα/β VCVFc antibodies described herein in assay media and added to the plates containing the cells and incubated together at 37° C., 5% $CO_2$ for 48 hours. Cells were pulsed with 1 µCi/well of Thymidine [Methyl-$^3$H] (PerkinElmer, Waltham, Mass.) and incubated at 37° C., 5% $CO_2$ for an additional 24 hours. Following incubation mitogenic activity was assessed by measuring the amount of $^3$H-Thymidine incorporation. Media was removed and cells trypsinized for 10 minutes at 37° C. before being harvested on FilterMate harvester (Packard Instrument Co., Meriden, Conn.) and read on TOPCOUNT® microplate scintillation counter (Packard Instrument Co., Meriden, Conn.) according to manufactures instructions. Increases in $^3$H-Thymidine incorporation were indicative of a PDGF-C or PDGF-D receptor-ligand interaction. Decreases in $^3$H-Thymidine incorporation were indicative of neutralization of the PDGF-C or PDGF-D receptor-ligand interaction. $IC_{50}$ (inhibitory concentration at 50 percent) values were calculated using GraphPad Prism 4 software (GraphPad Software, Inc., San Diego Calif.) for each PDGF-C/PDGF-D or PDGFRα/PDGFRβ VCVFc bispecific antibody.

IL-23/IL-17A/F VCVFc Bispecific Antibody Bioassay Activity; NIH/3T3/KZ170 NF-κB Luciferase Reporter Assay and Baf3/huIL-23Rα/huIL-12Rβ1 Transfectants Phospho-STAT3 Assay Results Human IL-17A, IL-17A/F and IL-17F induce activation of the NF-κB luciferase reporter in a dose dependent manner with an $EC_{50}$ concentration determined to be 0.15 nM for IL-17A, 0.5 nM for IL-17A/F and 0.5 nM for IL-17F and IL-23 induces STAT3 phosphorylation in a dose dependent manner with an $EC_{50}$ concentration determined to be 0.02 nM. The $IC_{50}$ data for the anti-human IL-23/IL-17A/F VCVFc bispecific antibodies are shown below in Tables 17, 18 and 19.

IL-23/17A/F VCVFc Bispecific Antibody Table

TABLE 17

| Name | Heavy Chain MVC# SEQ ID NO: | Light Chain MVC# SEQ ID NO: | IL-17A $IC_{50}$ nM | IL-17A/F $IC_{50}$ nM | IL-17F $IC_{50}$ nM | IL-23 $IC_{50}$ nM |
|---|---|---|---|---|---|---|
| 339-134 mAb IgG1.1 | MVC978 SEQ ID NO: 64 | MVC717 SEQ ID NO: 66 | 3 | 0.9 | 0.4 | Not Done |
| IL23.6 (7B7) mAb IgG1.1 | MVC1003 SEQ ID NO: 68 | MVC1002 SEQ ID NO: 17 | Not Done | Not Done | Not Done | 0.2 |
| 23/17VCV1 IgG1.1 | MVC1020 SEQ ID NO: 87 | MVC1021 SEQ ID NO: 89 | 20 | 3 | 3 | 0.008 |
| 23/17VCV2 IgG1.1 | MVC1022 SEQ ID NO: 91 | MVC1023 SEQ ID NO: 93 | 0.4 | 0.4 | 0.9 | 0.3 |

TABLE 18

| Name | Heavy Chain MVC# SEQ ID NO: | Light Chain MVC# SEQ ID NO: | IL-17A $IC_{50}$ nM | IL-17A/F $IC_{50}$ nM | IL-17F $IC_{50}$ nM | IL-23 $IC_{50}$ nM |
|---|---|---|---|---|---|---|
| 339-134 mAb IgG1.1 | MVC978 SEQ ID NO: 64 | MVC717 SEQ ID NO: 66 | 1.2 | 0.23 | 0.28 | Not Done |
| IL23.6 (7B7) mAb IgG1.1 | MVC1003 SEQ ID NO: 68 | MVC1002 SEQ ID NO: 17 | Not Done | Not Done | Not Done | 0.0030 |
| 23/17VCV3 IgG4.1 | MVC1119 SEQ ID NO: 95 | MVC1021 SEQ ID NO: 89 | 16 | 9.7 | 6.0 | 0.011 |
| 23/17VCV4 IgG4.1 | MVC1120 SEQ ID NO: 97 | MVC1023 SEQ ID NO: 93 | 0.20 | 0.34 | 0.20 | 0.47 |
| 23/17VCV5 IgG1.1 | MVC1122 SEQ ID NO: 99 | MVC1121 SEQ ID NO: 101 | 15 | 8.7 | 7.0 | 0.0038 |
| 23/17VCV6 IgG1.1 | MVC1124 SEQ ID NO: 103 | MVC1123 SEQ ID NO: 105 | 0.38 | 0.35 | 0.29 | 0.043 |

TABLE 19

| Name | Heavy Chain MVC# SEQ ID NO: | Light Chain MVC# SEQ ID NO: | IL-17A $IC_{50}$ nM | IL-17A/F $IC_{50}$ nM | IL-17F $IC_{50}$ nM | IL-23 $IC_{50}$ nM |
|---|---|---|---|---|---|---|
| 339.15.3.6 mAb Hybridoma line lot E10915 | N/A | N/A | 9.8 | 0.34 | 0.32 | Not Done |
| IL23.4 mAb IgG4.1-BDC Lot PC-1413-32 | SEQ ID NO: 107 | SEQ ID NO: 109 | Not Done | Not Done | Not Done | 0.029 |
| 23/17VCV7 IgG1.1 | MVC1108 SEQ ID NO: 111 | MVC1107 SEQ ID NO: 113 | 24 | 13 | 5.9 | 0.053 |

TABLE 19-continued

| Name | Heavy Chain MVC# SEQ ID NO: | Light Chain MVC# SEQ ID NO: | IL-17A $IC_{50}$ nM | IL-17A/F $IC_{50}$ nM | IL-17F $IC_{50}$ nM | IL-23 $IC_{50}$ nM |
|---|---|---|---|---|---|---|
| 23/17VCV8 IgG1.1 | MVC1110 SEQ ID NO: 115 | MVC1109 SEQ ID NO: 117 | 2.4 | 0.34 | 0.31 | 2.6 |

PDGF-C/PDGF-D and PDGFRα/PDGFβ VCVFc Bispecific Antibodies Bioassay Activity; Normal Human Lung Fibroblasts (NHLF) Proliferation Assay Results PDGF-C and PDGF-D induce proliferation of the NHLF cells in a dose dependent manner with a sub maximal concentration determined to be 0.1 nM for PDGF-C and 6 nM for PDGF-D. Table 20 and Table 21 present $IC_{50}$ data for the PDGF-C/PDGF-D or PDGFRα/PDGFRβ VCVFc bispecific antibody described herein.

PDGF-C/PDGF-D VCVFc Bispecific Antibody Table

TABLE 20

| Name | Heavy Chain MVC# SEQ ID NO: | Light Chain MVC# SEQ ID NO: | PDGFC $IC_{50}$ nM | PDGFD $IC_{50}$ nM |
|---|---|---|---|---|
| PDGFC mAb Hybridoma Lot-E2826 | N/A | N/A | .083 | Not Done |
| PDGFD mAb Hybridoma Lot-E4342 | N/A | N/A | Not Done | 3.5 |
| C/DVCV1 IgG1.1 | MVC1112 SEQ ID NO: 119 | MVC1111 SEQ ID NO: 121 | 0.090 | 20 |

PDGFRα/PDGFRβ VCVFc Bispecific Antibody Table

TABLE 21

| Name | Heavy Chain MVC# SEQ ID NO: | Light Chain MVC# SEQ ID NO: | PDGFC % Inhibition | PDGFD % Inhibition |
|---|---|---|---|---|
| PDGFRα mAb Hybridoma Lot-C5161 | N/A | N/A | 100% | 30% |
| PDGFRβ mAb Hybridoma Lot-C8938 | N/A | N/A | 50% | 100% |
| α/βVCV2 IgG1.1 | MVC1118 SEQ ID NO: 123 | MVC1117 SEQ ID NO: 125 | 70% | 100% |

IL-23/IL-17A/F VCVFc Bispecific Antibodies Bioassay Activity; Primary Human Fibroblast Assay to Measure Human IL-17A, IL-17A/F, and IL-17F Activity by IL-6 Induction The bioassay was pertextured as described in Example 3 hereinabove.

IL-23/IL-17A/F VCVFc Bispecific Antibodies Bioassay Activity; Primary Human Fibroblast Assay Results Human IL-17A, IL-17A/F and IL-17F induce human IL-6 production in a dose dependent manner with an $EC_{50}$ concentration determined to be 0.08 nM for IL-17A, 25 nM for IL-17A/F and 25 nM for IL-17F. Anti-human IL-23/IL-17A/F VCVFc bispecific antibody 23/17VCV2 (SEQ ID NO:91 and SEQ ID NO:93). Table 22 presents example $IC_{50}$ data for the IL-23/IL-17A/F VCVFc bispecific antibody described herein.

TABLE 22

| Profile | | 23/17VCV2 IgG1.1 SEQ ID NO: 91 SEQ ID NO: 93 | 339-134 mAbIgG1.1 SEQ ID NO: 64 SEQ ID NO: 66 | IL23.6(7B7) mAbIgG1.1 SEQ ID NO: 68 SEQ ID NO: 17 |
|---|---|---|---|---|
| Cellular Potency Hu. primary fibroblast cells (HFFF) $IC_{50}$ | IL-17A $EC_{50}$ = 0.08 nM | 0.3 nM | 2 nM | Not Done |
| | IL-17AF $EC_{50}$ = 25 nM | 26 nM | 22 nM | Not Done |
| | IL-17F $EC_{50}$ = 25 nM | 25 nM | 23 nM | Not Done |
| Cellular potency Primary T cell assay $IC_{50}$ | IL-23 $EC_{50}$ = 0.02 nM | 0.4 nM | Not Done | 0.02 nM |

IL-23/IL-17A/F VCVFc Bispecific Antibodies Co-Binding Activity; Primary Human Fibroblast Assay to Measure the Inhibition of Human IL-17A, IL-7A/F, or IL-F while Simultaneously Bound to Human IL-23. The Primary Human T Cell Phospho-STAT3 Assay to Measure the Inhibition of Human IL-23 while Simultaneously Bound to Human IL-17A, IL-7A/F, or IL-17F.

The primary human fibroblast assay was run in the presence of excess amounts of IL-23 at 30 nM. The primary human T cell phospho-STAT3 assay was run in the presence of excess amounts of IL-17A, IL-17A/F, and IL-17F at 30 nM.

IL-23/IL-17A/F VCVFc Bispecific Antibodies Bioassay Co-Binding Results

Bispecific antibody 23/17VCV2 (SEQ ID NO:91 and SEQ ID NO:93) when examined in the presence of human IL-23 did not interfere with human IL-17A, IL-17A/F, IL-17F inhibition. Bispecific antibody 23/17VCV2 when examined in the presence of human IL-17A, IL-17A/F, IL-17F did not interfere with human IL-23 inhibition.

Measurement of Binding Affinities of IL-23/IL-17A/F VCVFc Bispecific Antibodies to Human IL-17A, IL-17A/F, IL-17F, and Human IL-23 Via Surface Plasmon Resonance (Biacore)

Binding activities were determined as described in Example 3 hereinabove.

IL-23/IL-17A/F VCVFc Bispecific Antibodies Biacore Activity

The results of the binding experiments with human IL-17A, IL-17A/F, and IL-17F are shown in Tables 23, 24, and 25, respectively. The results of the binding experiments with the human IL-23/IL-12B heterodimer are shown in Table 26.

IL-23/IL-17A/F VCVFc Bispecific Antibodies Binding Affinity for IL-17A

TABLE 23

| Bispecific Antibody | $k_{a1}$ ($M^{-1}s^{-1}$) | $k_{d1}$ ($s^{-1}$) | $K_{D1}$ (M) | $K_{D1}$ (nM) |
|---|---|---|---|---|
| 339-134 mAb IgG1.1 SEQ ID NO: 64 SEQ ID NO: 66 | 2.E+06 | 3.E−03 | 1.E−9 | 1.0 |
| 23/17VCV2 IgG1.1 SEQ ID NO: 91 SEQ ID NO: 93 | 3.8E+06 | 3.4E−03 | 8.9E−10 | 0.9 |

TABLE 23-continued

| Bispecific Antibody | $k_{a1}$ (M$^{-1}$s$^{-1}$) | $k_{d1}$ (s$^{-1}$) | $K_{D1}$ (M) | $K_{D1}$ (nM) |
|---|---|---|---|---|
| 23/17VCV4 IgG4.1 SEQ ID NO: 97 SEQ ID NO: 93 | 5.4E+06 | 5.4E+03 | 1.0E+09 | 1.0 |
| 23/17VCV6 IgG1.1 SEQ ID NO: 103 SEQ ID NO: 105 | 4.0E+06 | 4.7E+03 | 1.2E+09 | 1.2 |

IL-23/IL-17AF VCVFc Bispecific Antibodies Binding Affinity for IL-17A/F

TABLE 24

| Bispecific Antibody | $k_{a1}$ (M$^{-1}$s$^{-1}$) | $k_{d1}$ (s$^{-1}$) | $K_{D1}$ (M) | $K_{D1}$ (nM) |
|---|---|---|---|---|
| 339-134 mAb IgG1.1 SEQ ID NO: 64 SEQ ID NO: 66 | 2.E+06 | 5.E−04 | 2.E−10 | 0.2 |
| 23/17VCV2 IgG1.1 SEQ ID NO: 91 SEQ ID NO: 93 | 1.8E+06 | 7.1E−04 | 3.9E−10 | 0.4 |
| 23/17VCV4 IgG4.1 SEQ ID NO: 97 SEQ ID NO: 93 | 1.5E+06 | 7.7E+04 | 5.1E+10 | 0.5 |
| 23/17VCV6 IgG1.1 SEQ ID NO: 103 SEQ ID NO: 105 | 1.2E+06 | 7.9E+04 | 6.6E+10 | 0.7 |

IL-23/IL-17A/F VCVFc Bispecific Antibodies Binding Affinity for IL-17F

TABLE 25

| Bispecific Antibody | $k_{a1}$ (M$^{-1}$s$^{-1}$) | $k_{d1}$ (s$^{-1}$) | $K_{D1}$ (M) | $K_{D1}$ (nM) |
|---|---|---|---|---|
| 339-134 mAb IgG1.1 SEQ ID NO: 64 SEQ ID NO: 66 | 2.E+06 | 2.E−04 | 1.E−10 | 0.1 |
| 23/17VCV2 IgG1.1 SEQ ID NO: 91 SEQ ID NO: 93 | 2.4E+06 | 5.1E−04 | 2.1E−10 | 0.2 |
| 23/17VCV4 IgG4.1 SEQ ID NO: 97 SEQ ID NO: 93 | 2.2E+06 | 3.5E+04 | 1.6E+10 | 0.2 |
| 23/17VCV6 IgG1.1 SEQ ID NO: 103 SEQ ID NO: 105 | 3.4E+06 | 1.2E+04 | 3.5E+11 | 0.04 |

IL-23/IL-17A/F VCVFc Bispecific Antibodies Binding Affinity for IL23/IL-12B

TABLE 26

| Antibody or Bispecific Antibody | $k_{a1}$ (M$^{-1}$s$^{-1}$) | $k_{d1}$ (s$^{-1}$) | $K_{D1}$ (M) | $K_{D1}$ (nM) |
|---|---|---|---|---|
| 7B7Mab SEQ ID NO: 68 SEQ ID NO: 17 | 3.E+05 | 2.E−04 | 7.E−10 | 0.7 |

TABLE 26-continued

| Antibody or Bispecific Antibody | $k_{a1}$ (M$^{-1}$s$^{-1}$) | $k_{d1}$ (s$^{-1}$) | $K_{D1}$ (M) | $K_{D1}$ (nM) |
|---|---|---|---|---|
| 23/17VCV2 IgG1.1 SEQ ID NO: 91 SEQ ID NO: 93 | 4.7E+04 | 2.1E−04 | 4.5E−09 | 4.5 |
| 23/17VCV4 IgG4.1 SEQ ID NO: 97 SEQ ID NO: 93 | No Binding | No Binding | No Binding | No Binding |
| 23/17VCV6 IgG1.1 SEQ ID NO: 103 SEQ ID NO: 105 | 5.6E+04 | 1.1E+04 | 2.0E+09 | 2.0 |

Simultaneous Co-binding of IL-17A/F and IL-23 to the IL-23/IL-17A/F VCVFc Bispecific Antibodies Via Surface Plasmon Resonance (Biacore)

This assay was performed as described in Example 3 hereinabove.

Simultaneous Co-binding of IL-17A/F and IL-23 to the IL-23/IL-17A/F VCVFc Bispecific Antibodies Via Surface Plasmon Resonance (Biacore) Results Bispecific antibody 23/17VCV2 (SEQ ID NO:91 and SEQ ID NO:93) was able to simultaneously co-bind both human IL-23 and human IL-17A/F, demonstrating that both arms of the bispecific antibodies were functional.

Example 7

IL-23p19 Epitope Mapping

The analysis described in this Example 7 aims to identify the epitopic residues on IL-23p19 for which the IL-23p19 antibody (7B7 antibody or Mab, 7B7 Fab and biAb3, all of which have a heavy chain variable domain as shown in SEQ ID NO:7 and light chain variable domain as shown in SEQ ID NO:9) binds. Fab 7B7, 7B7 antibody and biAb3 have all been used in the binding studies at various stages because they are interchangeable as far as their epitope on IL-23p19.

Proteolytic Digest and Peptide Data on Epitope

Mass spectrometry epitope sequence analysis of the IL-23p19 antibody was based on both epitope extraction and epitope excision methods. (Parker et al., "MALDI/MS-based epitope mapping of antigens bound to immobilized antibodies", *Mol. Biotechnol.*, 20(1):49-62 (January 2002)). In both cases the IL-23p19 antibody was directly immobilized via primary amines of the antibody on surface-activated beads at an average density of 2 mg mAb per 1 ml bed volume. Peptides from IL-23 his-tag antigen were generated with or without reduction and alkylation. Reduction of the antigen IL-23 was performed by incubating with 50 mM dithiothreitol in PBS and 4M guanidine HCl for 1 hour at 37° C. This was followed by alkylation with 100 mM iodoacetamide for 30 minutes at room temperature. Reduced and alkylated IL-23 was dialyzed against PBS overnight prior to fragmentation. For epitope extraction, antigen peptides were generated by proteolytic digestion with the endoproteinases trypsin, chymotrypsin, lys-C, arg-C, asp-N and or glu-C with an enzyme to antigen ratio of up to 2% (w/w). Incubations were performed at 37° C. with incubation times ranging from 2 hours to overnight. The resulting peptides were mixed with antibody resin at room temperature for 30 minutes. This resin was then washed three times to remove any non-specifically bound peptides. All digestion, incubation, and wash steps were performed in PBS pH 7. The same protocol was followed for epitope excision except that the intact antigen was incubated with the antibody for 30 minutes at room temperature prior to enzymatic digestion. In both methods antibody bound peptides were eluted and analyzed on ESI-MS.

These data indicate that IL-23p19 antibody has a discontinuous epitope comprised of three peptide regions in IL-23p19. Synthetic peptides were generated to further examine these three peptide regions, and their binding was tested and analyzed by both ELISA and mass spectrometry. Based on these observations, it is suggested that the following peptides represent the sequences of the IL-23p19 antibody epitope:

Peptide 1:
WQRLLLRFKILR (residues 156-167 of SEQ ID NO: 6)

Peptide 2:
SAHPLVGHMDLR (residues 46-57 of SEQ ID NO: 6)

Peptide 3:
IHQGLIFYEKLLGSDIFTGEPSLLP.
(residues 93-117 of SEQ ID NO: 6)

IL-23 Epitope Mapping by HDX-MS

Hydrogen/deuterium exchange mass spectrometry (HDX-MS) method probes protein conformation and conformational dynamics in solution by monitoring the rate and extent of deuterium exchange of backbone amide hydrogen atoms. The level of HDX depends on the solvent accessibility of backbone amide hydrogen atoms and the conformation of the protein. The mass increase of the protein upon HDX can be precisely measured by MS. When this technique is paired with enzymatic digestion, structural features at the peptide level can be resolved, enabling differentiation of surface exposed peptides from those folded inside. Typically, the deuterium labeling and subsequent quenching experiments are performed, followed by online pepsin digestion, peptide separation, and MS analysis. Prior to epitope mapping of BMS-986113 in IL-23 by HDX-MS, non-deuteriated experiments were performed to generate a list of common peptic peptides for IL-23 (4.4 mg/mL) and IL-23/BMS-986113 (1:1 molar ratio, 4.4 mg/mL & 3.36 mg/mL), achieving a sequence coverage of 97% for IL-23. In this experiment, 10 mM phosphate buffer (pH 7.0) was used during the labeling step, followed by adding quenching buffer (200 mM phosphate buffer with 1.5M GdnCl and 0.5M TCEP, pH 2.5, 1:1, v/v). For epitope mapping experiments, 5 µL of each sample (IL-23 or IL-23/BMS-986113 (1:1 molar ratio)) was mixed with 65 µL HDX labeling buffer (10 mM phosphate buffer in D$_2$O, pD 7.0) to start the labeling reactions at room temperature (~25° C.). The reactions were carried out for different periods of time: 20 sec, 1 min, 10 min, 60 min and 240 min. By the end of each labeling reaction period, the reaction was quenched by adding quenching buffer (1:1, v/v) and the quenched sample was injected into Waters HDX-MS system for analysis. The observed common peptic peptides were monitored for their deuterium uptake levels in the absence/presence of BMS-986113. The same protocol was followed for epitope mapping of anti-IL-23 7B7 Fab (4.91 mg/mL) in IL-23 by HDX-MS.

Epitope mapping of anti-IL-23 7B7 Fab in complex with IL-23 and biAb3 with IL-23 indicate that biAb3 has a discontinuous epitope comprised of five peptide regions in IL-23p19. Based on relative deuterium uptake levels, five peptide regions can be ranked as region 1>2>3>4>5 with region 1 having the most significant changes in deuterium uptakes and region 5 having the least significant changes in deuterium uptakes. The five peptide regions on IL-23p19 as determined by HDX-MS for the IL-23p19 antibody were determined as follows:

Region 1:
PDSPVGQL; (residues 117-124 of SEQ ID NO: 6)

Region 2:
IFTGEPSLL; (residues 108-116 of SEQ ID NO: 6)

Region 3:
KILRSLQAF; (residues 164-172 of SEQ ID NO: 6)

Region 4:
QQLSQKLCTLAWSAHPLVGHMD;
(residues 34-55 of SEQ ID NO: 6)
and

Region 5:
CLQRIHQGLIFYEKLLG. (residues 89-105 of SEQ ID NO: 6)

Computational Epitope Prediction and Design of Alanine Shave Mutants

Alanine shave mutagenesis is a strategy for mutating multiple residues in the same construct to alanine to remove the amino acid side chains in epitope of binding (Wells, J. A., "Systemic mutational analyses of protein-protein interfaces", *Enzym.*, 202:390-411 (1991)). Multiple sources of information on the involvement of residues in a potential epitope with the 7B7 Fab and biAb3 were combined to produce a targeted list of regional alanine shave mutants. The residues contained in the overlapping regions between both the HDX (see above in this Example 7) and the proteolytic digest peptide mapping (see above in this Example 7) were mapped onto the sequence of the IL-23p19 domain and three linear regions of common residues were identified as Regions A, B and C. Region A corresponds to amino acid residues 33-59 of SEQ ID NO:6. Region B corresponds to amino acid residues 89-125 of SEQ ID NO:6. Region C corresponds to amino acid residues 144-173 of SEQ ID NO:6. In order to calculate the residues whose side chains are exposed (solvent accessible surface area, SASA) and would therefore be located on the protein surface of the p19 domain of IL-23, an in-house structure of the IL-23 heterodimer was used. For each residue in the p19 domain of IL-23 the ratio of accessible surface to the standard exposed surface for the amino acid type was calculated and residues were grouped into bins. Residues were placed in accessibility bins as follows: <30%, 30-40%, 40-50%, 50-60%, 60-70%, 70-80%, >90% exposed. The standard residue accessibilities for each amino acid type were calculated in the extended tripeptide Gly-X-Gly. The second calculation performed was ODA (Optimal Docking Area) which is useful for predicting likely protein-protein interaction surfaces. The method identifies optimal surface patches with the lowest docking desolvation energy. The ODA was calculated for the p19 domain of IL-23 and these results used to prioritize residues for mutagenesis.

Residues in these three regions (A, B, C) were prioritized based upon a high score in both the ODA and SASA calculations and also weighted based on the extent of hydrogen-deuterium exchange relative to the uncomplexed IL-23 (peptide #1>#2>#3>#4>#5). Regions with non-identity to mouse were cloned as mouse swap mutants, instead of alanine shave mutants, which did not show an impact on binding in small scale testing. With the exception of M7 which contains a linear sequence of residues in an extended loop, residues were then combined into non-linear epitopes based on mapping them to the X-ray crystallographic structure of IL-23 (M5, M6, M8). Additional backup mutants were generated with the sub-epitopes of predominantly linear residues (M9, M10, M11). The alanine shave mutants designed by this method are shown below in Table 27.

TABLE 27

Alanine Shave Mutants of IL-23p19

| Name | Region Mutated | IL-23p19 (SEQ ID NO: 6) Residues Mutated to Alanine |
|---|---|---|
| M5 | A and B | H53A, M54A, E112A, L116A and D118A |
| M6 | A and C | T42A, W45A, H48A, F163A and Q170A |
| M7 | C | W142A, E143A, T144A, Q145A and Q146A |
| M8 | A, B and C | H53A, E112A, Q154A and W156A |
| M9 | B | L116A, D118A and Q123A |
| M10 | A | H53A, M54A, D55A and F163A |
| M11 | C | W142A, T144A and Q146A |

Cloning, Expression and Purification of IL-23 Epitope Mapping Alanine Mutants

Non-tagged wild-type IL-23 p40 subunit entry vector construct was generated by PCR and the fidelity of the PCR fragment was confirmed by sequencing. The transient expression construct was generated by Gateway LR recombination and sequence confirmed. The His-tagged wild-type IL-23 p19 subunit construct and all mutant constructs were generated by PCR and cloned into the transient expression vector directly. The fidelity of all PCR fragments was confirmed by sequencing. To generate the wild-type control, non-tagged wild-type IL-23 P40 subunit was co-expressed with the His-tagged wild-type P19 subunit transiently in HEK293-6E cells at 4 L scale for IL-23 complex purification. Briefly, HEK293-6E cells at $1 \times 10^6$ cells/ml were transfected with expression plasmids/PEI complex at the ratio of 0.5 (p19)/0.5(p40)/1.5 (PEI). Tryptone N1 feed was added 24 hours later and cells harvested on 120 hours post transfection. The conditioned media was filtered with 0.2 μM filters. Seven His-tagged IL-23 p19 mutant constructs were co-transfected with the non-tagged wild-type IL-23 p40 subunit at the 30 ml scale following the same transfection protocol described above. The conditioned media were transferred for analysis and the expression of all mutants was confirmed by anti-His Western-blot. Based on preliminary binding results, mutants M5, M7, M9, and M10 were selected and scaled up at 2 L scale with the same transfection protocol. The wild-type was also scaled up at 2 L. The scale-ups of wild-type and mutants of IL-23 at 2 liters of HEK cells were harvested and the supernatants were concentrated and buffer exchanged to PBS by tangential flow filtration with a 10 kDa membrane. The proteins were then purified by immobilized nickel affinity chromatography. The wild-type was eluted with 40 mM imidazole and then buffer exchanged by desalting gel filtration chromatography to PBS (5.6 mM $Na_2HPO_4$, 1.1 mM $KH_2PO_4$, 154 mM NaCl, pH 7.4). The purity of the wild-type was determined by SDS-PAGE to be >95%. The mutants were washed with 40 mM imidazole followed by elution at 500 mM Imidazole. The elution pools were then buffer exchanged by dialysis to PBS (7 mM $Na_2HPO_4$, 3 mM $NaH_2PO_4$, 130 mM NaCl, pH 7.1). The purity of the mutants was determined by SDS-PAGE to be >95%. Single alanine mutants of his-tagged IL-23p19 at key residues identified by alanine shave mutagenesis were generated by gene synthesis and then cloned into the transient transfection vector. Expression and purification were similar to the alanine shave mutants with the exception of M35A which was an affinity purified.

Biacore Binding Analysis of IL-23 Mutants to the IL-23p19 Antibody

The binding of the 30 mL small scale expression of all seven (7) alanine mutants (see Table 27) was measured by surface Plasmon resonance (SPR, Biacore)) on a BIACORE® T100 in PBST (7 mM $Na_2HPO_4$, 3 mM $NaH_2PO_4$, 130 mM NaCl, 0.05% Tween 20, pH 7.4) at 25° C. The relevant antibodies and receptors were captured at a level of about 60 RUs by protein A immobilized at 2000 RUs on a CM5 sensor chip. In addition to the biAb3, Merck's IL-23 p19 mAb (7G10) and STELARA® (IL-12/IL-23 p40 mAb) were used as controls for domain binding. In addition, the commercial receptors for IL-23 were used as controls: hIL-23R-Fc and hIL-12Rβ1-Fc (both from R&D Systems). The supernatants were diluted 1:5 into PBST and injected at 30 μL/min over the mAb or receptor surface for 3 minutes and, after a dissociation time, regenerated with 10 mM Glycine, pH 2.0. Binding to a reference surface of Protein A without any captured antibody was subtracted from all specific binding curves before analysis. The results shown in FIG. 9 show the response 10 seconds before the end of the injection.

The Biacore results demonstrate that the IL-23 alanine shave mutants maintain binding to the p40 specific antibody and the p19 specific IL-23 receptor (except for M8 which potentially describes the receptor binding site). Binding of another IL-23p19 mAb and IL-12Rβ1-Fc was also performed and is consistent with the results of FIG. 9. The M5 mutant shows a dramatic loss of binding to 7B7 Mab while M9 & M10 show partial loss of binding to 7B7 Mab (see FIG. 10). M7 does not show any impact to binding to the antibody or controls. Therefore, these four mutants were chosen for scale-up and purification, the three mutants that lose binding to the IL-23p19 antibody (7B7 antibody or Mab, 7B7 Fab and biAb3, all of which have a heavy chain variable domain as shown in SEQ ID NO:7 and light chain variable domain as shown in SEQ ID NO:9) and the M7 as a control.

Biacore analysis of the purified mutants used the same assay format as the supernatants except that the wild-type and mutant IL-23 was diluted to 25 nM and serially titrated 1:2 down to 1.5 nM. All results obtained with the purified IL-23 mutants confirmed the data obtained with the expression supernatants. The data were fit to a 1:1 Langmuir binding model to determine the Kd values shown in FIG. 10 and Table 28. The 1-2 RU of reference subtracted binding observed for M5 binding to the IL-23p19 antibody (7B7 antibody or Mab, 7B7 Fab and biAb3, all of which have a heavy chain variable domain as shown in SEQ ID NO:7 and light chain variable domain as shown in SEQ ID NO:9) was simulated using the BIAsimulation software 2.1 using the average Rmax determined from kinetic analysis of M9 & M10. The affinity was estimated to be ≥330 μM with a 1500 fold weaker Kd than wild-type as shown in Table 28.

TABLE 28

Biacore Kinetic Analysis of IL-23 Alanine Mutants Binding IL-23p19 Antibody

| | 7B7 mab | | | | | Merck |
|---|---|---|---|---|---|---|
| Variant | Kd (nM) | Kd-shift (from WT) | ΔΔG (kcal/mole) | BiAb3 ΔΔG (kcal/mole) | STELARA ® ΔΔG (kcal/mole) | 7G10 ΔΔG (kcal/mole) |
| WT | 0.14 | NA | NA | NA | NA | NA |
| M5 | ≥300 | 1500 | 4.6 | 3.8 | 0.1 | 1.9 |

TABLE 28-continued Biacore Kinetic Analysis of IL-23 Alanine Mutants Binding IL-23p19 Antibody

| | 7B7 mab | | | | STELARA® | Merck |
|---|---|---|---|---|---|---|
| Variant | Kd (nM) | Kd-shift (from WT) | ΔΔG (kcal/mole) | BiAb3 ΔΔG (kcal/mole) | ΔΔG (kcal/mole) | 7G10 ΔΔG (kcal/mole) |
| M7 | 0.4 | 3 | 0.5 | NM | 0.1 | 0.2 |
| M9 | 25 | 140 | 2.9 | 2.3 | 0.1 | 0.2 |
| M10 | 43 | 230 | 3.2 | 2.3 | 0.3 | 0.4 |

Biacore analysis of single alanine mutants was performed to confirm the non-linear epitope demonstrated by the M5, M9, and M10 alanine shave mutants. Most single alanine mutants in the three linear regions A, B, and C showed no change in binding to the 7B7 mAb or biAb3. Only three of the fourteen single alanine mutant of IL-23 tested showed a significant decrease in binding affinity greater than 1 kcal/mole. The affinity and the ΔΔG values for the key residues overlapping between alanine shave mutants M5, M9, and M10 shown in Table 29 and demonstrate that one major residue in linear region B and two residues in linear region A contribute predominantly to the binding energy of the IL-23p19 antibody-IL-23 complex.

TABLE 29

Biacore Kinetic Analysis of IL-23 Single Alanine Mutants Binding IL-23p19 Antibody

| | 7B7 mab | | | | | Merck |
|---|---|---|---|---|---|---|
| Variant | Kd (nM) | Kd-shift (from WT) | ΔΔG (kcal/mole) | BiAb3 ΔΔG (kcal/mole) | STELARA ® ΔΔG (kcal/mole) | 7G10 ΔΔG (kcal/mole) |
| WT | 0.14 | NA | NA | NA | NA | NA |
| His53 (region A) | 0.2 | 0 | 0.2 | 0.2 | 0.3 | 0 |
| Met 54 (region A) | 6.8 | 48 | 2.3 | 2.2 | 0.3 | 1.0 |
| Asp55 (region A) | 9.6 | 68 | 2.5 | 2.3 | 0.5 | 0.7 |
| Glu112 (region B) | 0.7 | 5 | 0.9 | 1.2 | 0.3 | 1.7 |
| Leu116 (region B) | 46 | 330 | 3.4 | 3.0 | 0.5 | 0.2 |
| Asp118 (region B) | 0.1 | 0 | 0 | −0.4 | −0.3 | −0.3 |

IL-23 Induced STAT3 Phosphorylation in BaF3 huIL-23Rα/huIL-12Rβ1 Transfectants

A murine bone marrow derived cell line (BaF3) was stably transfected with human IL-23Rα and human IL-12Rβ1 full length receptors and cloned. IL-23 induction of phosphorylation of STAT3 was monitored by ELISA for IL-23 Alanine shave mutants. BaF3/huIL-23Rα/huIL-12Rβ1 (clone 6) cells were washed three times with assay media before being plated at 50,000 cells per well in 96-well round-bottom tissue culture plates. BaF3/huIL-23Rα/huIL-12Rβ1 cells respond to IL-23 in a dose dependant manner by phosphorylation of STAT3. To assess antibody inhibition of IL-23 signaling, an $EC_{50}$ concentration of 20 pM IL-23 was premixed with three-fold serial dilutions of each antibody from 33 nM to 0.56 pM and incubated at 37° C. for 15 minutes in assay media prior to addition to the cells. Following pre-incubation, treatments were added in duplicate to plates containing cells and incubated at 37° C. for 15 minutes to stimulate phosphorylation of STAT3. Stimulation was stopped with the addition of ice-cold wash buffer and cells lysed according to manufacturer's instructions (Bio-Rad Laboratories Cell Lysis kit, Cat #171-304012). Phosphorylated STAT3 levels were determined by ELISA (Bio-Rad Laboratories Phospho-$STAT3^{(Tyr705)}$ kit, Cat #171-V22552) according to manufacturer's instructions. Data was analyzed and $IC_{50}$ values were calculated using GraphPad Prism 4 software. All the IL-23 Alanine shave mutants and all the IL-23 Alanine single mutants are active and equal potent as wt IL-23 (untagged and tagged) at inducing pSTAT3 activity on BaF3/huIL-23Rα/huIL-12Rβ1 transfectants (Table 30). Results for biAb3, STELARA® (IL-12/IL-23 p40 mAb), and Merck's IL-23p19 antibody (7G10) inhibition of IL-23 Alanine shave mutant induced pSTAT3 are shown in Table 31. biAb3 neutralizes the biological activity of wt IL-23 and IL-23 M7 Alanine shave mutant with equal potency, M9 and M10 with reduced potency, and does not neutralize the biological activity of M5 on BaF3/huIL-23Rα/huIL-12Rβ1 transfectants. STELARA® IL-12 p40 mAb neutralizes the biological activity of wt IL-23 and all the IL-23 Alanine shave mutants with equal potency on BaF3/huIL-23Rα/huIL-12Rβ1 transfectants. Positive control Merck IL-23 p19 mAb (7G10) neutralizes the biological activity of wt IL-23, M7, M9 and M10 Alanine shave mutants with equal potency and does not neutralize the biological activity of M5 on BaF3/huIL-23Rα/huIL-12Rβ1 transfectants.

TABLE 30

$EC_{50}$ values for IL-23 Alanine shave mutants and $IC_{50}$ Values for biAb3, STELARA ® (IL-12/IL-23 p40 mAb), and Merck's IL-23p19 antibody (7G10) inhibition of IL-23 Alanine shave mutants induced pSTAT3 in BaF3/huIL-23Rα/huIL-12Rβ1 transfectants

| Antibody | wt human IL-23 | IL-23 M5 | IL-23 M7 | IL-23 M9 | IL-23 M10 |
|---|---|---|---|---|---|
| None ($EC_{50}$) | 21 pM | 26 pM | 21 pM | 33 pM | 19 pM |
| biAb3 | 19 pM | NA | 17 pM | 2400 pM | 5300 pM |
| STELARA ® | 79 pM | 62 pM | 59 pM | 67 pM | 71 pM |
| Merck 7G10 | 380 pM | NA | 310 pM | 260 pM | 350 pM |

Single IL-23p19 mutations (H53A, M54A and D55A) were constructed and $IC_{50}$ Values for 7B7, STELARA® (IL-12/IL-23p40 mAb), and Merck's IL-23p19 antibody (7G10) (Table 31) to inhibit the single IL-23p19 mutated polypeptides to induce pSTAT3 in BaF3/huIL-23Rα/huIL-12Rβ1 transfectants was determined. The 7B7 mAb neutralizes the biological activity of IL-23 Alanine single mutants H53A, E112A, and D118A with equal potency, M54A and D55A mutants with significantly reduced potency, and does not neutralize the biological activity of L116A mutant compared to wt IL-23 on BaF3/huIL-23Rα/huIL-12Rβ1 transfectants (Table 31). STELARA® IL-12 p40 mAb neutralizes the biological activity of all the IL-23 Alanine single mutants with equal potency compared to wt IL-23 on BaF3/huIL-23Rα/huIL-12Rβ1 transfectants. Merck IL-23 p19 mAb neutralizes the biological activity of all the IL-23 Alanine single mutants with equal potency compared to wt IL-23 on BaF3/huIL-23Rα/huIL-12Rβ1 transfectants, except for IL-23 E112A mutant which it does not neutralize.

TABLE 31

IC$_{50}$ Values for 7B7, STELARA ® (IL-12 /IL-23p40 mAb), and Merck's IL-23p19 Antibody (7G10) to Inhibit IL-23p19 Single Mutations (H53A, M54A and D55A) to Induce pSTAT3 in BaF3/huIL-23Rα/huIL-12Rβ1 Transfectants

| Antibody | IL-23 wt IC$_{50}$ (nM) | IL-23 H53A IC$_{50}$ (nM) | IL-23 M54A IC$_{50}$ (nM) | IL-23 D55A IC$_{50}$ (nM) | IL-23 E112A IC$_{50}$ (nM) | IL-23 L116A IC$_{50}$ (nM) | IL-23 D118A IC$_{50}$ (nM) |
|---|---|---|---|---|---|---|---|
| 7B7/biAb3 | 0.020 | 0.015 | 0.71 | 1.2 | 0.025 | >3 | 0.012 |
| STELARA ® p40 | 0.067 | 0.078 | 0.081 | 0.077 | 0.033 | 0.054 | 0.052 |
| Merck 7G10 | 0.18 | 0.19 | 0.27 | 0.18 | >3 | 0.24 | 0.22 |

Taking all these results together, 7B7 mAb inhibition of IL-23 requires amino acids residues M54, D55, and L116, but does not require amino acid residues H53, E1112, or D118. STELARA® and Merck antibodies were able inhibit the IL-23 Alanine single mutants M54A, D55A and L116A with no loss in activity, suggesting the loss in activity seen with IL-23 M54, D55 and L116 Alanine mutants are specific to the 7B7 mAb and the biAb3.

Oligomeric State Analysis of IL-23 Mutants and 7B7 Fab Complexes

To confirm the oligomeric state of the heterodimeric IL-23 mutants and their ability to complex with the 7B7 Fab, the proteins were studied by analytical size-exclusion chromatography (SEC-MALS) separation using an AGILENT® 1100 series HPLC fitted with a diode-array absorbance detector, on a Shodex Protein KW-803 column in buffer (0.1 um filtered) containing 200 mM K$_2$PO$_4$ (pH 6.8 with HCl), 150 mM NaCl, and 0.02% sodium azide, at a flow rate of 0.5 mL/min. A Wyatt Technology MINIDAWN™ TREOS® laser light scattering instrument was plumbed downstream from the HPLC, followed by a Wyatt OPTILAB® T-REX™ differential refractometer. Sixty (60) µg of each IL-23 sample was injected after filtering at a concentration of 10.3 µM. For complex formation, 60 µg of the 7B7 Fab was premixed with a 6% molar excess and incubated with the IL-23 protein at a concentration of 10.9 µM at room temperature for at 3-6 hours before chromatographic separation. Particulates were removed from protein samples with a spin filter (NANOSEP® MF, 0.2m, Pall Corporation) prior to injection. Data were analyzed with ASTRA® 6 (Wyatt) and Chemstation (Agilent). All mutants were mostly monomeric, similar to the wild-type. The M5 mutant did not show significant complex formation after pre-incubation with the Fab and eluted close to where the M5 IL-23 alone elutes demonstrating that little if any complex was formed in the 10 µM concentration range of this experiment. M7 complexed and eluted similar to the wild-type. The M9 and M10 mutants form complex at these concentrations, but the mass was somewhat less than that of the wild-type and the retention time was slightly later than the wild-type and M7, suggesting that their affinity for 7B7 was weaker than the wild-type and M7. SEC-MALS analysis of the 14 single alanine mutants showed that all were mostly monomeric, similar to the wild-type, and only the L116A mutant showed a late-shifted elution time and a slight reduction in the expected mass of the complex suggesting that the affinity of the IL-23 for the 7B7 Fab was reduced. These results are consistent with the Biacore shift in Kd for these L116A. The effect of the reduced affinity of the complex of D54A and M55A with the Fab was not able to be resolved under the conditions of this assay.

Differential Scanning Calorimetry of IL-23 Mutants

The thermal stability profile for the wild type and mutant IL-23 heterodimers was measured by differential scanning calorimetry (DSC) using a MICROCAL® VP-capillary DSC instrument. 0.7 mg/ml protein samples in PBS (7 mM Na$_2$HPO$_4$, 3 mM NaH$_2$PO$_4$, 130 mM NaCl, pH 7.1) were scanned from 10-100° C. at 90°/hr, and the resulting thermograms were subjected to a buffer blank subtraction and fitting procedure. The denaturation of each molecule was characterized by two unfolding transitions and the fitted transition midpoint (Tm) values of each transition were within 1-4° C. of the wild type. The results show that none of the alanine shave mutants nor the 14 single alanine mutants show significant thermal destabilization relative to the wild type.

Fourier Transform Infrared Spectroscopy (FT-IR) Analysis of IL-23 Mutants

Secondary structure comparison of the alanine shave mutants and wild type of IL-23 was performed using a FT-IR spectroscopy on Biotools Prota FT-IR instrument with CaF$_2$ windows with a pathlength of ~7 µm and a Ne—He laser at 632.8 nm. Data were collected with a resolution of 2 cm$^{-1}$ and analyzed with Prota/Bomem-GRAMS/31 AI software. Duplicate measurements were made for each sample and the method variability is about 3%. Secondary structure content was calculated using Amide I peak as it is structure sensitive. Approximately an equal quantity of α-Helix and β-sheet was observed in all IL-23 samples as indicated by peaks at 1637 cm−1 for α-Helix and peak at 1637 cm−1 as well as shoulder at 1687 cm−1 for β-sheet. Overall no significant difference in FT-IR spectrum and calculated secondary structure result was observed in the alanine shave mutants compared to the wild type IL-23.

Circular Dichroism (CD) Analysis of IL-23 Mutants

Secondary structure comparison of the alanine shave mutants and wild type of IL-23 using CD spectroscopy was performed using a Jasco J-815 Spectrophotometer. The spectra were collected at 0.25 mg/mL IL-23 protein concentration in PBS pH7.1 using a 1 mm path length cells at 25° C. from 300-190 nm with a data interval of 0.1 nm, a 50 nm/min scanning speed, a 1 nm bandwidth, and 2 accumulations. Overall no significant difference in secondary structure profile was observed in the alanine shave mutants compared to the wild type IL-23 using circular dichroism.

Nuclear Magnetic Resonance (NMR) Spectroscopy Analysis of IL-23 Mutants

Proton NMR is a highly sensitive technique that allows one to assess the conformational state at atomic detail. 1D $^1$H NMR spectra were acquired for each of four mutant (M5, M7, M9, M10) and wild type IL23 proteins. All proteins were dialyzed simultaneously against NMR buffer (PBS in 8% D$_2$O/92% H$_2$O) to eliminate potential differences resulting from sample preparation. In addition, $^1$H signal intensities were corrected for differences in protein concentration by normalizing to the wild type spectrum. All NMR data was collected at 32° C. on a Bruker Avance 3 spectrometer operating at 600 MHz. 1D NMR spectra were acquired using the standard bruker pulse sequence (ZG) optimized for solvent and excipient suppression using the Watergate, WET, and Water flipback selective excitation pulse schemes. Two thousand forty-eight (2048) scans were signal averaged for each spectrum. Cosine squared apodization was applied prior to Fourier transformation, and a first order polynomial baseline correction was used to flatten the appearance of the baseline. Examination of each of the spectra for the individual proteins reveals that each mutant protein was properly folded, as evidenced by the well-dispersed resonances in both the high field (<0.5 ppm) and low field (>6.5 ppM)

regions of the spectra. The high field methyl resonances indicated the presence of an intact hydrophobic core; the downfield amide protons reflected the existence of well-formed secondary structure (alpha helices and beta sheets). Comparison of the spectra with that for wild type IL23 indicated a very close match, precluding the existence of large conformational changes in the protein structure induced by the amino acid substitutions. In addition, the NMR results also indicated that extra loss in activity in M5 is unlikely due to an extra large disruption in structural integrity at the mutation sites in M5. The fact that M5 was considerably closer to the wild-type protein by principle component analysis than M9 suggests, that the following M5-mutations which are missing in M9, i.e., H53A, M54A and E112A do not cause much of a disruption in the M5-structure. It was also observed that mutants M7 & M9 which contain the elimination of an aromatic residue appeared most similar to each other in the principle component analysis. All single mutants appear similar to wild-type with the exception of D118A and M54A, however other controls demonstrate that these mutants maintain stability and activity similar to wild-type.

Summary of IL-23 Epitope Analysis

The methods of Alanine Shave and Single Mutagenesis have been used to map the epitope of hIL-23 for the 7B7 Fab contained in both the 7B7 Fab, 7B7 antibody and biAb3. The targeted mutagenesis strategy was performed using epitope information generated by proteolytic digest LCMS analysis, peptide binding, hydrogen/deuterium exchange mass spectrometry, solvent accessible surface area calculations and docking algorithm calculations. Small scale screening by SPR and scale-up of select purified mutants demonstrated a specific epitope for 7B7/biAb3 binding hIL-23. The M5 mutant shows dramatic decrease in binding to 7B7/biAb3, while maintaining functional activity, binding to p40 and p19 specific reagents, monomeric oligomeric state, thermal stability, and secondary structural features similar to the wild-type. The M5 mutant showed a dramatic loss of binding to 7B7/biAb3 while M9 & M10, which each contained two of the same mutated residues as M5, each show partial loss of binding to 7B7/biAb3. The affinity of the M5 IL-23 mutant was ≥300 nM for 7B7/biAb3 which is approximately 1,500-fold weaker than wild-type IL-23 demonstrating that the residues in the M5 mutant define the epitope for 7B7/biAb3 binding to IL-23. Thus, the data suggests that the 7B7/biAb3 antibody binds to a discontinuous epitope on the p19 subunit of IL-23. This discontinuous epitope on IL-23p19 comprises at least two epitope regions (region A (amino acid residues 33-59 of SEQ ID NO:6) and region B (amino acid residues 89-125 of SEQ ID NO:6)). Specifically, with respect to the first epitope or region A of IL-23p19, amino acid residues 54 (Met) and 55 (Asp) of SEQ ID NO:6 contribute a significant amount of binding energy to 7B7/biAb3's ability to bind IL-23p19. With respect to the second epitope or region B of IL-23p19, amino acid residue 116 (Leu) is the primary residue within Region B energetically contributing to 7B7/biAb3's ability to bind IL-23p19.

Example 8

Marmoset EAE Model

Background and Rationale

Multiple sclerosis (MS) is a chronic autoimmune, inflammatory, neurodegenerative disease of the central nerve system (CNS) characterized by a loss of myelin in the brain and spinal cord. Although the mechanisms underlying disease initiation are not clearly understood, the disease processes that contribute to clinical progression of multiple sclerosis are inflammation, demyelination, and axonal loss, or neurodegeneration. Macrophages and microglia are the main immune cells of the CNS. These cells, as well as T cells, neutrophils, astrocytes, and microglia, can contribute to the immune-related pathology of, e.g., multiple sclerosis. Furthermore, T cell reactivity/autoimmunity to several myelin proteins, including myelin basic protein (MBP), proteolipid protein (PLP), myelin oligodendrocyte protein (MOG), and perhaps other myelin proteins, have been implicated in the induction and perpetuation of disease state and pathology of multiple sclerosis. This interaction of autoreactive T cells and myelin proteins can result in the release of proinflammatory cytokines, including TNF-alpha, IFN-gamma, and IL-17, among others. Additional consequences are the proliferation of T cells, activation of B cells and macrophages, upregulation of chemokines and adhesion molecules, and the disruption of the blood-brain barrier. The ensuing pathology is a loss of oligodendrocytes and axons, and the formation of a demyelinated "plaque". The plaque consists of a lesion in which the myelin sheath is now absent and the demyelinated axons are embedded within glial scar tissue. Demyelination can also occur as the result of specific recognition and opsinization of myelin antigens by autoantibodies, followed by complement- and/or activated macrophage-mediated destruction. It is this axonal loss and neurodegeneration that is thought to be primarily responsible for the irreversible neurological impairment that is observed in progressive multiple sclerosis.

Multiple sclerosis (MS) is classified into four types, characterized by the disease's progression.

(1) Relapsing-remitting MS (RRMS). RRMS is characterized by relapse (attacks of symptom flare-ups) followed by remission (periods of recovery). Symptoms may vary from mild to severe, and relapses and remissions may last for days or months. More than 80 percent of people who have MS begin with relapsing-remitting cycles.

(2) Secondary-progressive MS (SPMS). SPMS often develops in people who have relapsing-remitting MS. In SPMS, relapses and partial recoveries occur, but the disability doesn't fade away between cycles. Instead, it progressively worsens until a steady progression of disability replaces the cycles of attacks.

(3) Primary-progressive MS (PPMS). PPMS progresses slowly and steadily from its onset. There are no periods of remission and symptoms generally do not decrease in intensity. About 15 percent of people who have MS have PPMS.

(4) Progressive-relapsing MS (PRMS). In this relatively rare type of MS, people experience both steadily worsening symptoms and attacks during periods of remission.

Mayo Clinic (located on the internet at mayoclinic.org/multiple-sclerosis/types).

There is a large amount of clinical and pathological heterogeneity in the course of human multiple sclerosis. Symptoms most often begin between the ages of 18 and 50 years old, but can begin at any age. The clinical symptoms of multiple sclerosis can vary from mild vision disturbances and headaches, to blindness, severe ataxia and paralysis. The majority of the patients (approximately 70-75%) have relapsing-remitting multiple sclerosis, in which disease symptoms can recur within a matter of hours to days, followed by a much slower recovery; the absence of symptoms during stages of remission is not uncommon. The incidence and frequency of relapses and remissions can vary greatly, but as time progresses, the recovery phases can be incomplete and slow to occur. This worsening of disease in these cases is classified as secondary-progressive multiple sclerosis, and occurs in approximately 10-15% of multiple sclerosis patients. Another 10-15% of patients are diagnosed with primary-progressive multiple sclerosis, in which disease symptoms and physical impairment progress at a steady rate throughout the disease process.

Both IL-23 and IL-17 are overexpressed in the central nervous system of humans with multiple sclerosis and in mice undergoing an animal model of multiple sclerosis, experimental autoimmune encephalomyelitis (EAE). The overexpression is observed in mice when the EAE is induced by either myelin oligodendrocyte glycoprotein (MOG) 35-55 peptide- or proteolipid peptide (PLP). Furthermore, neutralization of either IL-23/p19 or IL-17 results in amelioration of EAE symptoms in mice (Park et al, Nat Immunol. 6:1133 (2005); and Chen et al, J Clin Invest. 116:1317 (2006)).

Methods

Experimental autoimmune encephalomyelitis (EAE) is a well-characterized and reproducible animal model which replicates certain aspects of MS. EAE is inducible in rodents and non-human primates, such as the common marmoset. Genain, C. P. and Hauser, S. L., "Creation of a model for multiple sclerosis in Callithrix jacchus marmosets," J. Mol. Med., 75:187-197 (1997). In marmoset EAE, animals are immunized with a recombinant human myelin oligodendrocyte glycoprotein (rHuMOG) to induce the development of a disease closely resembling human multiple sclerosis. Published studies of this model have employed MOG emulsified in complete Freund's adjuvant (CFA) as the immunogen, in a single inoculation. Our early attempts to induce EAE in the marmoset using the published methodology led to onset of clinical symptoms between 23 to 142 days after MOG injection (data not shown). Since this timeline was considered to be too long for pre-clinical efficacy studies, a modified protocol employing an initial priming dose followed by a booster immunization to induce disease was employed. Using the prime/boost protocol as described in this study, we evaluated the activity of a surrogate bispecific antibody having an IL-17A/F binding entity and an IL-23 binding entity in this non-human primate model of EAE. The surrogate bispecific antibody was a biAbFabL (see FIG. 2), having the same IL-17 A/F binding entity as biAb-1, biAb-2, biAb-3 and biAb-4, while having a surrogate IL-23 binding entity as the IL-23 binding entity of biAb-3, for example, has reduced affinity for marmoset IL-23p19. Accordingly, an alternative IL-23 binding entity was utilized in the surrogate bispecific antibody. The alternative IL-23 binding entity utilized in the surrogate bispecific antibody was the same IL-23 binding entity identified as IL-23 mAb in FIG. 13 and FIG. 14.

For induction of EAE, rHuMOG (BlueSky Biotech, Worcester, Mass.) was diluted in sterile PBS to 0.66 mg/ml and then emulsified with an equal volume of incomplete Freund's adjuvant (IFA, Sigma #F5506) containing 5 mg/mL of *M. tuberculosis* H37 RA (Difco #231141). 300 µL of the final CFA/MOG mixture (containing 0.33 mg/mL of MOG and 2.5 mg/ml of H37RA) was injected at 2 sites on the shaved shoulder area of each animal (150 µl×2 injection sites). All marmosets were immunized with CFA/MOG on the same day (Day 0).

On Day 21, the animals received a booster immunization of IFA/MOG, (prepared as above but without the H37 RA) injected at 2 injection sites over the shaved lumbar/hip area. Marmosets were anesthetized with Ketamine (15 mg/kg) via IM injection for the prime and boost inoculations.

The surrogate IL-23/17 AF bAb (IgG4.1k) was formulated in 20 mM succinic acid, 150 mM arginine buffer (pH 5.6). Dosing was started 1 day prior to the priming inoculation with CFA/MOG. Animals were given either placebo (PBS, SC, 2×/week) or IL-23/17 AF bAb (7 mg/kg, SC, 2×/week). Other treatment groups included BMS-938790 (IL-23 adnectin; 3 mg/kg, SC, 2×/week), ADX_PRD1651 (IL-23/17 binectin, 10 mg/kg, SC, 2×/week), and a surrogate IL-23 mAb IgG4.1 (IL-23.15-g4P, 9 mg/kg, SC, 2×/week). Doses were administered on Tuesdays and Fridays throughout the study period. Individual body weights were recorded weekly and animals were dosed based on individual body weight. All SC doses were administered into the flank area following topical swabbing with alcohol. The dose sites were alternated (left or right side) for each dose administration. Treatment groups at the start of the study consisted of 8 animals per group (mixed males and females). Animals were conscious and hand-restrained at the time of drug injection.

Visual assessments of disease status were made daily beginning on Day 12. Assessments were made and recorded by consensus of two investigators. Clinical scores were based on a modification of published disease score as described in Table 32 below.

TABLE 32

Marmoset EAE clinical scoring system

0 = No Clinical signs
0.5 = reduced alertness/slow movements, or losing appetite
1.0 = weight loss >10% (initial wt. at beginning of study Day 0)
1.5 = unilateral or bilateral visual defects, dissociated gaze abnormalities
2.0 = vision impairment and/or balance is weak, ataxia, or abnormal gait
2.5 = mono or paraparesis of front or back limbs and/or
sensory loss and/or brain stem syndrome
3.0 = hemi- or paraplegia (paralysis of the posterior half
of one side) (can also include 1 leg and 1 hand
paralysis at same time)
4.0 = quadriplegia
5.0 = moribund or spontaneous death Results The number of animals with signs/symptoms of EAE disease per groups was as follows:

Group A (PBS): 5 of 7 marmosets (71%) showed EAE-like disease and/or neurologic dysfunction at some point during the study. Disease presentation consisted of blindness and paralysis.

Group B (IL-23 adnectin, BMS-938790): 1 of 6 marmosets (17%) showed EAE-like disease. Disease presentation consisted of progressive blindness and paralysis.

Group C (IL-23/17 binectin, ADX_PRD1651): 6 of 7 marmosets (86%) showed EAE-like disease. However, 3 of the animals showed evidence of EAE signs/symptoms on only a single observation day.

Group D (IL-23 mAb): 3 of 6 marmosets (50%) showed EAE-like disease. Blindness was prevalent.

Group E (IL-23/17 AF bAb): 4 of 8 marmosets (50%) showed EAE-like disease; 3 of these 4 animals had transient symptoms with a "positive" score on only a single observation day. Disease consisted of mostly mild symptoms such as slow movement or reduced alertness.

Compared to the disease incidence in Group A (PBS), the difference in disease incidence in each of the other treatment groups was not statistically significant (p>0.05, Fisher's Exact Test).

A small subset of animals in the study did develop more severe signs/symptoms of EAE, with several marmosets requiring euthanasia to comply with pre-established humane endpoints. The number of animals in each group requiring euthanasia was as follows: Group A (2); Group B (1); Group C (1); Group D (0); Group E (0).

Figure 12:
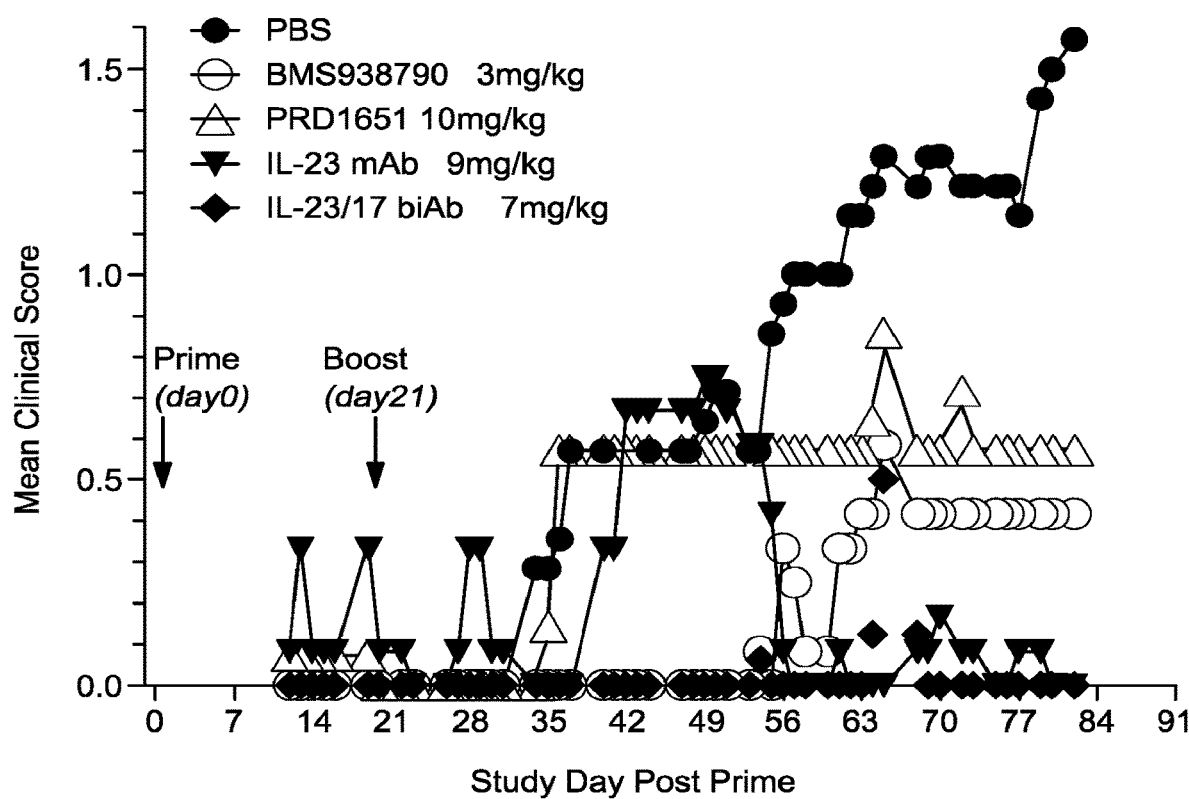
FIG. 12 schematically illustrates the clinical disease scores over time in the marmoset EAE model.

Animals that were euthanized for humane reasons as a result of EAE symptoms were assigned a clinical severity score of "4" at the time of euthanasia which was carried throughout the remainder of the study for the purpose of calculating a group mean clinical severity score. FIG. 12 depicts the mean clinical severity score for each treatment group over the course of the study. Group A (PBS) reached a peak score of approximately 1.6 by the end of the study. All other groups displayed lower mean clinical scores, with Group E (IL-23/17 AF bAb) showing only a brief period (~1 wk) when any signs of EAE disease were evident. Due to the limited numbers of animals in each group and the inter-animal variability in EAE disease scores among animals within a group, none of the differences between Group A (PBS) and the other treatment groups was statistically significant (Mann-Whitney U Test).

In summary, this study showed a trend toward reduced disease severity and reduced disease incidence in the marmoset EAE model by several of the compounds evaluated. Overall, the animals treated with IL-23/17 AF bAb (IgG4.1k) appeared to experience the most beneficial outcome (FIG. 12), though the differences between groups were not statistically significant. The finding that the animals treated with the IL-23/17 AF bAb were better protected than the animals treated with just the IL-23 mAb, suggests that dual targeting of both the IL-23 and IL-17AF pathways will result in greater efficacy in the treatment of human diseases in which these cytokine pathways play a role, including but not limited to multiple sclerosis.

Post-Mortem MRI

At the end of the study, the surviving marmosets were submitted for necropsy. The skull cap was removed and the brain was fixed in situ in formalin for 3 weeks. To assess lesions in white matter and the optic tracks, T2W and proton density MRI scans were conducted with the Bruker Biospec 7T system with a 72 mm Quad RF coil, using the following parameters: Total scan time ~15-20 mins per sample, 23 axial images were collected, TR/TE=5000/20 ms, slice thickness=1.2 mm, FOV=4 cm, matrix=256×256, in-plane resolution=156 mm$^2$.

Scans were reviewed and semi-quantitative interpretations were performed by consensus reading of 3 radiologists after review of all MRI images for each group of animals. Lesion scoring was based on lesion count in the white matter covering the entire brain. Optic nerve scoring was based on swelling and increased signal intensity reflecting inflammation in the optic tract and nerve.

Figure 13:
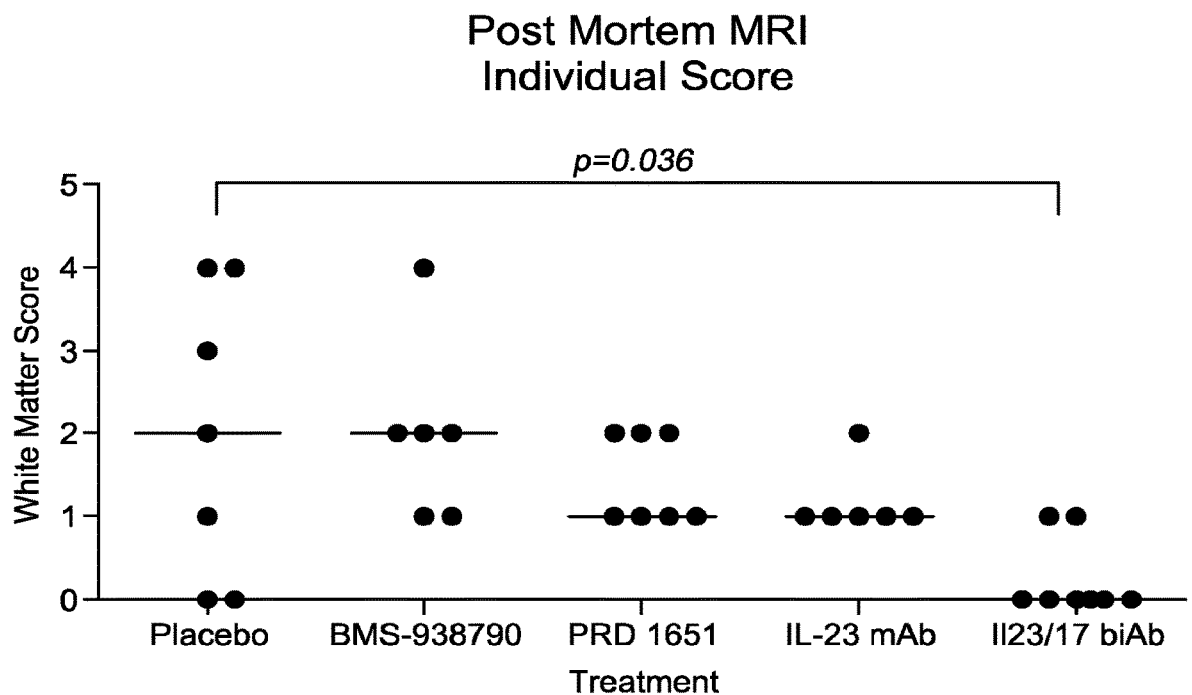
FIG. 13 schematically illustrates the MRI lesion score in the marmoset EAE model.
Figure 14:
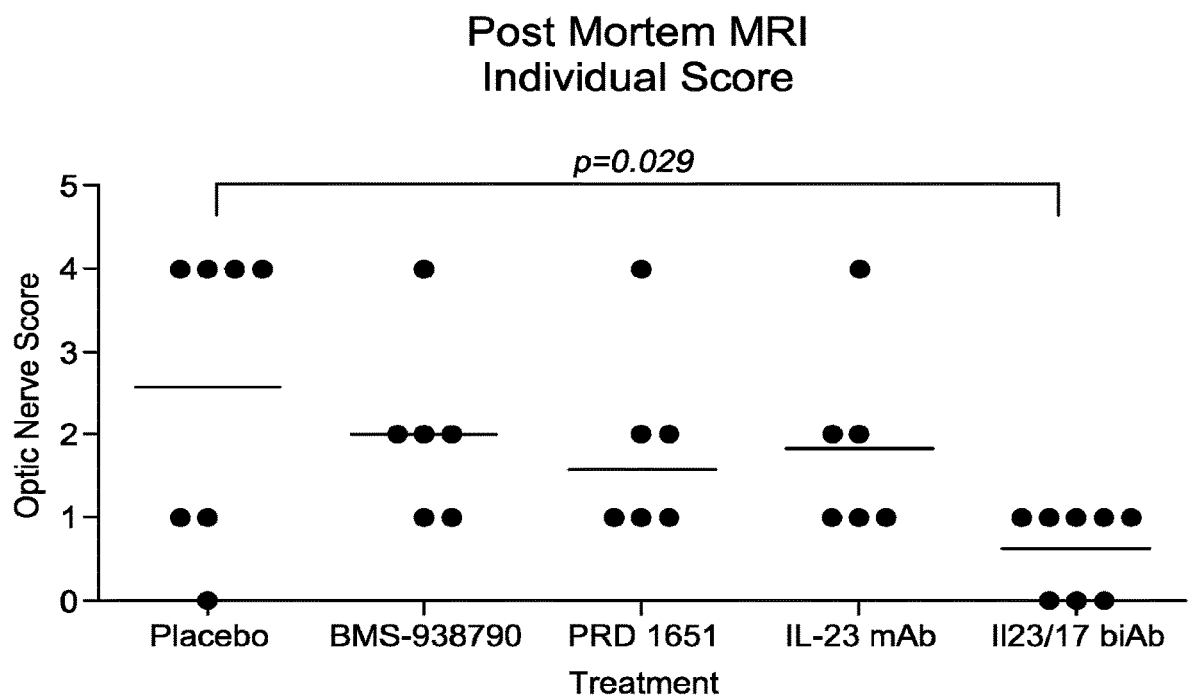
FIG. 14 schematically illustrates the MRI optic nerve score in the marmoset EAE model.

Overall, a significant ($p<0.05$) reduction in lesion load was observed for the IL-23/17 AF bAb group compared to the vehicle group (FIG. 13). The optic tract score was also significantly lower in the IL-23/17 AF bAb group compared to vehicle (FIG. 14). None of the other treatment groups were significantly different than vehicle-treated group for either of these MRI measurements. Thus, consistent with the clinical disease scores, the group of animals treated with the IL-23/17 AF bAb had the lowest mean MRI values again suggesting that dual targeting of both the IL-23 and IL-17AF pathways will result in greater efficacy in the treatment of diseases in humans.

Example 9

IL-17A and IL-17F Epitope Mapping

The analysis described in this Example 9 aims to identify the epitopic residues on IL-17A and IL-17F for which the IL-17A/F binding entity of biAb3 (heavy chain variable domain as shown in SEQ ID 13 and light chain variable domains as shown in SEQ ID NO:9) binds.

The strategy to identify the key differences between the epitope of the biAb3 and the mouse parent (339.15.5.3) utilized X-ray crystallography, site-directed mutagenesis, in-silico mutagenesis, and binding and functional assays to analyze the mutants. The heavy chain variable domain of the IL-17A/F binding entity of biAb3 is a humanized version of the heavy chain variable domain of clone 339.15.5.3, clone 339.15.3.6 or clone 339.15.5.3. The heavy chain CDR residues of the IL-17A/F binding entity of biAb3 and clone 339.15.5.3, clone 339.15.3.6 or clone 339.15.5.3 are identical. However, the two mAbs differ in the framework region of their heavy chain variable domains. The two mAbs have different light chains therefore the residues of IL-17 in contact with the light chain of each mAb was the focus of this study.

X-Ray Crystallography

IL17A Fab complex and IL17F Fab complex crystallography was performed to determine the contact interface residues for contact surface modeling for epitope/paratope residue predictions, and buried surface determination. The three-dimensional structures were also used for Protein Mutant energetic calculations based on modeled crystal structure complexes.

The Fabs of each antibody were cloned and expressed periplasmically in *E. coli* strain BL21 (humanized 339-134) or BL21 Star (BiAb). Purification for both included IMAC followed by SEC. Both IL-17A and IL-17F were expressed in *E. coli* strain W3110 as inclusion bodies and refolded, followed by a several step purification.

The Fab derived from the IL-17 arms of the biAb3 (heavy chain variable domain of SEQ ID NO:13 and heavy chain CH1 domain of SEQ ID NO:15; and a light chain of SEQ ID NO:17) and the Fab derived from the humanized lead of the parent (humanized anti-human IL-17A/F antibody 339-134 mAb (SEQ ID NO:65 and SEQ ID NO:67) were complexed with either human IL-17A or IL-17F. Complex formation of either IL-17A or IL-17F with the BiAb3 and the humanized anti-human IL-17A/F antibody 339-134 mAb was monitored by SEC.

Co-crystals of each of the four complexes were generated by broad screening followed by optimization of crystallization conditions. A data set on each sample was collected at the APS LS-CAT beamlines.

TABLE 33

Summary of X-ray crystallography dataset resolution.

| Complex | Resolution |
| --- | --- |
| IL-17A A2999F/Parent Fab A3052F | 2.85 Å |
| IL-17F A2768F/Parent Fab A3052F | 3.75 Å |
| IL-17A A2999F/Lead Fab A3185F | 3.4 Å |
| IL-17F A2768F/Lead Fab A3185F | 4.25 Å |

Each structure was determined by molecular replacement using Phaser MR from the CCP4 suite. The IL-17A search model was derived from PDB ID 2VXS. The IL-17F search model was taken from PDB ID 1JPY. For each Fab, search models were generated for the constant and variable domains using the humanized Fab from PDB ID 3IDX with the hypervariable loops deleted. The final models were obtained after iterative rounds of refinement in REFMAC5 and manual model building in Coot. In addition, additional rounds of refinement and map generation in Autobuster were performed for model building and refinement of all of the lower resolution structures. Crystallographic statistics for data collection and refinement are shown for the humanized parental Fab structures in Table 34 and the humanized lead Fab structures in Table 35. Each structure was assessed for geometry using MolProbity which had been downloaded to run on an internal server.

TABLE 34

Crystallographic statistics for the humanized parental Fab A3052F in complex with either IL-17A or IL-17F

|  | IL-17A/Parent Fab A3052F Overall | Highest shell | IL-17F/Parent Fab A3052F Overall | Highest shell |
|---|---|---|---|---|
| Crystal ID | 238318e7 |  | 238699f10 |  |
| Unique puck ID | 0yg0-1 |  | apa7-6 |  |
| Collection date | 1 November 2012 |  | 18 December 2012 |  |
| Δφ | 0.5° |  | 1.0° |  |
| Images | 71-260 (95°) |  | 1-180 (180°) |  |
| Wavelength | 0.97856 Å |  | 0.97856 Å |  |
| Space Group | P3$_2$21 |  | C2 |  |
| Unit Cell | a = b = 141.9 Å, c = 91.2 Å, α = β = 90°, γ = 120° |  | a = 226.1 Å, b = 62.3 Å, c = 117.3 Å, α = γ = 90°, β = 104.4° |  |
| Solvent content | 70% |  | 60% |  |
| $V_m$ | 4.1 Å$^3$/Da |  | 3.1 Å$^3$/Da |  |
| Resolution | 50-2.85 Å | 2.91-2.85 | 50-3.75 Å | 3.84-3.75 |
| I/σ | 18.2 | 2.3 | 16.7 | 2.0 |
| Completeness | 99.1% | 99.3% | 97.4% | 97.2% |
| $R_{merge}$ | 0.062 | 0.538 | 0.066 | 0.709 |
| Multiplicity | 5.9 | 6.0 | 3.4 | 3.5 |
| Reflections | 24,828 | 1821 | 16,223 | 1198 |
| Mosaicity | 0.4 |  | 0.3-0.8 |  |
| Refinement |  |  |  |  |
| R | 0.269 |  | 0.251 |  |
| $R_{free}$ | 0.309 |  | 0.300 |  |
| Validation |  |  |  |  |
| Ramachandran favored | 91.9% |  | 86.8% |  |
| Ramachandran outliers | 1.0% |  | 3.6% |  |
| Rotamer outliers | 3.2% |  | 10.3% |  |
| Clash score | 3.78 (100$^{th}$) |  | 10.08 (97$^{th}$) |  |
| Molprobity score | 2.04 (99$^{th}$) |  | 2.92 (91$^{st}$) |  |

TABLE 35

Crystallographic statistics for the humanized lead Fab A3185F alone or in complex with IL-17A or IL-17F

|  | Lead Fab A3185F Overall | Highest shell | IL-17A/Lead Fab A3185F Overall | Highest shell | IL-17F/Lead Fab A3185F Overall | Highest shell |
|---|---|---|---|---|---|---|
| Crystal ID | 243072a6 |  | 240719f6 |  | 238860g7 |  |
| Unique puck ID | koc5-3 |  | jsm6-5 |  | cum1-2 |  |
| Beamline | APS 21 ID-D |  | APS 21 ID-D |  | APS 21 ID-G |  |
| Collection date | Apr. 18, 2013 |  | Apr. 18, 2013 |  | Nov. 30, 2012 |  |
| Δφ | 1.0° |  | 1.0° |  | 0.5° |  |
| Images | 1-257 (257°) |  | 1-180 (180°) |  | 1-180 (180°) |  |
| Wavelength | 0.93005 Å |  | 0.93005 Å |  | 0.97856 Å |  |
| Space Group | C2 |  | C222$_1$ |  | P2$_1$ |  |
| Unit Cell | a = 92.1 Å, b = 60.1 Å, c = 73.0 Å, α = γ = 90°, β = 94.9° |  | a = 54.6 Å, b = 83.6 Å, c = 248.9 Å, α = β = γ = 90° |  | a = 115.0 Å, b = 61.8 Å, c = 124.9 Å, α = γ = 90°, β = 92.3° |  |
| Solvent content | 39% |  | 51% |  | 64% |  |
| $V_m$ | 2.0 Å$^3$/Da |  | 2.5 Å$^3$/Da |  | 3.4 Å$^3$/Da |  |
| Resolution | 50-2.1 Å | 2.14-2.10 Å | 50-3.4 Å | 3.48-3.40 Å | 50-4.25 Å | 4.35-4.25 Å |
| I/σ | 13.2 | 3.9 | 18.6 | 3.1 | 13.7 | 2.8 |
| Completeness | 99.6% | 99.4% | 98.1% | 97.5% | 98.2% | 98.9% |
| $R_{merge}$ | 0.108 | 0.450 | 0.090 | 0.583 | 0.066 | 0.556 |
| Multiplicity | 5.2 | 5.3 | 4.5 | 4.9 | 3.6 | 3.7 |
| Reflections | 23,262 | 1708 | 9200 | 653 | 12,522 | 931 |
| Mosaicity | 0.3 |  | 0.5 |  | 0.3 |  |
| Refinement |  |  |  |  |  |  |
| R | 0.175 |  | 0.243 |  | 0.285 |  |
| $R_{free}$ | 0.227 |  | 0.313 |  | 0.347 |  |
| Validation |  |  |  |  |  |  |
| Ramachandran favored | 97.3% |  | 94.1% |  | 92.5% |  |
| Ramachandran outliers | 0.0% |  | 0.8% |  | 1.4% |  |
| Rotamer outliers | 0.8% |  | 5.3% |  | 4.4% |  |
| Clash score | 2.91 (99$^{th}$) |  | 3.40 (100$^{th}$) |  | 3.98 (100$^{th}$) |  |
| Molprobity score | 1.22 (100$^{th}$) |  | 2.08 (100$^{th}$) |  | 2.14 (100$^{th}$) |  |

Each Fab primarily bound to one half-site of the IL-17 homodimer primarily through its heavy chain, and to a lesser extent through the light chain. Differences in binding of the humanized parent and humanized lead Fab appear consistent with higher affinity of the humanized lead Fab.

Figure 15:
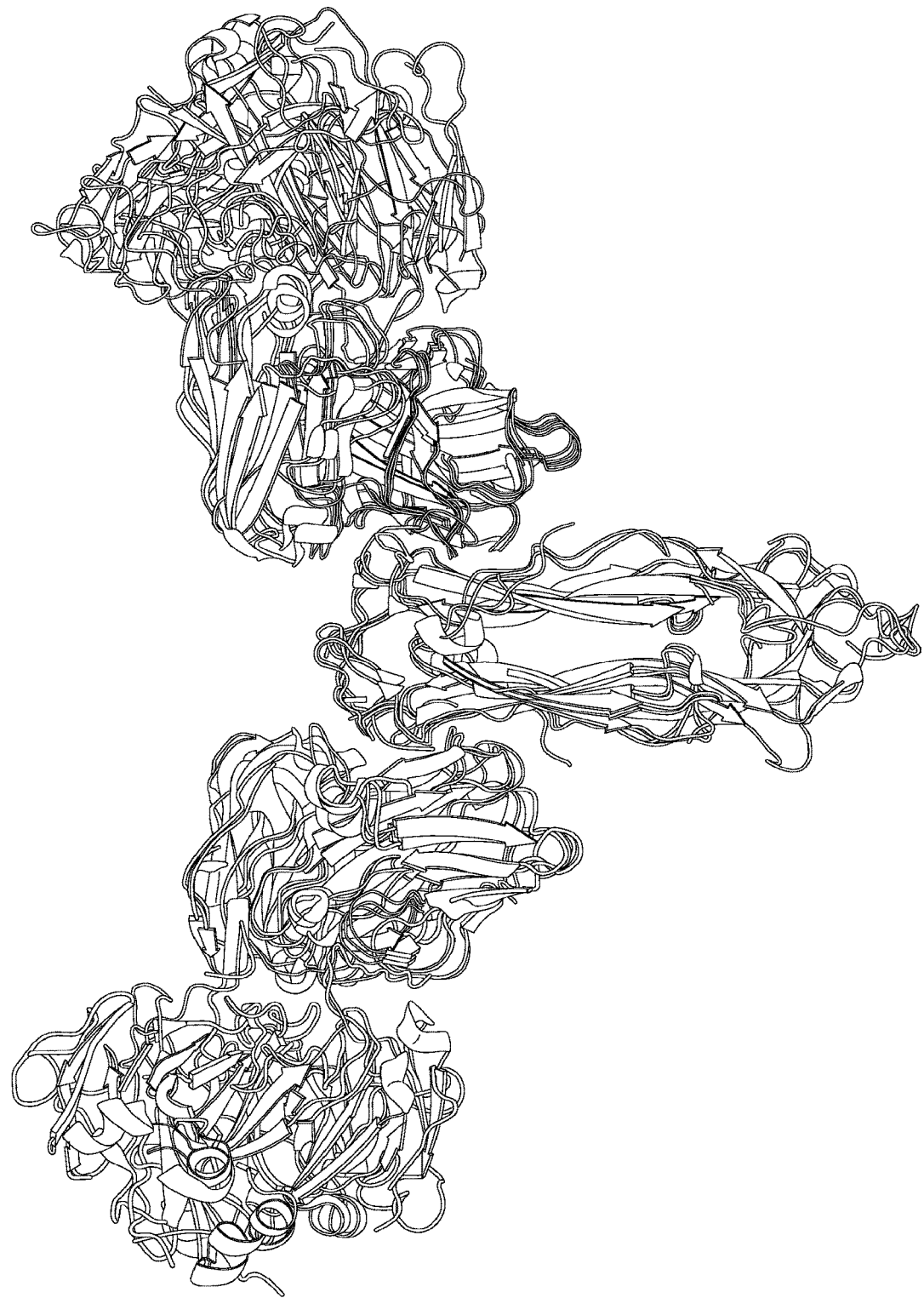
FIG. 15 shows the overlay of all four structures of the Fab with IL-17A or IL-17F, aligned by the interleukin.

Globally, each of the IL-17/BMS Fab complexes exhibited the same overall structure in which one Fab recognized one half-site of the IL-17 homodimer (FIG. 15). Thus, the binding stoichiometry is shown crystallographically to be two (2) Fabs to one (1) IL-17 homodimer (or two (2) Fabs to two (2) IL-17 protomers). The majority of the interactions with the interleukin are formed by the heavy chain with the hypervariable loop3 (or complementary determining region CDR3) forming the heart of the antibody-antigen interaction. In addition, a number of residues of CRD2 of the heavy chain interact with the interleukin. CDR1 of the heavy chain does not appear to interact with the interleukin significantly. For the light chain, CDR3 is involved in the recognition of IL-17. CDR1 of the light chain also appears to provide a weak, longer range binding interaction.

The crystal structure coordinates were used to define the contact interface as previously described (S. Sheriff, "Some Methods for Examining the Interaction between Two Molecules," Immunomethods, 3:191-196 (1993)), where a minimal definition, defined as residues in contact, was derived from the program CONTACSYM (Sheriff, S., Hendrickson, W. A., and Smith, J. L. (1987). Structure of Myohemerythrin in the Azidomet State at 1.7/1.3 Å Resolution. J. Mol. Biol. 197, 273-296.). A maximal definition of the interface, defined as residues at least partially buried by the interaction, was derived from Program MS (Connolly, M. L. (1983). Analytical Molecular Surface Calculation. J. Appl. Crystallogr. 16, 548-558).

TABLE 36

Contact and Buried Interface Residues of Complexes

| | IL17A (SEQ ID NO: 2) | | IL17F (SEQ ID NO: 4) | | | |
|---|---|---|---|---|---|---|
| IL17 Type mAb Type | Humanized Parent | Humanized Lead | Humanized Parent | | Humanized Lead | |
| Resolution | 2.85 Å | 3.4 Å | 3.75 Å | | 4.2Å | |
| Chain | | | A | B | A | B |
| | | Asn 75 | Asn 83 | Asn 83 | | Asn 83 |
| | Ala 92 | Ala 92 | Ala 100 | Ala 100 | Ala 100 | Ala 100 |
| | *Lys 93 | *Lys 93 | *Gln 101 | *Gln 101 | *Gln 101 | *Gln 101 |
| | *Cys 94 | *Cys 94 | *Cys 102 | *Cys 102 | *Cys 102 | *Cys 102 |
| | *Arg 95 | *Arg 95 | *Arg 103 | *Arg 103 | *Arg 103 | *Arg 103 |
| | *His 96 | *His 96 | *Asn 104 | *Asn 104 | *Asn 104 | *Asn 104 |
| | *Leu 97 | *Leu 97 | *Leu 105 | *Leu 105 | *Leu 105 | *Leu 105 |
| | *Gly 98 | | | | | Gly 106 |
| | Asp 103 | | | | | |
| | | | | Lys 113 | Lys 113 | |
| | *Val 106 | Val 106 | *Glu 114 | *Glu 114 | *Glu 114 | Glu 114 |
| | Asp 107 | Asp 107 | Asp 115 | Asp 115 | Asp 115 | Asp 115 |
| | *Tyr 108 | *Tyr 108 | *Ile 116 | *Ile 116 | *Ile 116 | *Ile 116 |
| | *His 109 | *His 109 | Ser 117 | *Ser 117 | *Ser 117 | *Ser 117 |
| | | | | | Met 118 | Met 118 |
| | *Asn 111 | *Asn 111 | *Asn 119 | *Asn 119 | *Asn 119 | *Asn 119 |
| | *Ser 112 | *Ser 112 | *Ser 120 | *Ser 120 | *Ser 120 | *Ser 120 |
| | *Val 113 | *Val 113 | *Val 121 | *Val 121 | *Val 121 | *Val 121 |
| | *Pro 114 | *Pro 114 | Pro 122 | Pro 122 | *Pro 122 | *Pro 122 |
| | | | *Gln 124 | Gln 124 | | *Gln 124 |
| | Ser 141 | Ser 141 | Thr 149 | Thr 149 | Thr 149 | Thr 149 |
| | Val 147 | *Val 147 | Val 155 | Val 155 | Val 155 | |
| | | Thr 148 | Thr 156 | Thr 156 | Thr 156 | Thr 156 |
| | *Pro 149 | *Pro 149 | *Pro 157 | *Pro 157 | *Pro 157 | *Pro 157 |
| | *Ile 150 | *Ile 150 | *Val 158 | *Val 158 | | Val 158 |
| | *Val 151 | *Val 151 | | | | |
| | His 152 | *His 152 | | | | |
| | His 153 | His 153 | | | | |

Residues with an asterick (*) are in contact at the complex interface.
Residues lacking an asterick are completely buried in the complex contact interface.

The main interaction of the Fab with IL-17A (SEQ ID NO:2) appears to be to residues L97 and a stretch of residues from H109-N111 (FIG. 15). I100, G98, N111, S112, V113, and P114 are conserved between IL-17A and IL-17F (amino acid residues I100, G98, N111, S112, V113, and P114 of SEQ ID NO:2 or IL-17A correspond to amino acid residues I108, G106, N119, S120, V121, and P122 of SEQ ID NO:4 or IL-17F). Thus, after obtaining this initial structure, it was expected that the humanized parent Fab A3052F would bind IL-17F in essentially an identical manner as that observed with IL-17A. However, near these residues there are several residues which differ between IL-17A (SEQ ID NO:2) and IL-17F (SEQ ID NO:4), such as K93 in IL-17A (Q101 in 17F), H95 in IL-17A (N104 in 17F), Y108 in IL-17A (I116 in 17F), and H109 in IL-17A (S117 in 17F). The C-terminus of IL-17A (SEQ ID NO:2) also appears to weakly interact with the Fab through residues P149 and I150, which correspond to residues P157 and V158 of IL-17F (SEQ ID NO:4). However, the differences between IL-17A and IL-17F would not be expected to alter the global antibody-antigen interaction significantly.

In comparison with the 2.85 Å resolution of the humanized parent Fab, the 3.4 Å resolution of the humanized lead Fab exhibits very similar interactions between the heavy chain and the interleukin as expected given the same sequence for the heavy chain. In contrast, the light chains between these two Fabs are completely different and as expected, these residues coordinate the interleukin in a different manner. The biAb Fab has one fewer residue in CDR3 which allows the loop to stretch out over the interleukin, allowing the backbone oxygen of G93 (G93 of SEQ ID NO:9 or G4 of SEQ ID NO:27) of the biAb Fab to form a direct hydrogen bond with the backbone nitrogen of Y108 of SEQ ID NO:2 (IL-17A). The same atom (backbone oxygen of N91 of SEQ ID NO:67 in the humanized parent Fab) was 2.3 Å away from the location in the parent Fab and was unable to hydrogen bond with the interleukin. Furthermore, the change of WN to YG allows Y33 of CDR1 (Y33 of SEQ ID NO:9) to approach the interleukin by 5.1 Å relative to its position in the lower affinity parent Fab thereby gaining additional packing interactions with H109 of IL-17A (SEQ ID NO:2). Finally, Y96 (Y96 of SEQ ID NO:9) of the biAb Fab may form a hydrogen bond with N106 (N106 of SEQ ID NO:13) of the heavy chain, assisting to align it in a hydrogen bond with the Y108 (Y108 of SEQ ID NO:2) backbone oxygen of the interleukin (IL-17A). Overall, these changes in the interface of CDR3 of the biAb Fab appear consistent with its higher affinity and have been tested by site-directed mutagenesis as shown below.

Unfortunately, crystal structures were not obtained for a complex consisting of the mouse parental Fab with either IL-17A or IL-17F. This suggests that the conditions for optimizing the interactions of these complexes are different from those used for successful crystallization of the humanized parental and lead Fabs.

In addition to interpretation of individual residue contacts, another measure of the differences in the humanized parent Fab vs. the biAb bound to the interleukin can be captured by calculating the total surface area buried by the interacting regions of the IL17/Fab complexes. This analysis was carried out using the MS algorithm for the IL-17A Fab complexes, as they were the highest resolution, and should provide the most reliable comparison. The two structures with IL-17F were over 3.5 Å and not considered reliable for this analysis. The parental Fab buried 720 Å$^2$ on IL-17A, while the biAb Fab buried 820 Å$^2$ (see Table 37). This difference (100 Å$^2$) in surface area is supported by the measured increased binding affinity of the lead Ab for IL-17A. Interestingly, the surface area of due to an extended side chain conformation for many amino acids is less than 100 Å$^2$ (A, N, D, C, G, L, P, S, T, V), see *Atlas of Protein Side-Chain Interactions V*1. Singh and Thornton 1992, 6-11). So, in aggregate by this measurement, the binding epitope difference on IL-17A for the lead vs. the parental structures might be described as approximately one (1) residue equivalent.

TABLE 37

| Surface Area | | |
|---|---|---|
| | Complex | |
| | IL-17A/Parent | IL-17A/Lead |
| Resolution | 2.85 Å | 3.4 Å |
| Buried on IL-17A | 720 | 820 |
| Buried on FAB | 740 | 830 |

Computational Epitope Prediction and Design of Alanine Shave Mutants

To provide detailed characterization of the different contributions of IL-17A and IL-17F epitope residues to the binding kinetics of the Parental and Lead Fabs, residues in the binding interfaces identified by X-ray crystallography were selected for site specific mutation to further distinguish differences between the binding of the human parent mAb and biAb.

A variety of criteria for selection of individual and multiple mutations on a single molecule were employed to select a set of representative and informative mutants to test. Crystal structures of IL-17A/Parental Fab, IL-17F/Lead Fab, described earlier herein were used to inform selection of residues to mutate. Residues at the ligand-Fab interaction interface were selected, while focusing on residues in contact with Fab light chain residues. Regions of poor definition in the crystal structure for one Fab but not the other were also selected because t his may suggest a difference in residue mobility within the complex in parent vs. biAb. In addition, residue positions where homologous IL-17 A/F residues differ were also selected because this may indicate tolerance to change for Fab binding, or may contribute to different binding affinities relative to the parental and biAb Fabs. The interface was modeled with the proposed mutants to look for differences in energetics in complex with parental vs. biAb Fabs. Clusters of contact residues (alanine shave mutants) were combined to generate mutants with additive or synergistic changes in binding affinity. The mutants of each interleukin which were generated for experimental analysis are shown in Table 38 and 39.

TABLE 38

| IL-17A mutants | |
|---|---|
| IL17A-WT | Residues 24-155 of SEQ ID NO: 2 |
| IL17A-M1 | N105A, Y108A, H109A |
| IL17A-M2 | L97A, Y108A, N111A |
| IL17A-M3 | K61A |
| IL17A-M4 | K61A, S64A, R69A |
| IL17A-M5 | N105A |
| IL17A-M6 | Y108A |
| IL17A-M7 | H109A |
| IL17A-M8 | V106A, D107A |
| IL17A-M9 | I150A, V151A |
| IL17A-M10 | Y108A, H109A, V151A, H152A |
| IL17A-M11 | Y108A, V151A |
| IL17A-M12 | H109A, I150A, H152A |

TABLE 39

| IL-17F mutants | |
|---|---|
| IL17F-WT | Residues 31-163 of SEQ ID NO: 4 |
| IL17F-M1 | L105A, I116A, N119A |
| IL17F-M2 | K113A, E114A, I116A |
| IL17F-M3 | S69A, R72A, R77A |
| IL17F-M4 | S69A |
| IL17F-M5 | R72A |
| IL17F-M6 | K113A |
| IL17F-M7 | E114A |
| IL17F-M8 | I116A |
| IL17F-M9 | D115A, S117A |
| IL17F-M10 | V158A, I159A |

Cloning & Expression of IL-17A & F Epitope Mapping Alanine Mutants

The mutant constructs of IL-17A and IL-17F were generated by gene synthesis and then cloned into the transient transfection vector for expression in HEK293-6E cells. 30 mL cultures of HEK293-6E cells at 1×10$^6$ cells/ml were transfected with expression plasmids/PEI complex and cells harvested on 120 hours post transfection.

Biacore Concentration Analysis of IL-17A&F Mutants

The concentration of each alanine mutant of IL-17A and IL-17F in the HEK harvest supernatants was quantitated by the level of capture on an anti-his Fab Biacore sensor surface. Protein A and huIgG surfaces were also immobilized as controls to assess non-specific binding of supernatants (no non-specific binding was observed). The concentration in each supernatant was quantitated using a standard curve of purified IL-17A-his or IL-17F-his ranging from 80 ug/mL to 0.039 ug/mL. The calibration curve was fit to a linear curve for the data from 0.3125 to 0.0039 ug/mL. The supernatants were run at 1:20, 1:60 and 1:180 dilution to allow multiple measurements in the linear range of the standard curve.

IL-17A mutant 8 had significantly reduced expression (only about 10% of the expression level of the wild-type). IL-17F mutants M2, M3, M7, and M9 had significantly reduced expression. The M9 mutant of IL-17F was virtually undetectable while the IL-17F M2 and M7 mutants were at less than 5% of the wild-type expression level.

TABLE 40

Expression levels of IL-17A and IL-17F constructs in HEK supernatants

| IL-17 variant | µg/mL expression level in HEK supernatants |
|---|---|
| IL17A-WT | 7.2 |
| IL17A-M1 | 6.3 |
| IL17A-M2 | 13.0 |
| IL17A-M3 | 15.3 |
| IL17A-M4 | 18.6 |
| IL17A-M5 | 10.3 |
| IL17A-M6 | 11.7 |
| IL17A-M7 | 12.4 |
| IL17A-M8 | 0.6 |
| IL17A-M9 | 13.6 |
| IL17A-M10 | 14.8 |
| IL17A-M11 | 13.2 |
| IL17A-M12 | 12.1 |
| IL17F-WT | 13.6 |
| IL17F-M1 | 16.2 |
| IL17F-M2 | 0.3 |
| IL17F-M3 | 1.4 |
| IL17F-M4 | 12.2 |
| IL17F-M5 | 6.8 |
| IL17F-M6 | 7.1 |
| IL17F-M7 | 0.3 |
| IL17F-M8 | 10.3 |
| IL17F-M9 | <0.1 |
| IL17F-M10 | 15.0 |

IL-17 Bioassay (NIH/3T3/KZ170 NF-κB Luciferase Reporter assay)

A murine fibroblast cell line (NIH/3T3, ATCC #CRL-1658) was stably transfected with an NF-κB luciferase reporter designated KZ170 and cloned out. NIH/3T3/KZ170 clone 1 cells were seeded at 10,000 cells/well in 96-well white opaque luciferase plates and incubated overnight at 37° C. The following day serial dilutions of recombinant human IL-17A, IL-17F, IL-17A Alanine mutants, and IL-17F Alanine mutants, using the Biacore determined concentrations, were made up in assay media and added to the plates containing the cells and incubated at 37° C. for 4 hours. Following incubation the media was removed and cells lysed before being read on the Berthold Centro XS$^3$ Luminometer using flash substrate according to manufactures instructions. Increases in mean fluorescence intensity (via activation of the NF-κB luciferase reporter) were indicative of an IL-17A or IL-17F receptor-ligand interaction. $EC_{50}$ (effective concentration at 50 percent) values were calculated using GraphPad Prism®4 software for each IL-17A and IL-17F Alanine mutant.

Figure 16:
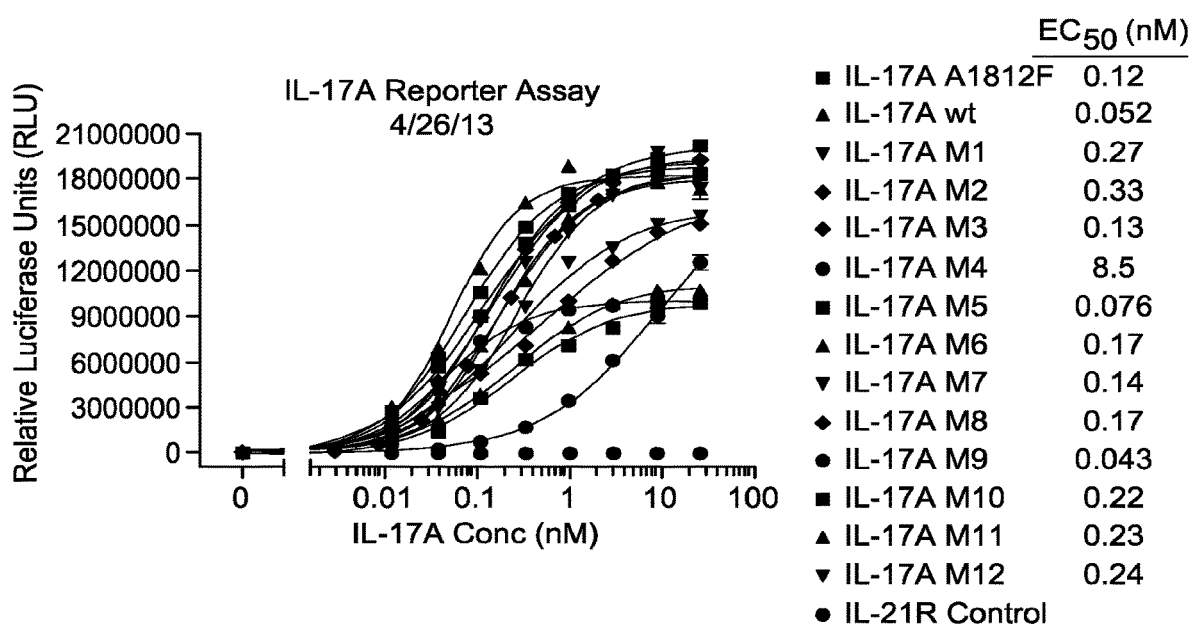
FIG. 16 graphically shows the cell functional activity of the IL-17A mutants.
Figure 17:
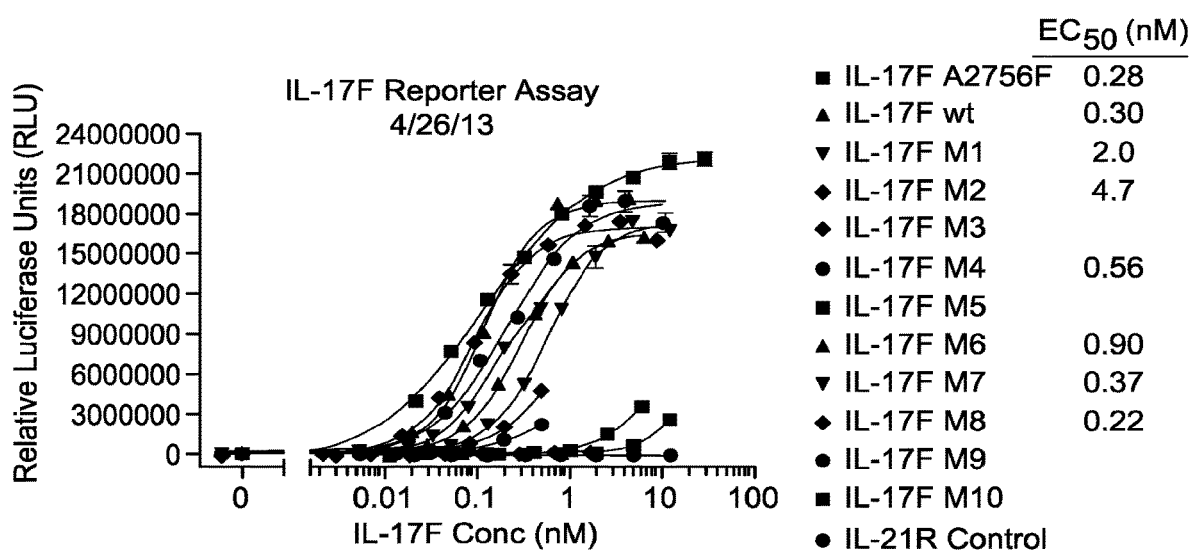
FIG. 17 graphically shows the cell functional activity of the IL-17F mutants.

All of the IL-17A mutants show cell functional activity, though some have lost a few fold in activity with respect to wild-type (FIG. 16). All IL-17F mutants except M3 show cell functional activity, though 3 of the mutants (M2, M5, M10) show significantly reduced activity (FIG. 17).

Biacore Binding Analysis of IL-17A&F Mutants for Binding to the BiAb3 and Other Related Antibodies The antibodies used for the Biacore binding assay were the biAb3 (heavy chain variable domain as shown in SEQ ID NO:7 and light chain variable domain as shown in SEQ ID NO:9) and the mouse parent antibody 339.15.5.3 (which contains the same variable region sequences as 339.15.3.5 and 339.15.3.6). Isotyping using the IsoStrip Mouse Monoclonal Antibody Isotyping Kit (Roche, Indianapolis, Ind., USA) demonstrates that the 339.15.5.3 antibody is the IgG2a/kappa just like the 339.15.3.5 used for humanization. No sequence or isotype differences have been determined between 339.15.3.5 and 339.15.5.3.

Figure 18:
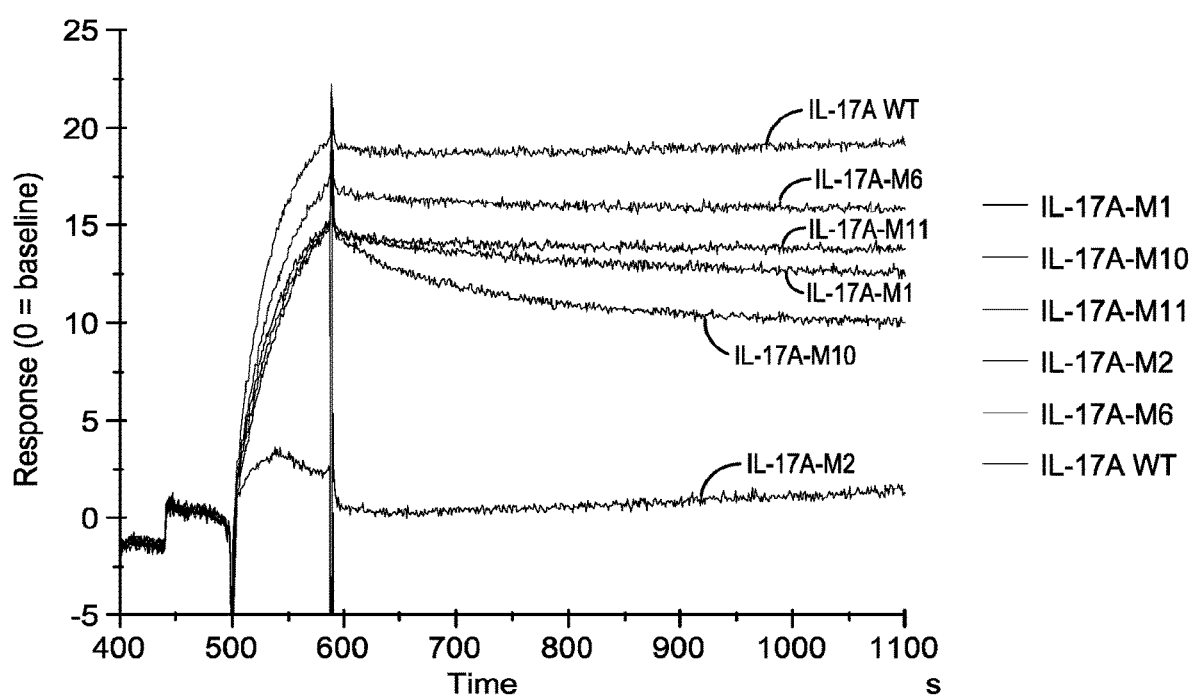
FIG. 18 is a schematic overly of the 9 nM IL-17A mutants binding BiAb3 demonstrating the accelerated off-rate of mutants containing Y108A mutation and combinations thereof.

The binding of the supernatants from the 30 mL expression of all 12 IL-17A and 10 IL-17F alanine mutants and a wild-type control supernatant for each (see Table 41 and Table 42) was measured by surface Plasmon resonance (SPR, Biacore)) on a Biacore T100 in HBS-EP (10 mM HEPES, 3 mM EDTA, 150 mM NaCl, 0.05% Tween 20, pH 7.4) at 25° C. The relevant antibodies and receptors were captured at a level of about 150-250 RUs by protein A immobilized at 3000 RUs on a CM5 sensor chip. In addition to the biAb3 and the parent mAb (339.15.3.5), other anti-IL-17 mAbs were used as controls for domain binding. In addition, the commercial receptor for IL-17A was used as a control: hIL-17RA-Fc (from R&D Systems) though a suitable IL-17RC reagent was not identified for this assay. The supernatants were diluted based on the anti-his quantitation determined concentration into HBS-EP at a concentration of 9 nM and diluted serially 1:3 and injected at 30 uL/min over the mAb or receptor surface for 90 seconds and, after a dissociation time, regenerated with 10 mM Glycine, pH 1.5. IL-17A M2 and IL-17F M1 were also run at higher concentration (in the 400-500 nM range at the expression level of the supernatant) because little to no binding signal was observed for the biAb captured surface. Binding to a reference surface of Protein A without any captured antibody was subtracted from all specific binding curves before analysis. All titration curves were fit to a 1:1 Langmuir binding model to determine the Kd values shown in FIG. 18 and Tables 41 and 42.

The Biacore results demonstrate that the IL-17A mutants M1, M2, M6, M10, and M11 show a reduction in binding affinity for the BiAb and contain residues that contribute to the binding epitope differences compared with the parent antibody. Most of these mutants show a 3-15 fold reduction (45-fold for M1) in binding to the IL-17RA-Fc likely because the receptor binding site has been altered. However, the cellular potency was maintained within a few fold for all mutants that impacted the BiAb3 interaction suggesting that these receptor disruptions are not significant for function.

The IL-17F mutants M1, M2, M7, and M8 show a reduction in binding affinity for the biAb however these same mutants show a similar reduced binding affinity for the parent antibody indicating that the epitope change between parent and biAb in IL-17A does not translate to IL-17F. These four mutants maintain potency in the cell functional assay similar to wild-type IL-17F, however many of the other mutants do not which limits our interpretation of the IL-17F mutagenesis.

TABLE 41

Biacore Kinetic Analysis of IL-17A Alanine Mutants Binding biAb3 and mouse parent antibodies

| | biAb3 | | | mouse parent | | |
|---|---|---|---|---|---|---|
| Variant | Kd (nM) | Kd-shift (from WT) | ΔΔG (kcal/mole) | Kd (nM) | Kd-shift (from WT) | ΔΔG (kcal/mole) |
| WT | 0.05 | none | 0 | 0.03 | none | 0 |
| M1 | 0.23 | 4.5 | 0.9 | 0.02 | none | −0.3 |
| M2 | >1 uM | >20,000 | >5.9 | >1 uM | >35,000 | >6.2 |
| M3 | 0.05 | none | 0 | 0.02 | none | −0.4 |
| M4 | 0.09 | 2 | 0.4 | 0.02 | none | −0.3 |
| M5 | 0.04 | none | −0.2 | 0.01 | none | −0.9 |
| M6 | 0.11 | 2.2 | 0.5 | 0.02 | none | −0.3 |
| M7 | 0.04 | none | −0.2 | 0.01 | none | −0.4 |
| M8 | 0.05 | none | 0 | 0.03 | none | 0.1 |
| M9 | 0.04 | none | −0.1 | 0.01 | none | −0.4 |
| M10 | 0.3 | 5.7 | 1.0 | 0.02 | none | −0.3 |
| M11 | 0.11 | 2.2 | 0.5 | 0.01 | none | −0.4 |
| M12 | 0.06 | none | 0.1 | 0.02 | none | −0.3 |

TABLE 42

Biacore Kinetic Analysis of IL-17F Alanine Mutants Binding biAb3 and mouse parent antibodies

| | biAb3 | | | Mouse parent | | |
|---|---|---|---|---|---|---|
| Variant | Kd (nM) | Kd-shift (from WT) | ΔΔG (kcal/mole) | Kd (nM) | Kd-shift (from WT) | ΔΔG (kcal/mole) |
| WT | 0.08 | none | 0 | 0.005 | none | 0 |
| M1 | >1 uM | >12,000 | >5.6 | >1 uM | >100,000 | >7.3 |
| M2 | 0.7 | 9.0 | 1.3 | 0.01 | 2 | 0.5 |
| M3 | 0.15 | 2.0 | 0.4 | <0.001 | none | −1.3 |
| M4 | 0.08 | none | 0 | <0.001 | none | −0.8 |
| M5 | 0.11 | none | 0.2 | <0.001 | none | −2.1 |
| M6 | 0.08 | none | 0 | <0.001 | none | −1.6 |
| M7 | 0.55 | 7.0 | 1.2 | 0.03 | 5.9 | 1.1 |
| M8 | 0.2 | 2.5 | 0.6 | 0.02 | 3.7 | 0.8 |
| M9 | NM | NM | NM | NM | NM | NM |
| M10 | 0.09 | none | 0 | <0.001 | none | −1.6 |

NM-not measured because the mutant was not expressed at detectable levels.

In Silico Mutagenesis

Energetic analyses were preformed for the IL-17A-Parent Fab, IL-17A-Lead Fab, and IL-17F-Lead Fab. Because the X-ray structures of the complexes were incomplete protein modeling was used to complete the structural models by building in the missing amino acid side chains using standard protocols (Maestro protein preparation wizard and Prime side chain modeling). The structural models were then used to calculate interaction energies for wildtype protein (IL-17A or IL-17F) or mutant IL-17 molecules with the Fabs. The interaction energies are a measure of the calculated affinity of the Fab towards the IL-17 (treated as ligand). In order to calculate the stability and delta-stability of mutant proteins the software MOE (ver. 2012.10, Chemical Computing Group) was used. The Residue Scanning protocol was used to perform computational site-directed mutagenesis to generate mutations and perform the affinity and stability calculations.

Figure 19:
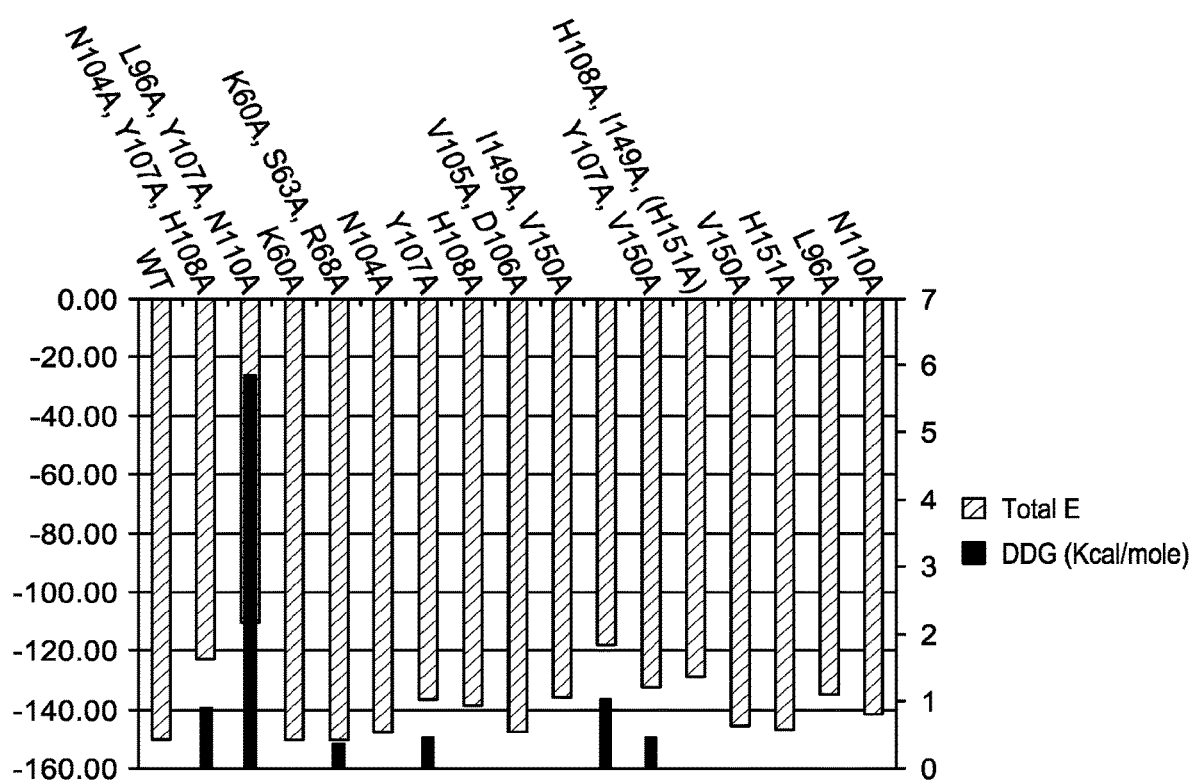
FIG. 19 shows the computational energetic analysis of IL-17A mutants binding to BiAb3.

A comparison of the computational predicted binding energies with the calculated ΔΔG values determined from the Biacore affinities for IL-17A mutants are shown in FIG. 19. The IL-17A mutants identified in FIG. 19 are mislabeled. The SEQ ID NO:2 numbering of IL-17A mutants identified in FIG. 19 are one less than they should be. The mutants are as identified as in Table 38. For example, N104A, Y107A and H108A should be N105A, Y108A and H109A and so on across the Figure. This comparison shows that the trend across the panel of mutants for the Biacore energetics are in agreement with the computational energetic prediction of the binding interface. Analysis of the IL-17A binding to the mouse parent were not possible because that complex failed to crystallize and an acceptable model could not be generated. An attempt to generate results for IL-17F mutants binding to the BiAb3 produced inconsistent results, likely because the structures used for these were at poor resolution and missing necessary residue information.

Summary of IL-17A&F Epitope Mapping

The strategy to identify the key differences between the epitope of the BiAb3 and the mouse parent (339.15.5.3) utilized X-ray crystallography, site-directed mutagenesis, in-silico mutagenesis, and binding and functional assays to analyze the mutants. The two mAbs differ in their light chain therefore the residues in contact with the light chain of each mAb were the focus of this study.

The IL-17A mutagenesis resulted in a panel of mutants with good expression and reasonable cellular potency. A significant change in the ΔΔG for binding to the biAb3 was measured for all mutants that contain Y108A with a 0.5 kcal/mole change measured for the Y108A single point mutant. These changes in ΔΔG were not observed for binding to the mouse parent antibody indicating that the Y108 is new residue in the epitope of IL-17A for the biAb3 compared with the mouse parent mAb. The energetic data is consistent with the interface analysis of the crystal structures showing that this residue is interacting with the light chain which is different in biAb3 compared with the mouse parent and that Y108A is brought into closer proximity to the biAb3 due to differences in the CDR3 of the biAb3 light chain compared with the mouse parent. The only IL-17A mutant shown here that impacts the binding of the mouse parent antibody is one that interacts with a heavy chain residue indicating that the light chain does not play much of a role in binding of the mouse parent antibody to IL-17A.

The IL-17F mutagenesis resulted in a panel of mutants with more variable and lower expression levels and significant losses in potency. The crystal structures obtained for IL-17F were also at poorer resolution than the IL-17A structures. This suggests that IL-17F is not as amenable to mutagenesis and potentially more dynamic in nature. However, the mutants with reduced binding to the biAb3 also reduced binding to the mouse parent mAb. And, all of the these mutants with reduced mAb binding were of reasonable potency and lower, but sufficient, expression levels for the analysis.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating an inflammatory and/or autoimmune disease or disorder characterized by an elevated expression of IL-23 in a human in need of such treatment comprising administering a therapeutically effective amount of a monoclonal antibody that binds to IL-23p19 and comprises a heavy chain variable domain and a light chain variable domain, wherein: a) the heavy chain variable domain comprises complementarity determining regions (CDRs), wherein: i) CDR1 has the amino acid sequence of SEQ ID NO: 19; ii) CDR2 has the amino acid sequence of SEQ ID NO:20; and iii) CDR3 has the amino acid sequence of SEQ ID NO:21; and wherein: b) the light chain variable domain comprises complementarity determining regions (CDRs), wherein: i) CDR1 has the amino acid sequence of SEQ ID NO:22; ii) CDR2 has the amino acid sequence of SEQ ID NO:23; and iii) CDR3 has the amino acid sequence of SEQ ID NO:24.

2. The method of claim 1, wherein the light chain variable domain comprises the amino acid sequence of SEQ ID NO:9.

3. The method of claim 1, wherein the heavy chain variable domain comprises the amino acid sequence of SEQ ID NO:7.

4. The method of claim 3, wherein the light chain variable domain comprises the amino acid sequence of SEQ ID NO:9.

5. The method of claim 1, wherein the antibody comprises a heavy chain constant domain comprising the amino acid sequence of SEQ ID NO:8 or SEQ ID NO:11.

6. The method of claim 1, wherein the antibody comprises a light chain comprising the amino acid sequence of SEQ ID NO:17.

7. The method of claim 1, wherein the heavy chain comprises a variable domain comprising the amino acid sequence of SEQ ID NO:7 and a constant domain comprising the amino acid sequence of SEQ ID NO:8.

8. The method of claim 7, wherein the antibody comprises a light chain comprising the amino acid sequence of SEQ ID NO:17.

9. The method of claim 1, wherein the antibody comprises a heavy chain and light chain, and wherein the heavy chain comprises a human immunoglobulin constant region.

10. The method of claim 9, wherein the isotype of the heavy chain is IgG1, IgG2, IgG3 or IgG4.

11. The method of claim 10, wherein the IgG4 heavy chain has a Serine to Proline mutation at position 241 according to Kabat.

12. The method of claim 1, wherein the disease or disorder is irritable bowel syndrome (IBS), inflammatory bowel disease (IBD), ulcerative colitis, Crohn's disease, atopic dermatitis, contact dermatitis, systemic sclerosis, systemic lupus erythematosus (SLE), antineutrophil cytoplasmic antibody (ANCA)-associated vasculitis (AAV), giant cell arteritis, multiple sclerosis (MS), relapsing-remitting multiple sclerosis, secondary-progressive multiple sclerosis, primary-progressive multiple sclerosis, progressive-relapsing multiple sclerosis, colitis, arthritis, rheumatoid arthritis (RA), osteoarthritis, Sjogren's syndrome, psoriasis, psoriatic arthritis, asthma, organ allograft rejection, graft vs. host disease (GVHD), lupus nephritis, IgA nephropathy, or scleroderma.

13. A method of treating an inflammatory and/or autoimmune disease or disorder characterized by an elevated expression of IL-23 in a human in need of such treatment comprising administering a therapeutically effective amount of a composition comprising a monoclonal antibody that binds to IL-23p19 and comprises a heavy chain variable domain and a light chain variable domain and a pharmaceutically acceptable carrier, wherein: a) the heavy chain variable domain comprises complementarity determining regions (CDRs), wherein: i) CDR1 has the amino acid sequence of SEQ ID NO: 19; ii) CDR2 has the amino acid sequence of SEQ ID NO:20; and iii) CDR3 has the amino acid sequence of SEQ ID NO:21; and wherein: b) the light chain variable domain comprises complementarity determining regions (CDRs), wherein: i) CDR1 has the amino acid sequence of SEQ ID NO:22; ii) CDR2 has the amino acid sequence of SEQ ID NO:23; and iii) CDR3 has the amino acid sequence of SEQ ID NO:24.

14. The method of claim 13, wherein the light chain variable domain comprises the amino acid sequence of SEQ ID NO:9.

15. The method of claim 13, wherein the heavy chain variable domain comprises the amino acid sequence of SEQ ID NO:7.

16. The method of claim 15, wherein the light chain variable domain comprises the amino acid sequence of SEQ ID NO:9.

17. The method of claim 13, wherein the antibody comprises a heavy chain constant domain comprising the amino acid sequence of SEQ ID NO:8 or SEQ ID NO:11.

18. The method of claim 13, wherein the antibody comprises a light chain comprising the amino acid sequence of SEQ ID NO:17.

19. The method of claim 13, wherein the heavy chain comprises a variable domain comprising the amino acid sequence of SEQ ID NO:7 and a constant domain comprising the amino acid sequence of SEQ ID NO:8.

20. The method of claim 19, wherein the antibody comprises a light chain comprising the amino acid sequence of SEQ ID NO:17.

21. The method of claim 13, wherein the antibody comprises a heavy chain and a light chain, and wherein the heavy chain comprises a human immunoglobulin constant region.

22. The method of claim 21, wherein the isotype of the heavy chain is IgG1, IgG2, IgG3 or IgG4.

23. The method of claim 22, wherein the IgG4 heavy chain has a Serine to Proline mutation at position 241 according to Kabat.

24. The method of claim 13, wherein the disease or disorder is irritable bowel syndrome (IBS), inflammatory bowel disease (IBD), ulcerative colitis, Crohn's disease, atopic dermatitis, contact dermatitis, systemic sclerosis, systemic lupus erythematosus (SLE), antineutrophil cytoplasmic antibody (ANCA)-associated vasculitis (AAV), giant cell arteritis, multiple sclerosis (MS), relapsing-remitting multiple sclerosis, secondary-progressive multiple sclerosis, primary-progressive multiple sclerosis, progressive-relapsing multiple sclerosis, colitis, arthritis, rheumatoid arthritis (RA), osteoarthritis, Sjogren's syndrome, psoriasis, psoriatic arthritis, asthma, organ allograft rejection, graft vs. host disease (GVHD), lupus nephritis, IgA nephropathy, or scleroderma.

* * * * *